US012565530B2

(12) United States Patent
Bacac et al.

(10) Patent No.: US 12,565,530 B2
(45) Date of Patent: Mar. 3, 2026

(54) COMBINATION THERAPY WITH TARGETED 4-1BB (CD137) AGONISTS/ANTI-FAP BINDING DOMAIN AND ANTI-CEA/ANTI-CD3 BISPECIFIC ANTIBODY

(71) Applicant: Hoffmann-La Roche Inc., Little Falls, NJ (US)

(72) Inventors: Marina Bacac, Schlieren (CH); Christina Claus, Schlieren (CH); Claudia Ferrara Koller, Schlieren (CH); Christian Klein, Schlieren (CH); Sabine Lang, Schlieren (CH); Viktor Levitski, Schlieren (CH); Pablo Umaña, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/166,783

(22) Filed: Feb. 9, 2023

(65) Prior Publication Data

US 2023/0357397 A1 Nov. 9, 2023

Related U.S. Application Data

(63) Continuation of application No. 16/825,773, filed on Mar. 20, 2020, now abandoned, which is a (Continued)

(30) Foreign Application Priority Data

Dec. 19, 2016 (EP) ..................................... 16205190
Mar. 1, 2017 (EP) ..................................... 17158771
(Continued)

(51) Int. Cl.
*C07K 16/28* (2006.01)
*A61P 35/00* (2006.01)
(Continued)

(52) U.S. Cl.
CPC .......... *C07K 16/2809* (2013.01); *A61P 35/00* (2018.01); *C07K 14/70575* (2013.01);
(Continued)

(58) Field of Classification Search
None
See application file for complete search history.

(56) References Cited

U.S. PATENT DOCUMENTS 8,945,571 B2 * 2/2015 Mossner ................. A61P 35/00
435/69.6
9,011,847 B2 4/2015 Bacac et al.
(Continued)

FOREIGN PATENT DOCUMENTS

WO 2014/131712 A1 9/2014
WO 2015/156268 A1 10/2015
(Continued)

OTHER PUBLICATIONS

Clinicaltrials.gov NCT02324257 (v20), Retrieved online: <URL: https://clinicaltrials.gov/study/NCT02324257?tab=history&a=20>, [retrieved on Aug. 4, 2022], Dec. 1, 2015.*
(Continued)

*Primary Examiner* — Claire Kaufman
(74) *Attorney, Agent, or Firm* — GENENTECH, INC.

(57) ABSTRACT

The present invention relates to combination therapies employing tumor targeted anti-CEA/CD3 bispecific antibodies and/or agents blocking PD-L1/PD-1 interaction in combination with 4-1BB (CD137) agonists, in particular 4-1BBL trimer containing antigen binding molecules that also target FAP, the use of these combination therapies for
(Continued)

- A:Vehicle
- B:CEA TCB(2,5mg/kg, twice/week)
- C: mono untarg-4-1BBL (10mg/kg, once/week)
- D: bi untarg-4-1BBL (10mg/kg, once/week)
- E: mono FAP (4B9)-4-1BBL (10mg/kg, once/week)
- F: 4-1BBLxFAP(4B9) bi (10mg/kg, once/week)
- G: CEA-TCB + mono untarg-4-1BBL
- H: CEA-TCB + bi untarg-4-1BBL
- I: CEA-TCB + mono FAP (4B9)-4-1BBL
- J: CEA-TCB + bi FAP (4B9)-4-1BBL the treatment of cancer and methods of using the combination therapies.

9 Claims, 65 Drawing Sheets

Specification includes a Sequence Listing.

Related U.S. Application Data continuation of application No. 16/446,484, filed on Jun. 19, 2019, now abandoned, which is a continuation of application No. PCT/EP2017/083235, filed on Dec. 18, 2017.

(30)    Foreign Application Priority Data

| | | | |
|---|---|---|---|
| Mar. 14, 2017 | (EP) | ................................... | 17160857 |
| Sep. 25, 2017 | (EP) | ................................... | 17192936 |

(51) Int. Cl.
| | |
|---|---|
| *C07K 14/705* | (2006.01) |
| *C07K 16/30* | (2006.01) |
| *C07K 16/40* | (2006.01) |
| *A61K 39/00* | (2006.01) |

(52) U.S. Cl.
CPC ...... *C07K 16/2863* (2013.01); *C07K 16/3007* (2013.01); *C07K 16/40* (2013.01); *A61K 2039/505* (2013.01); *C07K 2317/31* (2013.01); *C07K 2317/565* (2013.01)

(56)    References Cited

U.S. PATENT DOCUMENTS

| | | | |
|---|---|---|---|
| 9,266,938 B2 | 2/2016 | Ast et al. |
| 9,365,641 B2 | 6/2016 | June et al. |
| 9,447,159 B2 | 9/2016 | Ast et al. |
| 9,526,797 B2 | 12/2016 | Gerdes et al. |
| 9,926,379 B2 | 3/2018 | Bruenker et al. |
| 10,155,815 B2 | 12/2018 | Bacac et al. |
| 10,184,009 B2 | 1/2019 | Ast et al. |
| 10,202,464 B2 | 2/2019 | Ast et al. |
| 10,253,110 B2 | 4/2019 | Bacac et al. |
| 10,316,104 B2 | 6/2019 | Ast et al. |
| 10,323,098 B2 | 6/2019 | Ast et al. |
| 10,392,445 B2 | 8/2019 | Amann et al. |
| 10,464,981 B2 | 11/2019 | Amann et al. |
| 10,526,413 B2 | 1/2020 | Amann et al. |
| 10,577,429 B2 | 3/2020 | Bacac et al. |
| 10,603,360 B2 | 3/2020 | Gerdes et al. |
| 11,111,312 B2 | 9/2021 | Ast et al. |
| 11,130,822 B2 | 9/2021 | Ast et al. |
| 11,149,083 B2 | 10/2021 | Amann et al. |
| 11,214,622 B2 | 1/2022 | Bruenker et al. |
| 11,242,396 B2 | 2/2022 | Bruenker et al. |
| 11,267,903 B2 | 3/2022 | Amann et al. |
| 11,286,300 B2 | 3/2022 | Ferrara-Koller et al. |
| 11,306,154 B2 | 4/2022 | Amann et al. |
| 11,332,545 B2 | 5/2022 | Bacac et al. |
| 11,447,558 B2 | 9/2022 | Ferrara-Koller et al. |
| 2014/0242079 A1 | 8/2014 | Bacac et al. |
| 2014/0242080 A1 | 8/2014 | Jaeger et al. |
| 2014/0370019 A1 | 12/2014 | Bruenker et al. |
| 2017/0022287 A1 | 1/2017 | Igawa et al. |
| 2017/0174786 A1 | 6/2017 | Bacac et al. |
| 2017/0247467 A1 | 8/2017 | Amann et al. |
| 2018/0171017 A1 | 6/2018 | Taniguchi et al. |
| 2018/0230215 A1 | 8/2018 | Hofer et al. |
| 2018/0340030 A1 | 11/2018 | Bruenker et al. |
| 2019/0016771 A1 | 1/2019 | Amann et al. |
| 2019/0031784 A1 | 1/2019 | Bacac et al. |
| 2019/0033765 A1 | 1/2019 | Ast et al. |

| | | | |
|---|---|---|---|
| 2019/0185566 A1 | 6/2019 | Koller et al. |
| 2019/0194291 A1 | 6/2019 | Bruenker et al. |
| 2019/0211113 A1 | 7/2019 | Amann et al. |
| 2019/0322763 A1 | 10/2019 | Ast et al. |
| 2019/0322765 A1 | 10/2019 | Ast et al. |
| 2020/0071411 A1 | 3/2020 | Amann et al. |
| 2020/0188526 A1 | 6/2020 | Klein et al. |
| 2020/0190206 A1 | 6/2020 | Koller et al. |
| 2020/0197492 A1 | 6/2020 | Gerdes et al. |
| 2020/0199234 A1 | 6/2020 | Georges et al. |
| 2020/0223925 A1 | 7/2020 | Gasser et al. |
| 2020/0231691 A1 | 7/2020 | Grau-Richards et al. |
| 2020/0270321 A1 | 8/2020 | Amann et al. |
| 2020/0277392 A1 | 9/2020 | Amann et al. |
| 2020/0317774 A1 | 10/2020 | Hofer et al. |
| 2020/0325225 A1 | 10/2020 | Bacac et al. |
| 2020/0325238 A1 | 10/2020 | Bacac et al. |
| 2020/0347115 A1 | 11/2020 | Duerr et al. |
| 2020/0392237 A1 | 12/2020 | Bacac et al. |
| 2021/0009656 A1 | 1/2021 | Bruenker et al. |
| 2021/0024610 A1 | 1/2021 | Koller et al. |
| 2021/0054021 A1 | 2/2021 | Deak-Codarri et al. |
| 2021/0070882 A1 | 3/2021 | Bacac et al. |
| 2021/0095002 A1 | 4/2021 | Claus et al. |
| 2021/0163617 A1 | 6/2021 | Ferrara et al. |
| 2021/0188992 A1 | 6/2021 | Bruenker et al. |
| 2021/0253724 A1 | 8/2021 | Claus et al. |
| 2021/0292426 A1 | 9/2021 | Duerr et al. |
| 2021/0324108 A1 | 10/2021 | Amann et al. |
| 2022/0025046 A1 | 1/2022 | Amann et al. |
| 2022/0025069 A1 | 1/2022 | Claus et al. |
| 2022/0073646 A1 | 3/2022 | Amann et al. |
| 2022/0227878 A1 | 7/2022 | Bruenker et al. |
| 2022/0242971 A1 | 8/2022 | Ast et al. |
| 2022/0267395 A1 | 8/2022 | Amann et al. |
| 2022/0281995 A1 | 9/2022 | Bacac et al. |

FOREIGN PATENT DOCUMENTS

| | | | |
|---|---|---|---|
| WO | 2016/075278 A1 | 5/2016 |
| WO | 2016/079076 A1 | 5/2016 |
| WO | 2016/156291 A1 | 10/2016 |
| WO | 2020/260329 A1 | 12/2020 |
| WO | 2021/140130 A1 | 7/2021 |
| WO | 2021/198335 A1 | 10/2021 |
| WO | 2022/148853 A1 | 7/2022 |

OTHER PUBLICATIONS

Guo, "Extracellular Domain if 4-1BBL Enhanced the Antitumoral Efficacy of Blood Lymphocytes Mediated by Anti-CD3 x Anti-Pgp Bispecific Diabody Against Human Multidrug-Resistant Lukemia" Cell Immunol 251:102-108 (2008).

Herold, E., et al., "Determinants of the assembly and function of antibody variable domains" Sci Rep 7:12276 (1-17) (Sep. 25, 2017).

"International Search Report—PCT/EP2017/083235," :pp. 1-8 (Apr. 23, 2018).

Kranz, D., et al., "Restricted reassociation of heavy and light chains from hapten-specific monoclonal antibodies" PNAS USA 78(9):5807-5811 (Sep. 1, 1981).

Muller et al., "A Novel Antibody-4-1BBL Fusion Protein for Targeted Costimulation in Cancer Immunotherapy" J Immunother 31(8):714-722 (2008).

Oberst, M., et al., "CEA/CD3 bispecific antibody MEDI-565/AMG 211 activation of T cells and subsequent killing of human tumors is independent of mutations commonly found in colorectal adenocarcinomas" MABS 6(6):1571-1584 (Nov. 30, 2014).

Portolano, S., et al., "Lack of promiscuity in autoantigen-specific H and L chain combinations as revealed by human H and L chain 'Roulette'" J Immunol 150(3):880-887 (Feb. 1, 1993).

Sporn, M., et al., "Proliferative Diseases" Am J Med 70(6):1231-1235 (Jun. 1, 1981).

US CLINICALTRIALS.gov et al., "A Study of RO6958688 in Participants With Locally Advanced and/or Metastatic Carcinoembryonic Antigen Positive Solid Tumors—NCT02324257" (ClinicalTrials.

(56) References Cited

OTHER PUBLICATIONS gov Identifier: NCT02324257; First Posted: Dec. 24, 2014; Last Updated Posted: Apr. 17, 2020; History of Changes Retrieved; Aug. 4, 2022),:1-4 (Aug. 4, 2022).

Chen, S., et al., "Combination of 4-1BB Agonist and PD-1 Antagonist Promotes Antitumor Effector/Memory CD8 T Cells in a Poorly Immunogenic Tumor Model" Cancer Immunol Res 3(2):149-160 (Feb. 1, 2015).

Cytotoxic effect and mechanism of human 4-1BBL/anti-CD20 fusion protein to enhance anti-CD3/anti-CD20 bi-functional antibody. Liu, China Doctoral Dissertation Full-text Database: Medicine and Health Section, Issue 10, E059-53, 2010 (English abstract), pp. 99 (2010).

Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).

Zhang et al., "Research Progress of Monoclonal Antibody Drugs in Tumor Treatment" J Pract Oncology-China, 30(6):495-500 (Dec. 10, 2015).

* cited by examiner

FIG. 3A

CD3+ T-Cells in the tumor

FIG. 3B

Ratio of CD8+/CD4+ T-Cells in the tumor

CD8 quantification in tumors

FIG. 12A

CD8 quantification, d50, 6days after 4th therapy

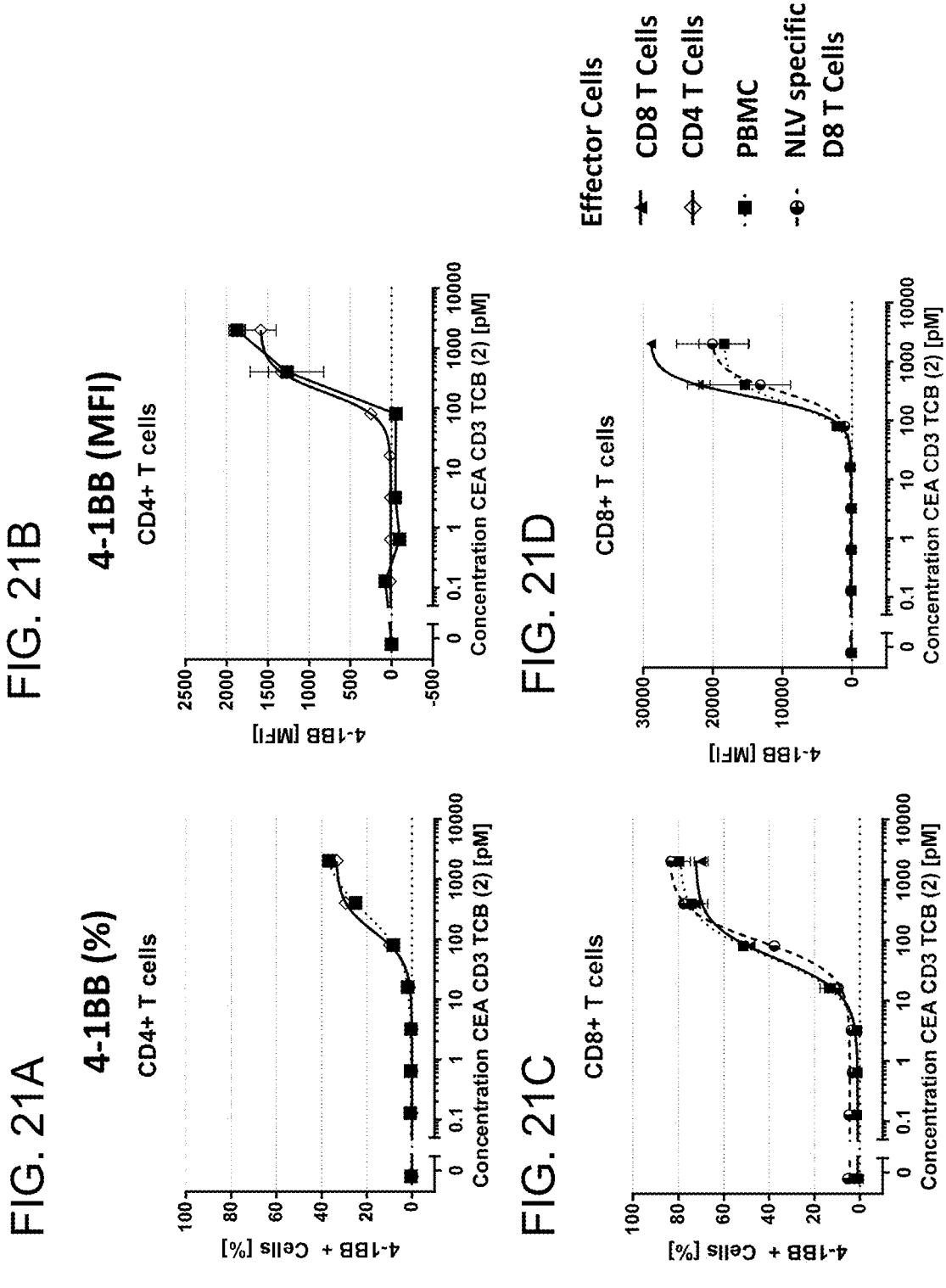

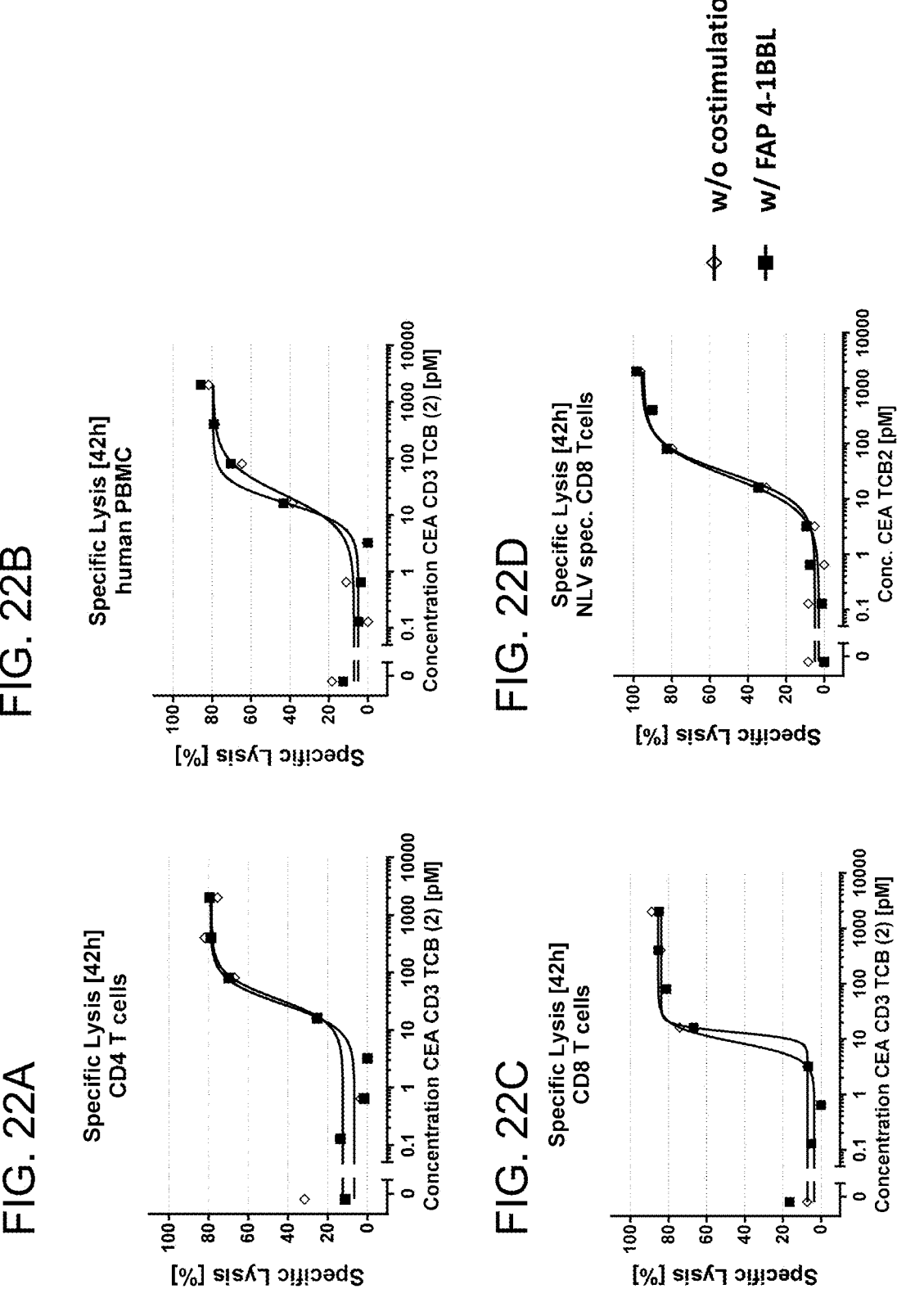

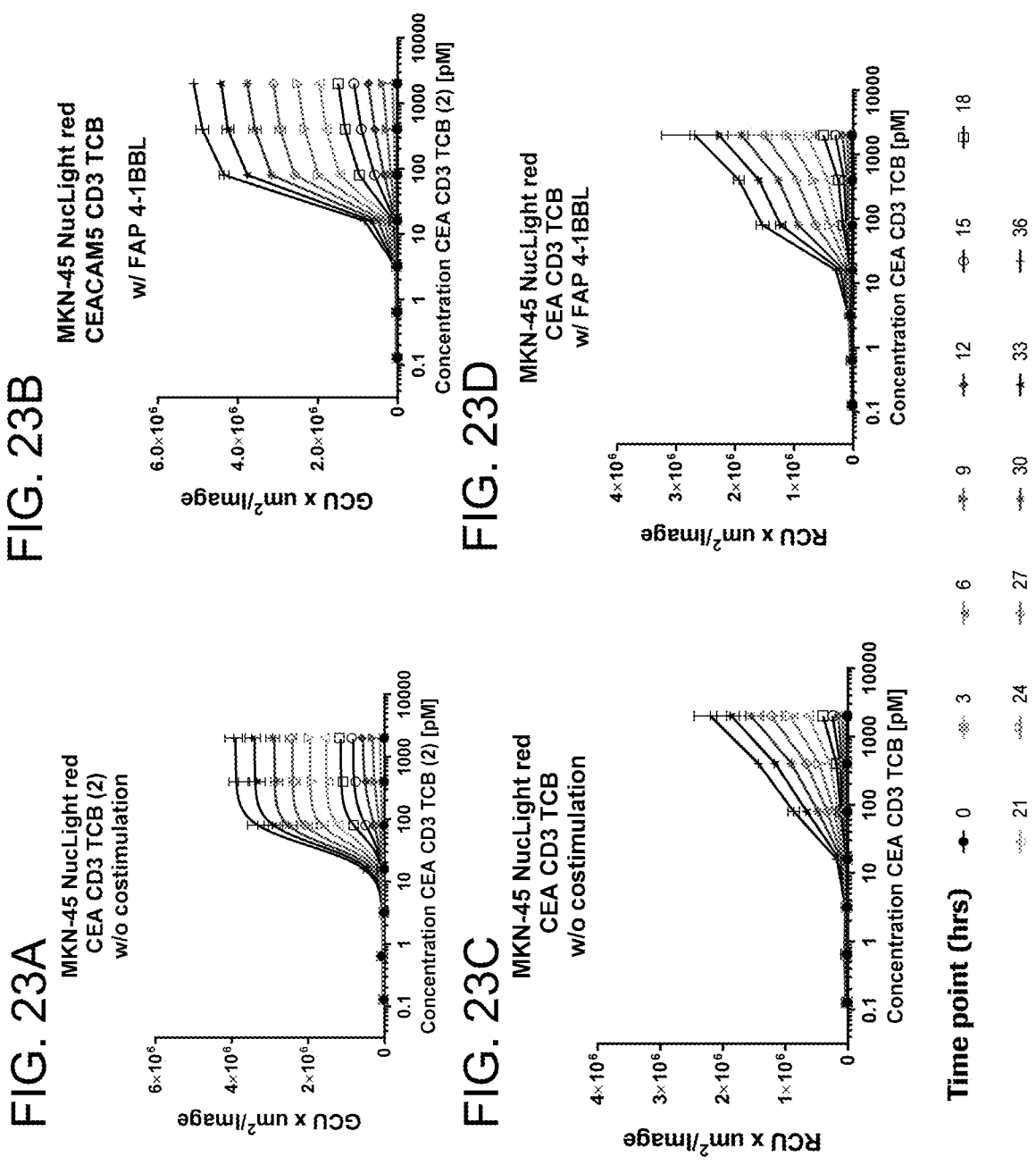

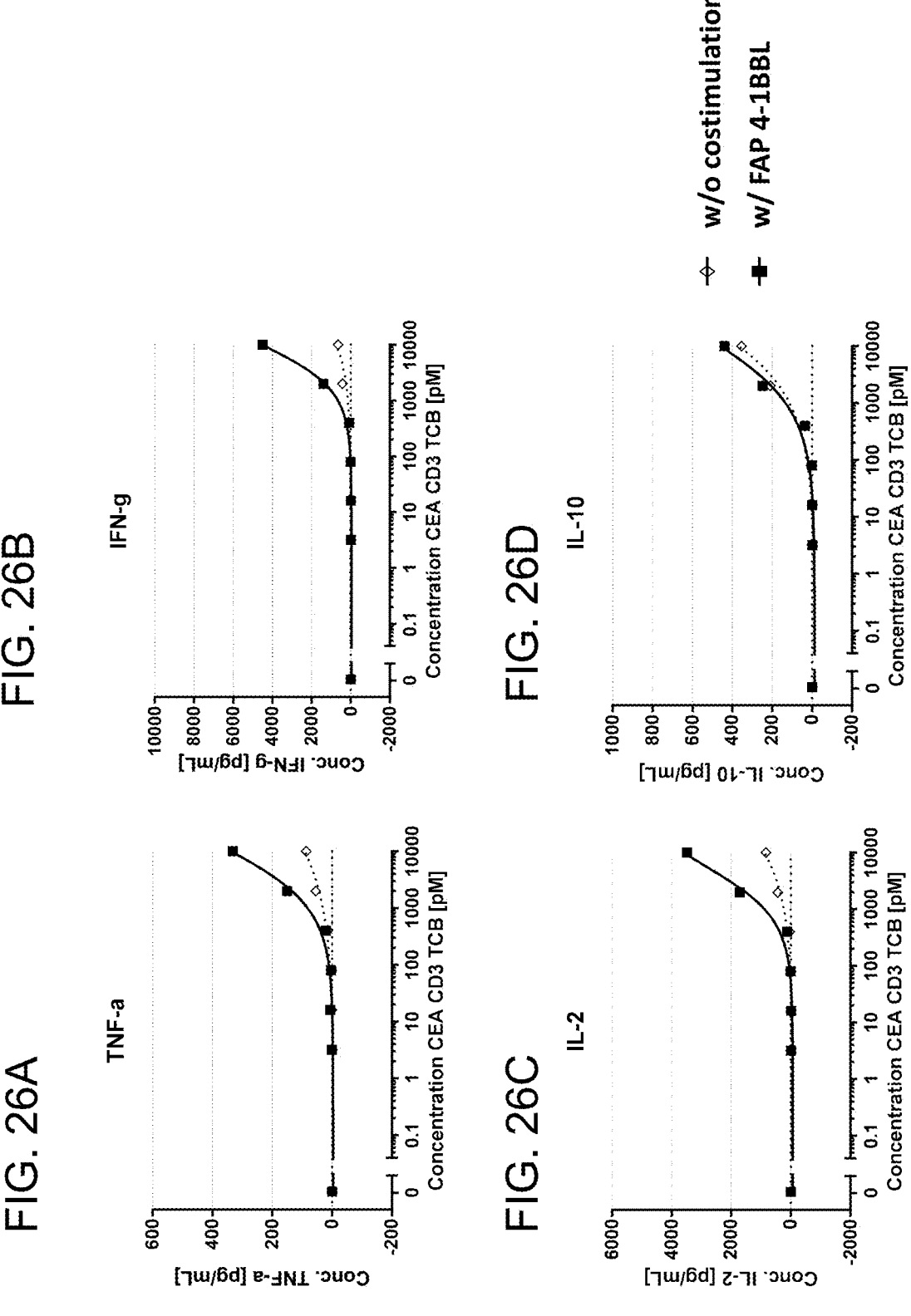

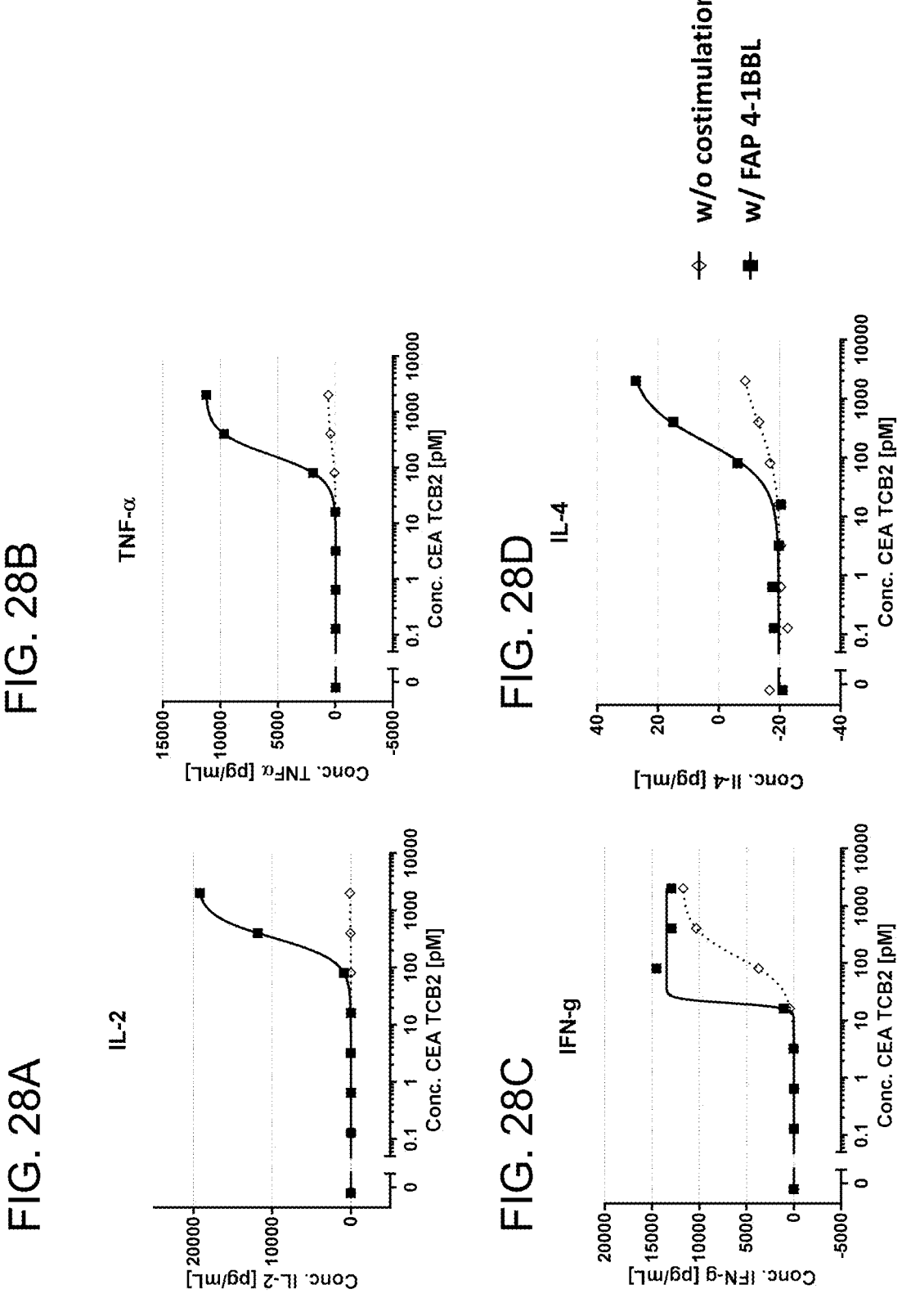

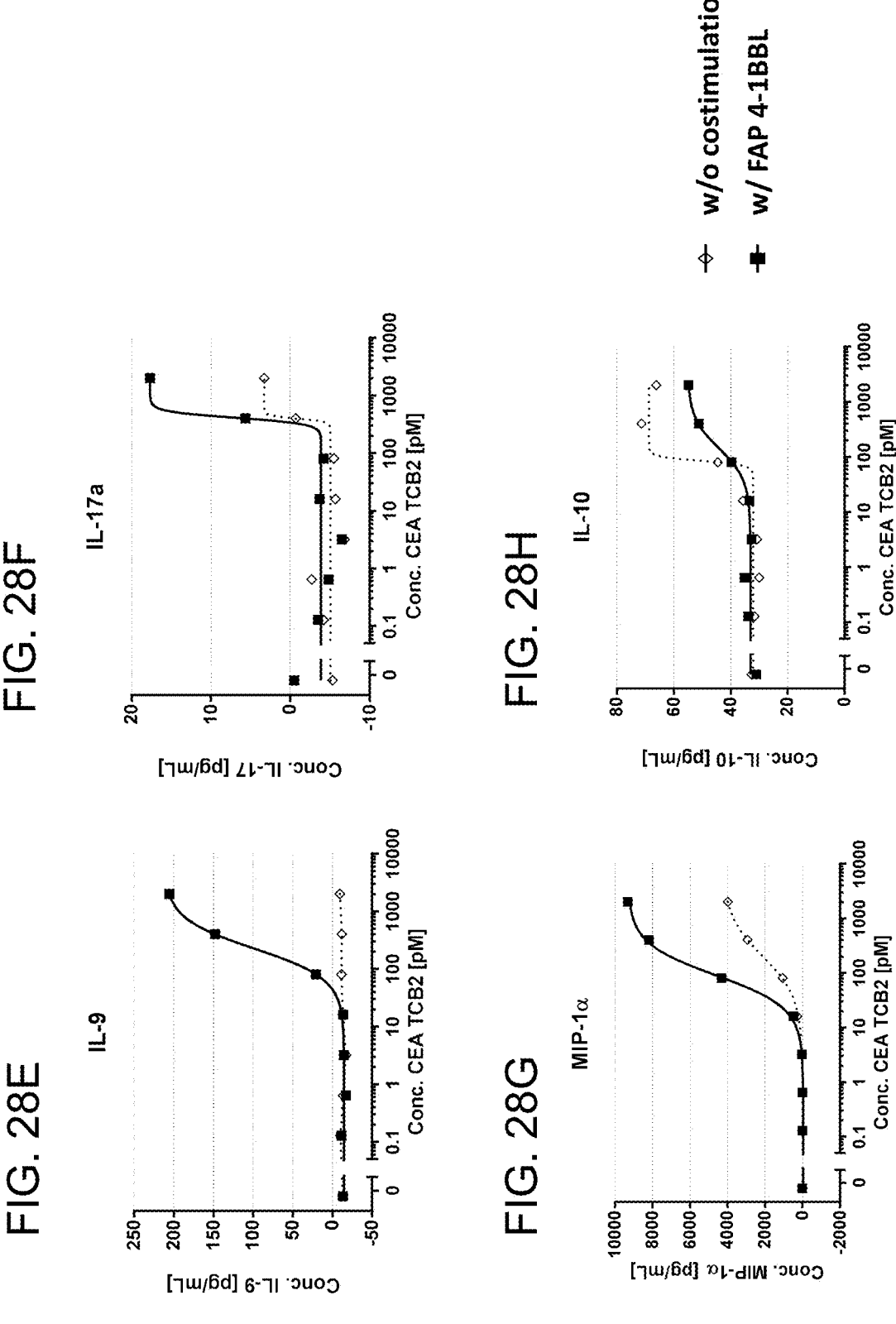

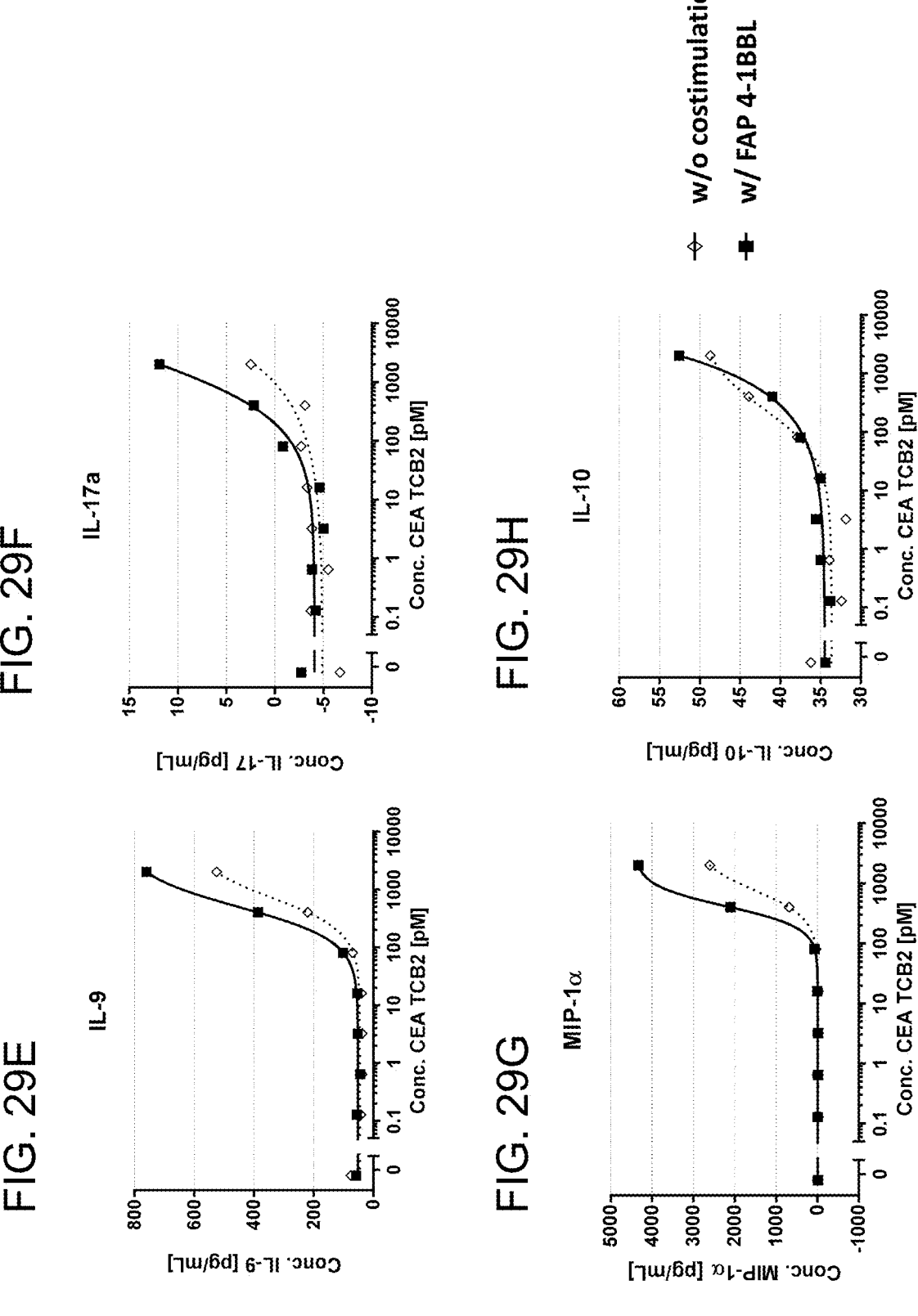

FIG. 38 donor 3

Figure 38:
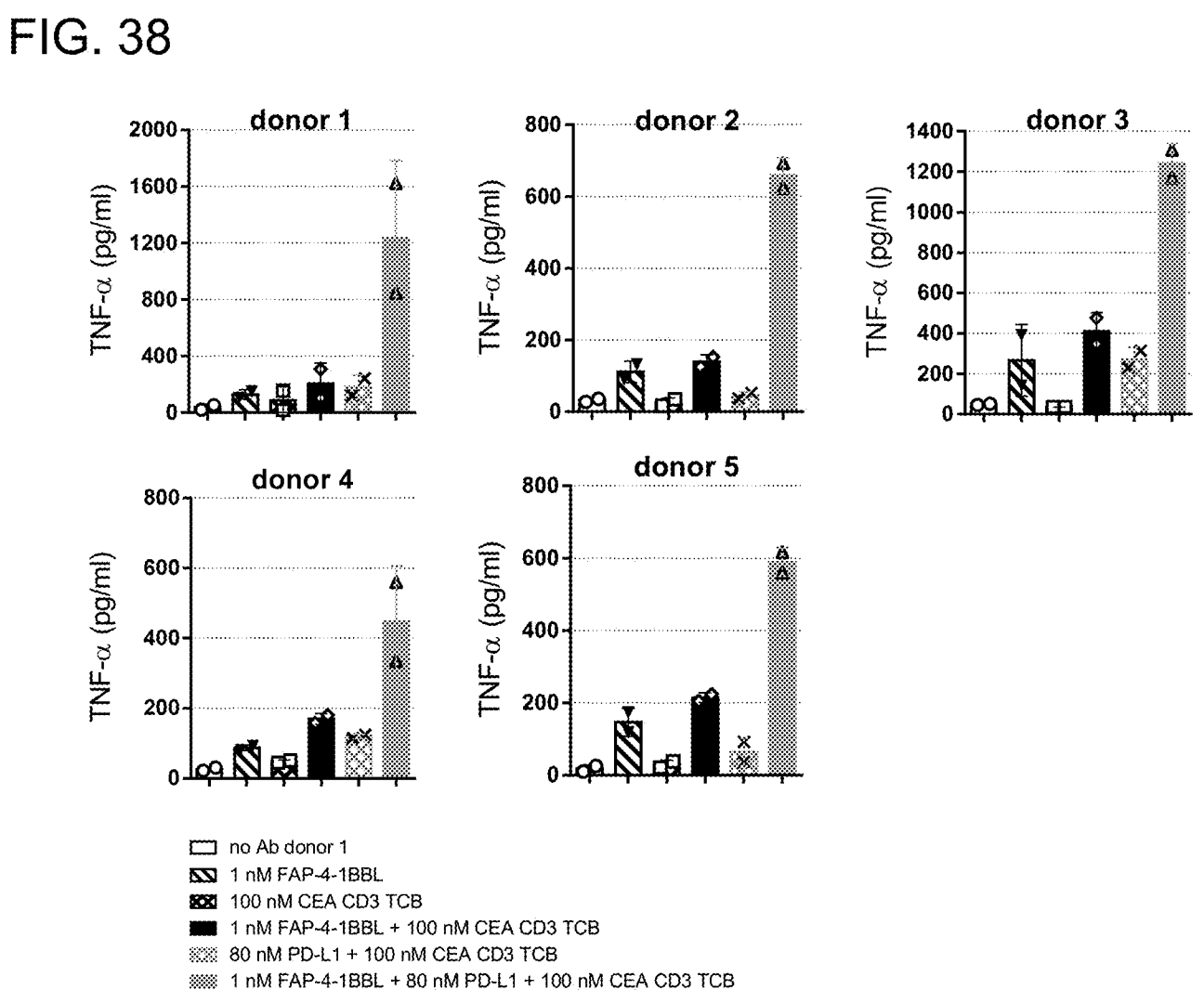

TNF-α (pg/ml)

donor 2

TNF-α (pg/ml)

donor 5

TNF-α (pg/ml)

donor 1

TNF-α (pg/ml)

donor 4

TNF-α (pg/ml)

no Ab donor 1
1 nM FAP-4-1BBL
100 nM CEA CD3 TCB
1 nM FAP-4-1BBL + 100 nM CEA CD3 TCB
80 nM PD-L1 + 100 nM CEA CD3 TCB
1 nM FAP-4-1BBL + 80 nM PD-L1 + 100 nM CEA CD3 TCB Exposure of 4-1BB targeted constructs after 1st therapy
ELISA: binding to hu4-1BB, detection of CH1-domain B) Untarg 4-1BBL: 197ug/mouse
D) Mono FAP-4-1BBL: 197 ug/mouse
E) FolR1 TCB + untarg 4-1BBL (197ug)
F) FolR1 TCB + mono FAP-4-1BBL (197 ug)
G) FolR1 TCB + mono FAP-4-1BBL (19.7 ug)

time after 1st therapy in hours concentration in ng/ml

CD3+ T-Cells in the tumor

CD4+ T-Cells in the tumor

CD8+ T-Cells in the tumor

Ratio of CD8+/CD4+ T-Cells in the tumor

FIG. 49
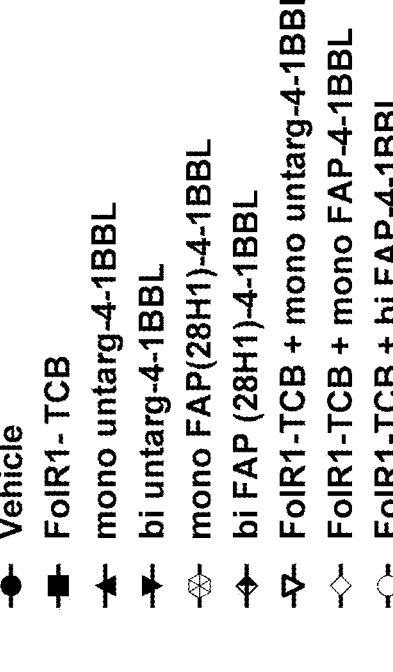
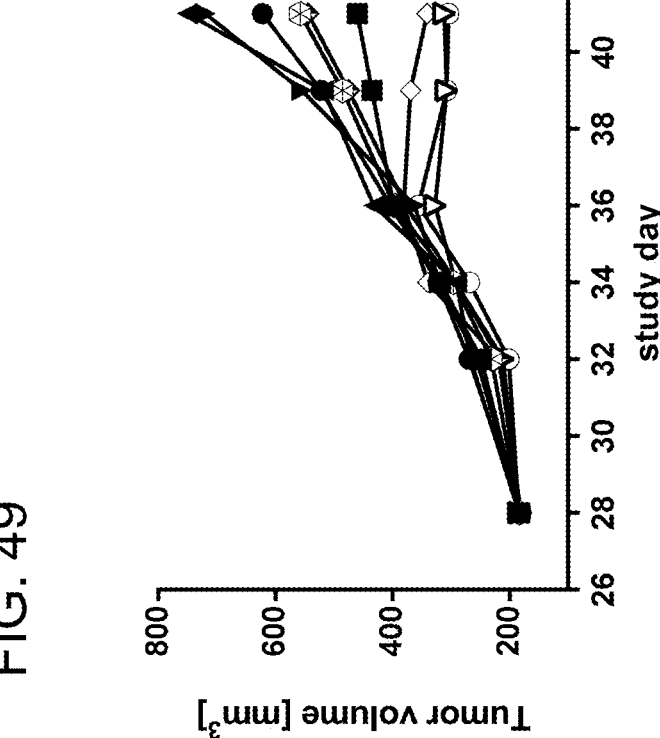

Exposure of 4-1BB targeted constructs after 1st therapy

ELISA: binding to hu 4-1BB, detection of CH1-domain

FIG. 51A

Tumor CD8+

FIG. 51B

Tumor CD4+

FIG. 51C

*Donor 1*

*Donor 2*

*Donor 3*

COMBINATION THERAPY WITH TARGETED 4-1BB (CD137) AGONISTS/ANTI-FAP BINDING DOMAIN AND ANTI-CEA/ANTI-CD3 BISPECIFIC ANTIBODY

CROSS REFERENCE TO RELATED APPLICATIONS

This application is a Continuation of U.S. application Ser. No. 16/825,773, filed Mar. 20, 2020, which is a Continuation of U.S. application Ser. No. 16/446,484, filed Jun. 19, 2019 (abandoned), which is a Continuation of International Application No. PCT/EP2017/083235, filed Dec. 18, 2017, which claims the benefit of priority to EP Application No. 16205190.8, filed Dec. 19, 2016, and EP Application No. 17158771.0, filed Mar. 1, 2017, and EP Application No. 17160857.3, filed Mar. 14, 2017, and EP Application No. 17192936.7, filed Sep. 25, 2017, each of which is incorporated herein by reference in its entirety.

SEQUENCE LISTING

This application contains a Sequence Listing, which has been submitted electronically in XML format and is hereby incorporated by reference in its entirety. Said XML copy, created on Jun. 7, 2023, is named P33996-US-2_SL.xml and is 236,744 bytes in size.

FIELD OF THE INVENTION

The present invention relates to combination therapies employing tumor targeted anti-CD3 bispecific antibodies and 4-1BB (CD137) agonists, in particular 4-1BBL trimer containing antigen binding molecules, the use of these combination therapies for the treatment of cancer and methods of using the combination therapies. Included are also combination therapies employing 4-1BB agonists comprising at least one antigen binding domain capable of specific binding to a tumor-associated antigen, in particular 4-1BBL trimer containing antigen binding molecules, with an agent blocking PD-L1/PD-1 interaction, in particular a PD-L1 antibody and/or with a tumor targeted anti-CD3 bispecific antibody.

BACKGROUND

Cancer is one of the leading causes of death worldwide. Despite advances in treatment options, prognosis of patients with advanced cancer remains poor. Consequently, there is a persisting and urgent medical need for optimal therapies to increase survival of cancer patients without causing unacceptable toxicity. Recent results from clinical trials have shown that immune therapies, particularly immune checkpoint inhibitors, can extend the overall survival of cancer patients and lead to durable responses. Despite these promising results, current immune-based therapies are only effective in a proportion of patients and combination strategies are needed to improve therapeutic benefit.

One way to recruit the patient's own immune system to fight cancer are T cell bispecific antibodies (TCB). An anti-CEA/anti-CD3 bispecific antibody is a molecule that targets CEA expressed on tumor cells and CD3 epsilon chain (CD3E) present on T cells. Simultaneous binding leads to T-cell activation and T-cell mediated killing of B cells. In the presence of CEA positive cancer cells, whether circulating or tissue resident, pharmacologically active doses will trigger T-cell activation and associated cytokine release. Parallel to tumor cell depletion anti-CEA/anti-CD3 bispecific antibody leads to a transient decrease of T cells in the peripheral blood within 24 hours after the first administration and to a peak in cytokine release, followed by rapid T-cell recovery and return of cytokine levels to baseline within 72 hours. Thus, in order to achieve complete elimination of tumor cells, there is a need of an additional agent that conserves T-cell activation and immune response to cancer cells.

4-1BB (CD137), a member of the TNF receptor superfamily, was first identified as an inducible molecule expressed by activated by T cells (Kwon and Weissman, 1989, Proc Natl Acad Sci USA 86, 1963-1967). Subsequent studies demonstrated that many other immune cells also express 4-1BB, including NK cells, B cells, NKT cells, monocytes, neutrophils, mast cells, dendritic cells (DCs) and cells of non-hematopoietic origin such as endothelial and smooth muscle cells (Vinay and Kwon, 2011, Cell Mol Immunol 8, 281-284). Expression of 4-1BB in different cell types is mostly inducible and driven by various stimulatory signals, such as T-cell receptor (TCR) or B-cell receptor triggering, as well as signaling induced through co-stimulatory molecules or receptors of pro-inflammatory cytokines (Diehl et al., 2002, J Immunol 168, 3755-3762; Zhang et al., 2010, Clin Cancer Res 13, 2758-2767).

4-1BB ligand (4-1BBL or CD137L) was identified in 1993 (Goodwin et al., 1993, Eur J Immunol 23, 2631-2641). It has been shown that expression of 4-1BBL was restricted on professional antigen presenting cells (APC) such as B-cells, DCs and macrophages. Inducible expression of 4-1BBL is characteristic for T-cells, including both $\alpha\beta$ and $\gamma\delta$ T-cell subsets, and endothelial cells (Shao and Schwarz, 2011, J Leukoc Biol 89, 21-29).

Co-stimulation through the 4-1BB receptor (for example by 4-1BBL ligation) activates multiple signaling cascades within the T cell (both CD4+ and CD8$^+$ subsets), powerfully augmenting T cell activation (Bartkowiak and Curran, 2015). In combination with TCR triggering, agonistic 4-1BB-specific antibodies enhance proliferation of T-cells, stimulate lymphokine secretion and decrease sensitivity of T-lymphocytes to activation-induced cells death (Snell et al., 2011, Immunol Rev 244, 197-217). This mechanism was further advanced as the first proof of concept in cancer immunotherapy. In a preclinical model administration of an agonistic antibody against 4-1BB in tumor bearing mice led to potent anti-tumor effect (Melero et al., 1997, Nat Med 3, 682-685). Later, accumulating evidence indicated that 4-1BB usually exhibits its potency as an anti-tumor agent only when administered in combination with other immunomodulatory compounds, chemotherapeutic reagents, tumor-specific vaccination or radiotherapy (Bartkowiak and Curran, 2015, Front Oncol 5, 117).

Signaling of the TNFR-superfamily needs cross-linking of the trimerized ligands to engage with the receptors, so does the 4-1BB agonistic antibodies which require wild type Fc-binding (Li and Ravetch, 2011, Science 333, 1030-1034). However, systemic administration of 4-1BB-specific agonistic antibodies with the functionally active Fc domain resulted in influx of CD8$^+$ T-cells associated with liver toxicity (Dubrot et al., 2010, Cancer Immunol Immunother 59, 1223-1233) that is diminished or significantly ameliorated in the absence of functional Fc-receptors in mice. In the clinic, an Fc-competent 4-1BB agonistic Ab (BMS-663513) (NCT00612664) caused a grade 4 hepatitis leading to termination of the trial (Simeone and Ascierto, 2012, J Immunotoxicol 9, 241-247). Therefore, there is a need for effective and safer 4-1BB agonists.

Fusion proteins composed of one extracellular domain of a 4-1BB ligand and a single chain antibody fragment (Hornig et al., 2012, J Immunother 35, 418-429; Müller et al., 2008, J Immunother 31, 714-722) or a single 4-1BB ligand fused to the C-terminus of a heavy chain (Zhang et al., 2007, Clin Cancer Res 13, 2758-2767) have been made. WO 2010/010051 discloses the generation of fusion proteins that consist of three TNF ligand ectodomains linked to each other and fused to an antibody part. In the present invention, antigen binding molecules composed of a trimeric and thus biologically active 4-1BB ligand and an antigen binding domain specific for the tumor-associated antigen FAP and an Fc inactive domain, are shown particularly stable and robust (herein named as FAP-4-1BBL). The FAP antigen binding domain replaces the unspecific FcγR-mediated crosslinking that is responsible for Fc-mediated toxicity in particular in the liver, by a FAP-targeted specific crosslinking. The cross-linking by a tumor (stroma) antigen makes it possible to administer the 4-1BB agonist.

It has been found that a better anti-tumor effect of 4-1BB agonism is achieved when the targeted 4-1BBL antigen binding molecule is combined with an anti-CEA/anti-CD3 bispecific antibody, i.e. a CEA TCB. The T-cell bispecific antibody provides the initial TCR activating signalling to T cells, and then the combination with FAP-4-1BBL leads to a further boost of anti-tumor T cell immunity. Thus, we herein describe a novel combination therapy for tumors expressing CEA (CEA-positive cancer). Furthermore, it has been shown that the combination of the targeted 4-1BB agonist FAP-4-1BBL with an agent blocking PD-L1/PD-1 interaction induced a strong tumor regression that cannot be observed with the agent blocking PD-L1/PD-1 interaction alone.

SUMMARY OF THE INVENTION

The present invention relates to anti-CD3 bispecific antibodies and their use in combination with 4-1BB (CD137) agonists, in particular 4-1BBL trimer containing antigen binding molecules, in particular to their use in a method for treating or delaying progression of cancer, more particularly for treating or delaying progression of advanced and/or metastatic solid tumors. It has been found that the combination therapy described herein is more effective in inhibiting tumor growth and eliminating tumor cells than treatment with the anti-CEA/anti-CD3 bispecific antibodies alone.

In one aspect, the invention provides a T-cell activating anti-CD3 bispecific antibody specific for a tumor-associated antigen for use in a method for treating or delaying progression of cancer, wherein the T-cell activating anti-CD3 bispecific antibody specific for a tumor-associated antigen is used in combination with a 4-1BB (CD137) agonist. In one aspect, the T-cell activating anti-CD3 bispecific antibody specific for a tumor-associated antigen is an anti-CEA/anti-CD3 bispecific antibody or an anti-FolR1/anti-CD3 bispecific antibody or an anti-MCSP/anti-CD3 bispecific antibody. Particularly, the T-cell activating anti-CD3 bispecific antibody specific for a tumor-associated antigen is an anti-CEA/anti-CD3 bispecific antibody or an anti-FolR1/anti-CD3 bispecific antibody. In a further aspect, the T-cell activating anti-CD3 bispecific antibody specific for a tumor-associated antigen is an anti-CEA/anti-CD3 bispecific antibody. Thus, the invention provides an anti-CEA/anti-CD3 bispecific antibody for use in a method for treating or delaying progression of cancer, wherein the anti-CEA/anti-CD3 bispecific antibody is used in combination with a 4-1BB (CD137) agonist.

In particular, the 4-1BB agonist is an antigen binding molecule comprising a tumor-associated antigen. In one aspect, the 4-1BB agonist is an antigen binding molecule comprising a Fc domain. In a particular aspect, the 4-1BB agonist is an antigen binding molecule comprising a Fc domain with modifications reducing Fcγ receptor binding and/or effector function. The crosslinking by a tumor associated antigen makes it possible to avoid unspecific FcγR-mediated crosslinking and thus higher and more efficacious doses of the 4-1BB agonists may be administered in comparison to common 4-1BB antibodies.

In a further aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the T-cell activating anti-CD3 bispecific antibody specific for a tumor-associated antigen and the 4-1BB agonist are administered together in a single composition or administered separately in two or more different compositions.

In a further aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the T-cell activating anti-CD3 bispecific antibody specific for a tumor-associated antigen is used in combination with a 4-1BB (CD137) agonist, and wherein the 4-1BB agonist acts synergistically with the T-cell activating anti-CD3 bispecific antibody.

In another aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the anti-CEA/anti-CD3 bispecific antibody is administered concurrently with, prior to, or subsequently to the 4-1BB agonist.

In one aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist comprises three ectodomains of 4-1BBL or fragments thereof. In a further aspect, provided is an anti-CEA/anti-CD3 bispecific antibody for use in a method for treating or delaying progression of cancer, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5. More particularly, the ectodomains of 4-1BBL comprise an amino acid sequence of SEQ ID NO:5.

In another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising at least one antigen binding domain capable of specific binding to a tumor-associated antigen. In one aspect, the the 4-1BB agonist is an antigen binding molecule comprising three ectodomains of 4-1BBL or fragments thereof and at least one antigen binding domain capable of specific binding to a tumor-associated antigen. In a further aspect, the 4-1BB agonist is an antigen binding molecule comprising an IgG Fc domain, specifically an IgG1 Fc domain or an IgG4 Fc domain.

In a further aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising three ectodomains of 4-1BBL or fragments thereof and at least one antigen binding domain capable of specific binding to a tumor-associated antigen, in particular to FAP. In one aspect, provided is an anti-CEA/anti-CD3 bispecific antibody for use in a method for treating or delaying progression of cancer, wherein the 4-1BB agonist is an antigen binding molecule comprising three ectodomains of 4-1BBL or fragments thereof and at least one moiety capable of specific binding to FAP, wherein the antigen binding domain capable of specific binding to FAP comprises (a) a heavy chain variable region (V$_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region (V$_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region (V$_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region (V$_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a particular aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region (V$_H$FAP) comprising an amino acid sequence of SEQ ID NO:21 and a light chain variable region (V$_L$FAP) comprising an amino acid sequence of SEQ ID NO:22 or wherein the antigen binding domain capable of specific binding to FAP comprises a heavy chain variable region (V$_H$FAP) comprising an amino acid sequence of SEQ ID NO:23 and a light chain variable region (V$_L$FAP) comprising an amino acid sequence of SEQ ID NO:24.

In one aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule further comprising a Fc domain composed of a first and a second subunit capable of stable association. In particular, the 4-1BB agonist is an antigen binding molecule comprising an IgG Fc domain, specifically an IgG1 Fc domain or an IgG4 Fc domain. More particularly, the 4-1BB agonist is an antigen binding molecule comprising a Fc domain that comprises one or more amino acid substitution that reduces binding to an Fc receptor and/or effector function. In a particular aspect, the 4-1BB agonist comprises an IgG1 Fc domain comprising the amino acid substitutions L234A, L235A and P329G.

In another aspect of the invention, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one antigen binding domain capable of specific binding to FAP, (b) a first and a second polypeptide that are linked to each other by a disulfide bond,
wherein the first polypeptide comprises two ectodomains of 4-1BBL or fragments thereof that are connected to each other by a peptide linker and in that the second polypeptide comprises one ectodomain of 4-1BBL or a fragment thereof.

In another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In one aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a particular aspect, there is provided a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68.

In another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

In one aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an anti-FAP/anti-4-1BB bispecific antibody.

In a further aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising three ectodomains of 4-1BBL or fragments thereof and at least one antigen binding domain capable of specific binding to CEA. In one aspect, provided is an anti-CEA/anti-CD3 bispecific antibody for use in a method for treating or delaying progression of cancer, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region ($V_L$CEA) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

In a particular aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:55 and a light chain variable region ($V_L$CEA) comprising an amino acid sequence of SEQ ID NO:56.

In one aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule further comprising a Fc domain composed of a first and a second subunit capable of stable association. In particular, the 4-1BB agonist is an antigen binding molecule comprising an IgG Fc domain, specifically an IgG1 Fc domain or an IgG4 Fc domain. More particularly, the 4-1BB agonist is an antigen binding molecule comprising a Fc domain that comprises one or more amino acid substitution that reduces binding to an Fc receptor and/or effector function. In a particular aspect, the 4-1BB agonist comprises an IgG1 Fc domain comprising the amino acid substitutions L234A, L235A and P329G.

In another aspect of the invention, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

In another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In one aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one Fab domain capable of specific binding to CEA comprising a heavy chain variable region ($V_H$CEA) comprising the amino acid sequence of SEQ ID NO:55 and a light chain variable region ($V_L$CEA) comprising the amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers.

In one aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the 4-1BB agonist is an anti-CEA/anti-4-1BB bispecific antibody.

In all these aspects, the invention further provides an anti-CEA/anti-CD3 bispecific antibody for use in a method for treating or delaying progression of cancer, wherein the anti-CEA/anti-CD3 bispecific antibody comprises a first antigen binding domain that binds to CD3, and a second antigen binding domain that binds to CEA. In particular, the anti-CEA/anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$CEA) and a light chain variable region ($V_L$CEA). In one aspect, the first antigen binding domain comprises a heavy chain variable region ($V_H$CD3) comprising CDR-H1 sequence of SEQ ID NO:33, CDR-H2 sequence of SEQ ID NO:34, and CDR-H3 sequence of SEQ ID NO:35; and/or a light chain variable region ($V_L$CD3) comprising CDR-L1 sequence of SEQ ID NO:36, CDR-L2 sequence of SEQ ID NO:37, and CDR-L3 sequence of SEQ ID NO:38. More particularly, the first antigen binding domain comprises a heavy chain variable region ($V_H$CD3) comprising the amino acid sequence of SEQ ID NO:39 and/or a light chain variable region ($V_L$CD3) comprising the amino acid sequence of SEQ ID NO:40. In another aspect, the second antigen binding domain comprises a heavy chain variable region (V$_H$CEA) comprising CDR-H1 sequence of SEQ ID NO:41, CDR-H2 sequence of SEQ ID NO:42, and CDR-H3 sequence of SEQ ID NO:43, and/or a light chain variable region (V$_L$CEA) comprising CDR-L1 sequence of SEQ ID NO:44, CDR-L2 sequence of SEQ ID NO:45, and CDR-L3 sequence of SEQ ID NO:46. In another aspect, the second antigen binding domain comprises a heavy chain variable region (V$_H$CEA) comprising CDR-H1 sequence of SEQ ID NO:49, CDR-H2 sequence of SEQ ID NO:50, and CDR-H3 sequence of SEQ ID NO:51, and/or a light chain variable region (V$_L$CEA) comprising CDR-L1 sequence of SEQ ID NO:52, CDR-L2 sequence of SEQ ID NO:53, and CDR-L3 sequence of SEQ ID NO:54.

More particularly, the second antigen binding domain comprises a heavy chain variable region (V$_H$CEA) comprising the amino acid sequence of SEQ ID NO:47 and/or a light chain variable region (V$_L$CEA) comprising the amino acid sequence of SEQ ID NO:48. More particularly, the second antigen binding domain comprises a heavy chain variable region (V$_H$CEA) comprising the amino acid sequence of SEQ ID NO:55 and/or a light chain variable region (V$_L$-CEA) comprising the amino acid sequence of SEQ ID NO:56.

In another aspect, the invention further provides an anti-CEA/anti-CD3 bispecific antibody for use in a method for treating or delaying progression of cancer, wherein the anti-CEA/anti-CD3 bispecific antibody further comprises a third antigen binding domain that binds to CEA. In particular, the third antigen binding domain comprises (a) a heavy chain variable region (V$_H$CEA) comprising CDR-H1 sequence of SEQ ID NO:41, CDR-H2 sequence of SEQ ID NO:42, and CDR-H3 sequence of SEQ ID NO:43, and/or a light chain variable region (V$_L$CEA) comprising CDR-L1 sequence of SEQ ID NO:44, CDR-L2 sequence of SEQ ID NO:45, and CDR-L3 sequence of SEQ ID NO:46, or (b) a heavy chain variable region (V$_H$CEA) comprising CDR-H1 sequence of SEQ ID NO:49, CDR-H2 sequence of SEQ ID NO:50, and CDR-H3 sequence of SEQ ID NO:51, and/or a light chain variable region (V$_L$CEA) comprising CDR-L1 sequence of SEQ ID NO:52, CDR-L2 sequence of SEQ ID NO:53, and CDR-L3 sequence of SEQ ID NO:54. More particularly, the third antigen binding domain comprises a heavy chain variable region (V$_H$CEA) comprising the amino acid sequence of SEQ ID NO:47 and/or a light chain variable region (V$_L$CEA) comprising the amino acid sequence of SEQ ID NO:48 or wherein the second antigen binding domain comprises a heavy chain variable region (V$_H$CEA) comprising the amino acid sequence of SEQ ID NO:55 and/or a light chain variable region (V$_L$CEA) comprising the amino acid sequence of SEQ ID NO:56.

In a further aspect, provided is an anti-CEA/anti-CD3 bispecific antibody for use in a method for treating or delaying progression of cancer, wherein the first antigen binding domain is a cross-Fab molecule wherein the variable domains or the constant domains of the Fab heavy and light chain are exchanged, and the second and third, if present, antigen binding domain is a conventional Fab molecule.

In a further aspect, provided is an anti-CEA/anti-CD3 bispecific antibody for use in a method for treating or delaying progression of cancer, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

In a further aspect, the invention provides an anti-CEA/anti-CD3 bispecific antibody for use in a method for treating or delaying progression of cancer, wherein the anti-CEA/anti-CD3 bispecific antibody comprises an Fc domain comprising one or more amino acid substitutions that reduce binding to an Fc receptor and/or effector function. More particularly, the anti-CEA/anti-CD3 bispecific antibody comprises an IgG1 Fc domain comprising the amino acid substitutions L234A, L235A and P329G.

In a further aspect, the invention provides a T-cell activating anti-CD3 bispecific antibody specific for a tumor-associated antigen, wherein the tumor-associated antigen is FolR1. Thus, the invention provides an anti-FolR1/anti-CD3 bispecific antibody for use in a method for treating or delaying progression of cancer, wherein the anti-FolR1/anti-CD3 bispecific antibody comprises a first antigen binding domain that binds to CD3, and a second antigen binding domain that binds to FolR1.

In one aspect, provided is a T-cell activating anti-CD3 bispecific antibody specific for a tumor-associated antigen for use in a method for treating or delaying progression of cancer, wherein the T-cell activating anti-CD3 bispecific antibody comprises a first antigen binding domain comprising a heavy chain variable region (V$_H$CD3), a second antigen binding domain comprising a heavy chain variable region (V$_H$FolR1) and a common light chain variable region.

In one aspect, provided is a T-cell activating anti-CD3 bispecific antibody specific for a tumor-associated antigen for use in a method for treating or delaying progression of cancer, wherein the first antigen binding domain comprises a heavy chain variable region (V$_H$CD3) comprising CDR-H1 sequence of SEQ ID NO:121, CDR-H2 sequence of SEQ ID NO:122, and CDR-H3 sequence of SEQ ID NO:123; the second antigen binding domain comprises a heavy chain variable region (V$_H$FolR1) comprising CDR-H1 sequence of SEQ ID NO:124, CDR-H2 sequence of SEQ ID NO:125, and CDR-H3 sequence of SEQ ID NO:126; and wherein the common light chain comprises a CDR-L1 sequence of SEQ ID NO:127, CDR-L2 sequence of SEQ ID NO:128, and CDR-L3 sequence of SEQ ID NO:129. In a further aspect, the first antigen binding domain comprises a heavy chain variable region (V$_H$CD3) comprising the sequence of SEQ ID NO:130; the second antigen binding domain comprises a heavy chain variable region (V$_H$FolR1) comprising the sequence of SEQ ID NO:131; and wherein the common light chain comprises the sequence of SEQ ID NO:132.

In a further aspect, provided is a T-cell activating anti-CD3 bispecific antibody specific for a tumor-associated antigen for use in a method for treating or delaying progression of cancer, wherein the anti-FolR1/anti-CD3 bispecific antibody comprises a third antigen binding domain that binds to FolR1. In particular, provided is an anti-FolR1/anti-CD3 bispecific antibody comprising a first heavy chain comprising the amino acid sequence of SEQ ID NO:133, a second heavy chain comprising the amino acid sequence of SEQ ID NO:134 and a common light chain of SEQ ID NO: 135.

In a further aspect, the invention provides a T-cell activating anti-CD3 bispecific antibody specific for a tumor-associated antigen, wherein the tumor-associated antigen is MCSP. Thus, the invention provides an anti-MCSP/anti-CD3 bispecific antibody for use in a method for treating or delaying progression of cancer, wherein the anti-MCSP/anti-CD3 bispecific antibody comprises a first antigen binding domain that binds to CD3, and a second antigen binding domain that binds to MCSP.

In particular, the anti-CEA/anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$MCSP) and a light chain variable region ($V_L$MCSP). In one aspect, the first antigen binding domain comprises a heavy chain variable region ($V_H$CD3) comprising CDR-H1 sequence of SEQ ID NO:33, CDR-H2 sequence of SEQ ID NO:34, and CDR-H3 sequence of SEQ ID NO:35; and/or a light chain variable region ($V_L$CD3) comprising CDR-L1 sequence of SEQ ID NO:36, CDR-L2 sequence of SEQ ID NO:37, and CDR-L3 sequence of SEQ ID NO:38. More particularly, the first antigen binding domain comprises a heavy chain variable region ($V_H$CD3) comprising the amino acid sequence of SEQ ID NO:39 and/or a light chain variable region ($V_L$CD3) comprising the amino acid sequence of SEQ ID NO:40. In another aspect, the second antigen binding domain comprises a heavy chain variable region ($V_H$MCSP) comprising CDR-H1 sequence of SEQ ID NO:151, CDR-H2 sequence of SEQ ID NO:152, and CDR-H3 sequence of FDY, and/or a light chain variable region ($V_L$MCSP) comprising CDR-L1 sequence of SEQ ID NO:154, CDR-L2 sequence of SEQ ID NO:155, and CDR-L3 sequence of SEQ ID NO:156. More particularly, the second antigen binding domain comprises a heavy chain variable region ($V_H$MCSP) comprising the amino acid sequence of SEQ ID NO:157 and/or a light chain variable region ($V_L$MCSP) comprising the amino acid sequence of SEQ ID NO:158.

In another aspect, the invention further provides an anti-MCSP/anti-CD3 bispecific antibody for use in a method for treating or delaying progression of cancer, wherein the anti-MCSP/anti-CD3 bispecific antibody further comprises a third antigen binding domain that binds to MCSP. In particular, the third antigen binding domain comprises (a) a heavy chain variable region ($V_H$MCSP) comprising CDR-H1 sequence of SEQ ID NO:151, CDR-H2 sequence of SEQ ID NO:152, and CDR-H3 sequence of FDY, and/or a light chain variable region ($V_L$MCSP) comprising CDR-L1 sequence of SEQ ID NO:154, CDR-L2 sequence of SEQ ID NO:155, and CDR-L3 sequence of SEQ ID NO:156. More particularly, the third antigen binding domain comprises a heavy chain variable region ($V_H$MCSP) comprising the amino acid sequence of SEQ ID NO:157 and/or a light chain variable region ($V_L$MCSP) comprising the amino acid sequence of SEQ ID NO:158.

In another aspect, provided is a T-cell activating anti-CD3 bispecific antibody specific for a tumor-associated antigen, in particular an anti-CEA/anti-CD3 bispecific antibody, for use in a method for treating or delaying progression of cancer, wherein the T-cell activating anti-CD3 bispecific antibody specific for a tumor-associated antigen is used in combination with a 4-1BB (CD137) agonist and wherein the combination is administered at intervals from about one week to three weeks.

In yet another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the T-cell activating anti-CD3 bispecific antibody specific for a tumor-associated antigen is used in combination with a 4-1BB (CD137) agonist and in combination with an agent blocking PD-L1/PD-1 interaction. In particular, the agent blocking PD-L1/PD-1 interaction is an anti-PD-L1 antibody or an anti-PD1 antibody. More particularly, the agent blocking PD-L1/PD-1 interaction is selected from the group consisting of atezolizumab, durvalumab, pembrolizumab and nivolumab. In a specific aspect, the agent blocking PD-L1/PD-1 interaction is atezolizumab.

In a further aspect, the invention provides a pharmaceutical product comprising (A) a first composition comprising as active ingredient a T-cell activating anti-CD3 bispecific antibody specific for a tumor-associated antigen, in particular an anti-CEA/anti-CD3 bispecific antibody, and a pharmaceutically acceptable carrier; and (B) a second composition comprising as active ingredient a 4-1BB agonist and a pharmaceutically acceptable carrier, for use in the combined, sequential or simultaneous treatment of a disease, in particular for the treatment of cancer.

In a further aspect, the T-cell activating anti-CD3 bispecific antibody specific for a tumor-associated antigen, in particular the anti-CEA/anti-CD3 bispecific antibody, is for use in a method for treating or delaying progression of cancer, wherein the T-cell activating anti-CD3 bispecific antibody specific for a tumor-associated antigen is used in combination with a 4-1BB agonist and wherein a pretreatment with an Type II anti-CD20 antibody, preferably obinutuzumab, is performed prior to the combination treatment, wherein the period of time between the pretreatment and the combination treatment is sufficient for the reduction of B-cells in the individual in response to the Type II anti-CD20 antibody, preferably obinutuzumab. In another aspect, provided is a pharmaceutical composition comprising a T-cell activating anti-CD3 bispecific antibody specific for a tumor-associated antigen, in particular an anti-CEA/anti-CD3 bispecific antibody, and a 4-1BB agonist. In one aspect, the pharmaceutical composition is for use in treating or delaying progression of cancer, in particular for the treatment of solid tumors. In a further aspect, the pharmaceutical composition is for use in treating a disease selected from the group consisting of colon cancer, lung cancer, ovarian cancer, gastric cancer, bladder cancer, pancreatic cancer, endometrial cancer, breast cancer, kidney cancer, esophageal cancer, and prostate cancer.

In an additional aspect, the invention provides a kit for treating or delaying progression of cancer in a subject, comprising a package comprising (A) a first composition comprising as active ingredient a T-cell activating anti-CD3 bispecific antibody specific for a tumor-associated antigen, in particular an anti-CEA/anti-CD3 bispecific antibody, and a pharmaceutically acceptable carrier; (B) a second composition comprising as active ingredient a 4-1BB agonist and a pharmaceutically acceptable carrier, and (C) instructions for using the compositions in a combination therapy.

In a further aspect, the invention relates to the use of a combination of a T-cell activating anti-CD3 bispecific antibody specific for a tumor-associated antigen, in particular an anti-CEA/anti-CD3 bispecific antibody, and a 4-1BB agonist in the manufacture of a medicament for treating or delaying progression of a proliferative disease, in particular cancer.

In particular, provided is the use of a combination of a T-cell activating anti-CD3 bispecific antibody specific for a tumor-associated antigen, in particular an anti-CEA/anti-CD3 bispecific antibody, and a 4-1BB agonist in the manufacture of a medicament for treating a disease selected from the group consisting of colon cancer, lung cancer, ovarian cancer, gastric cancer, bladder cancer, pancreatic cancer, endometrial cancer, breast cancer, kidney cancer, esophageal cancer, and prostate cancer.

In another aspect, the invention provides a method for treating or delaying progression of cancer in a subject comprising administering to the subject an effective amount of a T-cell activating anti-CD3 bispecific antibody specific for a tumor-associated antigen, in particular an anti-CEA/anti-CD3 bispecific antibody, and a 4-1BB agonist. In particular, the invention relates to a method for treating or delaying progression of cancer in a subject, wherein the 4-1BB agonist is an antigen binding molecule. In one aspect, the 4-1BB agonist is an antigen binding molecule comprising a Fc domain. In a particular aspect, the 4-1BB agonist is an antigen binding molecule comprising a Fc domain with modifications reducing Fcγ receptor binding and/or effector function. In a particular aspect, the 4-1BB agonist is an antigen binding molecule comprising three ectodomains of 4-1BBL or fragments thereof. In one aspect, the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5. In one aspect, the 4-1BB agonist is an antigen binding molecule comprising at least one antigen binding domain capable of specific binding to a tumor-associated antigen. In particular, the 4-1BB agonist is an antigen binding molecule comprising three ectodomains of 4-1BBL or fragments thereof and at least one antigen binding domain capable of specific binding to a tumor-associated antigen. More particularly, the 4-1BB agonist is an antigen binding molecule comprising three ectodomains of 4-1BBL or fragments thereof and an antigen binding domain capable of specific binding to FAP. In another particular aspect, the 4-1BB agonist is an antigen binding molecule comprising three ectodomains of 4-1BBL or fragments thereof and an antigen binding domain capable of specific binding to CEA.

In a further aspect, provided is a 4-1BB agonist comprising at least one antigen binding domain capable of specific binding to a tumor-associated antigen for use in a method for treating or delaying progression of cancer, wherein the 4-1BB agonist comprising at least one antigen binding domain capable of specific binding to a tumor-associated antigen is used in combination with an agent blocking PD-L1/PD-1 interaction. In particular, the agent blocking PD-L1/PD-1 interaction is an anti-PD-L1 antibody or an anti-PD1 antibody. More particularly, the agent blocking PD-L1/PD-1 interaction is selected from the group consisting of atezolizumab, durvalumab, pembrolizumab and nivolumab. In a specific aspect, the agent blocking PD-L1/PD-1 interaction is atezolizumab. Furthermore, the 4-1BB agonist comprising at least one antigen binding domain capable of specific binding to a tumor-associated antigen for use in the method described herein is one, wherein the tumor-associated antigen is selected from Fibroblast activation protein (FAP) or CEA. More particularly, the 4-1BB agonist is an antigen binding molecule comprising three ectodomains of 4-1BBL or fragments thereof and at least one antigen binding domain capable of specific binding to Fibroblast activation protein (FAP).

BRIEF DESCRIPTION OF THE DRAWINGS

In FIG. 1A an exemplary bispecific anti-CEA/anti-CD3 antibody in 2+1 format is shown (named CEA CD3 TCB or CEACAM5 CD3 TCB, respectively). FIG. 1B shows a monovalent FAP 4-1BBL-trimer containing antigen binding molecule with modifications in the CH1 and CL domain adjacent to the 4-1BBL dimer and 4-1BBL monomer. As it comprised the FAP binder 4B9, it was named mono FAP(4B9)-4-1BBL herein. FIG. 1C shows the bivalent construct with binder FAP(4B9), termed bi FAP(4B9)-4-1BBL. FIGS. 1D and 1E show untargeted control molecules (the FAP binder has been replaced by a non-binding DP47 Fab).

FIGS. 3A to 3F show that treatment with combinations of CEA CD3 TCB with monovalent or bivalent FAP(4B9)-4-1BBL led to increased infiltration of CD8 and CD4 positive T-cells in the tumor compared to treatment with the single agents. The letters A to J refer to the treatment groups as defined in FIG. 2.

FIG. 9A shows the increase of CD3 positive cells in the tumor, in FIG. 9B is shown the increase of CD8 positive cells in the tumor, in FIG. 9C the increase of CD4 positive cells in the tumor and in FIG. 9D the increase of CD3 positive cells in the spleen.

Figure 10A:
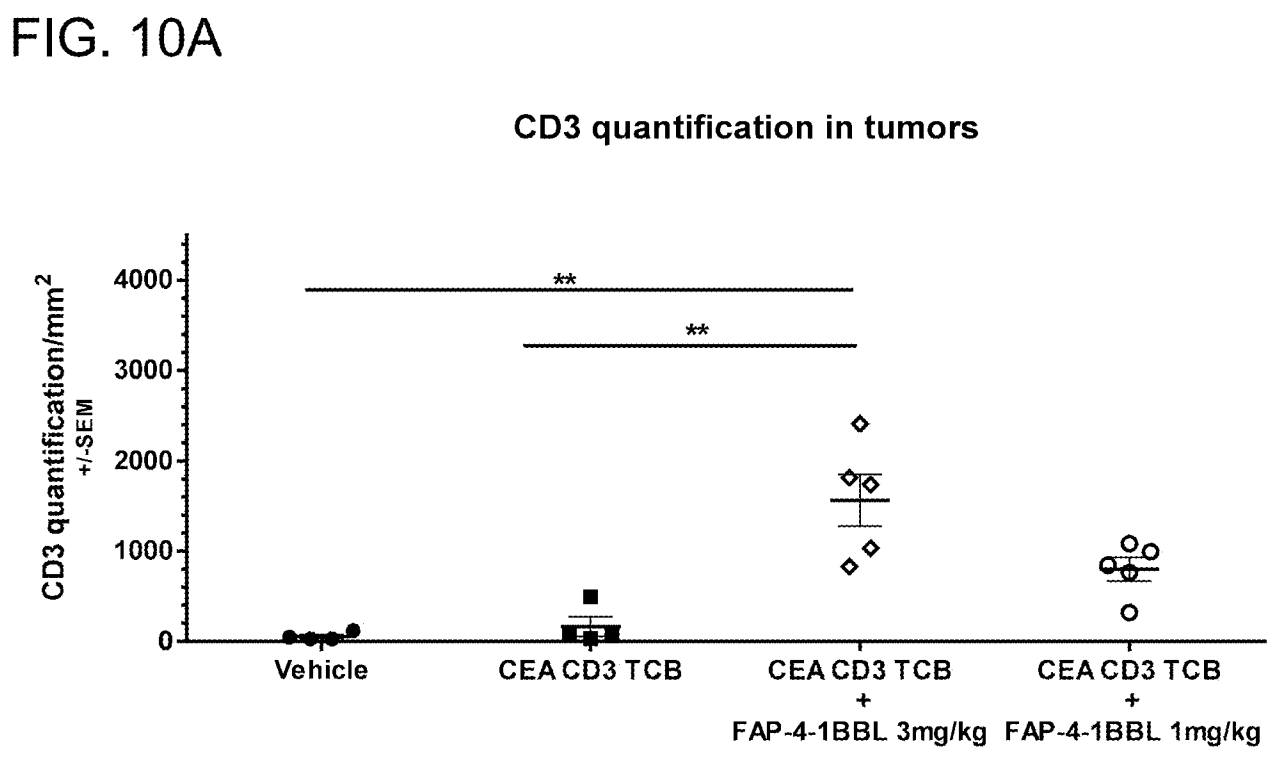
Figure 10B:
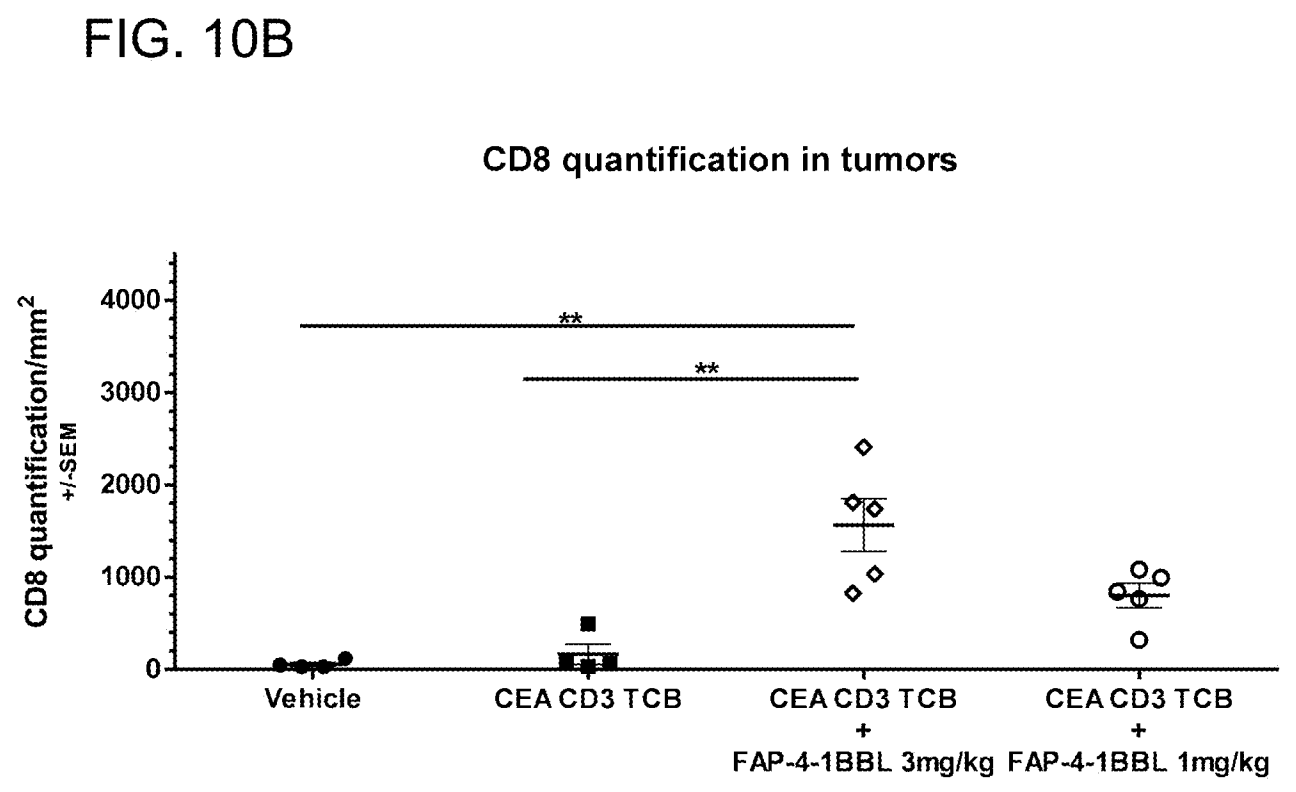
Figure 1:
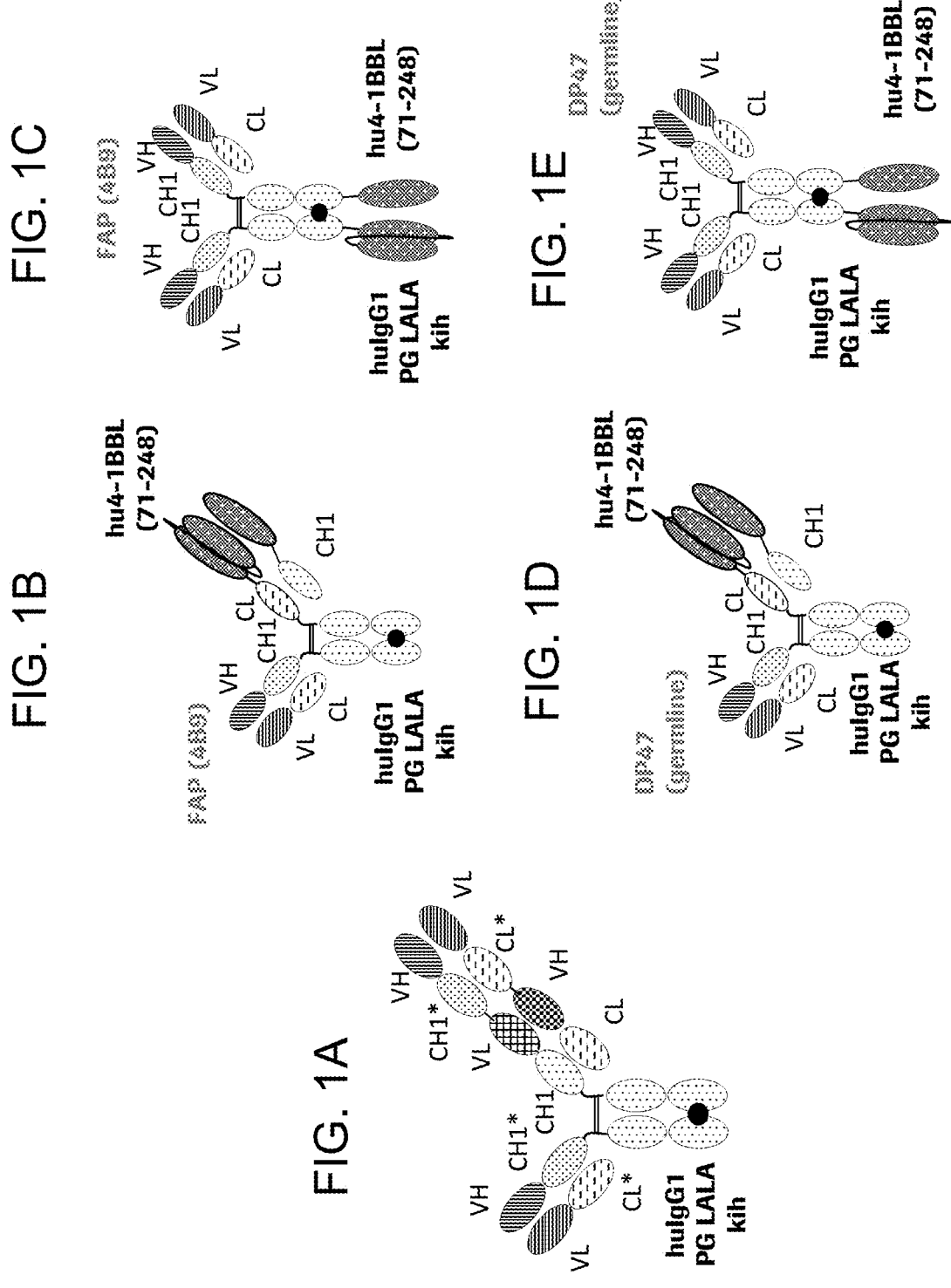
FIGS. 1A to 1E show particular FAP-4-1BBL antigen binding molecules and a particular anti-CEA/anti-CD3 bispecific antibody as used in the Examples. These molecules are described in more detail in Examples 1 and 2, respectively. The thick black point stands for the knob-into-hole modification. * symbolizes amino acid modifications in the CH1 and CL domain (so-called charged residues).

The histological analysis at the end of the study is illustrated in FIGS. 10A and 10B. Immunohistochemical images of human MKN45 gastric subcutaneous tumors cografted with 3T3 murine fibroblasts derived from the indicated treatment groups in humanized NOG mice were generated. Tissue samples were prepared for immunohistochemical staining. Subcutaneous tumors were harvested from animals at day 52 and during the experiment, fixed in formalin 10% (Sigma, Germany) and later processed for FFPET (Leica 1020, Germany). 4 μm paraffin sections were subsequently cut in a microtome (Leica RM2235, Germany). HuCD8 and HuCD3 immunohistochemistry was performed with anti-human CD8 (Cell Marque Corporation, California) and anti-human CD3 (ThermoFischer Scientific, USA) in the Leica autostainer (Leica ST5010, Germany) following the manufacture's protocols. Quantification of huCD3 (FIG. 10A) and huCD8 positive T cells (FIG. 10B) was performed with Definiens software (Definiens, Germany). Statistics were analyzed by one way ANOVA with multiple comparison tests. Results showed very low number of T cells in the MNK45/3T3 sc tumors from untreated mice. There is a significant increase of positive CD3 (A) and CD8 (B) T cell number in the CEA CD3 TCB+FAP-4-1BBL 3 mg/kg group compared to vehicle and CEA CD3 TCB monotherapy. (statistics: One Way ANOVA, Tukey's multiple comparison test, p<0.05). Animals analysed in histology are from different experiment delivery days to increase the number of samples. (Vehicle: 5× day 52; CEA CD3 TCB: 5× day 52; CEA CD3 TCB+FAP-4-1BBL 3 mg/kg: 2×day 52, 1×day 32, 2×day 29; CEA CD3 TCB+FAP-4-1BBL 1 mg/kg: 1×day 52, 2×day 50, 1×day 37, 1×day 35).

Figure 11:
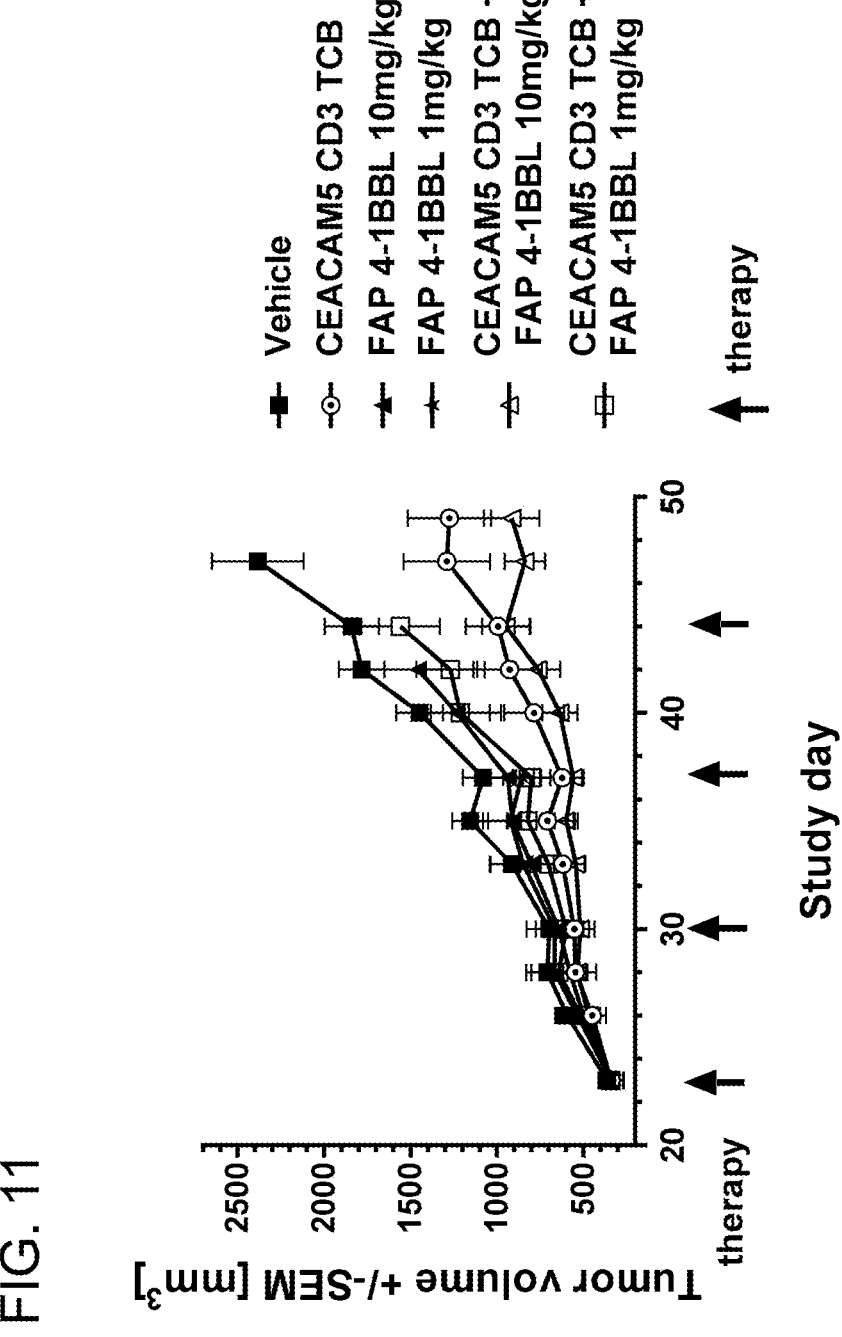

In FIG. 11 it is shown that the combinations of CEACAM5 CD3 TCB+FAP(4B9)-4-1BBL 10 mg/kg mediate slightly improved efficacy in terms of tumor growth inhibition compared to the other groups.

Figure 12A:
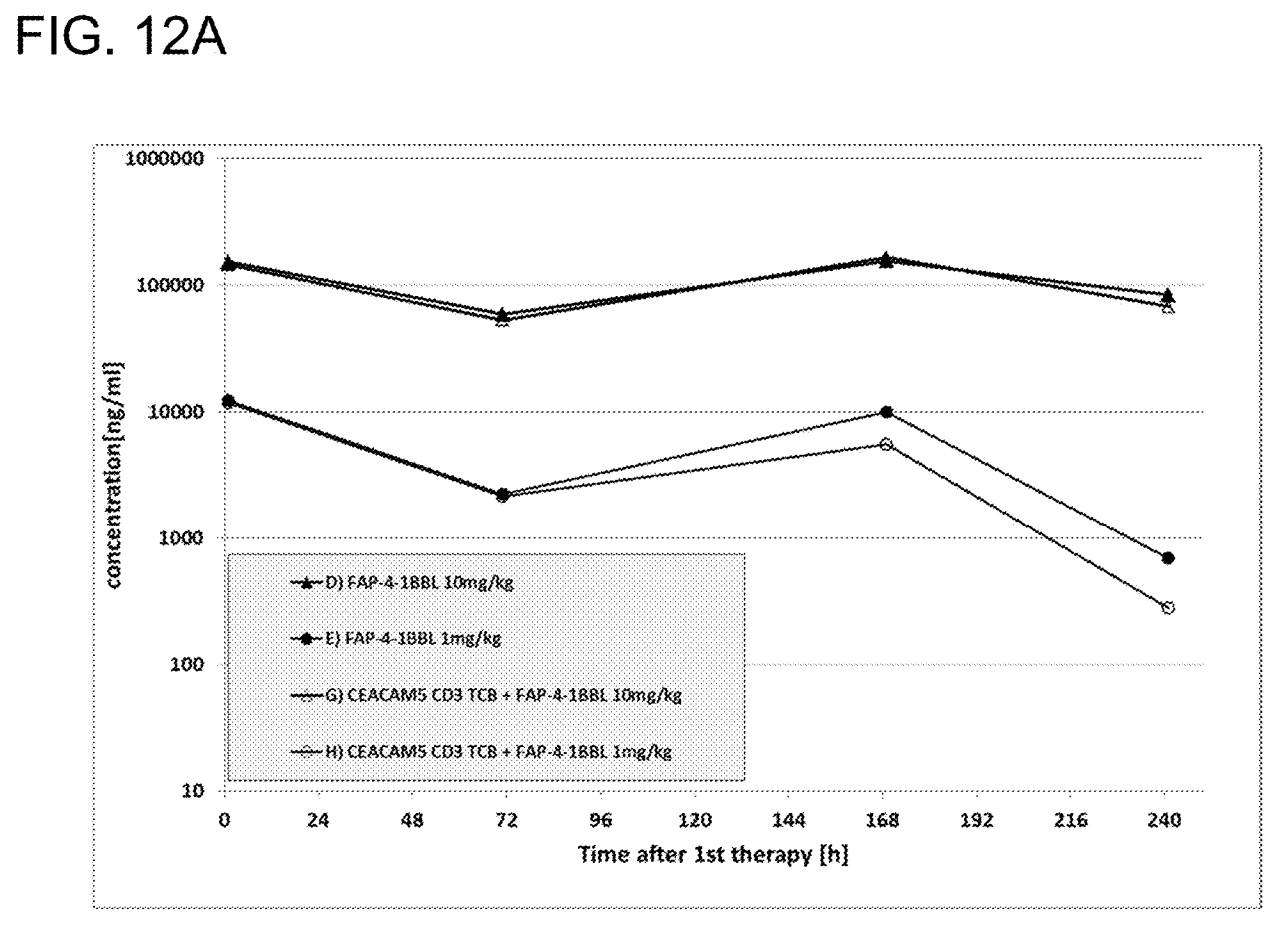
Figure 12B:
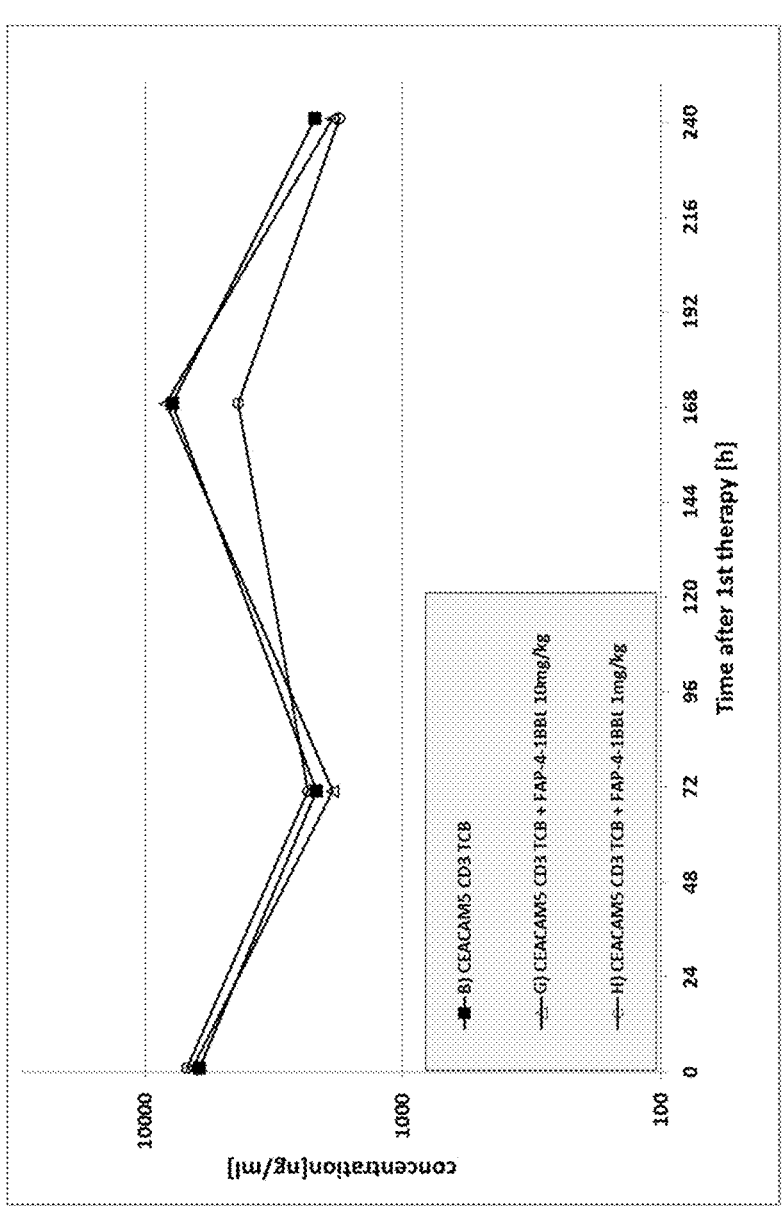

FIGS. 12A and 12B show the pharmacokinetic profile of injected compounds during the first week. 2 mice per Group were bled 1h and 72h after $1^{st}$ and $2^{nd}$ therapy. Injected compounds were analysed by ELISA as described in Example 5.

Figure 13A:
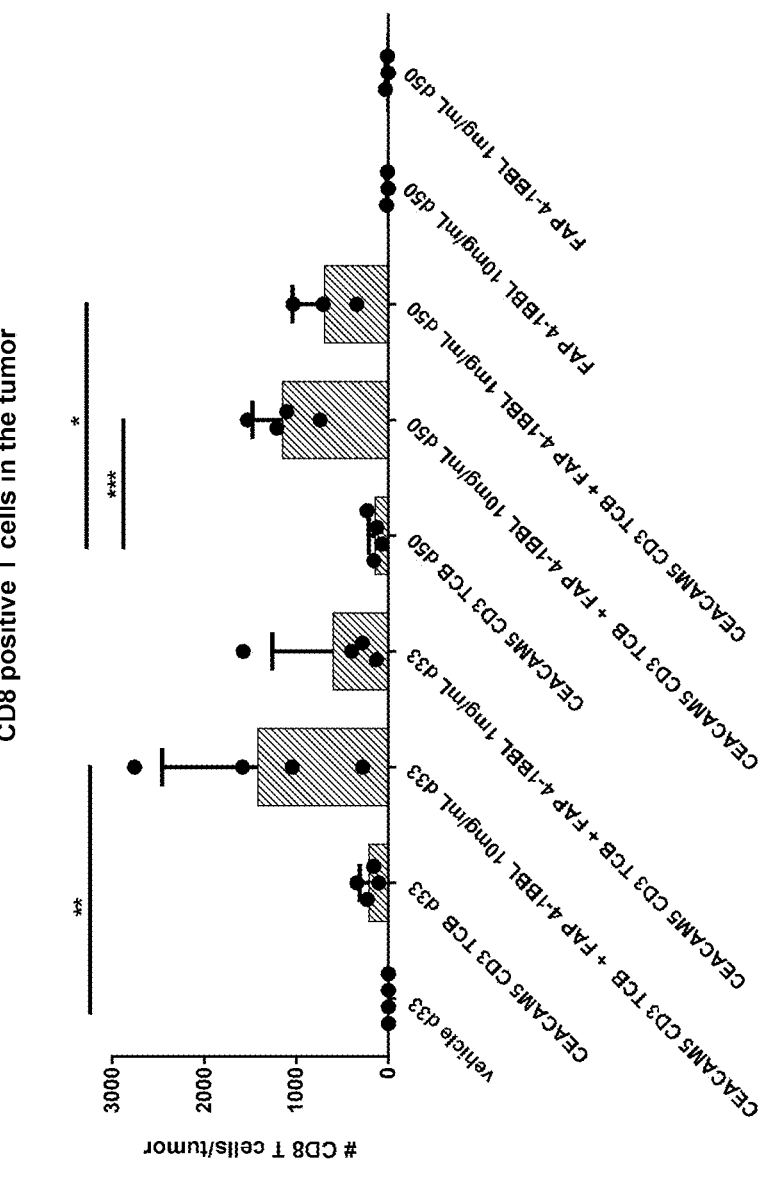
Figure 13B:
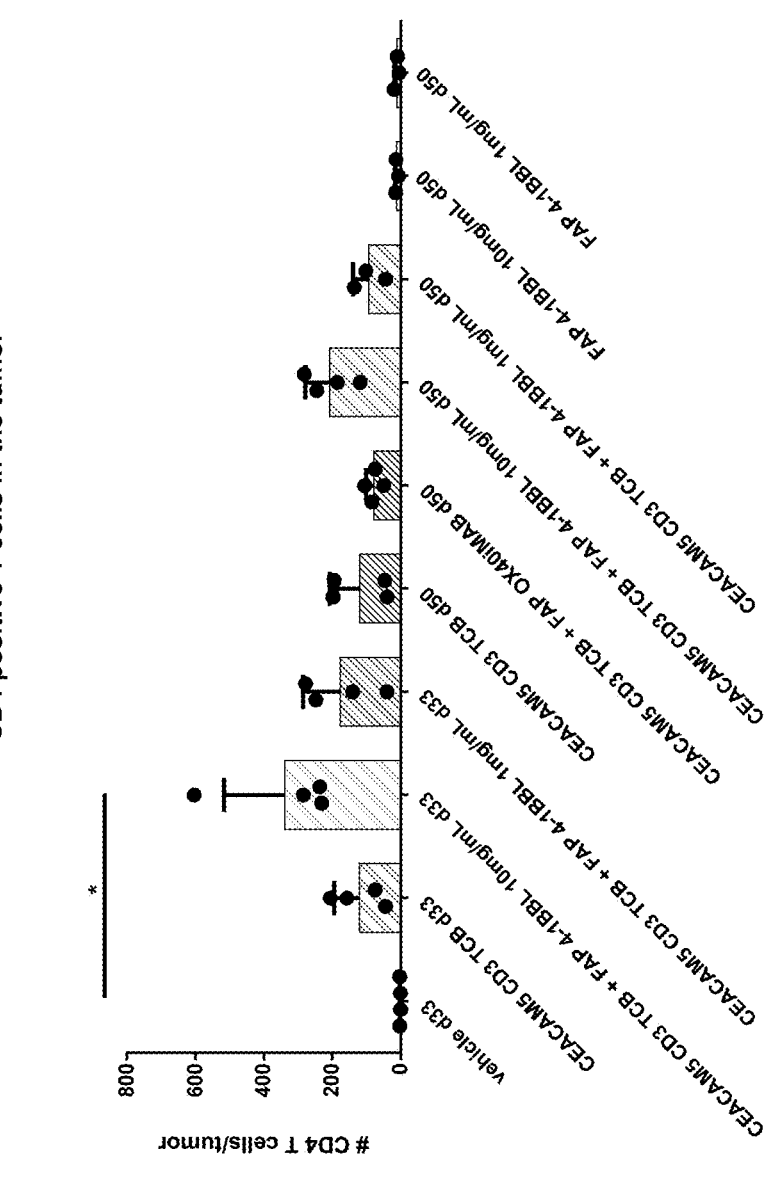

FIGS. 13A and 13B show the T cell infiltration in tumor at study termination as analysed by FACS. The increase of CD8 positive T cells in the tumor is shown in FIG. 13A and the increase of CD4 positive T cells in the tumor is illustrated in FIG. 13B.

Figure 14A:
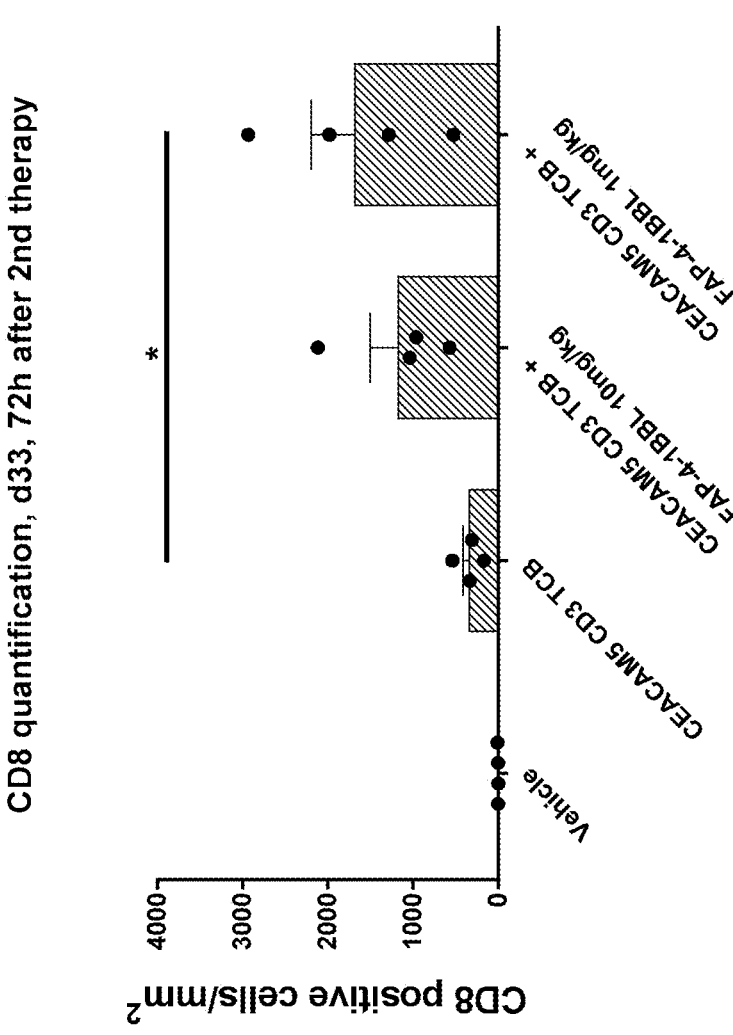
Figure 14B:
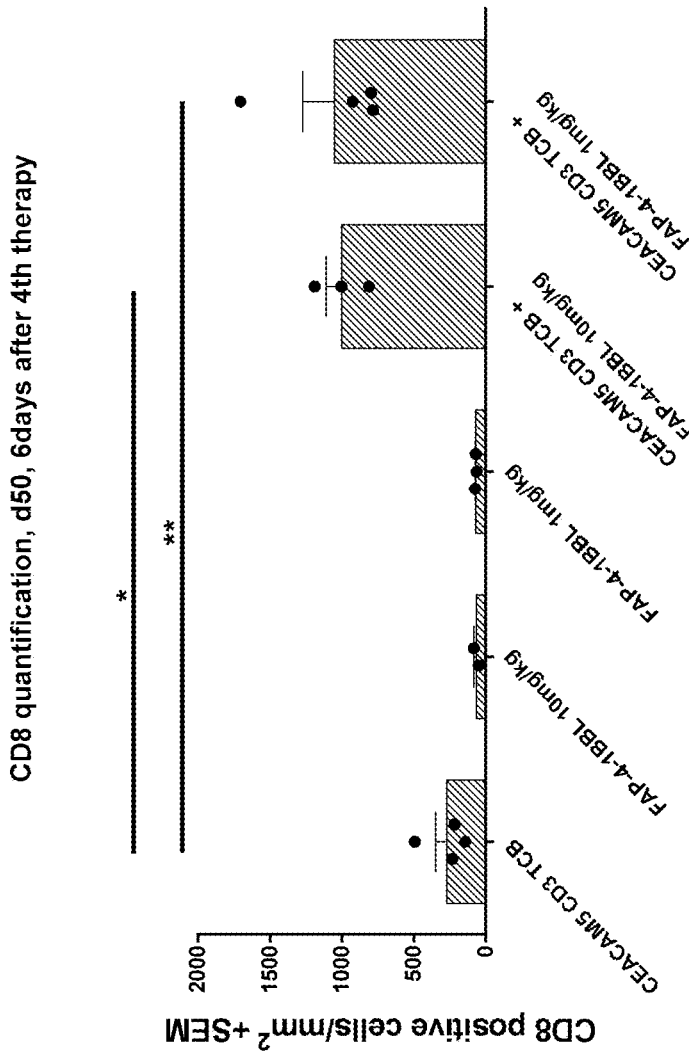
Figures 15A, 15B, 15C:
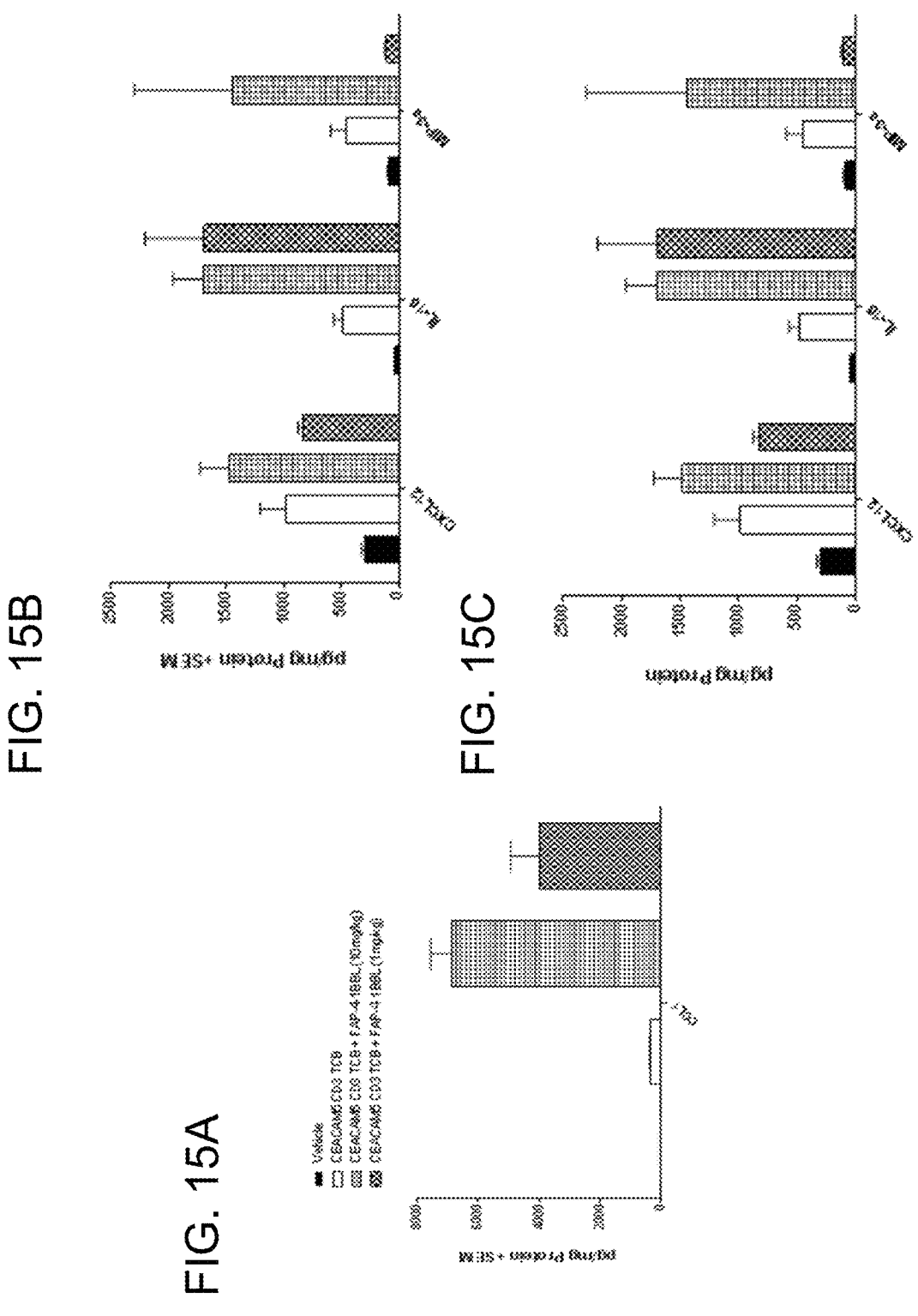

FIGS. 14A and 14B relate to the histological analysis at day 33 and the end of the study day 50 and FIGS. 15A, 15B and 15C refer to the cytokine analysis at the end of the study (see Example 5).

Figure 16:
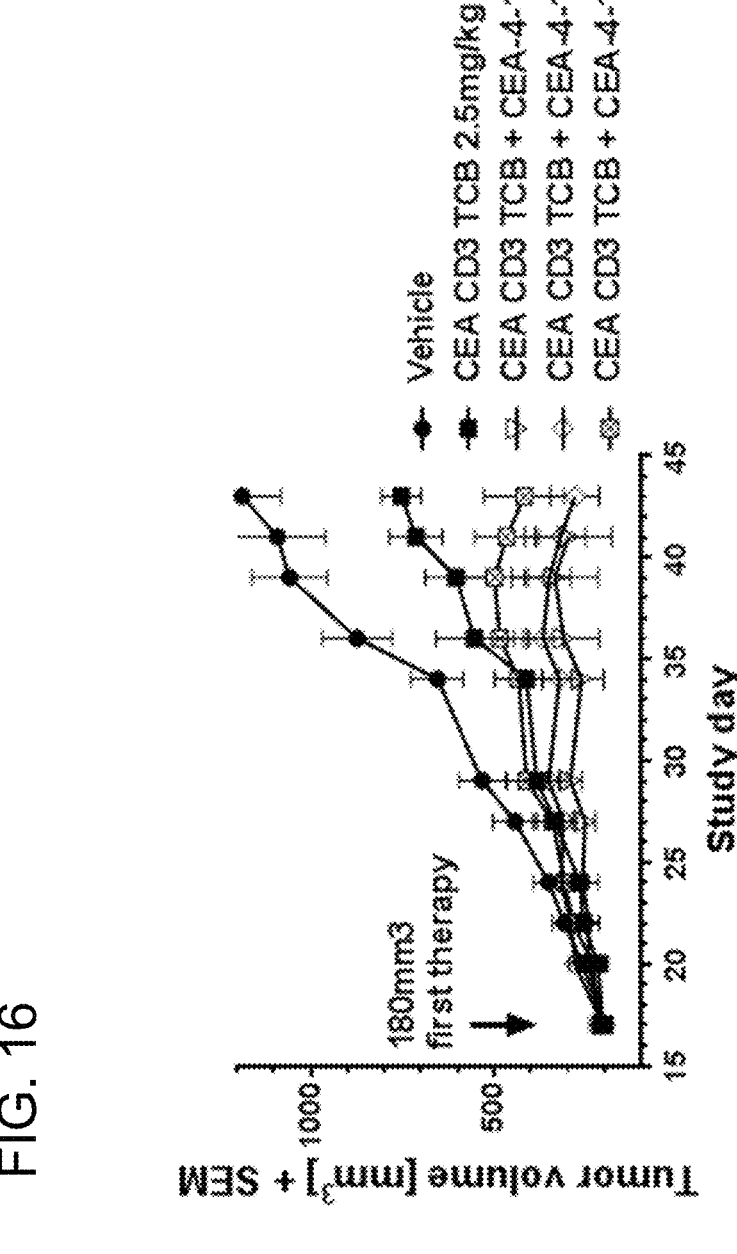

In FIG. 16 it is shown that combinations of CEA CD3 TCB+CEA-4-1BBL in the doses of 10 mg/kg and 3 mg/kg mediate improved efficacy in terms of tumor growth inhibition compared to CEA CD3 TCB monotherapy (see Example 7).

Figure 4A:
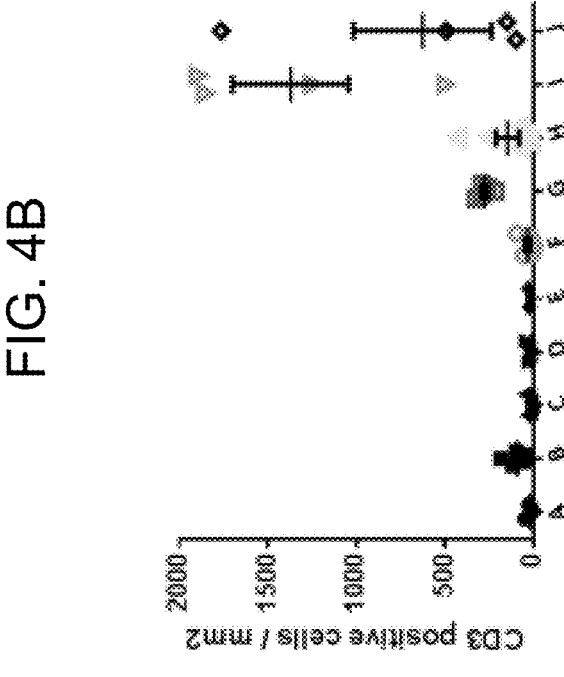
FIGS. 4A and 4B show the histological analysis at the end of the study, i.e. the amount of CD8 positive (FIG. 4A) and CD3 positive cells per mm² (FIG. 4B).
Figure 4B:
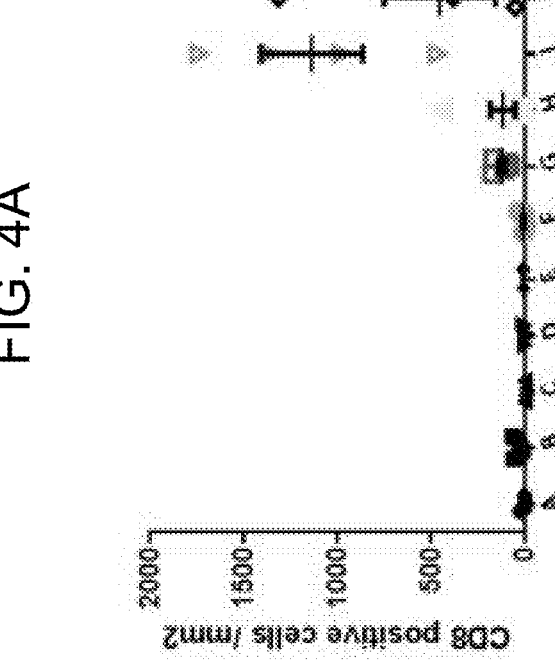
Figure 17A:
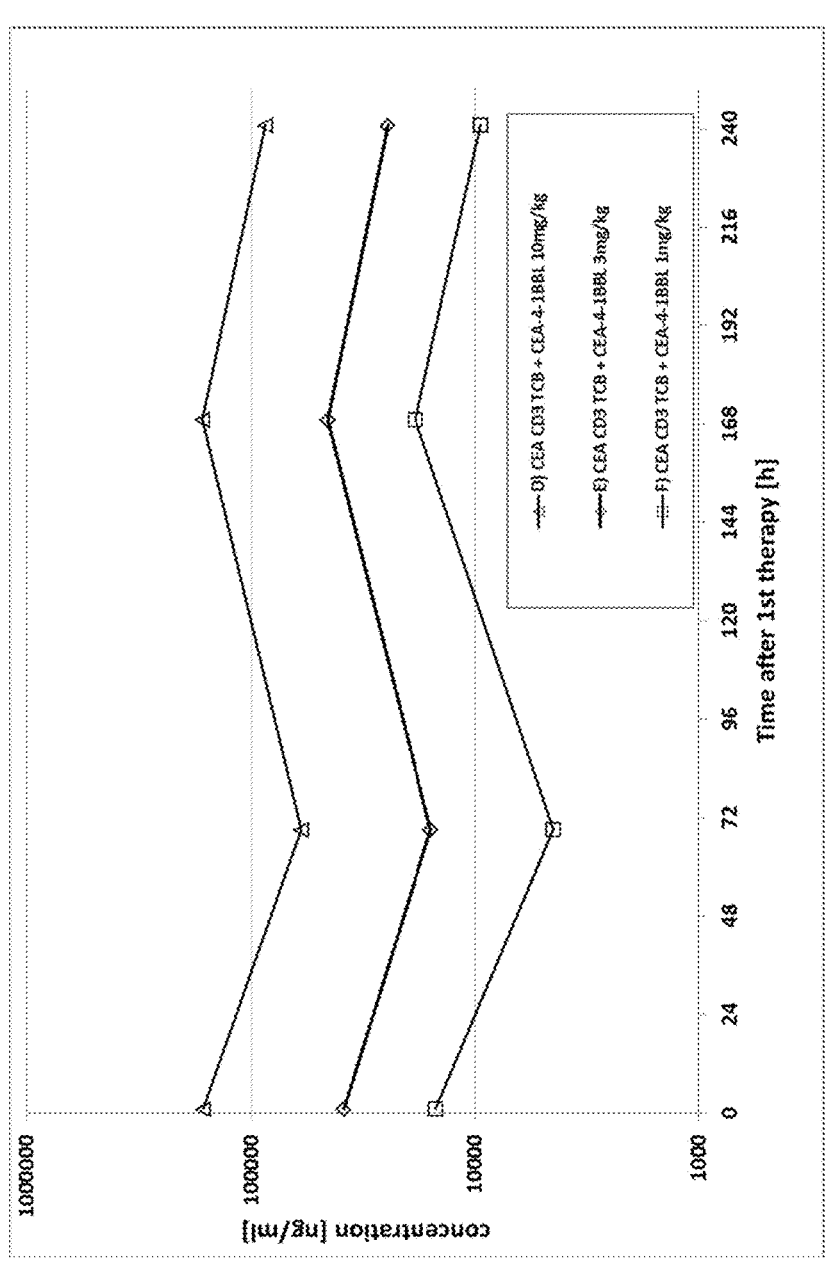
Figure 17B:
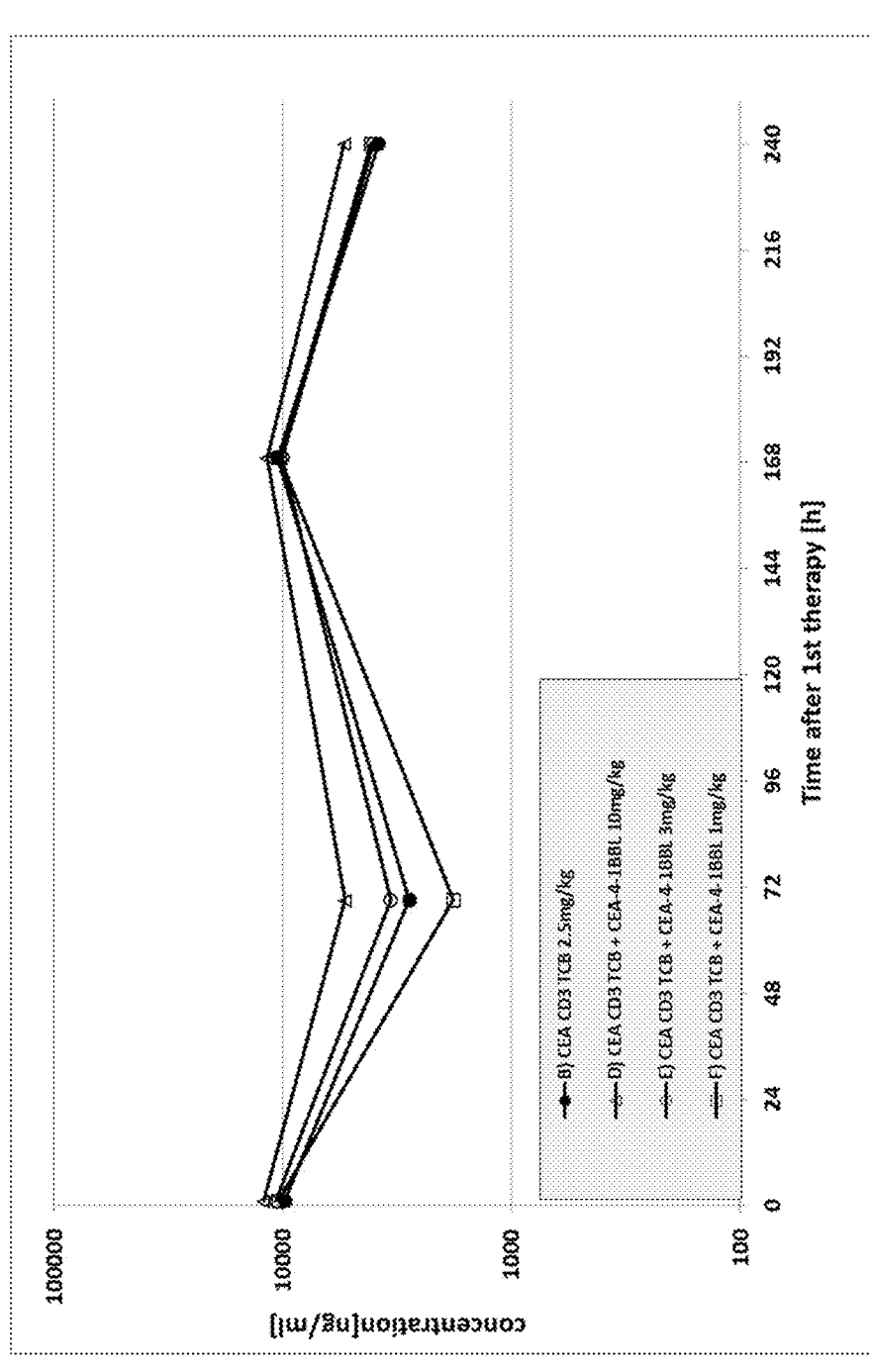

FIGS. 17A and 17B show the pharmacokinetic profile of injected compounds CEA CD3 TCB and CEA-4-1BBL during the first week. 2 mice per Group were bled 1h and 72h after $1^{st}$ and $2^{nd}$ therapy. Injected compounds were analysed by ELISA as described in Example 7. In FIG. 17A 4-1BBL was detected via 4-1BB binding whereas in FIG. 17B the concentration of CEA CD3 TCB was detected via binding to anti-CD3 CDR antibody.

Figure 18B:
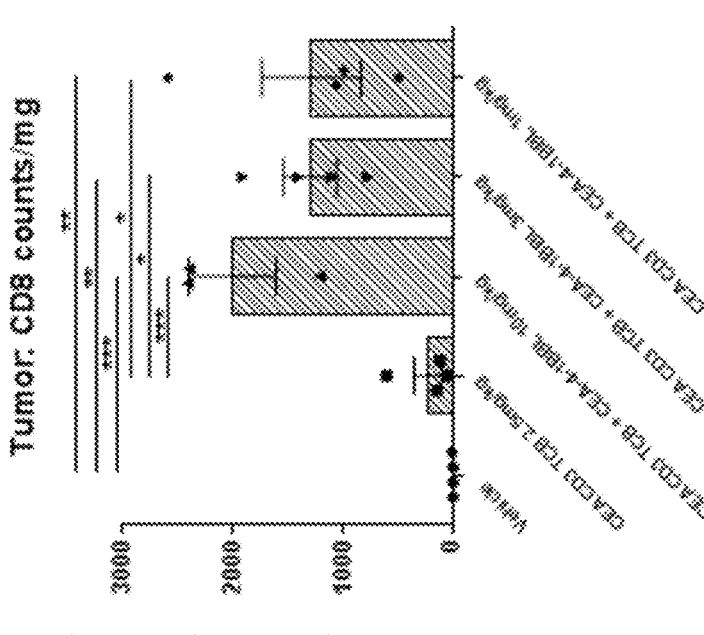
Figure 18A:
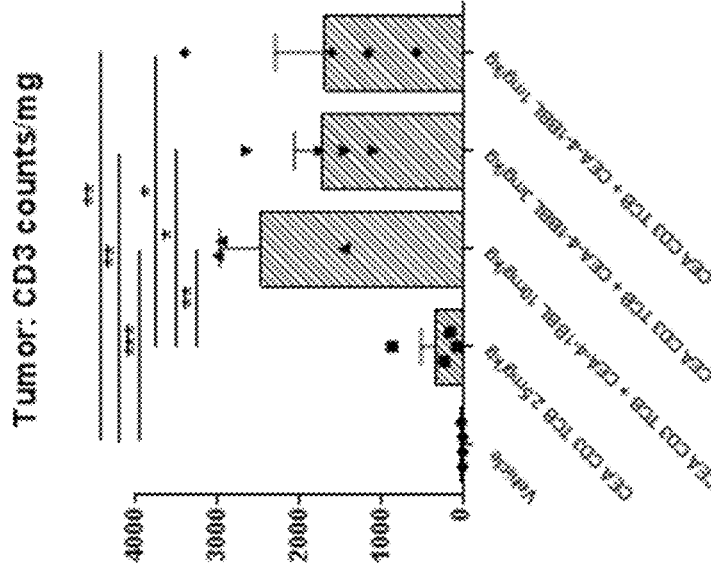

T cell infiltration in tumor at study termination as analysed by FACS is shown in FIGS. 18A (CD3 positive T cells), 18B (CD8 positive T cells) and 18C (CD4 positive T cells).

Figure 19A:
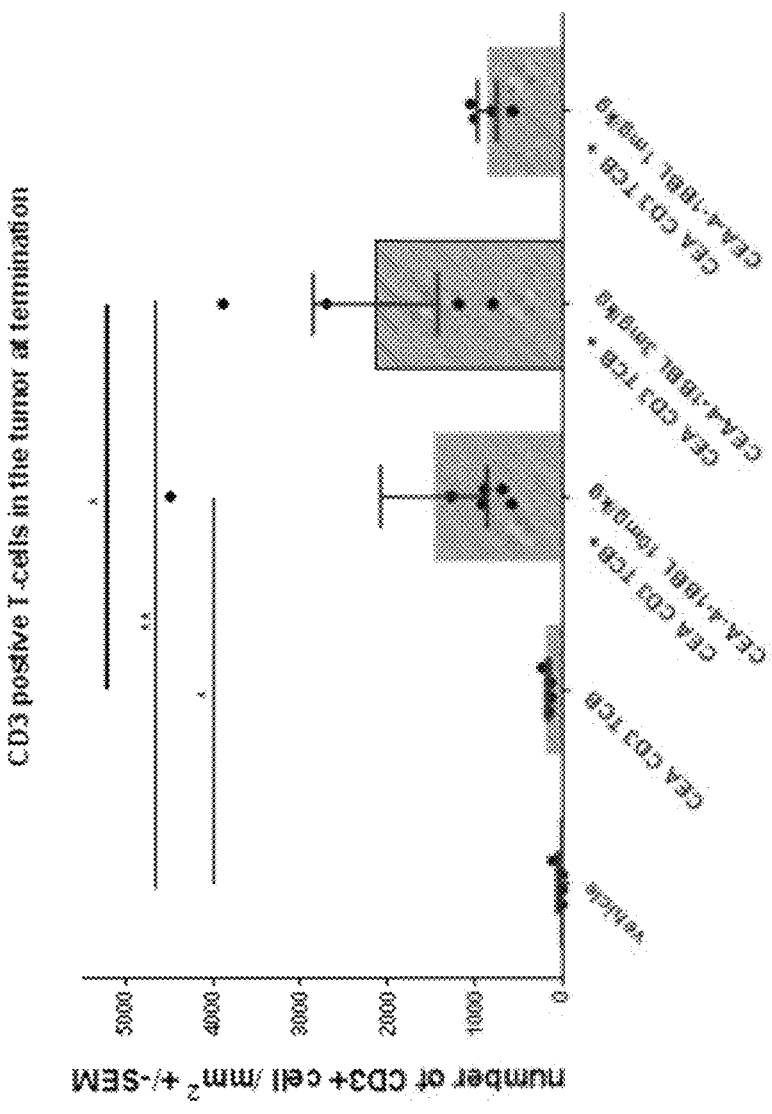
Figure 19B:
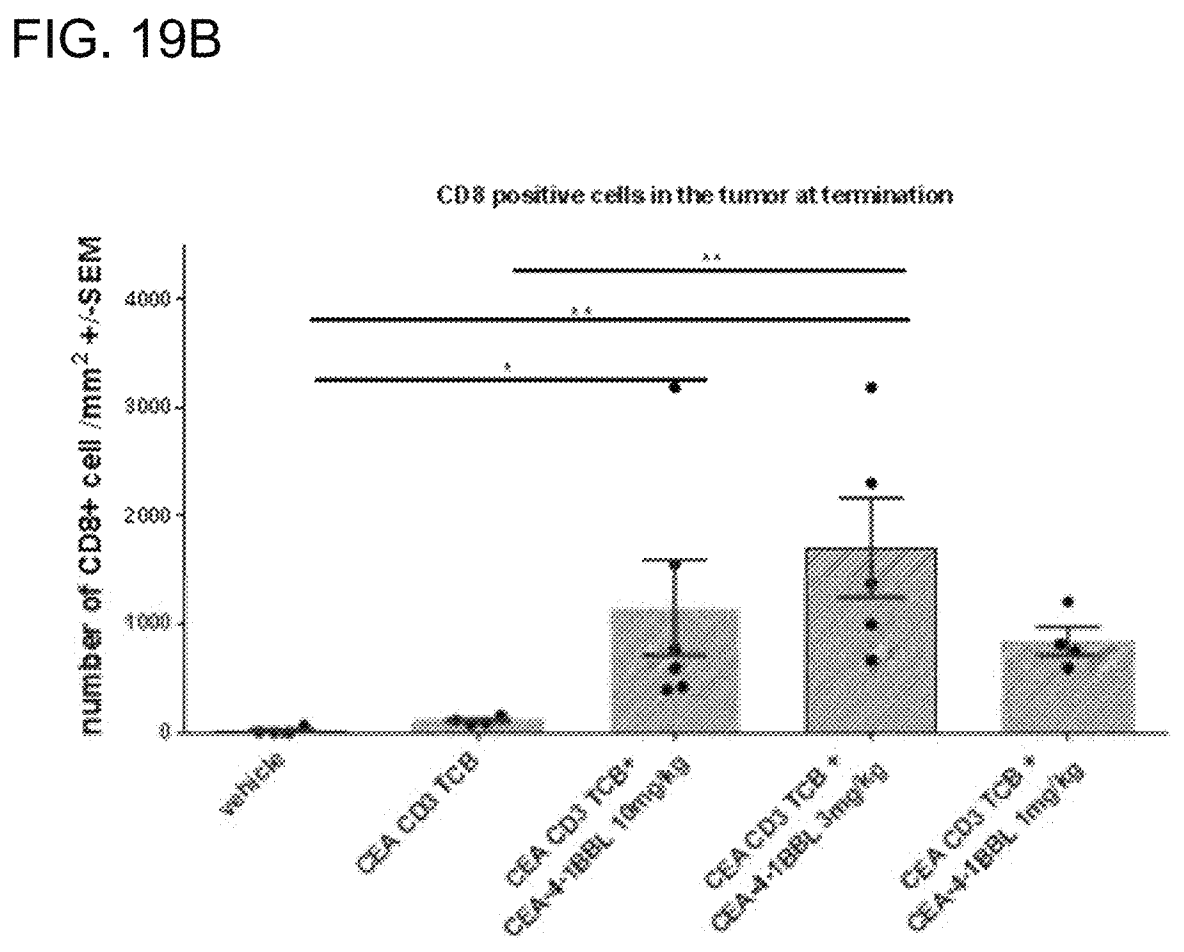

FIGS. 19A and 19B relate to the histological analysis at day 44 of the study (see Example 7). There is a significant increase of CD3 positive T cells (FIG. 19A) and CD8 positive T cells (FIG. 19B) positive T cells in the groups treated with CEA CD3 TCB+CEA-4-1BBL 10 mg/kg and 3 mg/kg group compared to CEA CD3 TCB monotherapy and vehicle.

Figure 20:
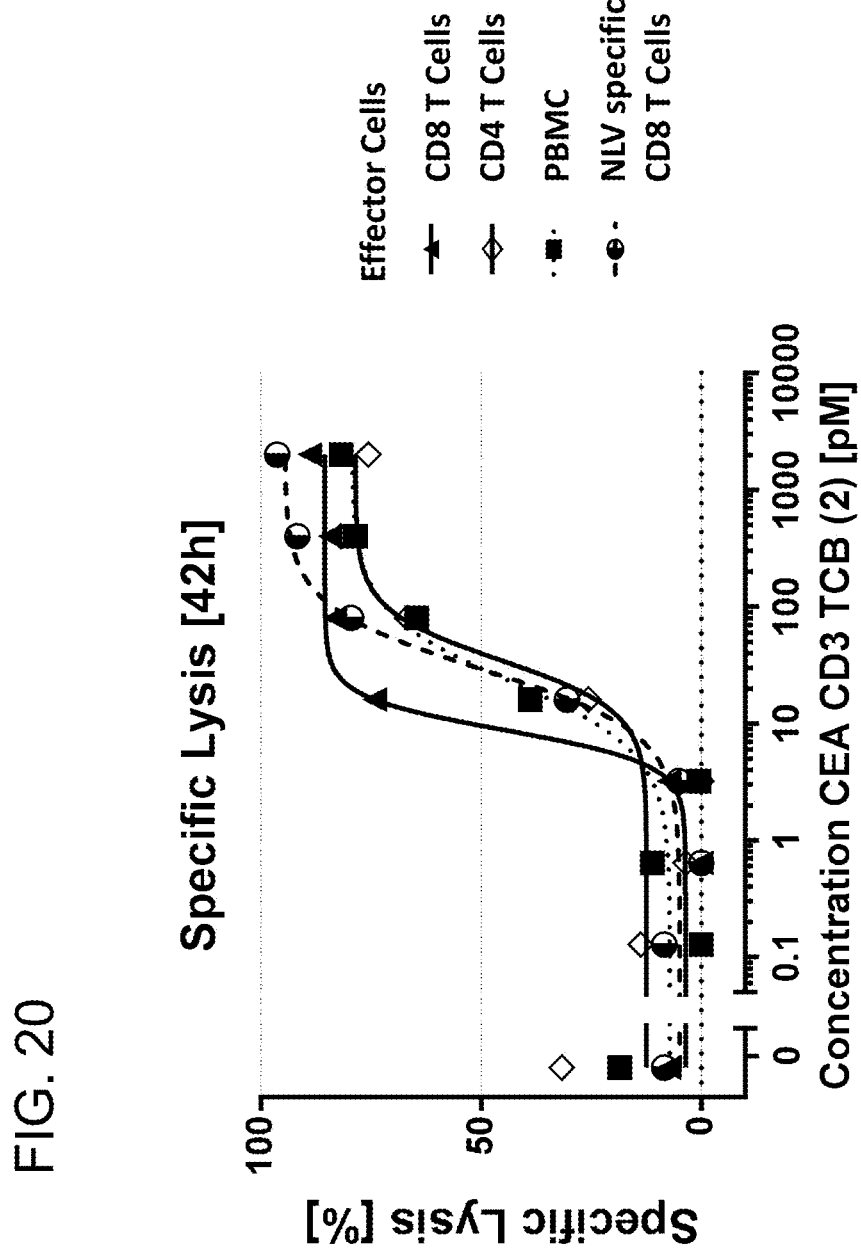

In FIG. 20 TCB mediated lysis of MKN45 NucLight red tumor cells by various human immune cell preparations is shown (Example 8). Different human immune effector cell preparations (resting PBMC, CD4 or CD8 T cells, NLV specific CD8 T effector memory cells) were cocultured with MKN-45 NucLight Red cells and irradiated NIH/3T3 huFAP in the presence of a serial dilution row of CEACAM5 CD3 TCB for 48 hours. The amount of living tumor cells was quantified by fluorescence microscopy high content life imaging using the Incucyte Zoom System (Essenbioscience, HD phase-contrast, green fluorescence and red fluorescence, 10× objective) in a 3 hours interval for 48 hours at 37° C. and 5% $CO_2$. The integrated red fluorescence of healthy tumor cells ($RCU \times pm^2$/image) of triplicates (median) was used to calculate the specific lysis which was plotted against the used TCB concentration to show the cytolytic potential of T cells.

FIGS. 21A to 21D show the expression of 4-1BB on T cells upon TCB stimulation. Different human immune effector cell preparations (resting PBMC, CD4 or CD8 T cells, NLV specific CD8 T effector memory cells) were cocultured with MKN-45 NucLight Red cells and irradiated NIH/3T3 huFAP in the presence of a serial dilution row of CEACAM5 CD3 TCB for 48 hours. The expression of 4-1BB was determined on CD4+ and CD8+ T cells by flow cytometry. The percentage of positive cells (FIGS. 21A and 21C) and MFI (FIGS. 21B and 21D) of triplicates (median) was plotted against the used TCB concentration for CD4 positive T cells (FIGS. 21A and 21B) and CD8 positive (FIGS. 21C and 21D) T cells. Error bars indicate the SEM. TCB mediate a dose dependent cell surface expression of 4-1BB on CD4+ T cells and on CD8+ T cell, albeit at a lower extent on CD4+ T cells.

FIGS. 22A to 22D demonstrate that 4-1BB costimulation did not influence the cytolytic potential of CEACAM5 CD3 TCB. Different human immune effector cell preparations (resting PBMC in FIG. 22B, CD4 T cells in FIG. 22A, CD8 T cells in FIG. 22C, NLV specific CD8 T effector memory cells in FIG. 22D) were cocultured for 48 hours with MKN-45 NucLight Red cells and irradiated NIH/3T3 huFAP in the presence of a serial dilution row of CEACAM5 CD3 TCB with or without a fixed concentration of FAP 4-1BBL. The amount of living tumor cells was quantified by fluorescence microscopy high content life imaging using the Incucyte Zoom System (Essenbioscience, HD phase-contrast, green fluorescence and red fluorescence, 10× objective) in a 3 hours interval for 48 hours at 37° C. and 5% $CO_2$. The integrated red fluorescence of healthy tumor cells (RCU×pm²/image) of triplicates (median) was used to calculate the specific lysis which was plotted against the used TCB concentration to show the cytolytic potential of T cells. Here, the 42 hours timepoint is shown exemplary. Error bars indicate the SEM.

In FIGS. 23A to 23D it is shown that 4-1BB costimulation did increase CEA CD3 TCB and CEACAM5 CD3 TCB mediated TNF-α, release. Resting CD4 T cells were cocultured for 48 hrs with MKN45 NucLight Red cells and irradiated NIH/3T3 huFAP in the presence of a serial dilution row of CEACAM5 CD3 TCB or CEA CD3 TCB with or without a fixed concentration of FAP 4-1BBL, respectively. The amount of TNF-α, was quantified as GFP induction in TNF-α, sensor cells by fluorescence microscopy high content life imaging using the Incucyte Zoom System (Essenbioscience, HD phase-contrast, green fluorescence and red fluorescence, 10× objective) in a 3 hours interval for 42 hours at 37° C. and 5% $CO_2$. The integrated green fluorescence of TNF-α sensor cells (GCU×pm²/image) of triplicates (median) was plotted against the used TCB concentration to quantify TNF-α, secretion of T cells. Error bars indicate the SEM. FIG. 23A shows the results for CEACAM5 CD3 TCB without the presence of FAP-4-1BBL, the increase with the addition of FAP-4-1BBL is shown in FIG. 23B. FIGS. 23C and 23D show the TNF-α, release mediated by CEA CD3 TCB without (FIG. 23C) and with (FIG. 23D) costimulation with FAP-4-1BBL.

Figures 24A, 24B:
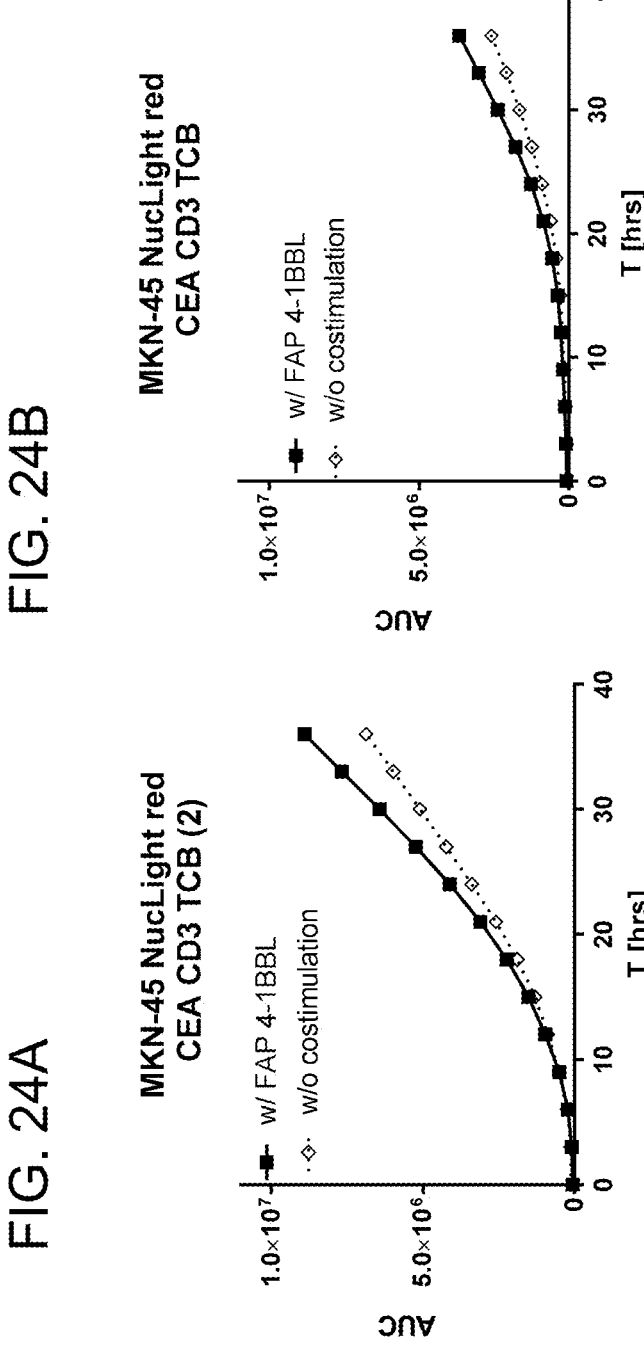
Figures 25A, 25B, 25C, 25D:
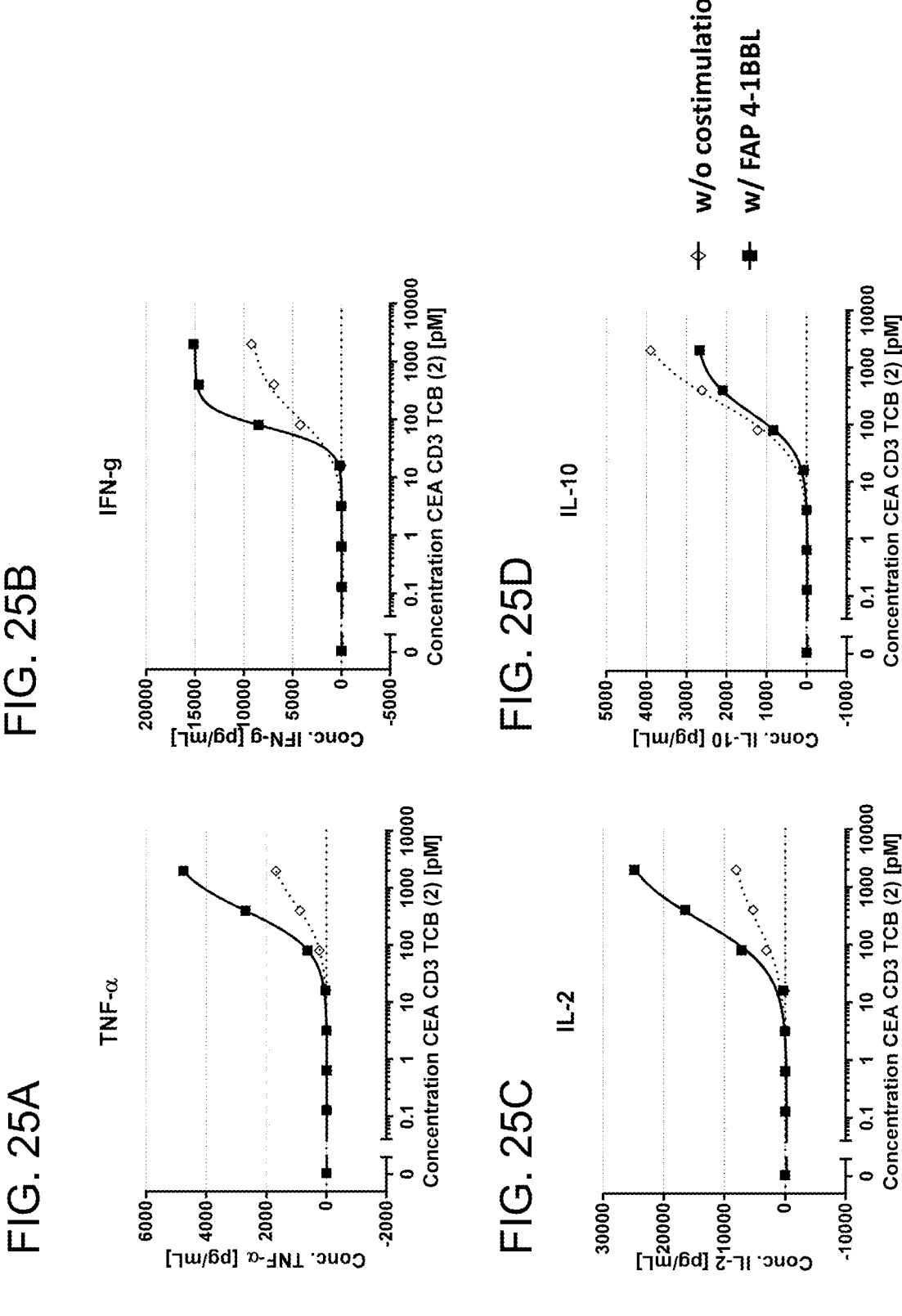

In FIGS. 24A and 24B the area under the curve (AUC) values are plotted against each timepoint. The amount of TNF-α, was quantified as GFP induction in TNF-α, sensor cells by fluorescence microscopy high content life imaging. The AUC of GFP was calculated for each condition and time point and was plotted against each timepoint to quantify TNF-α, secretion of T cells. It can be seen that the TNF-α release mediated by CEACAM5 CD3 TCB (FIG. 24A) and CEA CD3 TCB (FIG. 24B) did increase with 4-1BB costimulation through the presence of FAP-41BBL.

In FIGS. 25A to 25D it is shown how 4-1BB costimulation did modulate cytokine secretion by CEACAM5 CD3 TCB (called CEA CD3 TCB(2) in the graphs). Resting CD4 T cells were cocultured for 48 hrs with MKN-45 NucLight Red cells and irradiated NIH/3T3 huFAP in the presence of a serial dilution row of CEA CD3 TCB (2) with or without a fixed concentration of FAP 4-1BBL. The secreted amount of TNF-α, IFN-γ, IL-2 and IL-10 was quantified at the 48 hours end point using cytometric bead array technology. The respective cytokine concentrations were plotted against the TCB concentration. Off note—secretion of proinflammatory cytokine TNF-α (FIG. 25A), IFN-γ (FIG. 25B) and IL-2 (FIG. 25C) was enhanced by 4-1BB costimulation, whereas that of immunesuppressive IL-10 (FIG. 25D) was decreased.

In FIGS. 26A to 26D similar data are shown for CEA CD3 TCB mediated cytokine secretion. Resting CD4 T cells were cocultured for 48 hrs with MKN-45 NucLight Red cells and irradiated NIH/3T3 huFAP in the presence of a serial dilution row of CEA CD3 TCB with or without a fixed concentration of FAP 4-1BBL. The secreted amount of TNF-α, (FIG. 26A), IFN-γ (FIG. 26B), IL-2 (FIG. 26C) and IL-10 (FIG. 26D) was quantified at the 48h end point using cytometric bead array technology. The respective cytokine concentrations were plotted against the TCB concentration.

Figure 27:
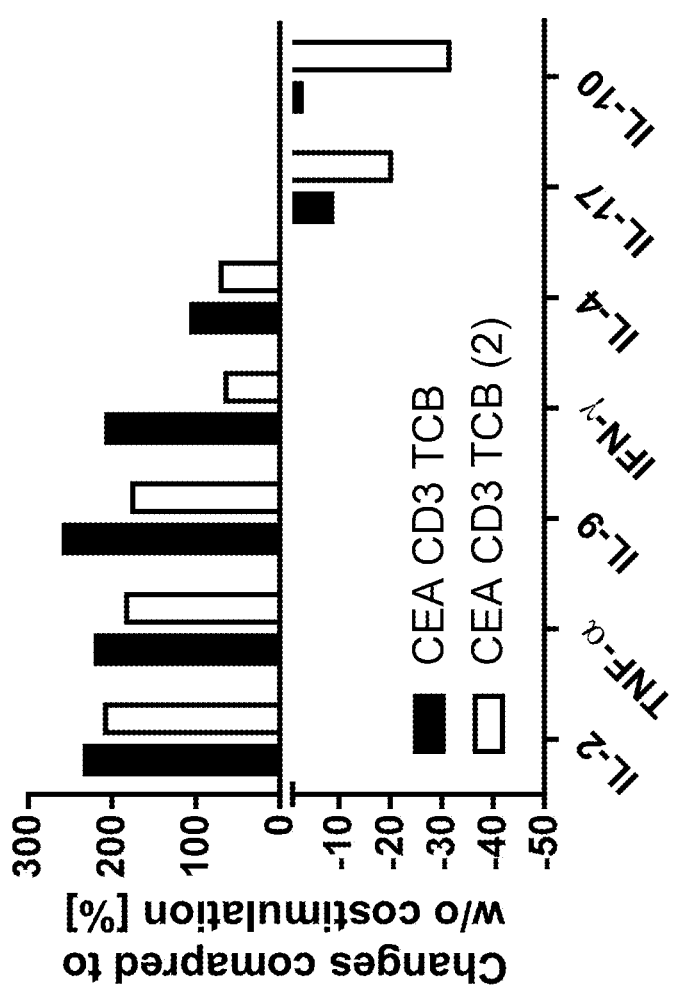
Figures 29A, 29B, 29C, 29D:
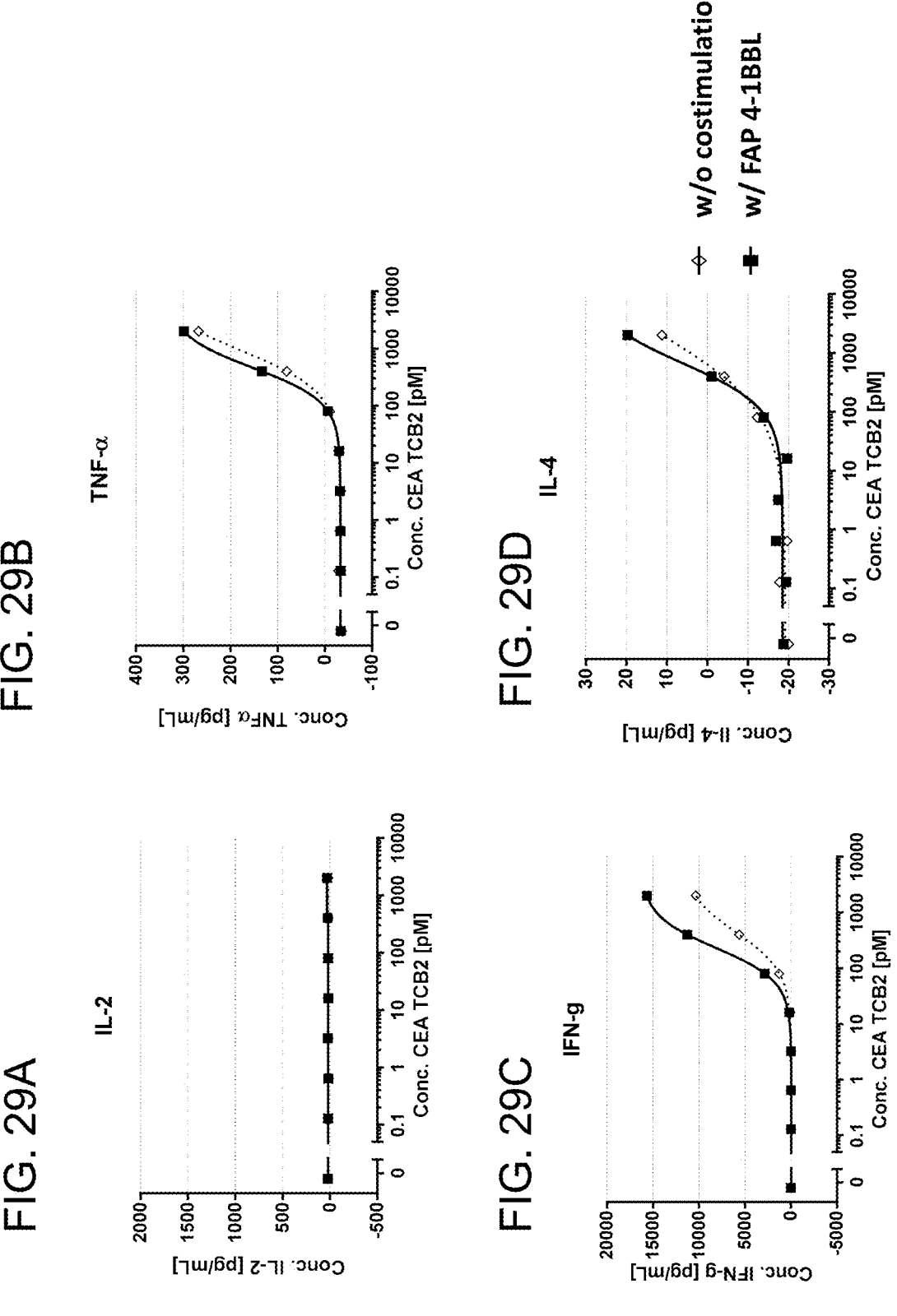

In FIG. 27 a comparison of FAP 4-1BBL costimulation mediated changes [%] in cytokine concentration in the presence of a high concentration of CEA CD3 TCB [50 nM]

or CEACAM5 CD3 TCB [2 nM](in the graph CEA CD3 TCB(2)) with or without a fixed concentration of FAP 4-1BBL are shown. The secreted amount of TNF-α, IFN-γ, IL-2, IL-10, IL-9 and IL-17A was quantified at the 48 hours end point using cytometric bead array technology. The changes of cytokine concentration were calculated in percent, whereby the respective sample w/o FAP 4-1BBL costimulation was considered 100%.

FIGS. 28A to 28H illustrate that 4-1BB costimulation did also modulate CEACAM5 CD3 TCB mediated cytokine secretion of resting CD8 T cells. Resting CD8 T cells were cocultured for 72 hrs with MKN-45 NucLight Red cells and irradiated NIH/3T3 huFAP in the presence of a serial dilution row of CEACAM5 CD3 TCB (called CEA TCB2 in the graphs) with or without a fixed concentration of FAP 4-1BBL. The secreted amount of IL-2 (FIG. 28A), TNF-α, (FIG. 28B), IFN-γ (FIG. 28C), IL-4 (FIG. 28D), IL-9 (FIG. 28E), IL-17a (FIG. 28F), MIP-1α (FIG. 28G) and IL-10 (FIG. 28H) was quantified at the 72 hours end point using cytometric bead array technology. The respective cytokine concentrations were plotted against the TCB concentration.

In FIGS. 29A to 29H it is shown that 4-1BB costimulation did modulate CEACAM5 CD3 TCB (CEA TCB2) mediated cytokine secretion of NLV specific effector memory CD8 T cells. NLV specific effector memory CD8 T cells were cocultured for 72 hours with MKN-45 NucLight Red cells and irradiated NIH/3T3 huFAP in the presence of a serial dilution row of CEA TCB2 with or without a fixed concentration of FAP 4-1BBL. The secreted amount of IL-2 (FIG. 29A), TNF-α (FIG. 29B), IFN-γ (FIG. 29C), IL-4 (FIG. 29D), IL-9 (FIG. 29E), IL-17a (FIG. 29F), MIP-1α (FIG. 29G) and IL-10 (FIG. 29H) was quantified at the 72 hours end point using cytometric bead array technology. The respective cytokine concentrations were plotted against the TCB concentration.

Figure 30:
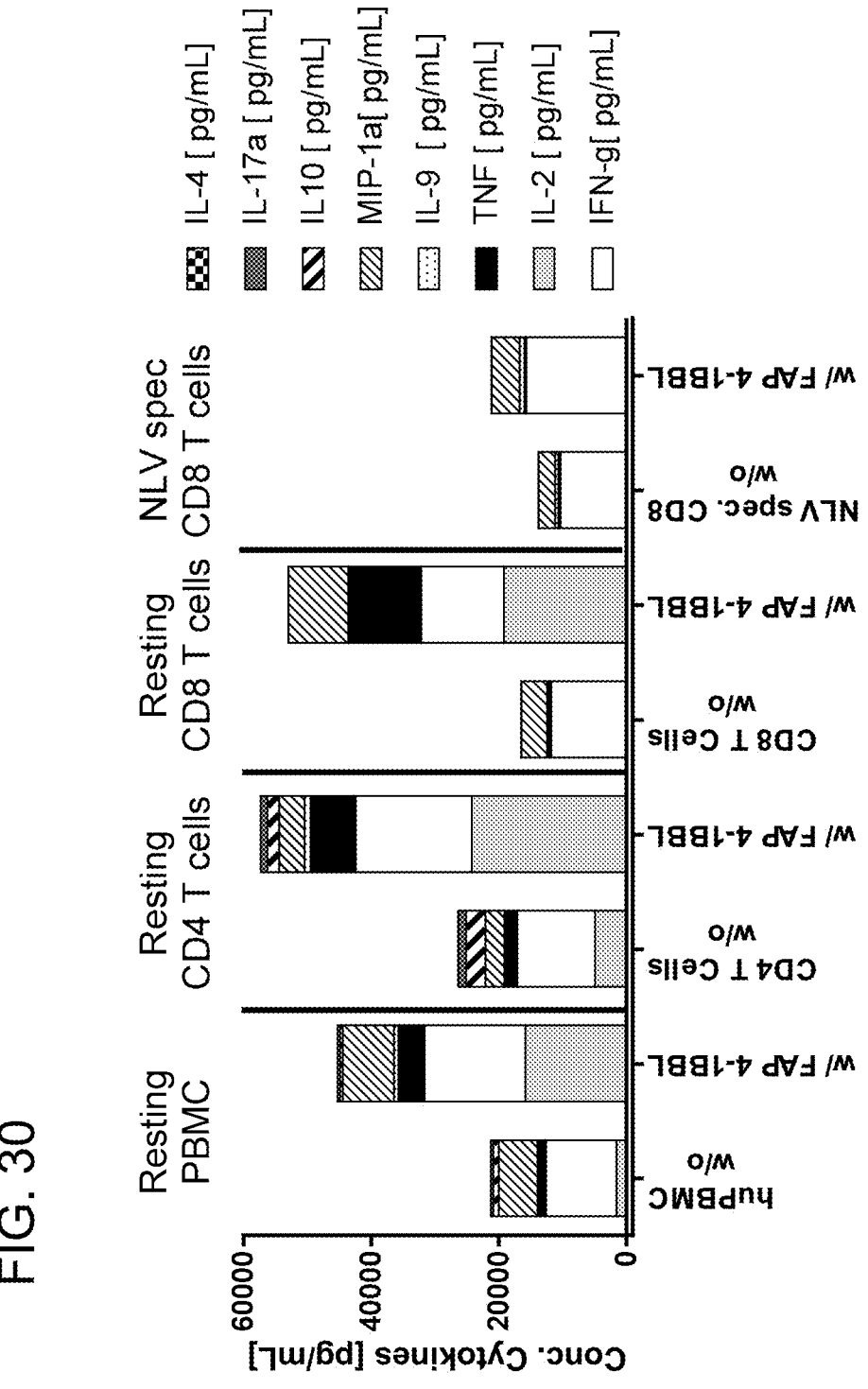

In FIG. 30 a comparison of FAP 4-1BBL costimulation mediated changes [%] in cytokine concentration in the presence of a high concentration of CEA CD3 TCB [50 nM] or CEACAM5 CD3 TCB [2 nM](in the graph CEA CD3 TCB(2)) with or without a fixed concentration of FAP 4-1BBL are shown. The secreted amount of TNF-α, IFN-γ, IL-2, IL-10, IL-9 and IL-17A was quantified at the 48 hours end point using cytometric bead array technology. The changes of cytokine concentration were calculated in percent, whereby the respective sample w/o FAP 4-1BBL costimulation was considered 100%.

Figure 31:
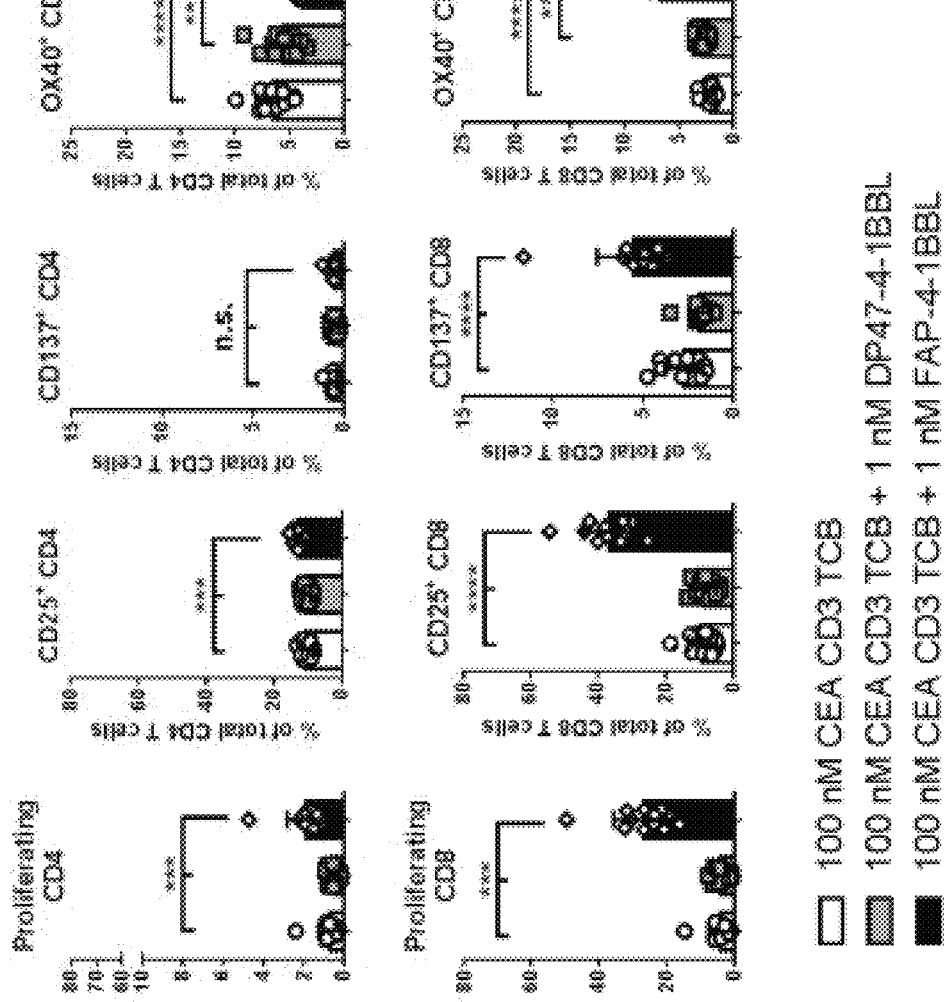
Figure 32:
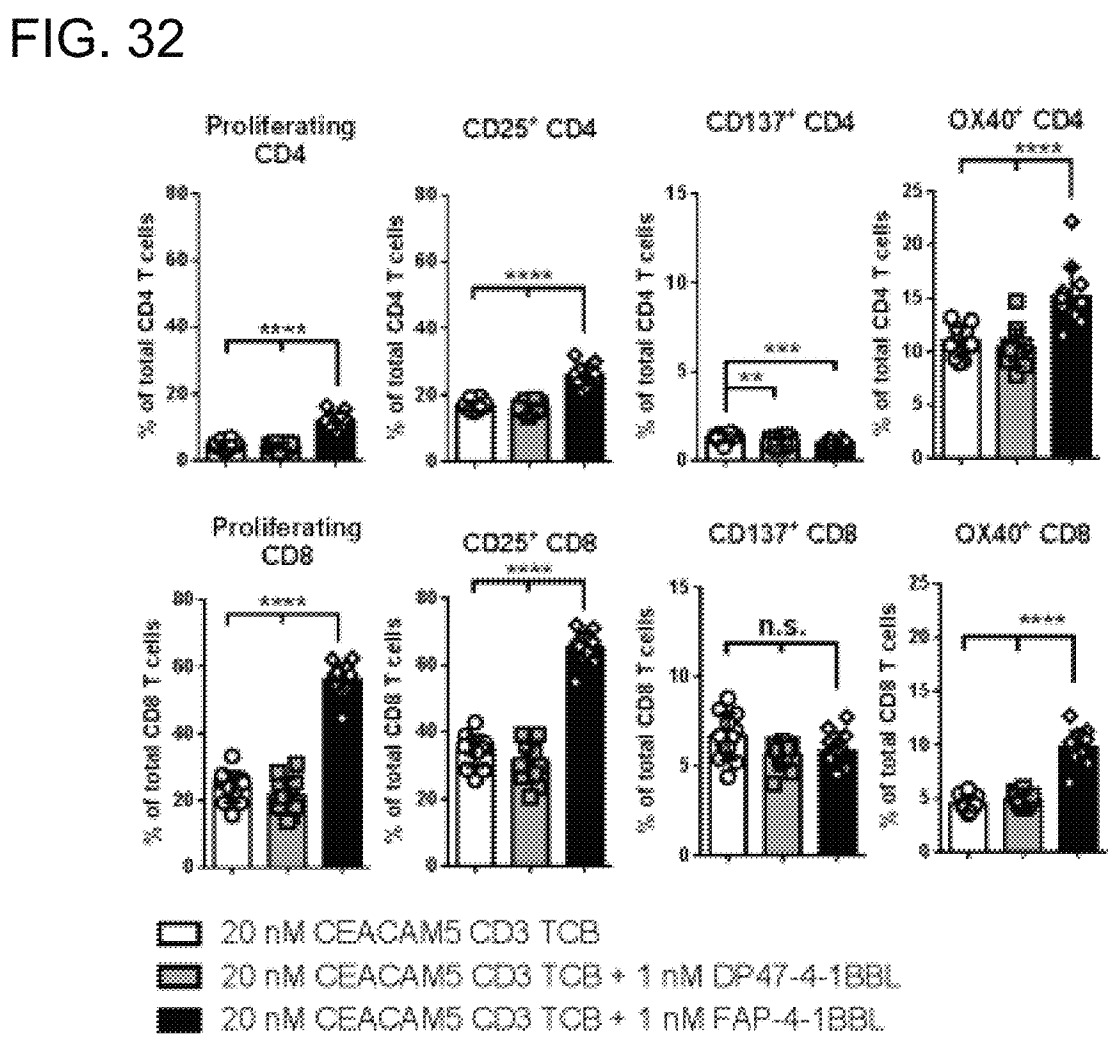

The results of in vitro co-culture assays of PBMCs with MKN45 cells expressing CEA and PDL-1 and NIH/3T3-FAP cells as described in Example 9 are shown in FIGS. 31 (for CEA CD3 TCB) and 32 (for CEACAM5 CD3 TCB). As can be seen in FIG. 31, a small increase of proliferating CD4 T cells and high increase of proliferating CD8 T cells was observed for the combination of CEA CD3 TCB and FAP-4-1BBL. As shown in FIG. 32, an even clearer increase of proliferating CD4 T cells and proliferating CD8 T cells was caused by the combination of CEACAM5 CD3 TCB and FAP-4-1BBL.

The results of an in vitro assay testing the efficacy of the combination of CEA CD3 TCB and FAP-4-1BBL as well as the triple combination of CEA CD3 TCB and FAP-4-1BBL with a PD-L1 antibody (Atezolizumab) are shown in FIGS. 33 to 40. PBMCs were incubated for four days in the presence of MKN45-PD-L1 and NIH/3T3-huFAP cells and different combinations of T cell activator CEA CD3 TCB, checkpoint inhibitor PD-L1 (Atezolizumab) and immunomodulator FAP-4-1BBL or control molecule DP47-4-1BBL. Each symbol indicate one well (each group were tested in triplicate), each color/pattern indicate a specific treatment combination, the bar indicates the mean with SD. Because different donors showed high diversity of frequencies, a graph for each donor is shown. The effect of the combinations compared to the single components and an untargeted 4-1BBL (DP47-4-1BBL) on proliferation (FIG. 33) and surface expression of CD25 (FIG. 34) and CD137 (4-1BB, FIG. 35) on CD8 T cells is shown for 5 different donors.

Figure 36:
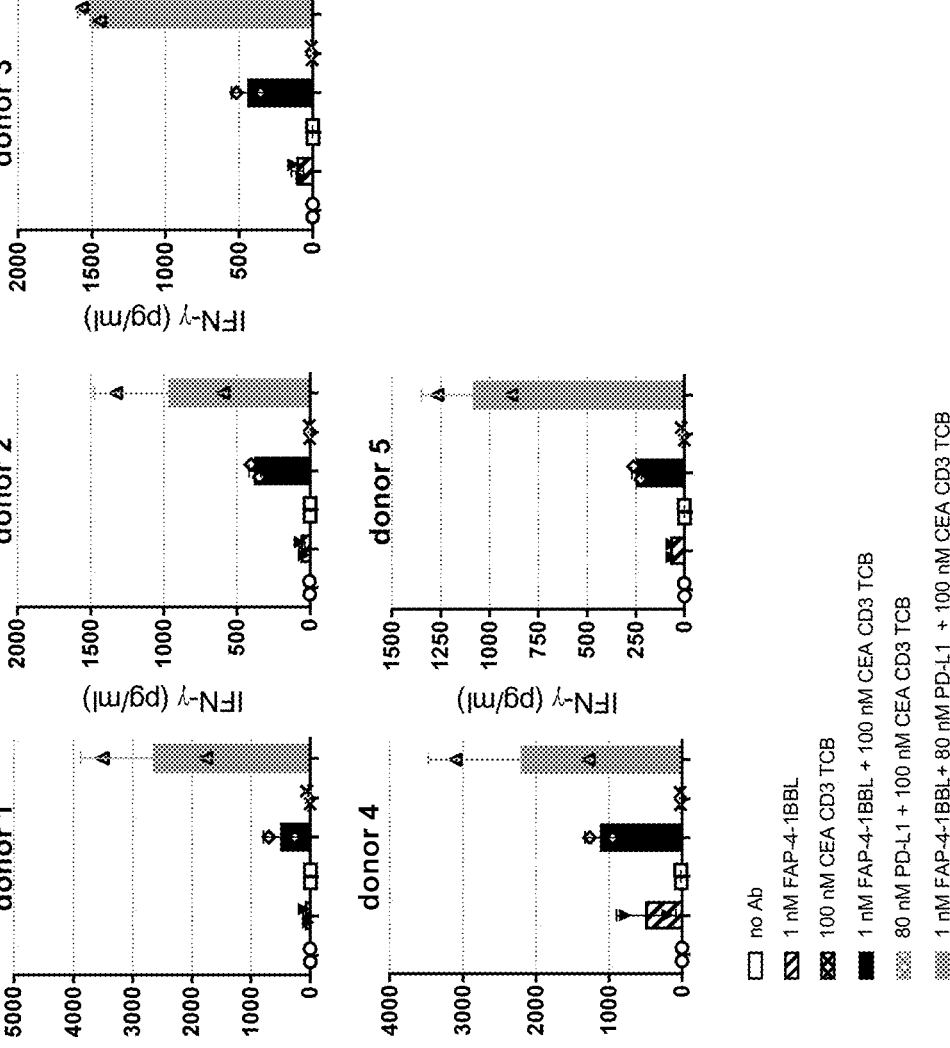
Figure 37:
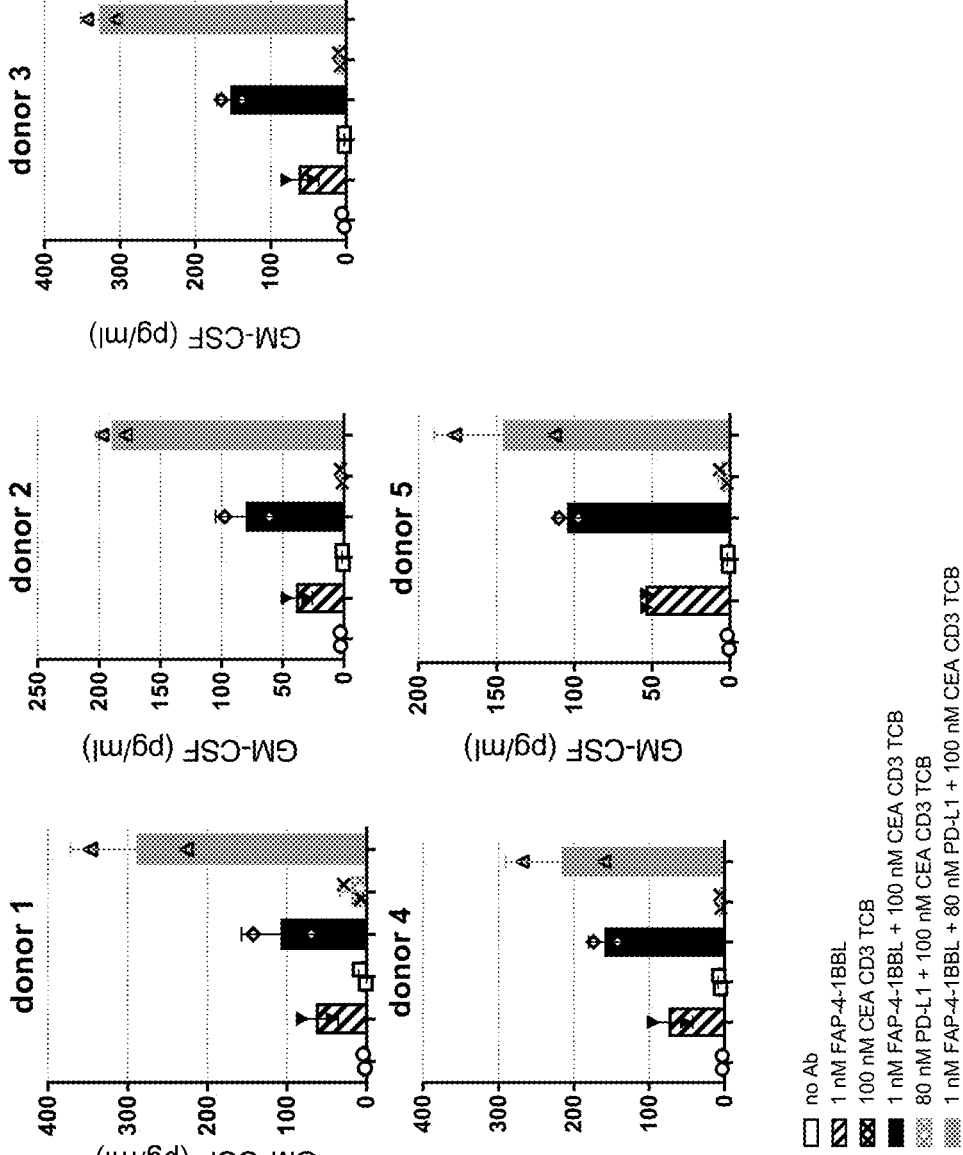

Secreted cytokines IFNγ, GM-CSF and TNFα were analyzed in the supernatant after 4 days of incubation using Bio-RAD Bio-Plex Pro Human Cytokine 8 plex. The increase in IFNγ release is shown in FIG. 36, FIG. 37 shows the increase in GM-CSF release and FIG. 38 shows the release of TNFα. Each symbol indicates one well (each group tested in duplicate), each color/pattern indicates a specific treatment combination, the bar indicates the mean with SD. Because different donors showed high diversity of frequencies, a graph for each donor is shown.

Figure 39:
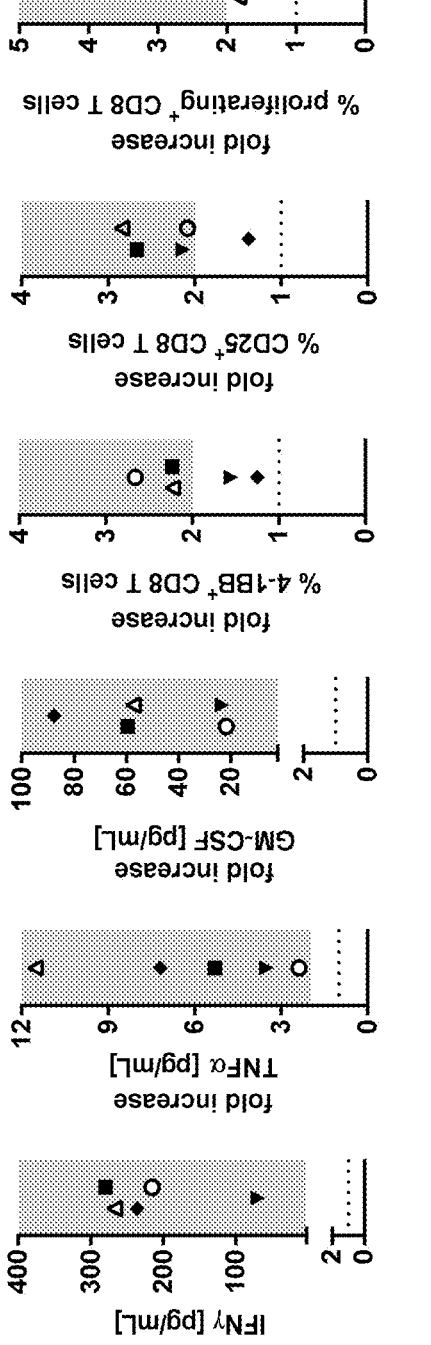

In FIG. 39 a comparison between the treatment with 100 nM CEA CD3 TCB and the the combination of 100 nM CEA CD3 TCB and 1 nM FAP-4-1BBL is shown. To analyze the improvement of T cell activation obtained by the combination and in consideration of the donor diversity the fold increase was calculated for each donor and each tested parameter. For each donor the mean is shown, whereby each donor is represented by a different symbol. A significant change is defined as a fold increase of 2 (grey area). No change (e.g. fold increase=1) is indicated as dotted line.

Figure 40:
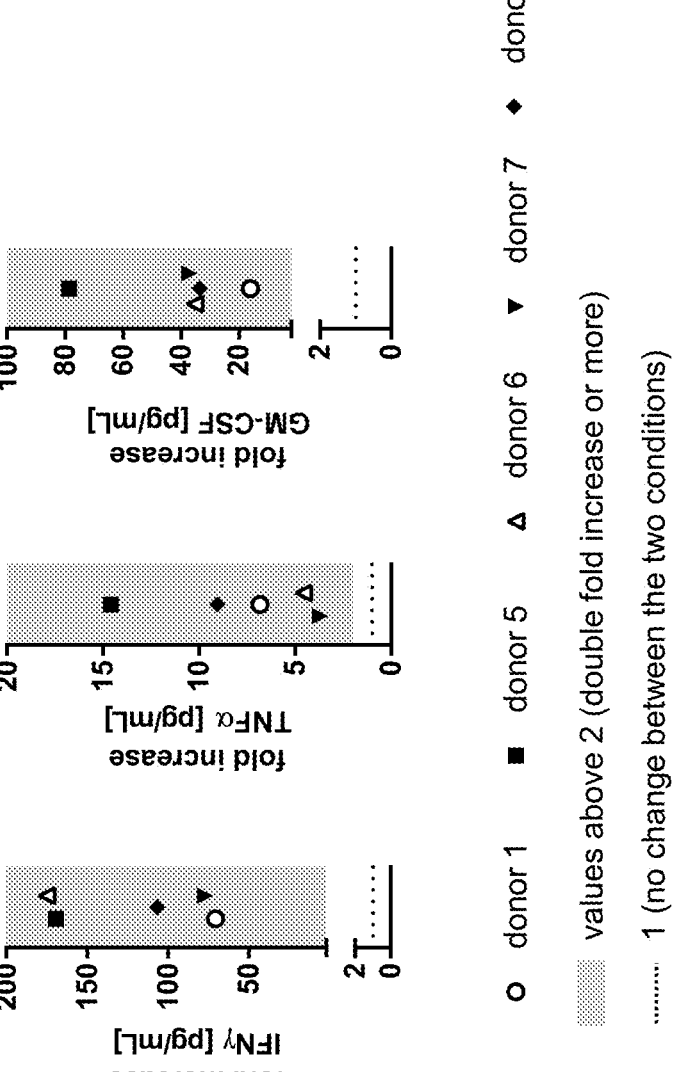

In FIG. 40 the combination treatment of CEA CD3 TCB with FAP-4-1BBL is compared versus the triple combination treatment of CEA CD3 TCB, FAP-4-1BBL and PD-L1 antibody (Atezolizumab). To analyze the improvement of T cell activation by combining CEA CD3TCB with FAP-4-1BBL and PD-L1 antibody (Atezolizumab) and in consideration of the donor diversity the fold increase was calculated for each donor and each tested parameter. For each donor the mean is shown, whereby each donor is represented by a different symbol. A significant change is defined as a fold increase of 2 (grey area). No change (e.g. fold increase=1) is indicated as dotted line.

Figure 41A:
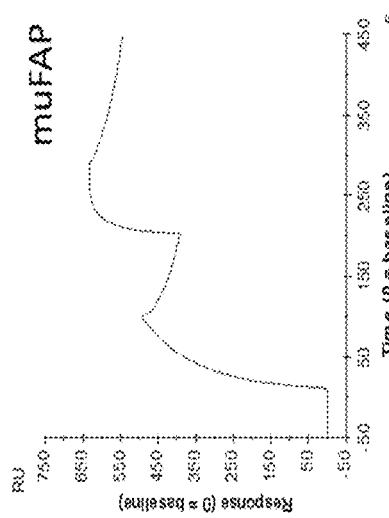
Figure 41B:
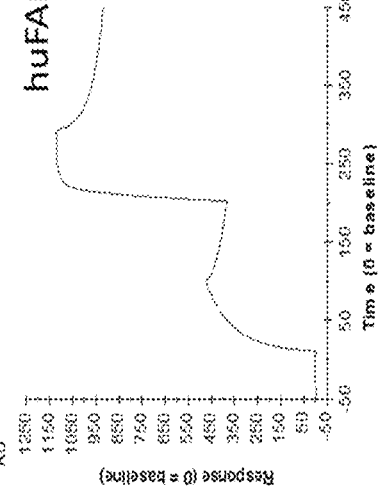
Figure 41C:
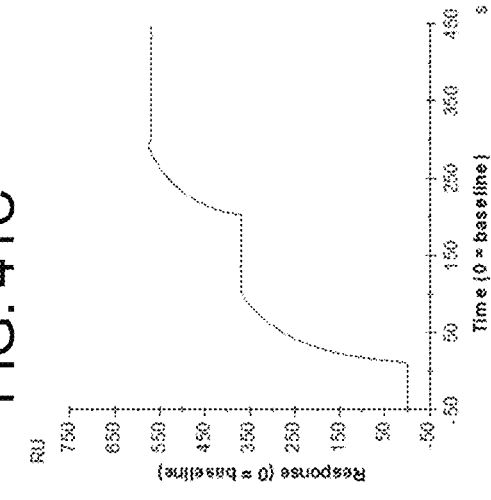

FIGS. 41A and 41B show the simultaneous binding of hybrid surrogate FAP-mu4-1BBL (Analyte 1) to immobilized murine 4-1BB and human FAP or murine FAP (Analyte 2), respectively. In FIG. 41C is shown the simultaneous binding of murine bispecific FAP-4-1BB antibody muFAP-4-1BB (Analyte 1) to immobilized murine 4-1BB and murine FAP (Analyte 2).

Figures 42, 43:
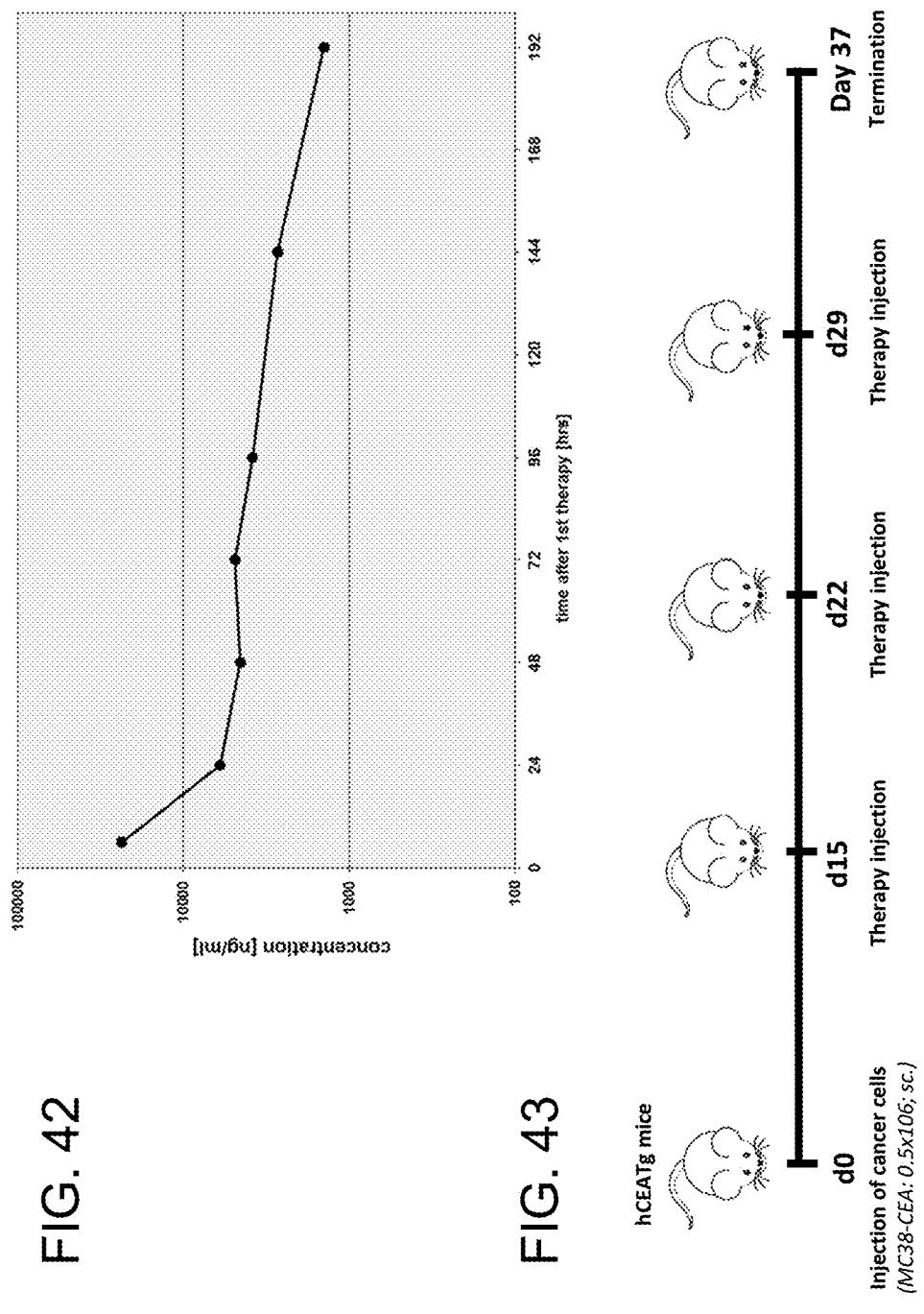

FIG. 42 shows the pharmacokinetic profile of muFAP-4-1BB after single injection in C57BL/6 mice as described in Example 13. A stable PK-behavior was observed which suggests that the compound can be administered in a once weekly schedule. This led to the treatment schedule of the efficacy study with muFAP-4-1BB and anti-PD-L1 antibody in the MC38-CEA model as shown in FIG. 43 and described in Example 14.

Figure 44A:
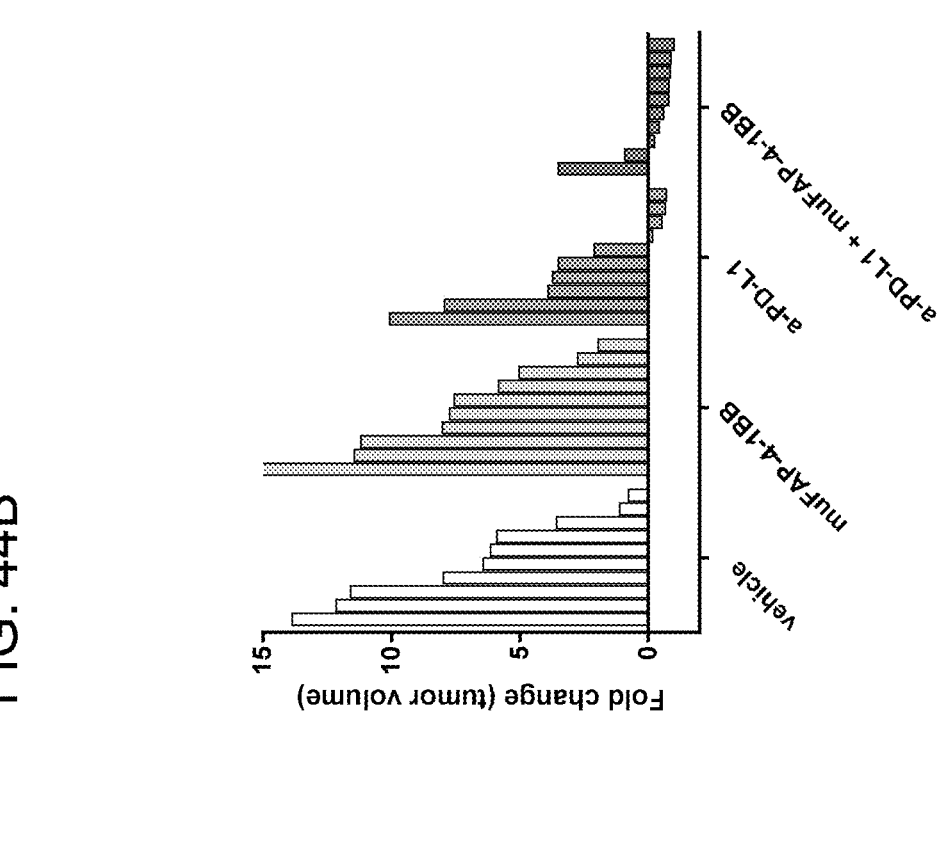
Figure 44B:
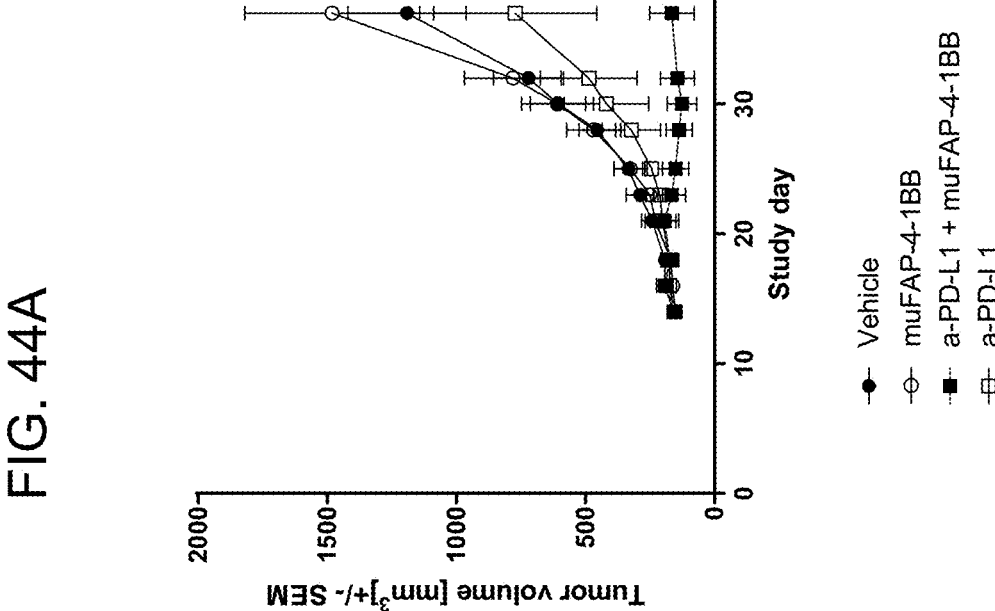

FIG. 44A shows the tumor growth kinetics (Mean+/−SEM) as observed in mice treated with muFAP-4-1BB alone, anti-PD-L1 antibody alone or with the combination of both. FIG. 44B shows a waterfall plot indicating the tumor growth change of any animal from start of treatment at day 15 until day 37. The individual tumor growth kinetics of each animal for all treatment groups is furthermore shown in more detail in FIG. 44C. Monotherapy of muFAP-4-1BB did not reveal any tumor growth inhibition. Treatment with anti-PD-L1 alone induced tumor growth inhibition with one mouse being tumor free at day 37. However, the combination of muFAP-4-1BB and a-PD-L1 induced strong tumor regression in 5 out of 10 mice resulting in 50% tumor free mice by day 37.

Figures 45A, 45B:
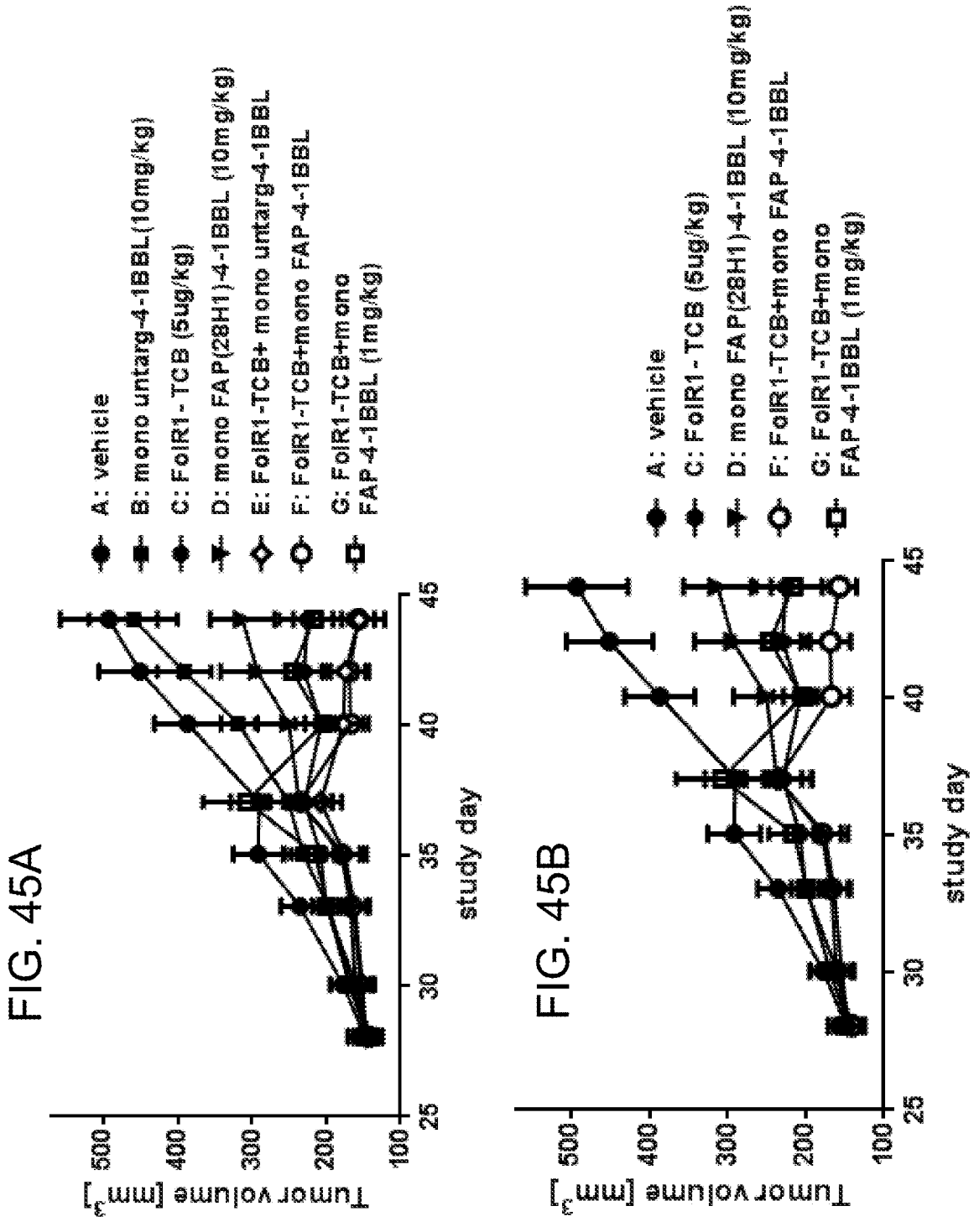

FIGS. 45A and 45B show that the groups treated with combinations of FolR1 CD3 TCB with monovalent FAP (28H1)-4-1BBL showed improved efficacy in terms of tumor growth inhibition compared to the other groups receiving FolR1 CD3 TCB alone or monovalent FAP (28H1)-4-1BBL as single agent (FIG. 45B). In FIG. 45A it can be seen that monovalent FAP(28H1)-4-1BBL is much more potent in inhibiting tumor growth as untargeted 4-1BBL, but less potent than in combination with FolR1 CD3 TCB.

Figure 46:

FIG. 46 shows the pharmacokinetic profile of injected compounds during the first week. 2-3 mice per Group were bled 10 min, 1 h, 8h, 24 h and 7d after the first therapy and injected compounds were analysed by ELISA. 4-1BBL was detected via 4-1BB binding. All groups injected with compounds show comparable exposure of the molecules between the different groups (dose dependent).

Figures 47A, 47B, 47C, 47D:
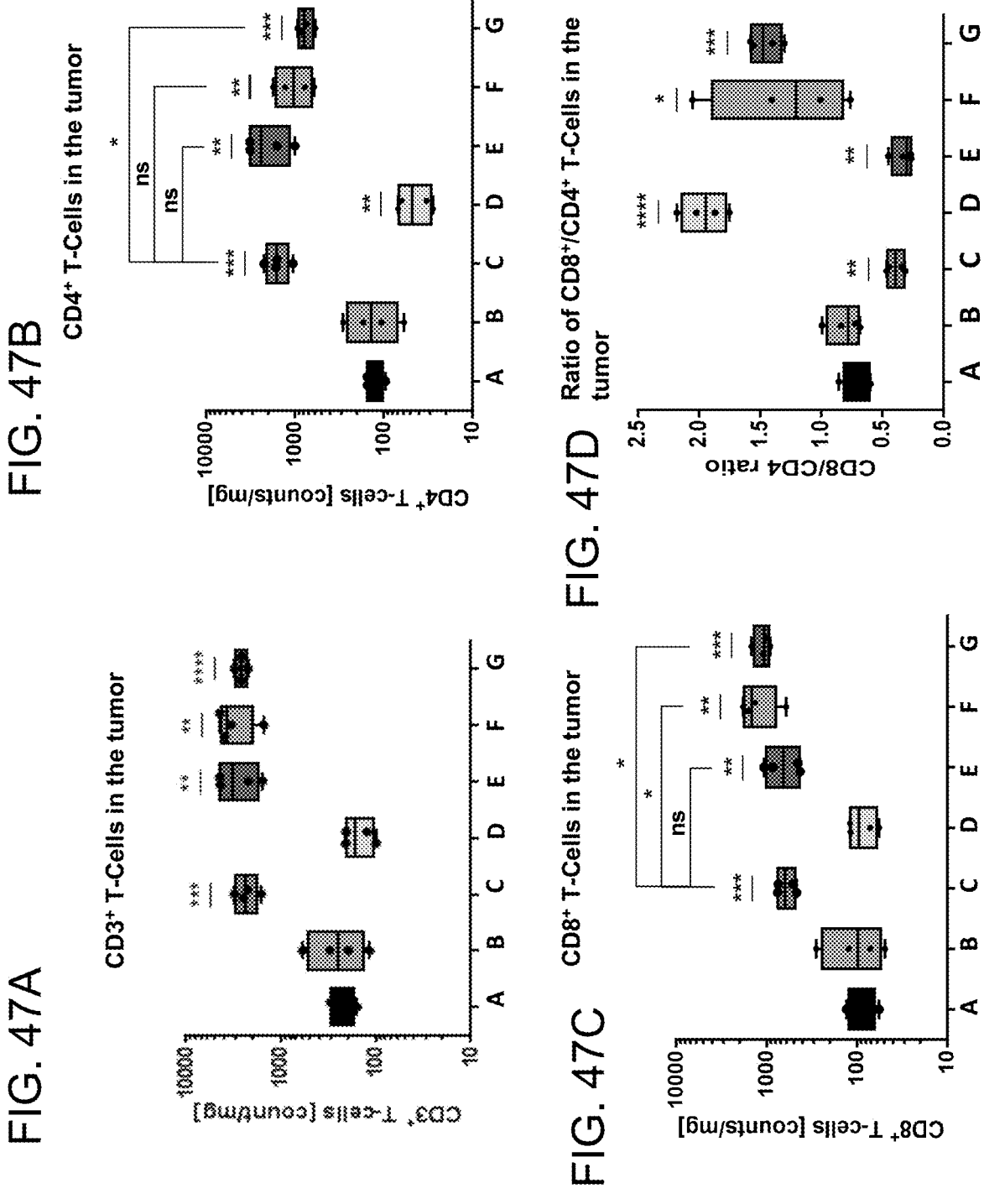

FIGS. 47A to 47D show that treatment with FolR1 CD3 TCB alone or combinations of FolR1 CD3 TCB with monovalent FAP(28H1)-4-1BBL led to increased infiltration of CD3$^+$ T-cells (FIG. 47A), CD8$^+$ T cells (FIG. 47C) and CD4$^+$ T-cells (FIG. 47B) in the tumor compared to treatment with 4-1BBL alone, however the ratio of CD8$^+$/CD4$^+$ T-cells is much higher in the combination groups compared to the group receiving FolR1 CD3 TCB alone (FIG. 47D).

Figures 48A, 48B, 48C:
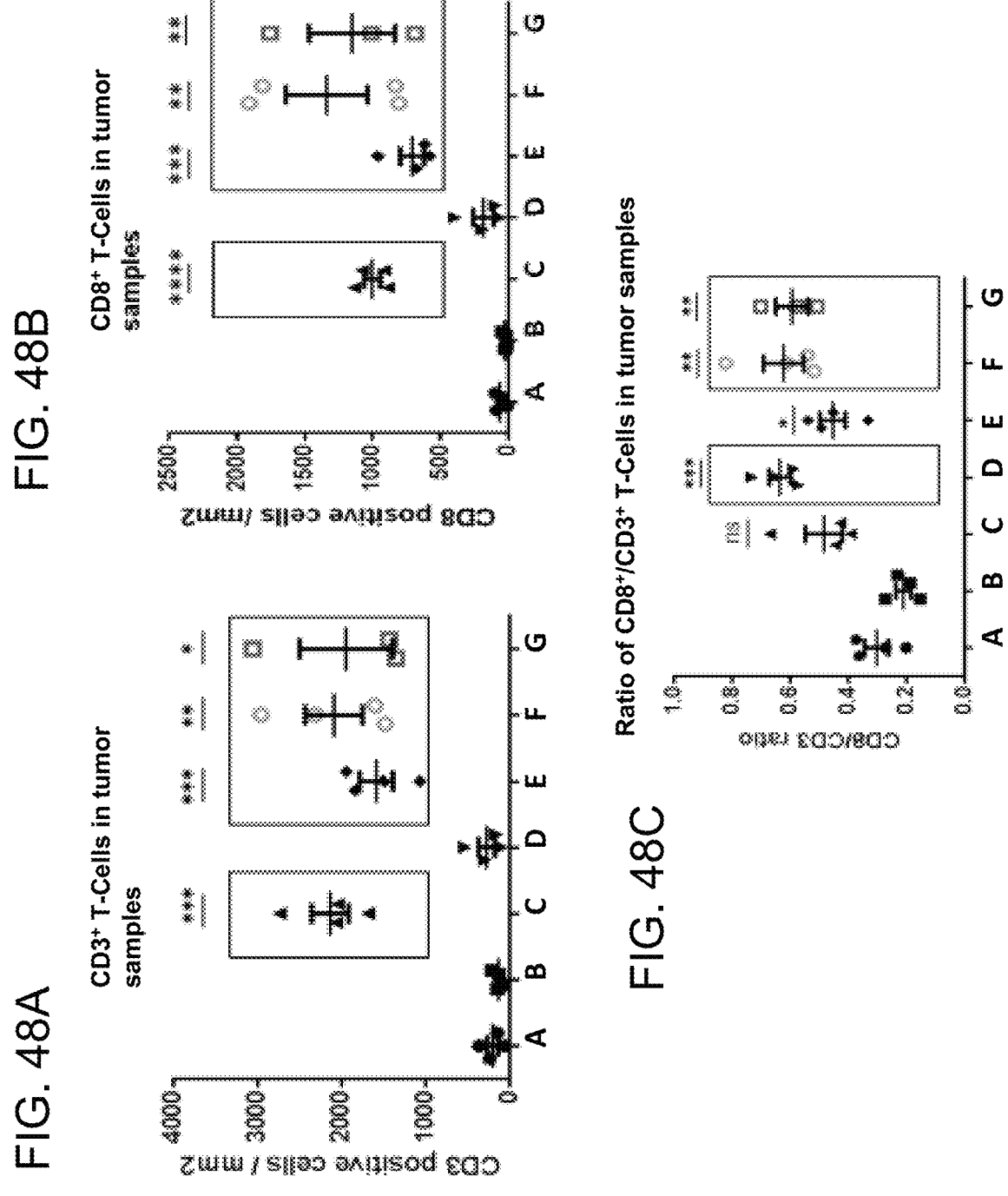

FIGS. 48A to 48C relate to the histological analysis at the end of the study, in particular to the quantification of CD3+(FIG. 48A) and CD8$^+$ T cells (FIG. 48B) in subcutaneous SKOV3 ovarian tumors collected at day 44, 1 day after last administration.

Immunohistochemistry staining of CD3 and CD8 T cells was performed on human SKOV3 ovarian subcutaneous tumors derived from the indicated treatment groups in PBMC transfer NOG mice. Tissue samples were prepared for immunohistochemical staining: subcutaneous tumors were harvested from animals at day 44, fixed in formalin 10% (Sigma, Germany) and later processed for FFPET (Leica 1020, Germany). 4 μm paraffin sections were subsequently cut in a microtome (Leica RM2235, Germany). HuCD8 and HuCD3 immunohistochemistry was performed with anti-human CD8 (Cell Marque Corporation, California) and anti-human CD3 (ThermoFischer Scientific, USA) in the Leica autostainer (Leica ST5010, Germany) following the manufacturer's protocols. Quantification of huCD3 and huCD8 positive T cells was performed with Definiens software (Definiens, Germany). Statistics were analyzed by t-test. There is a significant increase of positive CD3 and CD8 T cell number in the FolR1-TCB treated groups. The treatment of mono FAP-4-1BBL changes the ratio of CD8 to CD3.

FIG. 49 shows that the groups treated with combinations of FolR1 CD3 TCB with monovalent or bivalent FAP (28H1)-4-1BBL showed improved efficacy in terms of tumor growth inhibition compared to groups treated with the single agents.

Figure 50:

FIG. 50 shows the pharmacokinetic profile of injected compounds during the first week. 2 mice per Group were bled 10 min, 1 h, 8h, 24 h and 7d after the first therapy and injected compounds were analysed by ELISA. 4-1BBL was detected via 4-1BB binding. All groups injected with compounds show comparable exposure of the molecules between the different groups.

Figures 51A, 51B:
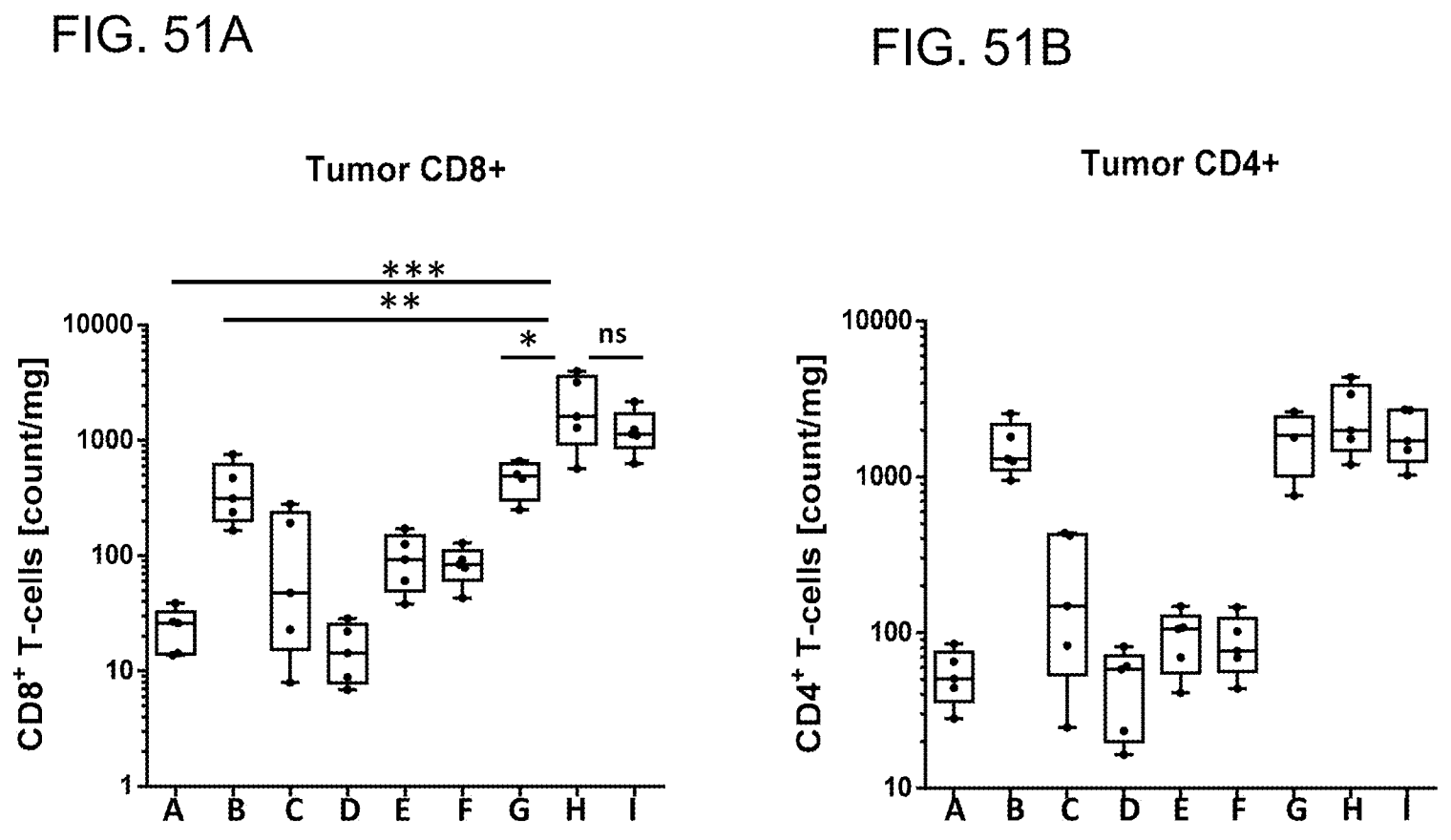
Figure 51C:
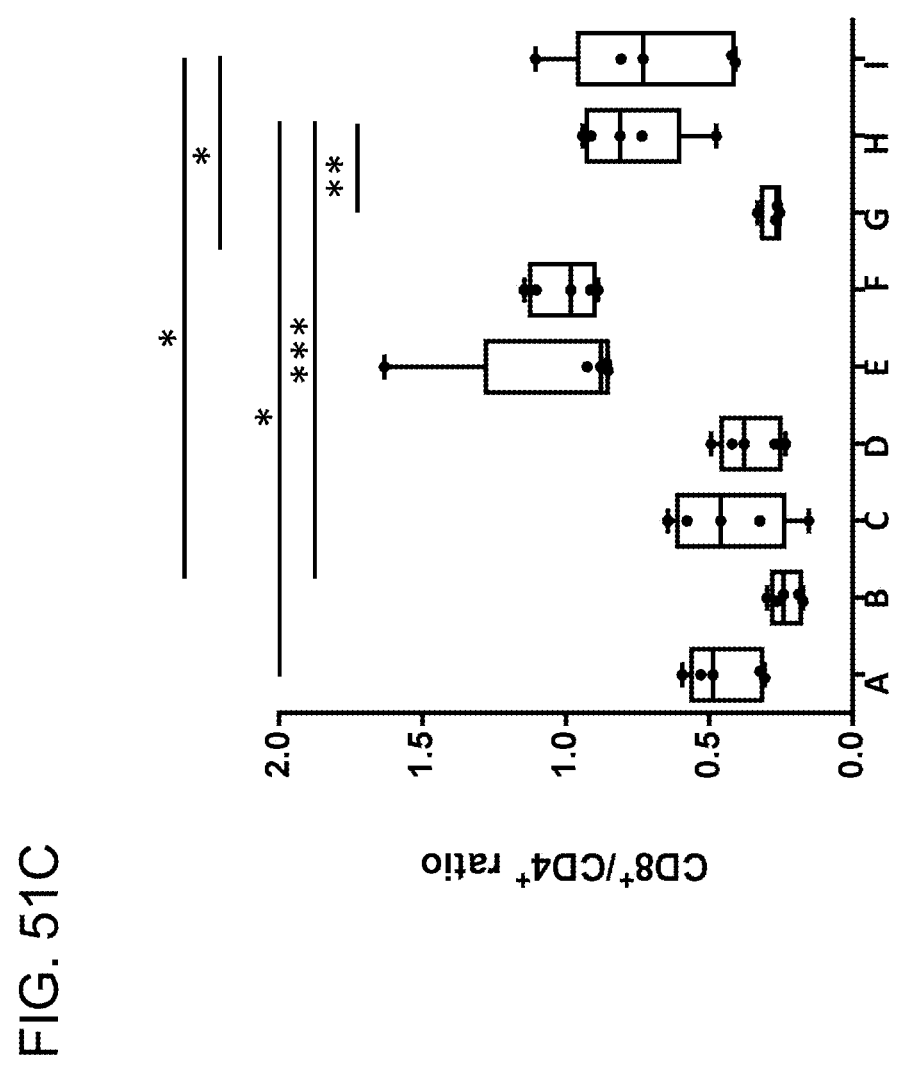

FIGS. 51A and 51B show that treatment with combinations of FolR1 CD3 TCB with monovalent or bivalent FAP(4B9)-4-1BBL led to increased infiltration of CD8 and CD4 positive T-cells in the tumor and blood compared to treatment with the single agents. FIG. 51C shows that the ratio of CD8$^+$/CD4$^+$ T-cells is much higher in the combination groups compared to the group receiving FolR1 CD3 TCB alone.

Figure 52:
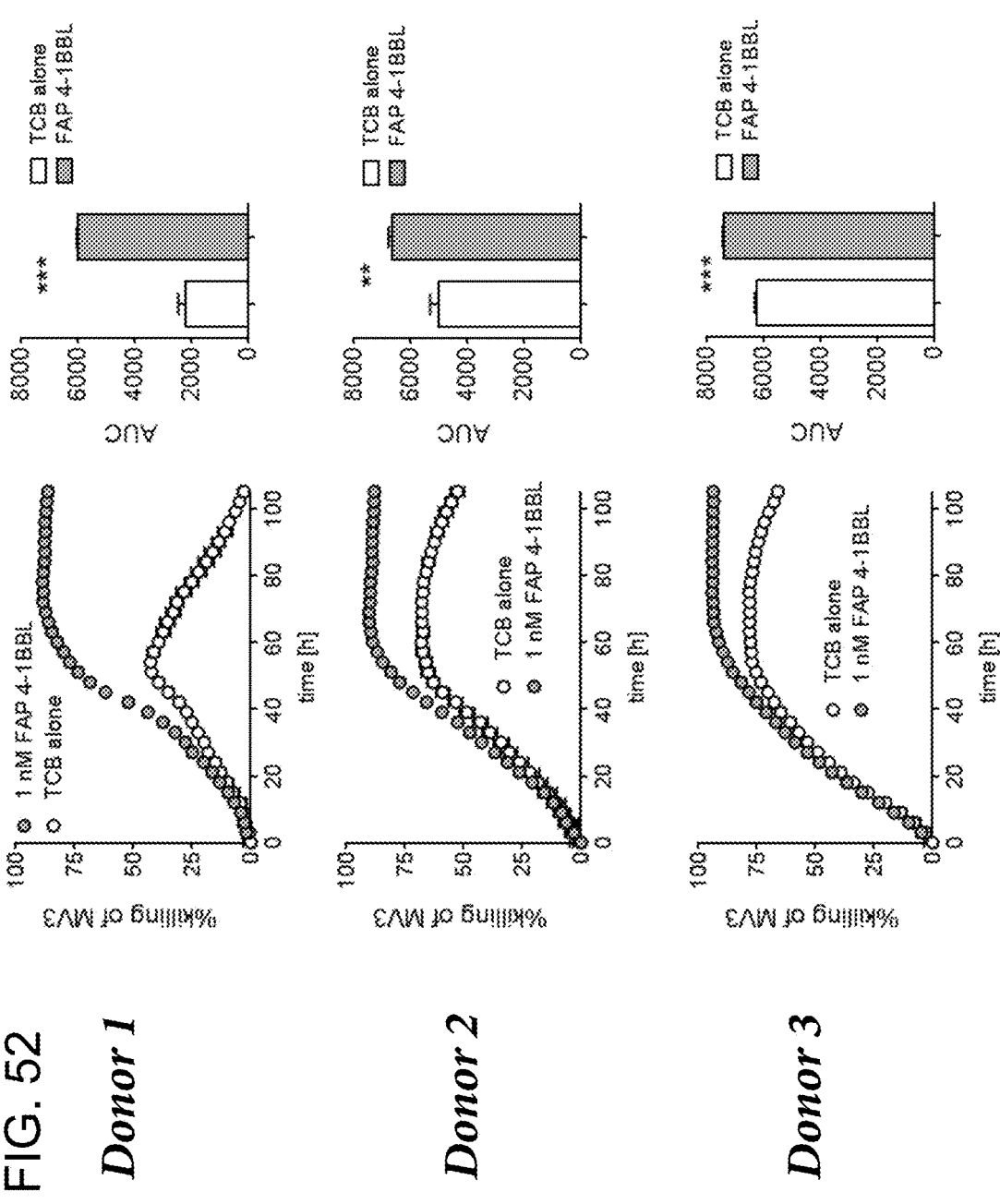
Figure 53:
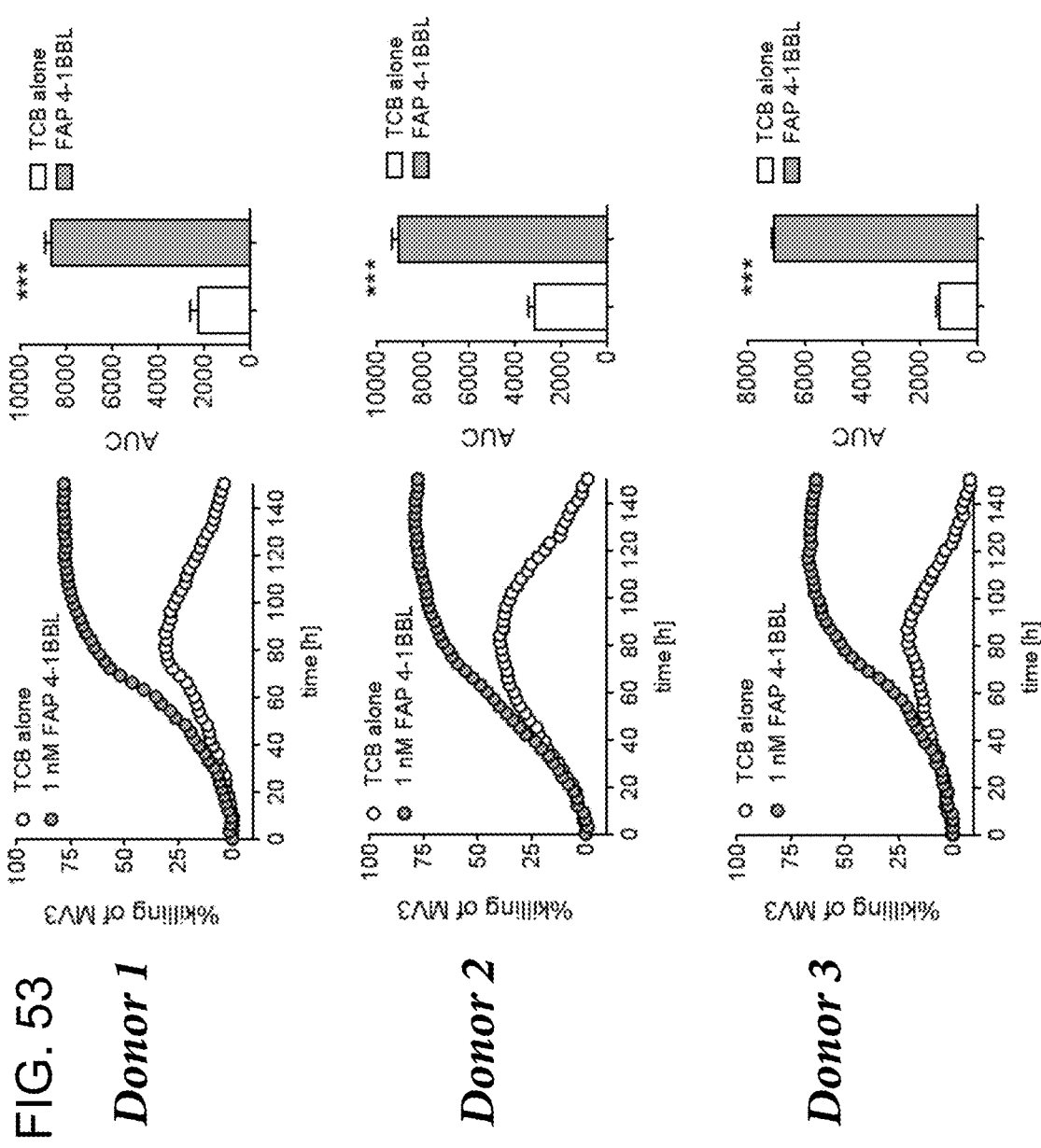

FIG. 52 shows a comparison of MCSP CD3 TCB-mediated killing of MV3 melanoma cells without or in the presence of FAP-4-1BBL with CD8$^+$ T cells of 3 donors (see Example 16). For all three donors a significantly increased tumor target cell killing was observed. FIG. 53 shows the comparison of TCB-mediated killing of MV3 melanoma cells without or in the presence of FAP-4-1BBL with pan T cells of 3 donors. Significantly increased tumor target cell killing was observed for all 3 donors.

DETAILED DESCRIPTION OF THE INVENTION

Definitions

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgAQ1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869, 046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an F(ab')$_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy (V$_H$) and light chains (V$_L$) of an antibody, connected with a short linker peptide of ten to about 25 amino acids. The linker is usually rich in glycine for flexibility, as well as serine or threonine for solubility, and can either connect the N-terminus of the VH with the C-terminus of the V$_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, a VH), V$_{NAR}$ fragments, a fibronectin (AdNectin), a C-type lectin domain (Tetranectin); a variable domain of a new antigen receptor beta-lactamase (V$_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin).

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633.

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment consisting of a single monomeric variable antibody domain. The first single domains were derived from the variable domain of the antibody heavy chain from camelids (nanobodies or VHH fragments). Furthermore, the term single-domain antibody includes an autonomous human heavy chain variable domain (a VH) or V$_{NAR}$ fragments derived from sharks.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM).

The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

The term "tumor-associated antigen" means any antigen that is highly expressed by tumor cells or in the tumor stroma. Particular tumor-associated antigens are CEA or FAP, but also other targets such as Folate Receptor.

The term "Fibroblast activation protein (FAP)", also known as Prolyl endopeptidase FAP or Seprase (EC 3.4.21), refers to any native FAP from any vertebrate source, including mammals such as primates (e.g. humans) non-human primates (e.g. cynomolgus monkeys) and rodents (e.g. mice and rats), unless otherwise indicated. The term encompasses "full-length," unprocessed FAP as well as any form of FAP which results from processing in the cell. The term also encompasses naturally occurring variants of FAP, e.g., splice variants or allelic variants. In one embodiment, the antigen binding molecule of the invention is capable of specific binding to human, mouse and/or cynomolgus FAP. The amino acid sequence of human FAP is shown in UniProt (www.uniprot.org) accession no. Q12884 (version 149, SEQ ID NO:80), or NCBI (www.ncbi.nlm.nih.gov/) RefSeq NP_004451.2. The extracellular domain (ECD) of human FAP extends from amino acid position 26 to 760. The amino acid sequence of a His-tagged human FAP ECD is shown in SEQ ID NO: 81. The amino acid sequence of mouse FAP is shown in UniProt accession no. P97321 (version 126, SEQ ID NO:82), or NCBI RefSeq NP_032012.1. The extracellular domain (ECD) of mouse FAP extends from amino acid position 26 to 761. SEQ ID NO: 83 shows the amino acid sequence of a His-tagged mouse FAP ECD. SEQ ID NO: 84 shows the amino acid sequence of a His-tagged cynomolgus FAP ECD. Preferably, an anti-FAP binding molecule of the invention binds to the extracellular domain of FAP. Exemplary anti-FAP binding molecules are described in International Patent Application No. WO 2012/020006 A2.

The term "Carcinoembroynic antigen (CEA)", also known as Carcinoembryonic antigen-related cell adhesion molecule 5 (CEACAM5), refers to any native CEA from any vertebrate source, including mammals such as primates (e.g. humans) non-human primates (e.g. cynomolgus monkeys) and rodents (e.g. mice and rats), unless otherwise indicated. The amino acid sequence of human CEA is shown in UniProt accession no. P06731 (version 151, SEQ ID NO:85). CEA has long been identified as a tumor-associated antigen (Gold and Freedman, J Exp Med., 121:439-462, 1965; Berinstein N. L., J Clin Oncol., 20:2197-2207, 2002). Originally classified as a protein expressed only in fetal tissue, CEA has now been identified in several normal adult tissues. These tissues are primarily epithelial in origin, including cells of the gastrointestinal, respiratory, and urogential tracts, and cells of colon, cervix, sweat glands, and prostate (Nap et al., Tumour Biol., 9(2-3):145-53, 1988; Nap et al., Cancer Res., 52(8):2329-23339, 1992). Tumors of epithelial origin, as well as their metastases, contain CEA as a tumor associated antigen. While the presence of CEA itself does not indicate transformation to a cancerous cell, the distribution of CEA is indicative. In normal tissue, CEA is generally expressed on the apical surface of the cell (Hammarström S., Semin Cancer Biol. 9(2):67-81 (1999)), making it inaccessible to antibody in the blood stream. In contrast to normal tissue, CEA tends to be expressed over the entire surface of cancerous cells (Hammarström S., Semin Cancer Biol. 9(2):67-81 (1999)). This change of expression pattern makes CEA accessible to antibody binding in cancerous cells. In addition, CEA expression increases in cancerous cells. Furthermore, increased CEA expression promotes increased intercellular adhesions, which may lead to metastasis (Marshall J., Semin Oncol., 30 (a Suppl. 8):30-6, 2003). The prevalence of CEA expression in various tumor entities is generally very high. In concordance with published data, own analyses performed in tissue samples confirmed its high prevalence, with approximately 95% in colorectal carcinoma (CRC), 90% in pancreatic cancer, 80% in gastric cancer, 60% in non-small cell lung cancer (NSCLC, where it is co-expressed with HER3), and 40% in breast cancer; low expression was found in small cell lung cancer and glioblastoma.

CEA is readily cleaved from the cell surface and shed into the blood stream from tumors, either directly or via the lymphatics. Because of this property, the level of serum CEA has been used as a clinical marker for diagnosis of cancers and screening for recurrence of cancers, particularly colorectal cancer (Goldenberg D M., The International Journal of Biological Markers, 7:183-188, 1992; Chau I., et al., J Clin Oncol., 22:1420-1429, 2004; Flamini et al., Clin Cancer Res; 12(23):6985-6988, 2006).

The term "FolR1" refers to Folate receptor alpha and has been identified as a potential prognostic and therapeutic target in a number of cancers. It refers to any native FolR1 from any vertebrate source, including mammals such as primates (e.g. humans) non-human primates (e.g. cynomolgus monkeys) and rodents (e.g. mice and rats), unless otherwise indicated. The amino acid sequence of human FolR1 is shown in UniProt accession no. P15328, murine FolR1 has the amino acid sequence of UniProt accession no. P35846 and cynomolgus FolR1 has the amino acid sequence as shown in UniProt accession no. G7PR14. FolR1 is an N-glycosylated protein expressed on plasma membrane of cells. FolR1 has a high affinity for folic acid and for several reduced folic acid derivatives and mediates delivery of the physiological folate, 5-methyltetrahydrofolate, to the interior of cells. FOLR1 is a desirable target for FOLR1-directed cancer therapy as it is overexpressed in vast majority of ovarian cancers, as well as in many uterine, endometrial, pancreatic, renal, lung, and breast cancers, while the expression of FOLR1 on normal tissues is restricted to the apical membrane of epithelial cells in the kidney proximal tubules, alveolar pneumocytes of the lung, bladder, testes, choroid plexus, and thyroid. Recent studies have identified that FolR1 expression is particularly high in triple negative breast cancers (Necela et al. PloS One 2015, 10(3). e0127133).

The term "MCSP" refers to Melanoma-associated Chondroitin Sulfate Proteoglycan, also known as Chondroitin Sulfate Proteoglycan 4 (CSPG4). It refers to any native FolR1 from any vertebrate source, including mammals such as primates (e.g. humans) non-human primates (e.g. cynomolgus monkeys) and rodents (e.g. mice and rats), unless otherwise indicated. The amino acid sequence of human MCSP is shown in UniProt accession no. Q6UVK1). MCSP is a highly glycosylated integral membrane chondroitin sulfate proteoglycan consisting of an N-linked 280 kDa glycoprotein component and a 450-kDa chondroitin sulfate proteoglycan component expressed on the cell membrane (Ross et al., *Arch. Biochem. Biophys.* 1983, 225:370-38). MCSP is more broadly distributed in a number of normal and transformed cells. In particular, MCSP is found in almost all basal cells of the epidermis. MCSP is differentially expressed in melanoma cells, and was found to be expressed in more than 90% of benign nevi and melanoma lesions analyzed. MCSP has also been found to be expressed in tumors of nonmelanocytic origin, including basal cell carcinoma, various tumors of neural crest origin, and in breast carcinomas.

A "T-cell antigen" as used herein refers to an antigenic determinant presented on the surface of a T lymphocyte, particularly a cytotoxic T lymphocyte.

A "T cell activating therapeutic agent" as used herein refers to a therapeutic agent capable of inducing T cell activation in a subject, particularly a therapeutic agent designed for inducing T-cell activation in a subject. Examples of T cell activating therapeutic agents include bispecific antibodies that specifically bind an activating T cell antigen, such as CD3, and a target cell antigen, such as CEA or Folate Receptor.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

The term "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD38). The amino acid sequence of human CD3E is shown in UniProt (www.uniprot.org) accession no. P07766 (version 144), or NCBI (www.ncbi.nlm-.nih.gov/) RefSeq NP_000724.1. See also SEQ ID NO: 106. The amino acid sequence of cynomolgus [*Macaca fascicularis*] CD3ε is shown in NCBI GenBank no. BAB71849.1. See also SEQ ID NO: 107.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences*

*of Proteins of Immunological Interest,* 5th Ed. Public Health Service, National Institutes of Health, Bethesda, MD (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table B as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
| --- | --- | --- | --- |
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fe receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote het-erodimerization of two non-identical antibody heavy chains as herein described. In one embodiment, a human IgG heavy chain Fc region extends from Cys226, or from Pro230, to the carboxyl-terminus of the heavy chain. However, the C-ter-minal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a pro-tuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific muta-genesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modifi-cation additionally comprises the amino acid substitution S354C, and the subunit of the Fc domain comprising the hole modification additionally comprises the amino acid substitution Y349C. Introduction of these two cysteine resi-dues results in the formation of a disulfide bridge between the two subunits of the Fc region, thus further stabilizing the dimer (Carter, J Immunol Methods 248, 7-15 (2001)).

A "region equivalent to the Fc region of an immunoglobu-lin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effec-tor functions include: C1q binding and complement depen-dent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that follow-ing engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

An "ectodomain" is the domain of a membrane protein that extends into the extracellular space (i.e. the space outside the target cell). Ectodomains are usually the parts of proteins that initiate contact with surfaces, which leads to signal transduction. The ectodomain of 4-1BBL as defined herein thus refers to the part of the 4-1BBL that extends into the extracellular space (the extracellular domain), but also includes shorter parts or fragments thereof that are respon-sible for the trimerization and for the binding to the corre-sponding receptor 4-1BB. The term "ectodomain of 4-1BBL or a fragment thereof" thus refers to the extracellular domain of 4-1BBL that forms the extracellular domain or to parts thereof that are still able to bind to the receptor (receptor binding domain).

"4-1BBL" or "4-1BB ligand" or "CD137L" is a costimu-latory TNF ligand family member, which is able to costimu-late proliferation and cytokine production of T-cells. Costimulatory TNF family ligands can costimulate TCR signals upon interaction with their corresponding TNF receptors and the interaction with their receptors leads to recruitment of TNFR-associated factors (TRAF), which initiate signalling cascades that result in T-cell activation. 4-1BBL is a type II transmembrane protein. Complete or full length 4-1BBL having the amino acid sequence of SEQ ID NO:86 has been described to form trimers on the surface of cells. The formation of trimers is enabled by specific motives of the ectodomain of 4-1BBL. Said motives are designated herein as "trimerization region". The amino acids 50-254 of the human 4-1BBL sequence (SEQ ID NO:87) form the extracellular domain of 4-1BBL, but even frag-ments thereof are able to form the trimers. In specific embodiments of the invention, the term "ectodomain of 4-1BBL or a fragment thereof" refers to a polypeptide having an amino acid sequence selected from SEQ ID NO:4 (amino acids 52-254 of human 4-1BBL), SEQ ID NO:1 (amino acids 71-254 of human 4-1BBL), SEQ ID NO:3 (amino acids 80-254 of human 4-1BBL), SEQ ID NO:2 (amino acids 85-254 of human 4-1BBL), SEQ ID NO:5 (amino acids 71-248 of human 4-1BBL), SEQ ID NO:6

(amino acids 85-248 of human 4-1BBL), SEQ ID NO:7 (amino acids 80-248 of human 4-1BBL) and SEQ ID NO:8 (amino acids 52-248 of human 4-1BBL), but also other fragments of the ectodomain capable of trimerization are included herein.

The term "4-1BB" or "CD137", as used herein, refers to any native 4-1BB from any vertebrate source, including mammals such as primates (e.g. humans) and rodents (e.g., mice and rats), unless otherwise indicated. The term encompasses "full-length," unprocessed 4-1BB as well as any form of 4-1BB that results from processing in the cell. The term also encompasses naturally occurring variants of 4-1BB, e.g., splice variants or allelic variants. The amino acid sequence of an exemplary human 4-1BB is shown in SEQ ID NO: 88 (Uniprot accession no. Q07011), the amino acid sequence of an exemplary murine 4-1BB is shown in SEQ ID NO: 89 (Uniprot accession no. P20334) and the amino acid sequence of an exemplary cynomolgous 4-1BB (from *Macaca* mulatta) is shown in SEQ ID NO:90 (Uniprot accession no. F6W5G6).

The terms "anti-4-1BB antibody", "anti-4-1BB", "4-1BB antibody and "an antibody that specifically binds to 4-1BB" refer to an antibody that is capable of binding 4-1BB with sufficient affinity such that the antibody is useful as a diagnostic and/or therapeutic agent in targeting 4-1BB. In one embodiment, the extent of binding of an anti-4-1BB antibody to an unrelated, non-4-1BB protein is less than about 10% of the binding of the antibody to 4-1BB as measured, e.g., by a radioimmunoassay (RIA) or flow cytometry (FACS). In certain embodiments, an antibody that binds to 4-1BB has a dissociation constant ($K_D$) of ≤1 μM, ≤100 nM, ≤10 nM, ≤1 nM, ≤0.1 nM, ≤0.01 nM, or ≤0.001 nM (e.g. $10^{-6}$ M or less, e.g. from $10^{-68}$ M to $10^{-13}$ M, e.g., from $10^{-8}$ M to $10^{-10}$ M).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$ (SEQ ID NO: 160), $(SG_4)_n$ (SEQ ID NO: 161) or $G_4(SG_4)$, peptide linkers (SEQ ID NO: 162), wherein "n" is generally a number between 1 and 10, typically between 2 and 4, in particular, i.e. the peptides selected from the group consisting of GGGGS (SEQ ID NO: 91) GGGGSGGGGS (SEQ ID NO:92), SGGGGSGGGG (SEQ ID NO:93) and GGGGSGGGGSGGGG (SEQ ID NO:94), but also include the sequences GSPGSSSSGS (SEQ ID NO:95), $(G4S)_3$ (SEQ ID NO:96), $(G4S)_4$ (SEQ ID NO:97), GSGSGSGS (SEQ ID NO:98), GSGSGNGS (SEQ ID NO:99), GGSGSGSG (SEQ ID NO:100), GGSGSG (SEQ ID NO:101), GGSG (SEQ ID NO:102), GGSGNGSG (SEQ ID NO:103), GGNGSGSG (SEQ ID NO:104) and GGNGSG (SEQ ID NO:105). Peptide linkers of particular interest are (G4S) (SEQ ID NO:91), $(G_4S)_2$ (SEQ ID NO: 92) and GGGGSGGGGS (SEQ ID NO:92).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a polypeptide and an ectodomain of 4-1BBL) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the antigen binding molecules provided herein are contemplated. For example, it may be desirable to improve the binding affinity and/or other biological properties of the antigen binding molecules. Amino acid sequence variants of the antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table C under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more CDR residues are mutated and the variant antigen binding molecules displayed on phage and screened for a particular biological activity (e.g. binding affinity). In certain embodiments, substitutions, insertions, or deletions may occur within one or more CDRs so long as such alterations do not substantially reduce the ability of the antigen binding molecule to bind antigen. For example, conservative alterations (e.g., conservative substitutions as provided herein) that do not substantially reduce binding affinity may be made in CDRs. A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antigen binding molecules with an N-terminal methionyl residue. Other insertional variants of the molecule include the fusion to the N- or C-terminus to a polypeptide which increases the serum half-life of the antigen binding molecules.

In certain embodiments, the antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the antigen binding molecule comprises an Fe region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antigen binding molecules may be made in order to create variants with certain improved properties. In one aspect, variants of antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the antigen binding molecules of the invention include those with bisected oligosaccharides, e.g., in which a biantennary oligosaccharide attached to the Fc region is bisected by GlcNAc. Such variants may have reduced fucosylation and/or improved ADCC function., see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the antigen binding molecules of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the 4-1BBL-containing antigen binding molecules provided herein maybe obtained. An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

The combination therapies in accordance with the invention have a synergistic effect. A "synergistic effect" of two compounds is one in which the effect of the combination of the two agents is greater than the sum of their individual effects and is statistically different from the controls and the single drugs. In another embodiment, the combination therapies disclosed herein have an additive effect. An "additive effect" of two compounds is one in which the effect of the combination of the two agents is the sum of their individual effects and is statistically different from either the controls and/or the single drugs.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as solid tumors, or melanoma.

"CD20" refers to B-lymphocyte antigen CD20, also known as B-lymphocyte surface antigen B1 or Leukocyte surface antigen Leu-16, and includes any native CD20 from any vertebrate source, including mammals such as primates (e.g. humans) non-human primates (e.g. cynomolgus monkeys) and rodents (e.g. mice and rats), unless otherwise indicated. The amino acid sequence of human CD20 is shown in Uniprot accession no. P11836 (version 149, SEQ ID NO:159). CD20 is a hydrophobic transmembrane protein with a molecular weight of approximately 35 kD expressed on pre-B and mature B lymphocytes. The corresponding human gene is membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein. The term "CD20" encompasses "full-length," unprocessed CD20 as well as any form of CD20 that results from processing in the cell. The term also encompasses naturally occurring variants of CD20, e.g., splice variants or allelic variants.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

By "Type II anti-CD20 antibody" is meant an anti-CD20 antibody having binding properties and biological activities of Type II anti-CD20 antibodies as described in Cragg et al., Blood 103 (2004) 2738-2743; Cragg et al., Blood 101

(2003) 1045-1052, Klein et al., mAbs 5 (2013), 22-33. A type II anti-CD20 antibody binds to class II epitope on CD20, it does not localize CD20 to lipid rafts, shows ADCC activity, but low CDC if it is a IgG1 isotype antibody, has less binding capacity to B cells compared with antibodies binding to the Class I CD20 epitope, shows homotypic aggregation and strong death induction. Examples of type II anti-CD20 antibodies include e.g. obinutuzumab (GA101), tositumumab (B1), humanized B-Ly1 antibody IgG1 (a chimeric humanized IgG1 antibody as disclosed in WO 2005/044859), 11B8 IgG1 (as disclosed in WO 2004/035607) and AT80 IgG1. In a particular aspect, the Type II anti-CD20 antibody is obinutuzumab (recommended INN, WHO Drug Information, Vol. 26, No. 4, 2012, p. 453). As used herein, obinutuzumab is synonymous for GA101. The tradename is GAZYVA® or GAZYVARO®. This replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In one aspect, the Type II anti-CD20 antibody is tositumomab.

Exemplary Anti-CEA/Anti-CD3 Bispecific Antibodies for Use in the Invention

The present invention relates to anti-CEA/anti-CD3 bispecific antibodies and their use in combination with 4-1BB (CD137) agonists, in particular to their use in a method for treating or delaying progression of cancer, more particularly for treating or delaying progression of solid tumors. The anti-CEA/anti-CD3 bispecific antibodies as used herein are bispecific antibodies comprising a first antigen binding domain that binds to CD3, and a second antigen binding domain that binds to CEA.

Thus, the anti-CEA/anti-CD3 bispecific antibody as used herein comprises a first antigen binding domain comprising a heavy chain variable region ($V_H$CD3) and a light chain variable region ($V_L$CD3), and a second antigen binding domain comprising a heavy chain variable region ($V_H$CEA) and a light chain variable region ($V_L$CEA).

In a particular aspect, the anti-CEA/anti-CD3 bispecific antibody for use in the combination comprises a first antigen binding domain comprising a heavy chain variable region ($V_H$CD3) comprising CDR-H1 sequence of SEQ ID NO:33, CDR-H2 sequence of SEQ ID NO:34, and CDR-H3 sequence of SEQ ID NO:35; and/or a light chain variable region ($V_L$CD3) comprising CDR-L1 sequence of SEQ ID NO:36, CDR-L2 sequence of SEQ ID NO:37, and CDR-L3 sequence of SEQ ID NO:38. More particularly, the anti-CEA/anti-CD3 bispecific antibody comprises a first antigen binding domain comprising a heavy chain variable region ($V_H$CD3) that is at least 90%, 95%, 96%, 97%, 98%, or 99% identical to the amino acid sequence of SEQ ID NO:39 and/or a light chain variable region ($V_L$CD3) that is at least 90%, 95%, 96%, 97%, 98%, or 99% identical to the amino acid sequence of SEQ ID NO:40. In a further aspect, the anti-CEA/anti-CD3 bispecific antibody comprises a heavy chain variable region ($V_H$CD3) comprising the amino acid sequence of SEQ ID NO:39 and/or a light chain variable region ($V_L$CD3) comprising the amino acid sequence of SEQ ID NO:40.

In one aspect, the antibody that specifically binds to CD3 is a full-length antibody. In one aspect, the antibody that specifically binds to CD3 is an antibody of the human IgG class, particularly an antibody of the human IgG₁ class. In one aspect, the antibody that specifically binds to CD3 is an antibody fragment, particularly a Fab molecule or a scFv molecule, more particularly a Fab molecule. In a particular aspect, the antibody that specifically binds to CD3 is a crossover Fab molecule wherein the variable domains or the constant domains of the Fab heavy and light chain are exchanged (i.e. replaced by each other). In one aspect, the antibody that specifically binds to CD3 is a humanized antibody.

In another aspect, the anti-CEA/anti-CD3 bispecific antibody comprises a second antigen binding domain comprising (a) a heavy chain variable region ($V_H$CEA) comprising CDR-H1 sequence of SEQ ID NO:41, CDR-H2 sequence of SEQ ID NO:42, and CDR-H3 sequence of SEQ ID NO:43, and/or a light chain variable region ($V_L$CEA) comprising CDR-L1 sequence of SEQ ID NO:44, CDR-L2 sequence of SEQ ID NO:45, and CDR-L3 sequence of SEQ ID NO:46, or (b) a heavy chain variable region ($V_H$CEA) comprising CDR-H1 sequence of SEQ ID NO:49, CDR-H2 sequence of SEQ ID NO:50, and CDR-H3 sequence of SEQ ID NO:51, and/or a light chain variable region ($V_L$CEA) comprising CDR-L1 sequence of SEQ ID NO:52, CDR-L2 sequence of SEQ ID NO:53, and CDR-L3 sequence of SEQ ID NO:54.

More particularly, the anti-CEA/anti-CD3 bispecific comprises a second antigen binding domain comprising a heavy chain variable region ($V_H$CEA) that is at least 90%, 95%, 96%, 97%, 98%, or 99% identical to the amino acid sequence of SEQ ID NO:47 and/or a light chain variable region ($V_L$CEA) that is at least 90%, 95%, 96%, 97%, 98%, or 99% identical to the amino acid sequence of SEQ ID NO:48. In a further aspect, the anti-CEA/anti-CD3 bispecific comprises a second antigen binding domain comprising a heavy chain variable region ($V_H$CEA) comprising the amino acid sequence of SEQ ID NO:47 and/or a light chain variable region ($V_L$CEA) comprising the amino acid sequence of SEQ ID NO:48. In another aspect, the anti-CEA/anti-CD3 bispecific comprises a second antigen binding domain comprising a heavy chain variable region ($V_H$CEA) that is at least 90%, 95%, 96%, 97%, 98%, or 99% identical to the amino acid sequence of SEQ ID NO:55 and/or a light chain variable region ($V_L$CEA) that is at least 90%, 95%, 96%, 97%, 98%, or 99% identical to the amino acid sequence of SEQ ID NO:56. In a further aspect, the anti-CEA/anti-CD3 bispecific comprises a second antigen binding domain comprising a heavy chain variable region ($V_H$CEA) comprising the amino acid sequence of SEQ ID NO:55 and/or a light chain variable region ($V_L$CEA) comprising the amino acid sequence of SEQ ID NO:56.

In another particular aspect, the anti-CEA/anti-CD3 bispecific antibody comprises a third antigen binding domain that binds to CEA. In particular, the anti-CEA/anti-CD3 bispecific antibody comprises a third antigen binding domain comprising (a) a heavy chain variable region ($V_H$CEA) comprising CDR-H1 sequence of SEQ ID NO:41, CDR-H2 sequence of SEQ ID NO:42, and CDR-H3 sequence of SEQ ID NO:43, and/or a light chain variable region ($V_L$CEA) comprising CDR-L1 sequence of SEQ ID NO:44, CDR-L2 sequence of SEQ ID NO:45, and CDR-L3 sequence of SEQ ID NO:46, or (b) a heavy chain variable region ($V_H$CEA) comprising CDR-H1 sequence of SEQ ID NO:49, CDR-H2 sequence of SEQ ID NO:50, and CDR-H3 sequence of SEQ ID NO:51, and/or a light chain variable region ($V_L$CEA) comprising CDR-L1 sequence of SEQ ID NO:52, CDR-L2 sequence of SEQ ID NO:53, and CDR-L3 sequence of SEQ ID NO:54.

More particularly, the anti-CEA/anti-CD3 bispecific comprises a third antigen binding domain comprising a heavy chain variable region ($V_H$CEA) that is at least 90%, 95%, 96%, 97%, 98%, or 99% identical to the amino acid sequence of SEQ ID NO:47 and/or a light chain variable region ($V_L$CEA) that is at least 90%, 95%, 96%, 97%, 98%, or 99% identical to the amino acid sequence of SEQ ID NO:48. In a further aspect, the anti-CEA/anti-CD3 bispecific comprises a third antigen binding domain comprising a heavy chain variable region ($V_H$CEA) comprising the amino acid sequence of SEQ ID NO:47 and/or a light chain variable region ($V_L$CEA) comprising the amino acid sequence of SEQ ID NO:48. In another particular aspect, the anti-CEA/anti-CD3 bispecific comprises a third antigen binding domain comprising a heavy chain variable region ($V_H$CEA) that is at least 90%, 95%, 96%, 97%, 98%, or 99% identical to the amino acid sequence of SEQ ID NO:55 and/or a light chain variable region ($V_L$CEA) that is at least 90%, 95%, 96%, 97%, 98%, or 99% identical to the amino acid sequence of SEQ ID NO:56. In a further aspect, the anti-CEA/anti-CD3 bispecific comprises a third antigen binding domain comprising a heavy chain variable region ($V_H$CEA) comprising the amino acid sequence of SEQ ID NO:55 and/or a light chain variable region ($V_L$CEA) comprising the amino acid sequence of SEQ ID NO:56.

In a further aspect, the anti-CEA/anti-CD3 bispecific antibody is bispecific antibody, wherein the first antigen binding domain is a cross-Fab molecule wherein the variable domains or the constant domains of the Fab heavy and light chain are exchanged, and the second and third, if present, antigen binding domain is a conventional Fab molecule.

In another aspect, the anti-CEA/anti-CD3 bispecific antibody is bispecific antibody, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

The Fab molecules may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$ (SEQ ID NO: 160), $(SG_4)_n$ (SEQ ID NO: 161), $(G_4S)_n$ (SEQ ID NO: 160) or $G_4(SG_4)_n$ peptide linkers (SEQ ID NO: 162). "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=0, 1, 2 or 3) (SEQ ID NOS 163 and 165, respectively, in order of appearance) or (x=4, n=2, 3, 4 or 5 and m=0, 1, 2 or 3) (SEQ ID NOS 164 and 166, respectively, in order of appearance), in one embodiment x=4 and n=2 or 3, in a further embodiment x=4 and n=2. In one embodiment said peptide linker is $(G_4S)_2$ (SEQ ID NO: 92). A particularly suitable peptide linker for fusing the Fab light chains of the first and the second Fab molecule to each other is $(G_4S)_2$ (SEQ ID NO: 92). An exemplary peptide linker suitable for connecting the Fab heavy chains of the first and the second Fab fragments comprises the sequence (D)-$(G_4S)_2$ (SEQ ID NO: 167). Another suitable such linker comprises the sequence $(G_4S)_4$ (SEQ ID NO: 97). Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

In a further aspect, the anti-CEA/anti-CD3 bispecific antibody comprises an Fc domain comprising one or more amino acid substitutions that reduce binding to an Fc receptor and/or effector function. In particular, the anti-CEA/anti-CD3 bispecific antibody comprises an IgG1 Fc domain comprising the amino acid substitutions L234A, L235A and P329G.

In a particular aspect, the anti-CEA/anti-CD3 bispecific antibody comprises a polypeptide that is at least 95%, 96%, 97%, 98%, or 99% identical to the sequence of SEQ ID NO: 61, a polypeptide that is at least 95%, 96%, 97%, 98%, or 99% identical to the sequence of SEQ ID NO: 62, a polypeptide that is at least 95%, 96%, 97%, 98%, or 99% identical to the sequence of SEQ ID NO: 63, and a polypeptide that is at least 95%, 96%, 97%, 98%, or 99% identical to the sequence of SEQ ID NO: 64. In a further particular embodiment, the bispecific antibody comprises a polypeptide sequence of SEQ ID NO: 61, a polypeptide sequence of SEQ ID NO: 62, a polypeptide sequence of SEQ ID NO: 63 and a polypeptide sequence of SEQ ID NO: 64 (CEA CD3 TCB).

In a further particular aspect, the anti-CEA/anti-CD3 bispecific antibody comprises a polypeptide that is at least 95%, 96%, 97%, 98%, or 99% identical to the sequence of SEQ ID NO:57, a polypeptide that is at least 95%, 96%, 97%, 98%, or 99% identical to the sequence of SEQ ID NO:58, a polypeptide that is at least 95%, 96%, 97%, 98%, or 99% identical to the sequence of SEQ ID NO:59, and a polypeptide that is at least 95%, 96%, 97%, 98%, or 99% identical to the sequence of SEQ ID NO:60. In a further particular embodiment, the bispecific antibody comprises a polypeptide sequence of SEQ ID NO:57, a polypeptide sequence of SEQ ID NO:58, a polypeptide sequence of SEQ ID NO:59 and a polypeptide sequence of SEQ ID NO:60 (CEACAM5 CD3 TCB).

Particular bispecific antibodies are described in PCT publication no. WO 2014/131712 A1.

In a further aspect, the anti-CEA/anti-CD3 bispecific antibody may also comprise a bispecific T cell engager (BiTE®). In a further aspect, the anti-CEA/anti-CD3 bispecific antibody is a bispecific antibody as described in WO 2007/071426 or WO 2014/131712. In another aspect, the bispecific antibody is MED1565.

Exemplary Anti-FolR1/Anti-CD3 Bispecific Antibodies for Use in the Invention

The present invention also relates to anti-FolR1/anti-CD3 bispecific antibodies and their use in combination with 4-1BB (CD137) agonists, in particular to their use in a method for treating or delaying progression of cancer, more particularly for treating or delaying progression of solid tumors. The anti-FolR1/anti-CD3 bispecific antibodies as used herein are bispecific antibodies comprising a first antigen binding domain that binds to CD3, and a second antigen binding domain that binds to FolR1. In a particular, the anti-FolR1/anti-CD3 bispecific antibodies as used herein comprise a third antigen binding domain that binds to FolR1.

In one aspect, the T-cell activating anti-CD3 bispecific antibody comprises a first antigen binding domain comprising a heavy chain variable region ($V_H$CD3), a second antigen binding domain comprising a heavy chain variable region ($V_H$FolR1), a third antigen binding domain comprising a heavy chain variable region ($V_H$FolR1) and three times a common light chain variable region.

In another aspect, the first antigen binding domain comprises a heavy chain variable region ($V_H$CD3) comprising CDR-H1 sequence of SEQ ID NO:121, CDR-H2 sequence of SEQ ID NO:122, and CDR-H3 sequence of SEQ ID NO:123; the second antigen binding domain comprises a heavy chain variable region ($V_H$FolR1) comprising CDR-H1 sequence of SEQ ID NO:124, CDR-H2 sequence of SEQ ID NO:125, and CDR-H3 sequence of SEQ ID NO:126; the third antigen binding domain comprises a heavy chain variable region ($V_H$FolR1) comprising CDR-H1 sequence of SEQ ID NO:124, CDR-H2 sequence of SEQ ID NO:125, and CDR-H3 sequence of SEQ ID NO:126; and the common light chains comprise a CDR-L1 sequence of SEQ ID NO:127, CDR-L2 sequence of SEQ ID NO:128, and CDR-L3 sequence of SEQ ID NO:129. In another aspect, the first antigen binding domain comprises a heavy chain variable region ($V_H$CD3) comprising the sequence of SEQ ID NO:130; the second antigen binding domain comprises a heavy chain variable region ($V_H$FolR1) comprising the sequence of SEQ ID NO:131; the third antigen binding domain comprises a heavy chain variable region ($V_H$FolR1) comprising the sequence of SEQ ID NO:131; and the common light chains comprise the sequence of SEQ ID NO:132.

In a particular aspect, the anti-FolR1/anti-CD3 bispecific antibody comprises a first heavy chain comprising the amino acid sequence of SEQ ID NO:133, a second heavy chain comprising the amino acid sequence of SEQ ID NO:134 and three times a common light chain of SEQ ID NO: 135.

Exemplary Anti-MCSP/Anti-CD3 Bispecific Antibodies for Use in the Invention

The present invention further relates to anti-MCSP/anti-CD3 bispecific antibodies and their use in combination with 4-1BB (CD137) agonists, in particular to their use in a method for treating or delaying progression of cancer, more particularly for treating or delaying progression of solid tumors. The anti-MCSP/anti-CD3 bispecific antibodies as used herein are bispecific antibodies comprising a first antigen binding domain that binds to CD3, and a second antigen binding domain that binds to MCSP. In a particular, the anti-MCSP/anti-CD3 bispecific antibodies as used herein comprise a third antigen binding domain that binds to MCSP.

In one aspect, the T-cell activating anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$MCSP) and a light chain variable region ($V_L$MCSP). a first antigen binding domain comprising a heavy chain variable region ($V_H$CD3), a second antigen binding domain comprising a heavy chain variable region ($V_H$FolR1), a third antigen binding domain comprising a heavy chain variable region ($V_H$FolR1) and three times a common light chain variable region.

In a particular aspect, the anti-MCSP/anti-CD3 bispecific antibody for use in the combination comprises a first antigen binding domain comprising a heavy chain variable region ($V_H$CD3) comprising CDR-H1 sequence of SEQ ID NO:33, CDR-H2 sequence of SEQ ID NO:34, and CDR-H3 sequence of SEQ ID NO:35; and/or a light chain variable region ($V_L$CD3) comprising CDR-L1 sequence of SEQ ID NO:36, CDR-L2 sequence of SEQ ID NO:37, and CDR-L3 sequence of SEQ ID NO:38. More particularly, the anti-MCSP/anti-CD3 bispecific antibody comprises a first antigen binding domain comprising a heavy chain variable region ($V_H$CD3) that is at least 90%, 95%, 96%, 97%, 98%, or 99% identical to the amino acid sequence of SEQ ID NO:39 and/or a light chain variable region ($V_L$CD3) that is at least 90%, 95%, 96%, 97%, 98%, or 99% identical to the amino acid sequence of SEQ ID NO:40. In a further aspect, the anti-MCSP/anti-CD3 bispecific antibody comprises a heavy chain variable region ($V_H$CD3) comprising the amino acid sequence of SEQ ID NO:39 and/or a light chain variable region ($V_L$CD3) comprising the amino acid sequence of SEQ ID NO:40.

In another aspect, the anti-MCSP/anti-CD3 bispecific antibody comprises a second antigen binding domain comprising a heavy chain variable region ($V_H$MCSP) comprising CDR-H1 sequence of SEQ ID NO:151, CDR-H2 sequence of SEQ ID NO:152, and CDR-H3 sequence of FDY, and/or a light chain variable region ($V_L$MCSP) comprising CDR-L1 sequence of SEQ ID NO:154, CDR-L2 sequence of SEQ ID NO:155, and CDR-L3 sequence of SEQ ID NO:156.

More particularly, the anti-MCSP/anti-CD3 bispecific comprises a second antigen binding domain comprising a heavy chain variable region ($V_H$MCSP) that is at least 90%, 95%, 96%, 97%, 98%, or 99% identical to the amino acid sequence of SEQ ID NO:157 and/or a light chain variable region ($V_L$MCSP) that is at least 90%, 95%, 96%, 97%, 98%, or 99% identical to the amino acid sequence of SEQ ID NO:158. In a further aspect, the anti-MCSP/anti-CD3 bispecific comprises a second antigen binding domain comprising a heavy chain variable region ($V_H$MCSP) comprising the amino acid sequence of SEQ ID NO:157 and/or a light chain variable region ($V_L$MCSP) comprising the amino acid sequence of SEQ ID NO:158.

In another particular aspect, the anti-MCSP/anti-CD3 bispecific antibody comprises a third antigen binding domain that binds to MCSP. In particular, the anti-MCSP/anti-CD3 bispecific antibody comprises a third antigen binding domain comprising (a) a heavy chain variable region ($V_H$MCSP) comprising CDR-H1 sequence of SEQ ID NO:151, CDR-H2 sequence of SEQ ID NO:152, and CDR-H3 sequence of FDY, and/or a light chain variable region ($V_L$MCSP) comprising CDR-L1 sequence of SEQ ID NO:154, CDR-L2 sequence of SEQ ID NO:155, and CDR-L3 sequence of SEQ ID NO:156.

In a further aspect, the anti-MCSP/anti-CD3 bispecific comprises a third antigen binding domain comprising a heavy chain variable region ($V_H$MCSP) comprising the amino acid sequence of SEQ ID NO:157 and/or a light chain variable region ($V_L$MCSP) comprising the amino acid sequence of SEQ ID NO:158.

In a further aspect, the anti-MCSP/anti-CD3 bispecific antibody comprises an Fc domain comprising one or more amino acid substitutions that reduce binding to an Fc receptor and/or effector function. In particular, the anti-MCSP/anti-CD3 bispecific antibody comprises an IgG1 Fc domain comprising the amino acid substitutions L234A, L235A and P329G.

In a particular aspect, the anti-MCSP/anti-CD3 bispecific antibody comprises a polypeptide that is at least 95%, 96%, 97%, 98%, or 99% identical to the sequence of SEQ ID NO: 147, a polypeptide that is at least 95%, 96%, 97%, 98%, or 99% identical to the sequence of SEQ ID NO: 148, a polypeptide that is at least 95%, 96%, 97%, 98%, or 99% identical to the sequence of SEQ ID NO: 149, and a polypeptide that is at least 95%, 96%, 97%, 98%, or 99% identical to the sequence of SEQ ID NO: 150. In a further particular embodiment, the bispecific antibody comprises a polypeptide sequence of SEQ ID NO: 147, a polypeptide sequence of SEQ ID NO: 148, a polypeptide sequence of SEQ ID NO: 149 and a polypeptide sequence of SEQ ID NO: 150 (MCSP CD3 TCB).

Particular anti-MCSP/anti-CD3 bispecific antibodies are described in PCT publication no. WO 2014/131712 A1.

Exemplary 4-1BB Agonists for Use in the Invention

In particular, the 4-1BB agonists as used in combination with the anti-CEA/anti-CD3 bispecific antibody are molecules comprising 4-1BBL. In particular, the 4-1BB agonist used in the invention comprises three ectodomains of 4-1BBL or fragments thereof.

In a particular aspect, the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

It has been shown herein, that the 4-1BB agonist is especially useful if it comprises an antigen binding domain that is specific for a tumor-associated antigen, in particular for a target on cancer cells or in the stroma. Thus, in a particular aspect, the 4-1BB agonist is an antigen binding molecule comprising three ectodomains of 4-1BBL or fragments thereof and at least one antigen binding domain capable of specific binding to FAP or CEA.

In a further aspect, the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises (a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a particular aspect, the antigen binding domain capable of specific binding to FAP comprises a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a further aspect, the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24. More particularly, the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

In another aspect, the 4-1BB agonist is an antigen binding molecule further comprising a Fc domain composed of a first and a second subunit capable of stable association. In one aspect, the 4-1BB agonist is an antigen binding molecule comprising an IgG Fc domain, specifically an IgG1 Fc domain or an IgG4 Fc domain. Particularly, the 4-1BB agonist is an antigen binding molecule comprising a Fc domain that comprises one or more amino acid substitution that reduces binding to an Fc receptor and/or effector function. In a particular aspect, the 4-1BB agonist is an antigen binding molecule comprising an IgG1 Fc domain comprising the amino acid substitutions L234A, L235A and P329G.

In one aspect, the 4-1BB agonist is an antigen binding molecule comprising (a) at least one antigen binding domain capable of specific binding to FAP, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

In a particular aspect, the 4-1BB agonist is an antigen binding molecule comprising (a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In another aspect, the 4-1BB agonist is an antigen binding molecule comprising (a) at least one Fab domain capable of specific binding to FAP comprising a heavy chain variable region $(V_H FAP)$ comprising the amino acid sequence of SEQ ID NO:21 and a light chain variable region $(V_L FAP)$ comprising the amino acid sequence of SEQ ID NO:22 or a heavy chain variable region $(V_H FAP)$ comprising the amino acid sequence of SEQ ID NO:23 and a light chain variable region $(V_L FAP)$ comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a particular aspect, the 4-1BB agonist is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72.

Particularly, the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68.

In another aspect, the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

In one aspect, the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

Particular bispecific antibodies are described in PCT publication No. WO 2016/075278 A1 or in PCT publication No. WO 2016/156291A1.

In a further aspect, the 4-1BB agonist is an anti-FAP/anti-4-1BB bispecific antibody.

In another aspect, the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region $(V_H CEA)$ comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region $(V_L CEA)$ comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

In a further aspect, the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region $(V_H CEA)$ comprising an amino acid sequence of SEQ ID NO:55 and a light chain variable region $(V_L CEA)$ comprising an amino acid sequence of SEQ ID NO:56.

In another aspect, the 4-1BB agonist is an antigen binding molecule further comprising a Fc domain composed of a first and a second subunit capable of stable association. In one aspect, the 4-1BB agonist is an antigen binding molecule comprising an IgG Fc domain, specifically an IgG1 Fc domain or an IgG4 Fc domain. Particularly, the 4-1BB agonist is an antigen binding molecule comprising a Fc domain that comprises one or more amino acid substitution that reduces binding to an Fc receptor and/or effector function. In a particular aspect, the 4-1BB agonist is an antigen binding molecule comprising an IgG1 Fc domain comprising the amino acid substitutions L234A, L235A and P329G.

In one aspect, the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

In a particular aspect, the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In another aspect, the 4-1BB agonist is an antigen binding molecule comprising (a) at least one Fab domain capable of specific binding to CEA comprising a heavy chain variable region ($V_H$CEA) comprising the amino acid sequence of SEQ ID NO:55 and a light chain variable region ($V_L$CEA) comprising the amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a particular aspect, the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

In another aspect, the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers.

In one aspect, the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In another aspect, the 4-1BB agonist comprises an anti-CEA/anti-4-1BB bispecific antibody.

Agents blocking PD-L1/PD-1 interaction for use in the invention

In one aspect of the invention, the T-cell activating anti-CD3 bispecific antibodies specific for a tumor-associated antigen, in particular the anti-CEA/anti-CD3 antibodies are for use in a method for treating or delaying progression of cancer, wherein the T-cell activating anti-CD3 bispecific antibodies specific for a tumor-associated antigen are used in combination with a 4-1BB (CD137) agonist and additionally they are combined with an agent blocking PD-L1/PD-1 interaction. In another aspect, the agent blocking PD-L1/PD-1 interaction is only combined with a targeted 4-1BB agonist. In all these aspects, an agent blocking PD-L1/PD-1 interaction is a PD-L1 binding antagonist or a PD-1 binding antagonist. In particular, the agent blocking PD-L1/PD-1 interaction is an anti-PD-L1 antibody or an anti-PD-1 antibody.

The term "PD-L1", also known as CD274 or B7-H1, refers to any native PD-L1 from any vertebrate source, including mammals such as primates (e.g. humans) non-human primates (e.g. cynomolgus monkeys) and rodents (e.g. mice and rats), in particular to "human PD-L1". The amino acid sequence of complete human PD-L1 is shown in UniProt (www.uniprot.org) accession no. Q9NZQ7 (SEQ ID NO:110). The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In particular, a PD-L1 binding antagonist is an anti-PD-L1 antibody. The term "anti-PD-L1 antibody" or "antibody binding to human PD-L1" or "antibody that specifically binds to human PD-L1" or "antagonistic anti-PD-L1" refers to an antibody specifically binding to the human PD-L1 antigen with a binding affinity of KD-value of $1.0 \times 10^{-8}$ mol/1 or lower, in one aspect of a KD-value of $1.0 \times 10^{-9}$ mol/1 or lower. The binding affinity is determined with a standard binding assay, such as surface plasmon resonance technique (BIAcore®, GE-Healthcare Uppsala, Sweden).

In a particular aspect, the agent blocking PD-L1/PD-1 interaction is an anti-PD-L1 antibody. In a specific aspect, the anti-PD-L1 antibody is selected from the group consisting of atezolizumab (MPDL3280A, RG7446), durvalumab (MEDI4736), avelumab (MSB0010718C) and MDX-1105. In a specific aspect, an anti-PD-L1 antibody is YW243.55.570 described herein. In another specific aspect, an anti-PD-L1 antibody is MDX-1105 described herein. In still another specific aspect, an anti-PD-L1 antibody is MEDI4736 (durvalumab). In yet a further aspect, an anti-PD-L1 antibody is MSB0010718C (avelumab). More particularly, the agent blocking PD-L1/PD-1 interaction is atezolizumab (MPDL3280A). In another aspect, the agent blocking PD-L1/PD-1 interaction is an anti-PD-L1 antibody comprising a heavy chain variable domain VH(PDL-1) of SEQ ID NO: 112 and a light chain variable domain VL(PDL-1) of SEQ ID NO: 113. In another aspect, the agent blocking PD-L1/PD-1 interaction is an anti-PD-L1 antibody comprising a heavy chain variable domain VH(PDL-1) of SEQ ID NO: 114 and a light chain variable domain VL(PDL-1) of SEQ ID NO:115.

The term "PD-1", also known as CD279, PD1 or programmed cell death protein 1, refers to any native PD-L1 from any vertebrate source, including mammals such as primates (e.g. humans) non-human primates (e.g. cynomolgus monkeys) and rodents (e.g. mice and rats), in particular to the human protein PD-1 with the amino acid sequence as shown in UniProt (www.uniprot.org) accession no. Q15116 (SEQ ID NO:111). The term "PD-1 binding antagonist" refers to a molecule that inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In particular, a PD-L1 binding antagonist is an anti-PD-L1 antibody. The term "anti-PD-1 antibody" or "antibody binding to human PD-1" or "antibody that specifically binds to human PD-1" or "antagonistic anti-PD-1" refers to an antibody specifically binding to the human PD1 antigen with a binding affinity of KD-value of $1.0 \times 10^{-8}$ mol/1 or lower, in one aspect of a KD-value of $1.0 \times 10^{-9}$ mol/1 or lower. The binding affinity is determined with a standard binding assay, such as surface plasmon resonance technique (BIAcore®, GE-Healthcare Uppsala, Sweden).

In one aspect, the agent blocking PD-L1/PD-1 interaction is an anti-PD-1 antibody. In a specific aspect, the anti-PD-1 antibody is selected from the group consisting of MDX 1106 (nivolumab), MK-3475 (pembrolizumab), CT-011 (pidilizumab), MEDI-0680 (AMP-514), PDR001, REGN2810, and BGB-108, in particular from pembrolizumab and nivolumab. In another aspect, the agent blocking PD-L1/PD-1 interaction is an anti-PD-1 antibody comprising a heavy chain variable domain VH(PD-1) of SEQ ID NO:116 and a light chain variable domain VL(PD-1) of SEQ ID NO:117. In another aspect, the agent blocking PD-L1/PD-1 interaction is an anti-PD-1 antibody comprising a heavy chain variable domain VH(PD-1) of SEQ ID NO:118 and a light chain variable domain VL(PD-1) of SEQ ID NO:119.

Exemplary 4-1BB agonists for use in combination with agents blocking PD-L1/PD-1 interaction The present invention also relates to 4-1BB agonists comprising at least one antigen binding domain capable of specific binding to a tumor-associated antigen for use in a method for treating or delaying progression of cancer, wherein the 4-1BB agonist comprising at least one antigen binding domain capable of specific binding to a tumor-associated antigen is used in combination with an agent blocking PD-L1/PD-1 interaction. In one aspect, the 4-1BB agonist is for use in a method for treating or delaying progression of cancer, wherein the agent blocking PD-L1/PD-1 interaction is an anti-PD-L1 antibody or an anti-PD1 antibody, in particular the agent blocking PD-L1/PD-1 interaction is selected from the group consisting of atezolizumab, durvalumab, pembrolizumab and nivolumab. More particularly, the agent blocking PD-L1/PD-1 interaction is atezolizumab.

The 4-1BB agonist comprising at least one antigen binding domain capable of specific binding to a tumor-associated antigen for use in in combination with an agent blocking PD-L1/PD-1 interaction is particularly one, wherein the tumor-associated antigen is selected from Fibroblast activation protein (FAP) or CEA. More particularly, the 4-1BB agonist comprising at least one antigen binding domain capable of specific binding to a tumor-associated antigen is an antigen binding molecule comprising three ectodomains of 4-1BBL or fragments thereof and at least one antigen binding domain capable of specific binding to Fibroblast activation protein (FAP).

In one aspect, the 4-1BB agonist comprising at least one antigen binding domain capable of specific binding to a tumor-associated antigen for use in a method for treating or delaying progression of cancer in combination with an agent blocking PD-L1/PD-1 interaction is an antigen binding molecule comprising three ectodomains of 4-1BBL or fragments thereof and at least one antigen binding domain capable of specific binding to FAP, wherein the antigen binding domain capable of specific binding to FAP comprises (a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region ($V_L$FAP) comprising (iv)

CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

In a particular aspect, the 4-1BB agonist comprising at least one antigen binding domain capable of specific binding to a tumor-associated antigen for use in a method for treating or delaying progression of cancer in combination with an agent blocking PD-L1/PD-1 interaction is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

In another aspect, the 4-1BB agonist comprising at least one antigen binding domain capable of specific binding to a tumor-associated antigen for use in the method is an antigen binding molecule comprising an IgG Fc domain, specifically an IgG1 Fc domain or an IgG4 Fc domain. In a further aspect, the 4-1BB agonist comprising at least one antigen binding domain capable of specific binding to a tumor-associated antigen for use in the method is an antigen binding molecule comprising a Fc domain that comprises one or more amino acid substitution that reduces binding to an Fc receptor and/or effector function.

In a further aspect, the 4-1BB agonist comprising at least one antigen binding domain capable of specific binding to a tumor-associated antigen a method for treating or delaying progression of cancer in combination with an agent blocking PD-L1/PD-1 interaction is an antigen binding molecule comprising (a) at least one antigen binding domain capable of specific binding to FAP, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

In another aspect, the 4-1BB agonist comprising at least one antigen binding domain capable of specific binding to a tumor-associated antigen for use in a method for treating or delaying progression of cancer in combination with an agent blocking PD-L1/PD-1 interaction is an antigen binding molecule comprising (a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

In a particular aspect, the 4-1BB agonist comprising at least one antigen binding domain capable of specific binding to a tumor-associated antigen for use in the method an antigen binding molecule comprising (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

In a specific aspect, the 4-1BB agonist comprising at least one antigen binding domain capable of specific binding to a tumor-associated antigen for use in the method is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72.

In another aspect, the 4-1BB agonist comprising at least one antigen binding domain capable of specific binding to a tumor-associated antigen for use in a method as described herein before is an antigen binding molecule comprising (a) at least one antigen binding domain capable of specific binding to FAP, (b) a polypeptide comprising three ectodomains of 4-1BBL or fragments thereof that are connected to each other by peptide linkers.

In a further aspect, the 4-1BB agonist comprising at least one antigen binding domain capable of specific binding to a tumor-associated antigen for use in the method is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In yet another aspect, the 4-1BB agonist comprising at least one antigen binding domain capable of specific binding to a tumor-associated antigen for use in in a method for treating or delaying progression of cancer in combination with an agent blocking PD-L1/PD-1 interaction is an anti-FAP/anti-4-1BB bispecific antibody.

In a further aspect, the 4-1BB agonist comprising at least one antigen binding domain capable of specific binding to a tumor-associated antigen for use in the method is an antigen binding molecule comprising three ectodomains of 4-1BBL or fragments thereof and at least one antigen binding domain capable of specific binding to CEA.

In particular the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises (a) a heavy chain variable region ($V_H$CEA) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region ($V_L$CEA) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54. More particularly, the 4-1BB agonist comprising at least one antigen binding domain capable of specific binding to a tumor-associated antigen for use in the method is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:55 and a light chain variable region ($V_L$CEA) comprising an amino acid sequence of SEQ ID NO:56. In one aspect, the 4-1BB agonist is an antigen binding molecule comprising an IgG Fc domain, specifically an IgG1 Fc domain or an IgG4 Fc domain. In one aspect, the 4-1BB agonist is an antigen binding molecule comprising a Fc domain that comprises one or more amino acid substitution that reduces binding to an Fc receptor and/or effector function.

In a further aspect, the 4-1BB agonist comprising at least one antigen binding domain capable of specific binding to a tumor-associated antigen for use in the method described herein before is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

In a particular aspect, the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CHT domain and the second polypeptide contains a VL-CHT domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

More particularly, the 4-1BB agonist for use in the method is an antigen binding molecule comprising (a) at least one Fab domain capable of specific binding to CEA comprising a heavy chain variable region ($V_H$-CEA) comprising the amino acid sequence of SEQ ID NO:55 and a light chain variable region ($V_L$CEA) comprising the amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8. In a specific aspect, the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

In another aspect, the 4-1BB agonist comprising at least one antigen binding domain capable of specific binding to a tumor-associated antigen for use in the method is an antigen binding molecule comprising (a) at least one antigen binding domain capable of specific binding to CEA, and (b) a polypeptide comprising three ectodomains of 4-1BBL or fragments thereof that are connected to each other by peptide linkers. In a further aspect, the 4-1BB agonist for use in the method is an antigen binding molecule comprising (a) at least one antigen binding domain capable of specific binding to CEA, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

In yet another aspect, the 4-1BB agonist comprising at least one antigen binding domain capable of specific binding to a tumor-associated antigen for use in the method is an anti-CEA/anti-4-1BB bispecific antibody.

Preparation of bispecific antibodies for use in the invention

In certain aspects, the therapeutic agents used in the combination comprise multispecific antibodies, e.g. bispecific antibodies. Multispecific antibodies are monoclonal antibodies that have binding specificities for at least two different sites. In certain aspects, the binding specificities are for different antigens. In certain aspects, the binding specificities are for different epitopes on the same antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking of two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J.

Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibodies or fragments herein also include a "Dual Acting FAb" or "DAF" comprising an antigen binding site that binds to two different antigens (see, US 2008/0069820, for example). "Crossmab" antibodies are also included herein (see e.g. WO 2009/080251, WO 2009/080252, WO2009/080253, or WO2009/080254).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain (VH) and a variable light chain (VL) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species. In one aspect, the bispecific bispecific antibodies used in the invention are composed of a single polypeptide chain comprising two single chain FV fragments (scFV) fused to each other by a peptide linker.

Fc Domain Modifications Reducing Fc Receptor Binding and/or Effector Function

The Fc domain of the antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells.

Accordingly, in particular aspects, the Fc domain of the antigen binding molecules of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In a particular aspect, the invention provides an antibody, wherein the Fc domain comprises one or more amino acid substitution that reduces binding to an Fc receptor, in particular towards Fcγ receptor.

In one aspect, the Fc domain of the antibody of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antibody according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or cell activating antibodies comprising an Fc domain for Fc receptors may be evaluated using cell lines known to express particular Fc receptors, such as human NK cells expressing FcγIIIa receptor.

Effector function of an Fc domain, or antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some aspects, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Fc Domain Modifications Promoting Heterodimerization

The bispecific antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antigen binding molecules of the invention a modification promoting the association of the desired polypeptides.

Accordingly, in particular aspects the invention relates to the bispecific antigen binding molecule comprising (a) at least one antigen binding domain capable of specific binding to a tumor-associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of said 4-1BBL or a fragment thereof, and (c) a Fc domain composed of a first and a second subunit capable of stable association, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to an antigen binding molecule comprising (a) at least one antigen binding domain capable of specific binding to a tumor-associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and (c) a Fc domain composed of a first and a second subunit capable of stable association, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a 4-1BBL-containing antigen binding molecule, comprising (a) a Fab fragment capable of specific binding to a tumor-associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and (c) a Fc domain composed of a first and a second subunit capable of stable association, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific antigen binding molecule comprising (a) a first Fab fragment capable of specific binding to a tumor associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and wherein each of them is linked to a CH1 or CL domain, and (c) a Fc domain composed of a first and a second subunit capable of stable association, wherein the constant domains CL and CH1 adjacent to 4-1BBL are replaced by each other so that the CH1 domain is part of the light chain and the CL domain is part of the heavy chain.

In another aspect, the invention relates to a bispecific antigen binding molecule, comprising (a) two light chains and two heavy chains of an antibody comprising two Fab fragments capable of specific binding to 4-1BB and the Fc domain, and (b) two additional Fab fragments capable of specific binding to a tumor associated antigen, wherein said additional Fab fragments are each connected via a peptide linker to the C-terminus of the heavy chains of (a). In a particular aspect, the additional Fab fragments are Fab fragments, wherein the variable domains VL and VH are replaced by each other so that the VH domain is part of the light chain and the VL domain is part of the heavy chain.

In another aspect, and to further improve correct pairing, the bispecific antigen binding molecule comprising (a) a first Fab fragment capable of specific binding to a tumor associated antigen, (b) a first and a second polypeptide that are linked to each other by a disulfide bond, wherein the antigen binding molecule is characterized in that the first polypeptide comprises two ectodomains of 4-1BBL or two fragments thereof that are connected to each other by a peptide linker and in that the second polypeptide comprises only one ectodomain of 4-1BBL or a fragment thereof, and wherein each of them is linked to a CH1 or CL domain, and (c) a Fc domain composed of a first and a second subunit capable of stable association, can contain different charged amino acid substitutions (so-called "charged residues"). These modifications are introduced in the crossed or non-crossed CH1 and CL domains. In a particular aspect, the invention relates to a bispecific antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

More particularly, the invention relates to a bispecific binding molecule comprising a Fab, wherein in the CL domain adjacent to 4-1BBL the amino acid at position 123 (EU numbering) has been replaced by arginine (R) and the amino acid at position 124 (EU numbering) has been substituted by lysine (K), and wherein in the CH1 domain adjacent to 4-1BBL the amino acids at position 147 (EU numbering) and at position 213 (EU numbering) have been substituted by glutamic acid (E).

Polynucleotides

The invention further provides isolated polynucleotides encoding an antibody as described herein or a fragment thereof.

The isolated polynucleotides encoding the antibodies of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes the entire antibody according to the invention as described herein. In other embodiments, the isolated polynucleotide encodes a polypeptide comprised in the antibody according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Bispecific antibodies as used in the invention may be obtained, for example, by solid-state peptide synthesis (e.g. Merrifield solid phase synthesis) or recombinant production. For recombinant production one or more polynucleotide encoding the antibody or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y.

(1989). The expression vector can be part of a plasmid, virus, or may be a nucleic acid fragment. The expression vector includes an expression cassette into which the polynucleotide encoding the antibody or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit a-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or polypeptide fragments thereof is desired, DNA encoding a signal sequence may be placed upstream of the nucleic acid an antibody of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse 0-glucuronidase.

DNA encoding a short protein sequence that could be used to facilitate later purification (e.g. a histidine tag) or assist in labeling the fusion protein may be included within or at the ends of the polynucleotide encoding an antibody of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) an antibody of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NSO, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NSO, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing an antibody of the invention or polypeptide fragments thereof is provided, wherein the method comprises culturing a host cell comprising polynucleotides encoding the antibody of the invention or polypeptide fragments thereof, as provided herein, under conditions suitable for expression of the antibody of the invention or polypeptide fragments thereof, and recovering the antibody of the invention or polypeptide fragments thereof from the host cell (or host cell culture medium).

In certain embodiments the moieties capable of specific binding to a target cell antigen (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the antibodies are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, NJ). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, NY).

Antibodies of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the antigen binding molecule or fragments thereof can be determined by any of a variety of well-known analytical methods including gel electrophoresis, high pressure liquid chromatography, and the like. For example, the 4-1BBL-containing antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art.

1. Affinity assays

The affinity of the bispecific antigen binding molecules provided herein for the corresponding receptor can be determined in accordance with the methods set forth in the Examples by surface plasmon resonance (SPR), using standard instrumentation such as a BIAcore instrument (GE Healthcare), and receptors or target proteins such as may be obtained by recombinant expression. The affinity of the bispecific antigen binding molecule for the target cell antigen can also be determined by surface plasmon resonance (SPR), using standard instrumentation such as a BIAcore instrument (GE Healthcare), and receptors or target proteins such as may be obtained by recombinant expression. For the FAP-4-1BBL antigen binding molecules the methods have been described in more detail in International Patent Appl. Publ. No. WO 2016/075278 A1. According to one aspect, $K_D$ is measured by surface plasmon resonance using a BIACORE® T100 machine (GE Healthcare) at 25° C.

2. Binding assays and other assays

In one aspect, the FAP-4-1BBL antigen binding molecules as reported herein are tested for its antigen binding activity as described in more detail in International Patent Appl. Publ. No. WO 2016/075278 A1.

3. Activity assays

In one aspect, assays are provided for identifying the biological activity of FAP-4-1BBL antigen binding molecules.

In certain embodiments, an antibody as reported herein is tested for such biological activity in the in vitro co-culture assays with human immune effector cells as described in Example 8, in the in vitro co-culture assays with MKN45 cells expressing CEA and PDL-1 as described in Example 9 or in the in vitro PBMC activation assay as described in Example 10.

Pharmaceutical Compositions, Formulations and Routes of Administration

In a further aspect, the invention provides pharmaceutical compositions comprising the T-cell activating anti-CD3 bispecific antibody specific for a tumor-associated antigen, in particular an anti-CEA/anti-CD3 bispecific antibody, and 4-1BB agonists provided herein, e.g., for use in any of the below therapeutic methods. In one embodiment, a pharmaceutical composition comprises an antibody provided herein and at least one pharmaceutically acceptable excipient. In another embodiment, a pharmaceutical composition comprises an antibody provided herein and at least one additional therapeutic agent, e.g., as described below.

In another aspect, provided are pharmaceutical compositions comprising the T-cell activating anti-CD3 bispecific antibody specific for a tumor-associated antigen, in particular an anti-CEA/anti-CD3 bispecific antibody, and 4-1BB agonists provided herein In yet another aspect, the invention provides a T-cell activating anti-CD3 bispecific antibody specific for a tumor-associated antigen, in particular an anti-CEA/anti-CD3 bispecific antibody, for use in a method for treating or delaying progression of cancer, wherein the T-cell activating anti-CD3 bispecific antibody specific for a tumor-associated antigen is used in combination with a 4-1BB (CD137) agonist and in combination with an agent blocking PD-L1/PD-1 interaction. In particular, the agent blocking PD-L1/PD-1 interaction is an anti-PD-L1 antibody or an anti-PD1 antibody. More particularly, the agent blocking PD-L1/PD-1 interaction is selected from the group consisting of atezolizumab, durvalumab, pembrolizumab and nivolumab. In a specific aspect, the agent blocking PD-L1/PD-1 interaction is atezolizumab.

Pharmaceutical compositions of the present invention comprise a therapeutically effective amount of one or more antibodies dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one antibody and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the antigen binding molecules may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies of the invention may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Administration of the T-cell activating anti-CD3 bispecific antibody and the 4-1BB agonist Both the T-cell activating anti-CD3 bispecific antibody, in particular the anti-CEA/anti-CD3 bispecific antibody and the 4-1BB agonist (both called substance herein) can be administered by any suitable means, including parenteral, intrapulmonary, and intranasal, and, if desired for local treatment, intralesional administration. The methods of the present invention are particularly useful, however, in relation to therapeutic agents administered by parenteral, particularly intravenous, infusion.

Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In one embodiment, the therapeutic agent is administered parenterally, particularly intravenously. In a particular embodiment, the therapeutic agent is administered by intravenous infusion.

Both the T-cell activating anti-CD3 bispecific antibody, in particular the anti-CEA/anti-CD3 bispecific antibody, and the 4-1BB agonist would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. Both the T-cell activating anti-CD3 bispecific antibody, in particular the anti-CEA/anti-CD3 bispecific antibody, and the 4-1BB agonist need not be, but are optionally formulated with one or more agents currently used to prevent or treat the disorder in question. The effective amount of such other agents depends on the amount of therapeutic agent present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the T-cell activating anti-CD3 bispecific antibody, in particular the anti-CEA/anti-CD3 bispecific antibody and the 4-1BB agonist (when used in their combination or with one or more other additional therapeutic agents) will depend on the type of disease to be treated, the type of 4-1BB agent, the severity and course of the disease, whether both agents are administered for preventive or therapeutic purposes, previous therapy, the patient's clinical history and response to the therapeutic agent, and the discretion of the attending physician. Each substance is suitably administered to the patient at one time or over a series of treatments. Depending on the type and severity of the disease, about 1 µg/kg to 15 mg/kg (e.g. 0.1 mg/kg-10 mg/kg) of the substance can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of each substance would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the subject. Such doses may be administered intermittently, e.g. every week, every two weeks, or every three weeks (e.g. such that the subject receives from about two to about twenty, or e.g. about six doses of the therapeutic agent). An initial higher loading dose, followed by one or more lower doses, or an initial lower dose, followed by one or more higher doses may be administered. An exemplary dosing regimen comprises administering an initial dose of about 10 mg, followed by a bi-weekly dose of about 20 mg of the therapeutic agent. However, other dosage regimens may be useful. The progress of this therapy is easily monitored by conventional techniques and assays.

In one aspect, the administration of both the T-cell activating anti-CD3 bispecific antibody, in particular the anti-CEA/anti-CD3 bispecific antibody and the 4-1BB agonist is a single administration. In certain aspects, the administration of the therapeutic agent is two or more administrations. In one such aspect, the substances are administered every week, every two weeks, or every three weeks, particularly every two weeks. In one aspect, the substance is administered in a therapeutically effective amount. In one aspect the substance is administered at a dose of about 50 µg/kg, about 100 µg/kg, about 200 µg/kg, about 300 µg/kg, about 400 µg/kg, about 500 µg/kg, about 600 µg/kg, about 700 µg/kg, about 800 µg/kg, about 900 µg/kg or about 1000 µg/kg. In one embodiment, the T-cell activating anti-CD3 bispecific antibody, in particular the anti-CEA/anti-CD3 bispecific antibody is administered at a dose which is higher than the dose of the T-cell activating anti-CD3 bispecific antibody, in particular the anti-CEA/anti-CD3 bispecific antibody, in a corresponding treatment regimen without the administration of the 4-1BB agonist. In one aspect the administration of the T-cell activating anti-CD3 bispecific antibody, in particular the anti-CEA/anti-CD3 bispecific antibody comprises an initial administration of a first dose of the T-cell activating anti-CD3 bispecific antibody, in particular the anti-CEA/anti-CD3 bispecific antibody, and one or more subsequent administrations of a second dose of the T-cell activating anti-CD3 bispecific antibody, in particular the anti-CEA/anti-CD3 bispecific antibody, wherein the second dose is higher than the first dose. In one aspect, the administration of the T-cell activating anti-CD3 bispecific antibody, in particular the anti-CEA/anti-CD3 bispecific antibody comprises an initial administration of a first dose of the T-cell activating anti-CD3 bispecific antibody, in particular the anti-CEA/anti-CD3 bispecific antibody, and one or more subsequent administrations of a second dose of the T-cell activating anti-CD3 bispecific antibody, in particular the anti-CEA/anti-CD3 bispecific antibody, wherein the first dose is not lower than the second dose.

In one aspect, the administration of the T-cell activating anti-CD3 bispecific antibody, in particular the anti-CEA/anti-CD3 bispecific antibody in the treatment regimen according to the invention is the first administration of said T-cell activating anti-CD3 bispecific antibody, in particular the anti-CEA/anti-CD3 bispecific antibody to the subject (at least within the same course of treatment). In one aspect, no administration of the 4-1BB agonist is made to the subject prior to the administration of the T-cell activating anti-CD3 bispecific antibody, in particular the anti-CEA/anti-CD3 bispecific antibody. In another aspect, the 4-1BB agonist is administered prior to the administration of the T-cell activating anti-CD3 bispecific antibody, in particular the anti-CEA/anti-CD3 bispecific antibody.

In another aspect, the T-cell activating anti-CD3 bispecific antibody, in particular the anti-CEA/anti-CD3 bispecific antibody is for use in combination with a 4-1BB agonist, wherein a pretreatment with an Type II anti-CD20 antibody, preferably obinutuzumab, is performed prior to the combination treatment, wherein the period of time between the pretreatment and the combination treatment is sufficient for the reduction of B-cells in the individual in response to the Type II anti-CD20 antibody, preferably obinutuzumab.

Activation of T cells can lead to severe cytokine release syndrome (CRS). In a phase 1 study conducted by TeGenero (Suntharalingam et al., N Engl J Med (2006) 355, 1018-1028), all 6 healthy volunteers experienced near fatal, severe cytokine release syndrome (CRS) rapidly post-infusion of an inappropriately-dosed, T-cell stimulating super-agonist anti-CD28 monoclonal antibody. The cytokine release associated with administration of a T-cell activating therapeutic agent, such as the anti-CEA/anti-CD3 bispecific antibody, to a subject can be significantly reduced by pre-treatment of said subject with a Type II anti-CD20 antibody, such as obinutuzumab. the use of GAZYVA® pre-treatment (Gpt) should aid in the rapid depletion of B cells, both in the peripheral blood and in secondary lymphoid organs, such that the risk of highly relevant adverse events (AEs) from strong systemic T cell activation by T-cell activating therapeutic agents (e.g. CRS) is reduced, while supporting exposure levels of T-cell activating therapeutic agents that are high enough from the start of dosing to mediate tumour cell elimination. To date, the safety profile of obinutuzumab (including cytokine release) has been assessed and managed in hundreds of patients in ongoing obinutuzumab clinical trials. Finally, in addition to supporting the safety profile of T-cell activating anti-CD3 bispecific antibodies such as the anti-CEA/anti-CD3 bispecific antibody, Gpt should also help prevent the formation of anti-drug antibodies (ADAs) to these unique molecules.

In the present invention, the combination of the T-cell activating anti-CD3 bispecific antibody, in particular the anti-CEA/anti-CD3 bispecific antibody and the 4-1BB agonist can be used in combination with further agents in a therapy. For instance, at least one additional therapeutic agent may be co-administered. In certain aspects, an additional therapeutic agent is an immunotherapeutic agent.

In one aspect, the combination of the T-cell activating anti-CD3 bispecific antibody, in particular the anti-CEA/anti-CD3 bispecific antibody, and the 4-1BB agonist can be used in combination with a PD-1 axis binding antagonist. In one aspect, the PD-1 axis binding antagonist is selected from the group consisting of a PD-1 binding antagonist, a PD-L1 binding antagonist and a PD-L2 binding antagonist. In a particular aspect, PD-1 axis binding antagonist is a PD-1 binding antagonist. In one aspect, the PD-1 axis binding antagonist is selected MDX 1106 (nivolumab), MK-3475 (pembrolizumab), CT-011 (pidilizumab), MEDI-0680 (AMP-514), PDR001, REGN2810, and BGB-108. In another particular aspect, the PD-1 axis binding antagonist is a PD-L1 binding antagonist. In one aspect, the PD-1 axis binding antagonist is selected from MPDL3280A (atezolizumab), YW243.55.S70, MDX-1105, MEDI4736 (durvalumab), and MSB0010718C (avelumab). More particularly, the combination of the T-cell activating anti-CD3 bispecific antibody, in particular the anti-CEA/anti-CD3 bispecific antibody, and the 4-1BB agonist can be used in combination with MPDL3280A (atezolizumab).

The period of time between the administration of the PD-1 axis binding antagonist and the administration of the combination therapy comprising T-cell activating anti-CD3 bispecific antibody, in particular the anti-CEA/anti-CD3 bispecific antibody, and the 4-1BB agonist and the doses are chosen such as to effectively shrink the tumor in the subject prior to administration of the combination therapy.

Such combination therapies noted above encompass combined administration (where two or more therapeutic agents are included in the same or separate formulations), and separate administration, in which case, administration of the therapeutic agent can occur prior to, simultaneously, and/or following, administration of an additional therapeutic agent or agents. In one embodiment, administration of the therapeutic agent and administration of an additional therapeutic agent occur within about one month, or within about one, two or three weeks, or within about one, two, three, four, five, or six days, of each other.

Administration of the 4-1BB Agonist Comprising at Least One Antigen Binding Domain Capable of Specific Binding to a Tumor-Associated Antigen and the Agent Blocking PD-L1/PD-1 Interaction Both the 4-1BB agonist comprising at least one antigen binding domain capable of specific binding to a tumor-associated antigen and the agent blocking PD-L1/PD-1 interaction (both called substance herein) can be administered by any suitable means, including parenteral, intrapulmonary, and intranasal, and, if desired for local treatment, intralesional administration. The methods of the present invention are particularly useful, however, in relation to therapeutic agents administered by parenteral, particularly intravenous, infusion.

Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In one embodiment, the therapeutic agent is administered parenterally, particularly intravenously. In a particular embodiment, the therapeutic agent is administered by intravenous infusion.

Both the 4-1BB agonist comprising at least one antigen binding domain capable of specific binding to a tumor-associated antigen and the agent blocking PD-L1/PD-1 interaction would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. Both the 4-1BB agonist comprising at least one antigen binding domain capable of specific binding to a tumor-associated antigen and the agent blocking PD-L1/PD-1 interaction need not be, but are optionally formulated with one or more agents currently used to prevent or treat the disorder in question. The effective amount of such other agents depends on the amount of therapeutic agent present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the 4-1BB agonist comprising at least one antigen binding domain capable of specific binding to a tumor-associated antigen and the agent blocking PD-L1/PD-1 interaction (when used in their combination or with one or more other additional therapeutic agents) will depend on the type of disease to be treated, the type of 4-1BB agonist, the severity and course of the disease, whether both agents are administered for preventive or therapeutic purposes, previous therapy, the patient's clinical history and response to the therapeutic agent, and the discretion of the attending physician. Each substance is suitably administered to the patient at one time or over a series of treatments. Depending on the type and severity of the disease, about 1 µg/kg to 15 mg/kg (e.g. 0.1 mg/kg-10 mg/kg) of the substance can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of each substance would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the subject. Such doses may be administered intermittently, e.g. every week, every two weeks, or every three weeks (e.g. such that the subject receives from about two to about twenty, or e.g. about six doses of the therapeutic agent). An initial higher loading dose, followed by one or more lower doses, or an initial lower dose, followed by one or more higher doses may be administered. An exemplary dosing regimen comprises administering an initial dose of about 10 mg, followed by a bi-weekly dose of about 20 mg of the therapeutic agent. However, other dosage regimens may be useful. The progress of this therapy is easily monitored by conventional techniques and assays.

In one aspect, the administration of both the 4-1BB agonist comprising at least one antigen binding domain capable of specific binding to a tumor-associated antigen and the agent blocking PD-L1/PD-1 interaction is a single administration. In certain aspects, the administration of the therapeutic agent is two or more administrations. In one such aspect, the substances are administered every week, every two weeks, or every three weeks, particularly every two weeks. In one aspect, the substance is administered in a therapeutically effective amount. In one aspect the substance is administered at a dose of about 50 µg/kg, about 100 µg/kg, about 200 µg/kg, about 300 µg/kg, about 400 µg/kg, about 500 µg/kg, about 600 µg/kg, about 700 µg/kg, about 800 µg/kg, about 900 µg/kg or about 1000 µg/kg. In one embodiment, the agent blocking PD-L1/PD-1 interaction is administered at a dose which is higher than the dose of the agent blocking PD-L1/PD-1 interaction, in a corresponding treatment regimen without the administration of the 4-1BB agonist. In another embodiment, the agent blocking PD-L1/PD-1 interaction is administered at a dose which is lower than the dose of the agent blocking PD-L1/PD-1 interaction, in a corresponding treatment regimen without the administration of the 4-1BB agonist. In one aspect the administration of the agent blocking PD-L1/PD-1 interaction comprises an initial administration of a first dose of the agent blocking PD-L1/PD-1 interaction and one or more subsequent administrations of a second dose of the agent blocking PD-L1/PD-1 interaction wherein the second dose is higher than the first dose. In one aspect, the administration of the agent blocking PD-L1/PD-1 interaction comprises an initial administration of a first dose of the agent blocking PD-L1/PD-1 interaction and one or more subsequent administrations of a second dose of the agent blocking PD-L1/PD-1 interaction wherein the first dose is not lower than the second dose.

In one aspect, the administration of the 4-1BB agonist comprising at least one antigen binding domain capable of specific binding to a tumor-associated antigen in the treatment regimen according to the invention is the first administration of said 4-1BB agonist comprising at least one antigen binding domain capable of specific binding to a tumor-associated antigen to the subject (at least within the same course of treatment). In one aspect, no administration of the 4-1BB agonist is made to the subject prior to the administration of the agent blocking PD-L1/PD-1 interaction. In another aspect, the 4-1BB agonist is administered prior to the administration of the agent blocking PD-L1/PD-1 interaction.

In another aspect, the 4-1BB agonist comprising at least one antigen binding domain capable of specific binding to a tumor-associated antigen is for use in combination with the agent blocking PD-L1/PD-1 interaction, wherein a pretreatment with an Type II anti-CD20 antibody, preferably obinutuzumab, is performed prior to the combination treatment, wherein the period of time between the pretreatment and the combination treatment is sufficient for the reduction of B-cells in the individual in response to the Type II anti-CD20 antibody, preferably obinutuzumab.

In the present invention, the combination of the T-cell activating anti-CD3 bispecific antibody, in particular the anti-CEA/anti-CD3 bispecific antibody and the 4-1BB agonist can be used in combination with further agents in a therapy. For instance, at least one additional therapeutic agent may be co-administered. In certain aspects, an additional therapeutic agent is an immunotherapeutic agent.

Such combination therapies noted above encompass combined administration (where two or more therapeutic agents are included in the same or separate formulations), and separate administration, in which case, administration of the therapeutic agent can occur prior to, simultaneously, and/or following, administration of an additional therapeutic agent or agents. In one embodiment, administration of the therapeutic agent and administration of an additional therapeutic agent occur within about one month, or within about one, two or three weeks, or within about one, two, three, four, five, or six days, of each other.

Therapeutic Methods and Compositions

Bispecific antibodies recognizing two cell surface proteins on different cell populations hold the promise to redirect cytotoxic immune cells for destruction of pathogenic target cells.

In one aspect, provided is a method for treating or delaying progression of cancer in a subject comprising administering to the subject an effective amount of a T-cell activating anti-CD3 bispecific antibody, in particular a anti-CEA/anti-CD3 bispecific antibody, and a 4-1BB agonist.

In one such aspect, the method further comprises administering to the subject an effective amount of at least one additional therapeutic agent. In further embodiments, herein is provided a method for tumor shrinkage comprising administering to the subject an effective amount of a T-cell activating anti-CD3 bispecific antibody, in particular an anti-CEA/anti-CD3 bispecific antibody, and a 4-1BB agonist. An "individual" or a "subject" according to any of the above aspects is preferably a human.

In further aspects, a composition for use in cancer immunotherapy is provided comprising a T-cell activating anti-CD3 bispecific antibody, in particular a anti-CEA/anti-CD3 bispecific antibody, and a 4-1BB agonist. In certain embodiments, a composition comprising a T-cell activating anti-CD3 bispecific antibody, in particular a anti-CEA/anti-CD3 bispecific antibody, and a 4-1BB agonist for use in a method of cancer immunotherapy is provided.

In a further aspect, herein is provided for the use of a composition comprising a T-cell activating anti-CD3 bispecific antibody, in particular a anti-CEA/anti-CD3 bispecific antibody, and a 4-1BB agonist in the manufacture or preparation of a medicament. In one embodiment, the medicament is for treatment of solid tumors. In a further embodiment, the medicament is for use in a method of tumor shrinkage comprising administering to an individual having a solid tumor an effective amount of the medicament. In one such embodiment, the method further comprises administering to the individual an effective amount of at least one additional therapeutic agent. In a further embodiment, the medicament is for treating solid tumors. In some aspects, the individual has CEA positive cancer. In some aspects, CEA positive cancer is colon cancer, lung cancer, ovarian cancer, gastric cancer, bladder cancer, pancreatic cancer, endometrial cancer, breast cancer, kidney cancer, esophageal cancer, or prostate cancer. In some aspects, the breast cancer is a breast carcinoma or a breast adenocarcinoma. In some aspects, the breast carcinoma is an invasive ductal carcinoma. In some aspects, the lung cancer is a lung adenocarcinoma. In some embodiments, the colon cancer is a colorectal adenocarcinoma. An "individual" according to any of the above embodiments may be a human.

The combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of a T-cell activating anti-CD3 bispecific antibody, in particular a anti-CEA/anti-CD3 bispecific antibody, and a 4-1BB agonist and optionally the administration of an additional therapeutic agent occur within about one month, or within about one, two or three weeks, or within about one, two, three, four, five, or six days, of each other.

Both the T-cell activating anti-CD3 bispecific antibody, in particular a anti-CEA/anti-CD3 bispecific antibody, and the 4-1BB agonist as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Both the T-cell activating anti-CD3 bispecific antibody, in particular a anti-CEA/anti-CD3 bispecific antibody, and the 4-1BB agonist as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibodies need not be, but are optionally formulated with one or more agents currently used to prevent or treat the disorder in question. The effective amount of such other agents depends on the amount of antibodies present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Articles of Manufacture (Kits)

In another aspect of the invention, a kit containing materials useful for the treatment, prevention and/or diagnosis of the disorders described above is provided. The kit comprises at least one container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least two active agents in the kit are a T-cell activating anti-CD3 bispecific antibody, in particular a anti-CEA/anti-CD3 bispecific antibody, and an 4-1BB agonist of the invention.

In a particular aspect, provided is a kit for treating or delaying progression of cancer in a subject, comprising a package comprising (A) a first composition comprising as active ingredient a T-cell activating anti-CD3 bispecific antibody, in particular a anti-CEA/anti-CD3 bispecific antibody, and a pharmaceutically acceptable carrier; (B) a second composition comprising as active ingredient a 4-1BB agonist and a pharmaceutically acceptable carrier, and (C) instructions for using the compositions in a combination therapy.

The label or package insert indicates how the composition is used for treating the condition of choice and provides the instructions for using the compositions in a combination therapy. Moreover, the kit may comprise (a) a first container with a composition contained therein, wherein the composition comprises a T-cell activating anti-CD3 bispecific antibody, in particular a anti-CEA/anti-CD3 bispecific antibody, of the invention; and (b) a second container with a composition contained therein, wherein the composition comprises an 4-1BB agonist of the invention. In addition, the kit may comprise one or more further containers comprising further active ingredients that can be used in combination. The article of manufacture in this embodiment of the invention may further comprise a package insert indicating that the compositions can be used to treat a particular condition.

Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C (Sequences):

| SEQ ID NO: | Name | Sequence |
|---|---|---|
| 1 | Human (hu) 4-1BBL (71-254) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFG FQGRLLHLSAGQRLGVHLHTEARARHAWQLTQ GATVLGLFRVTPEIPAGLPSPRSE |
| 2 | hu 4-1BBL (85-254) | LDLRQGMFAQLVAQNVLLIDGPLSWYSDPGLA GVSLTGGLSYKEDTKELVVAKAGVYYVFFQLE LRRVVAGEGSGSVSLALHLQPLRSAAGAAALA LTVDLPPASSEARNSAFGFQGRLLHLSAGQRL GVHLHTEARARHAWQLTQGATVLGLFRVTPEI PAGLPSPRSE |
| 3 | hu 4-1BBL (80-254) | DPAGLLDLRQGMFAQLVAQNVLLIDGPLSWYS DPGLAGVSLTGGLSYKEDTKELVVAKAGVYYV FFQLELRRVVAGEGSGSVSLALHLQPLRSAAG AAALALTVDLPPASSEARNSAFGFQGRLLHLS AGQRLGVHLHTEARARHAWQLTQGATVLGLFR VTPEIPAGLPSPRSE |
| 4 | hu 4-1BBL (52-254) | PWAVSGARASPGSAASPRLREGPELSPDDPAG LLDLRQGMFAQLVAQNVLLIDGPLSWYSDPGL AGVSLTGGLSYKEDTKELVVAKAGVYYVFFQL ELRRVVAGEGSGSVSLALHLQPLRSAAGAAAL ALTVDLPPASSEARNSAFGFQGRLLHLSAGQR LGVHLHTEARARHAWQLTQGATVLGLFRVTPE IPAGLPSPRSE |
| 5 | Human (hu) 4-1BBL (71-248) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFG FQGRLLHLSAGQRLGVHLHTEARARHAWQLTQ GATVLGLFRVTPEIPAGL |
| 6 | hu 4-1BBL (85-248) | LDLRQGMFAQLVAQNVLLIDGPLSWYSDPGLA GVSLTGGLSYKEDTKELVVAKAGVYYVFFQLE LRRVVAGEGSGSVSLALHLQPLRSAAGAAALA LTVDLPPASSEARNSAFGFQGRLLHLSAGQRL GVHLHTEARARHAWQLTQGATVLGLFRVTPEI PAGL |

TABLE C-continued

| SEQ ID NO: | Name | Sequence |
|---|---|---|
| 7 | hu 4-1BBL (80-248) | DPAGLLDLRQGMFAQLVAQNVLLIDGPLSWYS DPGLAGVSLTGGLSYKEDTKELVVAKAGVYYV FFQLELRRVVAGEGSGSVSLALHLQPLRSAAG AAALALTVDLPPASSEARNSAFGFQGRLLHLS AGQRLGVHLHTEARARHAWQLTQGATVLGLFR VTPEIPAGL |
| 8 | hu 4-1BBL (52-248) | PWAVSGARASPGSAASPRLREGPELSPDDPAG LLDLRQGMFAQLVAQNVLLIDGPLSWYSDPGL AGVSLTGGLSYKEDTKELVVAKAGVYYVFFQL ELRRVVAGEGSGSVSLALHLQPLRSAAGAAAL ALTVDLPPASSEARNSAFGFQGRLLHLSAGQR LGVHLHTEARARHAWQLTQGATVLGLFRVTPE IPAGL |
| 9 | FAP (28H1) CDR-H1 | SHAMS |
| 10 | FAP (28H1) CDR-H2 | AIWASGEQYYADSVKG |
| 11 | FAP (28H1) CDR-H3 | GWLGNFDY |
| 12 | FAP (28H1) CDR-L1 | RASQSVSRSYLA |
| 13 | FAP (28H1) CDR-L2 | GASTRAT |
| 14 | FAP (28H1) CDR-L3 | QQGQVIPPT |
| 15 | FAP(4B9) CDR-H1 | SYAMS |
| 16 | FAP(4B9) CDR-H2 | AIIGSGASTYYADSVKG |
| 17 | FAP(4B9) CDR-H3 | GWFGGFNY |
| 18 | FAP(4B9) CDR-L1 | RASQSVTSSYLA |
| 19 | FAP(4B9) CDR-L2 | VGSRRAT |
| 20 | FAP(4B9) CDR-L3 | QQGIMLPPT |
| 21 | FAP(28H1) VH | EVQLLESGGGLVQPGGSLRLSCAASGFTFSSH AMSWVRQAPGKGLEWVSAIWASGEQYYADSVK GRFTISRDNSKNTLYLQMNSLRAEDTAVYYCA KGWLGNFDYWGQGTLVTVSS |
| 22 | FAP(28H1) VL | EIVLTQSPGTLSLSPGERATLSCRASQSVSRS YLAWYQQKPGQAPRLLIIGASTRATGIPDRFS GSGSGTDFTLTISRLEPEDFAVYYCQQGQVIP PTFGQGTKVEIK |
| 23 | FAP(4B9) VH | EVQLLESGGGLVQPGGSLRLSCAASGFTFSSY AMSWVRQAPGKGLEWVSAIIGSGASTYYADSV KGRFTISRDNSKNTLYLQMNSLRAEDTAVYYC AKGWFGGFNYWGQGTLVTVSS |
| 24 | FAP(4B9) VL | EIVLTQSPGTLSLSPGERATLSCRASQSVTSS YLAWYQQKPGQAPRLLINVGSRRATGIPDRFS GSGSGTDFTLTISRLEPEDFAVYYCQQGIMLP PTFGQGTKVEIK |
| 25 | dimeric hu 4-1BBL (71-254) connected by (G4S)$_2$ linker (SEQ ID NO: 92) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFG FQGRLLHLSAGQRLGVHLHTEARARHAWQLTQ GATVLGLFRVTPEIPAGLPSPRSEGGGGSGGG GSREGPELSPDDPAGLLDLRQGMFAQLVAQNV LLIDGPLSWYSDPGLAGVSLTGGLSYKEDTKE LVVAKAGVYYVFFQLELRRVVAGEGSGSVSLA LHLQPLRSAAGAAALALTVDLPPASSEARNSA FGFQGRLLHLSAGQRLGVHLHTEARARHAWQL TQGATVLGLFRVTPEIPAGLPSPRSE |
| 26 | dimeric hu 4-1BBL (85-254) connected by (G4S)$_2$ linker (SEQ ID NO: 92) | LDLRQGMFAQLVAQNVLLIDGPLSWYSDPGLA GVSLTGGLSYKEDTKELVVAKAGVYYVFFQLE LRRVVAGEGSGSVSLALHLQPLRSAAGAAALA |

TABLE C-continued

| (Sequences): | | |
|---|---|---|
| SEQ ID NO: | Name | Sequence |

|  |  | LTVDLPPASSEARNSAFGFQGRLLHLSAGQRL<br>GVHLHTEARARHAWQLTQGATVLGLFRVTPEI<br>PAGLPSPRSEGGGGSGGGGSLDLRQGMFAQLV<br>AQNVLLIDGPLSWYSDPGLAGVSLTGGLSYKE<br>DTKELVVAKAGVYYVFFQLELRRVVAGEGSGS<br>VSLALHLQPLRSAAGAAALALTVDLPPASSEA<br>RNSAFGFQGRLLHLSAGQRLGVHLHTEARARH<br>AWQLTQGATVLGLFRVTPEIPAGLPSPRSE |
| 27 | dimeric hu 4-1BBL (80-254)<br>connected by (G4S)₂ linker<br>(SEQ ID NO: 92) | DPAGLLDLRQGMFAQLVAQNVLLIDGPLSWYS<br>DPGLAGVSLTGGLSYKEDTKELVVAKAGVYYV<br>FFQLELRRVVAGEGSGSVSLALHLQPLRSAAG<br>AAALALTVDLPPASSEARNSAFGFQGRLLHLS<br>AGQRLGVHLHTEARARHAWQLTQGATVLGLFR<br>VTPEIPAGLPSPRSEGGGGSGGGGSDPAGLLD<br>LRQGMFAQLVAQNVLLIDGPLSWYSDPGLAGV<br>SLTGGLSYKEDTKELVVAKAGVYYVFFQLELR<br>RVVAGEGSGSVSLALHLQPLRSAAGAAALALT<br>VDLPPASSEARNSAFGFQGRLLHLSAGQRLGV<br>HLHTEARARHAWQLTQGATVLGLFRVTPEIPA<br>GLPSPRSE |
| 28 | dimeric hu 4-1BBL (52-254)<br>connected by (G4S)₂ linker<br>(SEQ ID NO: 92) | PWAVSGARASPGSAASPRLREGPELSPDDPAG<br>LLDLRQGMFAQLVAQNVLLIDGPLSWYSDPGL<br>AGVSLTGGLSYKEDTKELVVAKAGVYYVFFQL<br>ELRRVVAGEGSGSVSLALHLQPLRSAAGAAAL<br>ALTVDLPPASSEARNSAFGFQGRLLHLSAGQR<br>LGVHLHTEARARHAWQLTQGATVLGLFRVTPE<br>IPAGLPSPRSEGGGGSGGGGSPWAVSGARASP<br>GSAASPRLREGPELSPDDPAGLLDLRQGMFAQ<br>LVAQNVLLIDGPLSWYSDPGLAGVSLTGGLSY<br>KEDTKELVVAKAGVYYVFFQLELRRVVAGEGS<br>GSVSLALHLQPLRSAAGAAALALTVDLPPASS<br>EARNSAFGFQGRLLHLSAGQRLGVHLHTEARA<br>RHAWQLTQGATVLGLFRVTPEIPAGLPSPRSE |
| 29 | dimeric hu 4-1BBL (71-248)<br>connected by (G4S)2 linker<br>(SEQ ID NO: 92) | REGPELSPDDPAGLLDLRQGMFAQLVAQNVLL<br>IDGPLSWYSDPGLAGVSLTGGLSYKEDTKELV<br>VAKAGVYYVFFQLELRRVVAGEGSGSVSLALH<br>LQPLRSAAGAAALALTVDLPPASSEARNSAFG<br>FQGRLLHLSAGQRLGVHLHTEARARHAWQLTQ<br>GATVLGLFRVTPEIPAGLGGGGSGGGGSREGP<br>ELSPDDPAGLLDLRQGMFAQLVAQNVLLIDGP<br>LSWYSDPGLAGVSLTGGLSYKEDTKELVVAKA<br>GVYYVFFQLELRRVVAGEGSGSVSLALHLQPL<br>RSAAGAAALALTVDLPPASSEARNSAFGFQGR<br>LLHLSAGQRLGVHLHTEARARHAWQLTQGATV<br>LGLFRVTPEIPAGL |
| 30 | dimeric hu 4-1BBL (85-248)<br>connected by (G4S)2 linker<br>(SEQ ID NO: 92) | LDLRQGMFAQLVAQNVLLIDGPLSWYSDPGLA<br>GVSLTGGLSYKEDTKELVVAKAGVYYVFFQLE<br>LRRVVAGEGSGSVSLALHLQPLRSAAGAAALA<br>LTVDLPPASSEARNSAFGFQGRLLHLSAGQRL<br>GVHLHTEARARHAWQLTQGATVLGLFRVTPEI<br>PAGLGGGGSGGGGSLDLRQGMFAQLVAQNVLL<br>IDGPLSWYSDPGLAGVSLTGGLSYKEDTKELV<br>VAKAGVYYVFFQLELRRVVAGEGSGSVSLALH<br>LQPLRSAAGAAALALTVDLPPASSEARNSAFG<br>FQGRLLHLSAGQRLGVHLHTEARARHAWQLTQ<br>GATVLGLFRVTPEIPAGL |
| 31 | dimeric hu 4-1BBL (80-248)<br>connected by (G4S)2 linker<br>(SEQ ID NO: 92) | DPAGLLDLRQGMFAQLVAQNVLLIDGPLSWYS<br>DPGLAGVSLTGGLSYKEDTKELVVAKAGVYYV<br>FFQLELRRVVAGEGSGSVSLALHLQPLRSAAG<br>AAALALTVDLPPASSEARNSAFGFQGRLLHLS<br>AGQRLGVHLHTEARARHAWQLTQGATVLGLFR<br>VTPEIPAGLGGGGSGGGGSDPAGLLDLRQGMF<br>AQLVAQNVLLIDGPLSWYSDPGLAGVSLTGGL<br>SYKEDTKELVVAKAGVYYVFFQLELRRVVAGE<br>GSGSVSLALHLQPLRSAAGAAALALTVDLPPA<br>SSEARNSAFGFQGRLLHLSAGQRLGVHLHTEA<br>RARHAWQLTQGATVLGLFRVTPEIPAGL |

TABLE C-continued

| | | |
|---|---|---|
| | (Sequences): | |

| SEQ ID NO: | Name | Sequence |
|---|---|---|
| 32 | dimeric hu 4-1BBL (52-248) connected by (G4S)2 linker (SEQ ID NO: 92) | PWAVSGARASPGSAASPRLREGPELSPDDPAG LLDLRQGMFAQLVAQNVLLIDGPLSWYSDPGL AGVSLTGGLSYKEDTKELVVAKAGVYYVFFQL ELRRVVAGEGSGSVSLALHLQPLRSAAGAAAL ALTVDLPPASSEARNSAFGFQGRLLHLSAGQR LGVHLHTEARARHAWQLTQGATVLGLFRVTPE IPAGLGGGGSGGGGSPWAVSGARASPGSAASP RLREGPELSPDDPAGLLDLRQGMFAQLVAQNV LLIDGPLSWYSDPGLAGVSLTGGLSYKEDTKE LVVAKAGVYYVFFQLELRRVVAGEGSGSVSLA LHLQPLRSAAGAAALALTVDLPPASSEARNSA FGFQGRLLHLSAGQRLGVHLHTEARARHAWQL TQGATVLGLFRVTPEIPAGL |
| 33 | CD3-HCDR1 | TYAMN |
| 34 | CD3-HCDR2 | RIRSKYNNYATYYADSVKG |
| 35 | CD3-HCDR3 | HGNFGNSYVSWFAY |
| 36 | CD3-LCDR1 | GSSTGAVTTSNYAN |
| 37 | CD3-LCDR2 | GTNKRAP |
| 38 | CD3-LCDR3 | ALWYSNLWV |
| 39 | CD3 VH | EVQLLESGGGLVQPGGSLRLSCAASGFTFSTY AMNWVRQAPGKGLEWVSRIRSKYNNYATYYAD SVKGRFTISRDDSKNTLYLQMNSLRAEDTAVY YCVRHGNFGNSYVSWFAYWGQGTLVTVSS |
| 40 | CD3 VL | QAVVTQEPSLTVSPGGTVTLTCGSSTGAVTTS NYANWVQEKPGQAFRGLIGGTNKRAPGTPARF SGSLLGGKAALTLSGAQPEDEAEYYCALWYSN LWVFGGGTKLTVL |
| 41 | CEA-HCDR1 | EFGMN |
| 42 | CEA-HCDR2 | WINTKTGEATYVEEFKG |
| 43 | CEA-HCDR3 | WDFAYYVEAMDY |
| 44 | CEA-LCDR1 | KASAAVGTYVA |
| 45 | CEA-LCDR2 | SASYRKR |
| 46 | CEA-LCDR3 | HQYYTYPLFT |
| 47 | CEA VH | QVQLVQSGAEVKKPGASVKVSCKASGYTFTEF GMNWVRQAPGQGLEWMGWINTKTGEATYVEEF KGRVTFTTDTSTSTAYMELRSLRSDDTAVYYC ARWDFAYYVEAMDYWGQGTTVTVSS |
| 48 | CEA VL | DIQMTQSPSSLSASVGDRVTITCKASAAVGTY VAWYQQKPGKAPKLLIYSASYRKRGVPSRFSG SGSGTDFTLTISSLQPEDFATYYCHQYYTYPL FTFGQGTKLEIK |
| 49 | CEA-HCDR1 (CEACAM5) | DTYMH |
| 50 | CEA-HCDR2 (CEACAM5) | RIDPANGNSKYVPKFQG |
| 51 | CEA-HCDR3 (CEACAM5) | FGYYVSDYAMAY |
| 52 | CEA-LCDR1 (CEACAM5) | RAGESVDIFGVGFLH |
| 53 | CEA-LCDR2 (CEACAM5) | RASNRAT |
| 54 | CEA-LCDR3 (CEACAM5) | QQTNEDPYT |
| 55 | CEA VH (CEACAM5) | QVQLVQSGAEVKKPGSSVKVSCKASGFNIKDT YMHWVRQAPGQGLEWMGRIDPANGNSKYVPKF QGRVTITADTSTSTAYMELSSLRSEDTAVYYC APFGYYVSDYAMAYWGQGTLVTVSS |

TABLE C-continued

| SEQ ID NO: | Name | Sequence |
|---|---|---|
| 56 | CEA VL (CEACAM5) | EIVLTQSPATLSLSPGERATLSCRAGESVDIF GVGFLHWYQQKPGQAPRLLIYRASNRATGIPA RFSGSGSGTDFTLTISSLEPEDFAVYYCQQTN EDPYTFGQGTKLEIK |
| 57 | CD3 VH-CL (CEACAM5 TCB) | EVQLLESGGGLVQPGGSLRLSCAASGFTFSTY AMNWVRQAPGKGLEWVSRIRSKYNNYATYYAD SVKGRFTISRDDSKNTLYLQMNSLRAEDTAVY YCVRHGNFGNSYVSWFAYWGQGTLVTVSSASV AAPSVFIFPPSDEQLKSGTASVVCLLNNFYPR EAKVQWKVDNALQSGNSQESVTEQDSKDSTYS LSSTLTLSKADYEKHKVYACEVTHQGLSSPVT KSFNRGEC |
| 58 | humanized CEA VH-CH1(EE)-Fc (hole, P329G LALA) (CEACAM5 TCB) | QVQLVQSGAEVKKPGSSVKVSCKASGFNIKDT YMHWVRQAPGQGLEWMGRIDPANGNSKYVPKF QGRVTITADTSTSTAYMELSSLRSEDTAVYYC APFGYYVSDYAMAYWGQGTLVTVSSASTKGPS VFPLAPSSKSTSGGTAALGCLVEDYFPEPVTV SWNSGALTSGVHTFPAVLQSSGLYSLSSVVTV PSSSLGTQTYICNVNHKPSNTKVDEKVEPKSC DKTHTCPPCPAPEAAGGPSVFLFPPKPKDTLM ISRTPEVTCVVVDVSHEDPEVKFNWYVDGVEV HNAKTKPREEQYNSTYRVVSVLTVLHQDWLNG KEYKCKVSNKALGAPIEKTISKAKGQPREPQV CTLPPSRDELTKNQVSLSCAVKGFYPSDIAVE WESNGQPENNYKTTPPVLDSDGSFFLVSKLTV DKSRWQQGNVFSCSVMHEALHNHYTQKSLSLS P |
| 59 | humanized CEA VH-CH1(EE)-CD3 VL-CH1-Fc (knob, P329G LALA) (CEACAM5 TCB) | QVQLVQSGAEVKKPGSSVKVSCKASGFNIKDT YMHWVRQAPGQGLEWMGRIDPANGNSKYVPKF QGRVTITADTSTSTAYMELSSLRSEDTAVYYC APFGYYVSDYAMAYWGQGTLVTVSSASTKGPS VFPLAPSSKSTSGGTAALGCLVEDYFPEPVTV SWNSGALTSGVHTFPAVLQSSGLYSLSSVVTV PSSSLGTQTYICNVNHKPSNTKVDEKVEPKSC DGGGGSGGGGSQAVVTQEPSLTVSPGGTVTLT CGSSTGAVTTSNYANWVQEKPGQAFRGLIGGT NKRAPGTPARFSGSLLGGKAALTLSGAQPEDE AEYYCALWYSNLWVFGGGTKLTVLSSASTKGP SVFPLAPSSKSTSGGTAALGCLVKDYFPEPVT VSWNSGALTSGVHTFPAVLQSSGLYSLSSVVT VPSSSLGTQTYICNVNHKPSNTKVDKKVEPKS CDKTHTCPPCPAPEAAGGPSVFLFPPKPKDTL MISRTPEVTCVVVDVSHEDPEVKFNWYVDGVE VHNAKTKPREEQYNSTYRVVSVLTVLHQDWLN GKEYKCKVSNKALGAPIEKTISKAKGQPREPQ VYTLPPCRDELTKNQVSLWCLVKGFYPSDIAV EWESNGQPENNYKTTPPVLDSDGSFFLYSKLT VDKSRWQQGNVFSCSVMHEALHNHYTQKSLSL SP |
| 60 | humanized CEA VL-CL(RK) (CEACAM5 TCB) | EIVLTQSPATLSLSPGERATLSCRAGESVDIF GVGFLHWYQQKPGQAPRLLIYRASNRATGIPA RFSGSGSGTDFTLTISSLEPEDFAVYYCQQTN EDPYTFGQGTKLEIKRTVAAPSVFIFPPSDRK LKSGTASVVCLLNNFYPREAKVQWKVDNALQS GNSQESVTEQDSKDSTYSLSSTLTLSKADYEK HKVYACEVTHQGLSSPVTKSFNRGEC |
| 61 | Light chain „CEA₂F₁" (CEA TCB) | DIQMTQSPSSLSASVGDRVTITCKASAAVGTY VAWYQQKPGKAPKLLIYSASYRKRGVPSRFSG SGSGTDFTLTISSLQPEDFATYYCHQYYTYPL FTFGQGTKLEIKRTVAAPSVFIFPPSDEQLKS GTASVVCLLNNFYPREAKVQWKVDNALQSGNS QESVTEQDSKDSTYSLSSTLTLSKADYEKHKV YACEVTHQGLSSPVTKSFNRGEC |

TABLE C-continued

| SEQ ID NO: | Name | Sequence |
|---|---|---|
| 62 | Light Chain humanized CD3$_{CH2527}$ (Crossfab, VL-CH1) (CEA TCB) | QAVVTQEPSLTVSPGGTVTLTCGSSTGAVTTS NYANWVQEKPGQAFRGLIGGTNKRAPGTPARF SGSLLGGKAALTLSGAQPEDEAEYYCALWYSN LWVFGGGTKLTVLSSASTKGPSVFPLAPSSKS TSGGTAALGCLVKDYFPEPVTVSWNSGALTSG VHTFPAVLQSSGLYSLSSVVTVPSSSLGTQTY ICNVNHKPSNTKVDKKVEPKSC |
| 63 | CEA$_{CH1A1A\ 98/99}$ - humanized CD3$_{CH2527}$ (Crossfab VH-Ck)-Fc(knob) P329GLALA (CEA TCB) | QVQLVQSGAEVKKPGASVKVSCKASGYTFTEF GMNWVRQAPGQGLEWMGWINTKTGEATYVEEF KGRVTFTTDTSTSTAYMELRSLRSDDTAVYYC ARWDFAYYVEAMDYWGQGTTVTVSSASTKGPS VFPLAPSSKSTSGGTAALGCLVKDYFPEPVTV SWNSGALTSGVHTFPAVLQSSGLYSLSSVVTV PSSSLGTQTYICNVNHKPSNTKVDKKVEPKSC DGGGGSGGGGSEVQLLESGGGLVQPGGSLRLS CAASGFTFSTYAMNWVRQAPGKGLEWVSRIRS KYNNYATYYADSVKGRFTISRDDSKNTLYLQM NSLRAEDTAVYYCVRHGNFGNSYVSWFAYWGQ GTLVTVSSASVAAPSVFIFPPSDEQLKSGTAS VVCLLNNFYPREAKVQWKVDNALQSGNSQESV TEQDSKDSTYSLSSTLTLSKADYEKHKVYACE VTHQGLSSPVTKSFNRGECDKTHTCPPCPAPE AAGGPSVFLFPPKPKDTLMISRTPEVTCVVVD VSHEDPEVKFNWYVDGVEVHNAKTKPREEQYN STYRVVSVLTVLHQDWLNGKEYKCKVSNKALG APIEKTISKAKGQPREPQVYTLPPCRDELTKN QVSLWCLVKGFYPSDIAVEWESNGQPENNYKT TPPVLDSDGSFFLYSKLTVDKSRWQQGNVFSC SVMHEALHNHYTQKSLSLSPGK |
| 64 | CEA$_{CH1A1A\ 98/99}$ (VH-CH1)-Fc(hole) P329GLALA (CEA TCB) | QVQLVQSGAEVKKPGASVKVSCKASGYTFTEF GMNWVRQAPGQGLEWMGWINTKTGEATYVEEF KGRVTFTTDTSTSTAYMELRSLRSDDTAVYYC ARWDFAYYVEAMDYWGQGTTVTVSSASTKGPS VFPLAPSSKSTSGGTAALGCLVKDYFPEPVTV SWNSGALTSGVHTFPAVLQSSGLYSLSSVVTV PSSSLGTQTYICNVNHKPSNTKVDKKVEPKSC DKTHTCPPCPAPEAAGGPSVFLFPPKPKDTLM ISRTPEVTCVVVDVSHEDPEVKFNWYVDGVEV HNAKTKPREEQYNSTYRVVSVLTVLHQDWLNG KEYKCKVSNKALGAPIEKTISKAKGQPREPQV CTLPPSRDELTKNQVSLSCAVKGFYPSDIAVE WESNGQPENNYKTTPPVLDSDGSFFLVSKLTV DKSRWQQGNVFSCSVMHEALHNHYTQKSLSLS PGK |
| 65 | Dimeric hu 4-1BBL (71-248)-CL* Fc knob chain (Construct 2.4 and 5.4) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFG FQGRLLHLSAGQRLGVHLHTEARARHAWQLTQ GATVLGLFRVTPEIPAGLGGGGSGGGGSREGP ELSPDDPAGLLDLRQGMFAQLVAQNVLLIDGP LSWYSDPGLAGVSLTGGLSYKEDTKELVVAKA GVYYVFFQLELRRVVAGEGSGSVSLALHLQPL RSAAGAAALALTVDLPPASSEARNSAFGFQGR LLHLSAGQRLGVHLHTEARARHAWQLTQGATV LGLFRVTPEIPAGLGGGGSGGGGSRTVAAPSV FIFPPSDRKLKSGTASVVCLLNNFYPREAKVQ WKVDNALQSGNSQESVTEQDSKDSTYSLSSTL TLSKADYEKHKVYACEVTHQGLSSPVTKSFNR GECDKTHTCPPCPAPEAAGGPSVFLFPPKPKD TLMISRTPEVTCVVVDVSHEDPEVKFNWYVDG VEVHNAKTKPREEQYNSTYRVVSVLTVLHQDW LNGKEYKCKVSNKALGAPIEKTISKAKGQPRE PQVYTLPPCRDELTKNQVSLWCLVKGFYPSDI AVEWESNGQPENNYKTTPPVLDSDGSFFLYSK LTVDKSRWQQGNVFSCSVMHEALHNHYTQKSL SLSPGK |
| 66 | Monomeric hu 4-1BBL (71-248)-CH1* (Construct 2.4 and 5.4) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFG |

TABLE C-continued

| (Sequences): | | |
|---|---|---|
| SEQ ID NO: | Name | Sequence |

|  |  | FQGRLLHLSAGQRLGVHLHTEARARHAWQLTQ GATVLGLFRVTPEIPAGLGGGGSGGGGSASTK GPSVFPLAPSSKSTSGGTAALGCLVEDYFPEP VTVSWNSGALTSGVHTFPAVLQSSGLYSLSSV VTVPSSSLGTQTYICNVNHKPSNTKVDEKVEP KSC |
|---|---|---|
| 67 | anti-FAP (4B9) Fc hole chain (Construct 2.4) | EVQLLESGGGLVQPGGSLRLSCAASGFTFSSY AMSWVRQAPGKGLEWVSAIIGSGASTYYADSV KGRFTISRDNSKNTLYLQMNSLRAEDTAVYYC AKGWFGGFNYWGQGTLVTVSSASTKGPSVFPL APSSKSTSGGTAALGCLVKDYFPEPVTVSWNS GALTSGVHTFPAVLQSSGLYSLSSVVTVPSSS LGTQTYICNVNHKPSNTKVDKKVEPKSCDKTH TCPPCPAPEAAGGPSVFLFPPKPKDTLMISRT PEVTCVVVDVSHEDPEVKFNWYVDGVEVHNAK TKPREEQYNSTYRVVSVLTVLHQDWLNGKEYK CKVSNKALGAPIEKTISKAKGQPREPQVCTLP PSRDELTKNQVSLSCAVKGFYPSDIAVEWESN GQPENNYKTTPPVLDSDGSFFLVSKLTVDKSR WQQGNVFSCSVMHEALHNHYTQKSLSLSPGK |
| 68 | anti-FAP (4B9) light chain (Construct 2.4) | EIVLTQSPGTLSLSPGERATLSCRASQSVTSS YLAWYQQKPGQAPRLLINVGSRRATGIPDRFS GSGSGTDFTLTISRLEPEDFAVYYCQQGIMLP PTFGQGTKVEIKRTVAAPSVFIFPPSDEQLKS GTASVVCLLNNFYPREAKVQWKVDNALQSGNS QESVTEQDSKDSTYSLSSTLTLSKADYEKHKV YACEVTHQGLSSPVTKSFNRGEC |
| 69 | Dimeric hu 4-1BBL (71-254)-CL* Fc knob chain (Construct 1.2) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFG FQGRLLHLSAGQRLGVHLHTEARARHAWQLTQ GATVLGLFRVTPEIPAGLPSPRSEGGGGSGGG GSREGPELSPDDPAGLLDLRQGMFAQLVAQNV LLIDGPLSWYSDPGLAGVSLTGGLSYKEDTKE LVVAKAGVYYVFFQLELRRVVAGEGSGSVSLA LHLQPLRSAAGAAALALTVDLPPASSEARNSA FGFQGRLLHLSAGQRLGVHLHTEARARHAWQL TQGATVLGLFRVTPEIPAGLPSPRSEGGGGSG GGGSRTVAAPSVFIFPPSDRKLKSGTASVVCL LNNFYPREAKVQWKVDNALQSGNSQESVTEQD SKDSTYSLSSTLTLSKADYEKHKVYACEVTHQ GLSSPVTKSFNRGECDKTHTCPPCPAPEAAGG PSVFLFPPKPKDTLMISRTPEVTCVVVDVSHE DPEVKFNWYVDGVEVHNAKTKPREEQYNSTYR VVSVLTVLHQDWLNGKEYKCKVSNKALGAPIE KTISKAKGQPREPQVYTLPPCRDELTKNQVSL WCLVKGFYPSDIAVEWESNGQPENNYKTTPPV LDSDGSFFLYSKLTVDKSRWQQGNVFSCSVMH EALHNHYTQKSLSLSPGK |
| 70 | Monomeric hu 4-1BBL (71-254)-CH1* (Construct 1.2) | REGPELSPDDPAGLLDLRQGMFAQLVAQNVLL IDGPLSWYSDPGLAGVSLTGGLSYKEDTKELV VAKAGVYYVFFQLELRRVVAGEGSGSVSLALH LQPLRSAAGAAALALTVDLPPASSEARNSAFG FQGRLLHLSAGQRLGVHLHTEARARHAWQLTQ GATVLGLFRVTPEIPAGLPSPRSEGGGGSGGG GSASTKGPSVFPLAPSSKSTSGGTAALGCLVE DYFPEPVTVSWNSGALTSGVHTFPAVLQSSGL YSLSSVVTVPSSSLGTQTYICNVNHKPSNTKV DEKVEPKSC |
| 71 | anti-FAP(28H1) Fc hole chain | EVQLLESGGGLVQPGGSLRLSCAASGFTFSSH AMSWVRQAPGKGLEWVSAIWASGEQYYADSVK GRFTISRDNSKNTLYLQMNSLRAEDTAVYYCA KGWLGNFDYWGQGTLVTVSSASTKGPSVFPLA PSSKSTSGGTAALGCLVKDYFPEPVTVSWNSG ALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTP EVTCVVVDVSHEDPEVKFNWYVDGVEVHNAKT KPREEQYNSTYRVVSVLTVLHQDWLNGKEYKC |

TABLE C-continued

| | (Sequences): | |
|---|---|---|
| SEQ ID NO: | Name | Sequence |
| | | KVSNKALGAPIEKTISKAKGQPREPQVCTLPP SRDELTKNQVSLSCAVKGFYPSDIAVEWESNG QPENNYKTTPPVLDSDGSFFLVSKLTVDKSRW QQGNVFSCSVMHEALHNHYTQKSLSLSPGK |
| 72 | anti-FAP (28H1) light chain | EIVLTQSPGTLSLSPGERATLSCRASQSVSRS YLAWYQQKPGQAPRLLIIGASTRATGIPDRFS GSGSGTDFTLTISRLEPEDFAVYYCQQGQVIP PTFGQGTKVEIKRTVAAPSVFIFPPSDEQLKS GTASVVCLLNNFYPREAKVQWKVDNALQSGNS QESVTEQDSKDSTYSLSSTLTLSKADYEKHKV YACEVTHQGLSSPVTKSFNRGEC |
| 73 | DP47 Fc hole chain | EVQLLESGGGLVQPGGSLRLSCAASGFTFSSY AMSWVRQAPGKGLEWVSAISGSGGSTYYADSV KGRFTISRDNSKNTLYLQMNSLRAEDTAVYYC AKGSGFDYWGQGTLVTVSSASTKGPSVFPLAP SSKSTSGGTAALGCLVKDYFPEPVTVSWNSGA LTSGVHTFPAVLQSSGLYSLSSVVTVPSSSLG TQTYICNVNHKPSNTKVDKKVEPKSCDKTHTC PPCPAPEAAGGPSVFLFPPKPKDTLMISRTPE VTCVVVDVSHEDPEVKFNWYVDGVEVHNAKTK PREEQYNSTYRVVSVLTVLHQDWLNGKEYKCK VSNKALGAPIEKTISKAKGQPREPQVCTLPPS RDELTKNQVSLSCAVKGFYPSDIAVEWESNGQ PENNYKTTPPVLDSDGSFFLVSKLTVDKSRWQ QGNVFSCSVMHEALHNHYTQKSLSLSPGK |
| 74 | anti-FAP (4B9) Fc hole chain fused to dimeric hu 4-1BBL (71-254) | EVQLLESGGGLVQPGGSLRLSCAASGFTFSSY AMSWVRQAPGKGLEWVSAIIGSGASTYYADSV KGRFTISRDNSKNTLYLQMNSLRAEDTAVYYC AKGWFGGFNYWGQGTLVTVSSASTKGPSVFPL APSSKSTSGGTAALGCLVKDYFPEPVTVSWNS GALTSGVHTFPAVLQSSGLYSLSSVVTVPSSS LGTQTYICNVNHKPSNTKVDKKVEPKSCDKTH TCPPCPAPEAAGGPSVFLFPPKPKDTLMISRT PEVTCVVVDVSHEDPEVKFNWYVDGVEVHNAK TKPREEQYNSTYRVVSVLTVLHQDWLNGKEYK CKVSNKALGAPIEKTISKAKGQPREPQVCTLP PSRDELTKNQVSLSCAVKGFYPSDIAVEWESN GQPENNYKTTPPVLDSDGSFFLVSKLTVDKSR WQQGNVFSCSVMHEALHNHYTQKSLSLSPGGG GGSGGGGSREGPELSPDDPAGLLDLRQGMFAQ LVAQNVLLIDGPLSWYSDPGLAGVSLTGGLSY KEDTKELVVAKAGVYYVFFQLELRRVVAGEGS GSVSLALHLQPLRSAAGAAALALTVDLPPASS EARNSAFGFQGRLLHLSAGQRLGVHLHTEARA RHAWQLTQGATVLGLFRVTPEIPAGLPSPRSE GGGGSGGGGSREGPELSPDDPAGLLDLRQGMF AQLVAQNVLLIDGPLSWYSDPGLAGVSLTGGL YKEDTKELVVAKAGVYYVFFQLELRRVVAGEG SGSVSLALHLQPLRSAAGAAALALTVDLPPAS SEARNSAFGFQGRLLHLSAGQRLGVHLHTEAR ARHAWQLTQGATVLGLFRVTPEIPAGLPSPRS E |
| 75 | anti-FAP (4B9) Fc knob chain fused to monomeric hu 4-1BBL (71-254) | EVQLLESGGGLVQPGGSLRLSCAASGFTFSSY AMSWVRQAPGKGLEWVSAIIGSGASTYYADSV KGRFTISRDNSKNTLYLQMNSLRAEDTAVYYC AKGWFGGFNYWGQGTLVTVSSASTKGPSVFPL APSSKSTSGGTAALGCLVKDYFPEPVTVSWNS GALTSGVHTFPAVLQSSGLYSLSSVVTVPSSS LGTQTYICNVNHKPSNTKVDKKVEPKSCDKTH TCPPCPAPEAAGGPSVFLFPPKPKDTLMISRT PEVTCVVVDVSHEDPEVKFNWYVDGVEVHNAK TKPREEQYNSTYRVVSVLTVLHQDWLNGKEYK CKVSNKALGAPIEKTISKAKGQPREPQVYTLP PCRDELTKNQVSLWCLVKGFYPSDIAVEWESN GQPENNYKTTPPVLDSDGSFFLYSKLTVDKSR WQQGNVFSCSVMHEALHNHYTQKSLSLSPGGG |

TABLE C-continued

| (Sequences): | | |
|---|---|---|
| SEQ ID NO: | Name | Sequence |
| | | GGSGGGGSREGPELSPDDPAGLLDLRQGMFAQ LVAQNVLLIDGPLSWYSDPGLAGVSLTGGLSY KEDTKELVVAKAGVYYVFFQLELRRVVAGEGS GSVSLALHLQPLRSAAGAAALALTVDLPPASS EARNSAFGFQGRLLHLSAGQRLGVHLHTEARA RHAWQLTQGATVLGLFRVTPEIPAGLPSPRSE |
| 76 | anti-FAP (28H1) Fc hole chain fused to dimeric hu 4-1BBL (71-254) | EVQLLESGGGLVQPGGSLRLSCAASGFTFSSH AMSWVRQAPGKGLEWVSAIWASGEQYYADSVK GRFTISRDNSKNTLYLQMNSLRAEDTAVYYCA KGWLGNFDYWGQGTLVTVSSASTKGPSVFPLA PSSKSTSGGTAALGCLVKDYFPEPVTVSWNSG ALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTP EVTCVVVDVSHEDPEVKFNWYVDGVEVHNAKT KPREEQYNSTYRVVSVLTVLHQDWLNGKEYKC KVSNKALGAPIEKTISKAKGQPREPQVCTLPP SRDELTKNQVSLSCAVKGFYPSDIAVEWESNG QPENNYKTTPPVLDSDGSFFLVSKLTVDKSRW QQGNVFSCSVMHEALHNHYTQKSLSLSPGGGG GSGGGGSREGPELSPDDPAGLLDLRQGMFAQL VAQNVLLIDGPLSWYSDPGLAGVSLTGGLSYK EDTKELVVAKAGVYYVFFQLELRRVVAGEGSG SVSLALHLQPLRSAAGAAALALTVDLPPASSE ARNSAFGFQGRLLHLSAGQRLGVHLHTEARAR HAWQLTQGATVLGLFRVTPEIPAGLPSPRSEG GGGSGGGGSREGPELSPDDPAGLLDLRQGMFA QLVAQNVLLIDGPLSWYSDPGLAGVSLTGGLS YKEDTKELVVAKAGVYYVFFQLELRRVVAGEG SGSVSLALHLQPLRSAAGAAALALTVDLPPAS SEARNSAFGFQGRLLHLSAGQRLGVHLHTEAR ARHAWQLTQGATVLGLFRVTPEIPAGLPSPRS E |
| 77 | anti-FAP (28H1) Fc knob chain fused to monomeric hu 4-1BBL (71-254) | EVQLLESGGGLVQPGGSLRLSCAASGFTFSSH AMSWVRQAPGKGLEWVSAIWASGEQYYADSVK GRFTISRDNSKNTLYLQMNSLRAEDTAVYYCA KGWLGNFDYWGQGTLVTVSSASTKGPSVFPLA PSSKSTSGGTAALGCLVKDYFPEPVTVSWNSG ALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTP EVTCVVVDVSHEDPEVKFNWYVDGVEVHNAKT KPREEQYNSTYRVVSVLTVLHQDWLNGKEYKC KVSNKALGAPIEKTISKAKGQPREPQVYTLPP CRDELTKNQVSLWCLVKGFYPSDIAVEWESNG QPENNYKTTPPVLDSDGSFFLYSKLTVDKSRW QQGNVFSCSVMHEALHNHYTQKSLSLSPGGGG GSGGGGSREGPELSPDDPAGLLDLRQGMFAQL VAQNVLLIDGPLSWYSDPGLAGVSLTGGLSYK EDTKELVVAKAGVYYVFFQLELRRVVAGEGSG SVSLALHLQPLRSAAGAAALALTVDLPPASSE ARNSAFGFQGRLLHLSAGQRLGVHLHTEARAR HAWQLTQGATVLGLFRVTPEIPAGLPSPRSE |
| 78 | DP47 Fc hole chain fused to dimeric hu 4-1BBL (71-254) | EVQLLESGGGLVQPGGSLRLSCAASGFTFSSY AMSWVRQAPGKGLEWVSAIIGSGASTYYADSV KKGRFTISRDNSKNTLYLQMNSLRAEDTAVYY CAKGWFGGFNYWGQGTLVTVSSASTKGPSVFP LAPSSKSTSGGTAALGCLVKDYFPEPVTVSWN SGALTSGVHTFPAVLQSSGLYSLSSVVTVPSS SLGTQTYICNVNHKPSNTKVDKKVEPKSCDKT HTCPPCPAPEAAGGPSVFLFPPKPKDTLMISR TPEVTCVVVDVSHEDPEVKFNWYVDGVEVHNA KTKPREEQYNSTYRVVSVLTVLHQDWLNGKEY KCKVSNKALGAPIEKTISKAKGQPREPQVCTL PPSRDELTKNQVSLSCAVKGFYPSDIAVEWES NGQPENNYKTTPPVLDSDGSFFLVSKLTVDKS RWQQGNVFSCSVMHEALHNHYTQKSLSLSPGG GGGSGGGGSREGPELSPDDPAGLLDLRQGMFA QLVAQNVLLIDGPLSWYSDPGLAGVSLTGGLS YKEDTKELVVAKAGVYYVFFQLELRRVVAGEG SGSVSLALHLQPLRSAAGAAALALTVDLPPAS SEARNSAFGFQGRLLHLSAGQRLGVHLHTEAR |

TABLE C-continued

| | | |
|---|---|---|
| | (Sequences): | |
| SEQ ID NO: | Name | Sequence |
| | | ARHAWQLTQGATVLGLFRVTPEIPAGLPSPRS EGGGGSGGGGSREGPELSPDDPAGLLDLRQGM FAQLVAQNVLLIDGPLSWYSDPGLAGVSLTGG LSYKEDTKELVVAKAGVYYVFFQLELRRVVAG EGSGSVSLALHLQPLRSAAGAAALALTVDLPP ASSEARNSAFGFQGRLLHLSAGQRLGVHLHTE ARARHAWQLTQGATVLGLFRVTPEIPAGLPSP RSE |
| 79 | DP47 Fc knob chain fused to monomeric hu 4-1BBL (71-254) | EVQLLESGGGLVQPGGSLRLSCAASGFTFSSY AMSWVRQAPGKGLEWVSAIIGSGASTYYADSV KKGRFTISRDNSKNTLYLQMNSLRAEDTAVYY CAKGWFGGFNYWGQGTLVTVSSASTKGPSVFP LAPSSKSTSGGTAALGCLVKDYFPEPVTVSWN SGALTSGVHTFPAVLQSSGLYSLSSVVTVPSS SLGTQTYICNVNHKPSNTKVDKKVEPKSCDKT HTCPPCPAPEAAGGPSVFLFPPKPKDTLMISR TPEVTCVVVDVSHEDPEVKFNWYVDGVEVHNA KTKPREEQYNSTYRVVSVLTVLHQDWLNGKEY KCKVSNKALGAPIEKTISKAKGQPREPQVYTL PPCRDELTKNQVSLWCLVKGFYPSDIAVEWES NGQPENNYKTTPPVLDSDGSFFLYSKLTVDKS RWQQGNVFSCSVMHEALHNHYTQKSLSLSPGG GGGSGGGGSREGPELSPDDPAGLLDLRQGMFA QLVAQNVLLIDGPLSWYSDPGLAGVSLTGGLS YKEDTKELVVAKAGVYYVFFQLELRRVVAGEG SGSVSLALHLQPLRSAAGAAALALTVDLPPAS SEARNSAFGFQGRLLHLSAGQRLGVHLHTEAR ARHAWQLTQGATVLGLFRVTPEIPAGLPSPRS E |
| 80 | Human (hbu) FAP | UniProt no. Q12884 |
| 81 | hu FAP ectodomain + poly-lys-tag + his6-tag ("His6" disclosed as SEQ ID NO: 168) | RPSRVHNSEENTMRALTLKDILNGTFSYKTFF PNWISGQEYLHQSADNNIVLYNIETGQSYTIL SNRTMKSVNASNYGLSPDRQFVYLESDYSKLW RYSYTATYYIYDLSNGEFVRGNELPRPIQYLC WSPVGSKLAYVYQNNIYLKQRPGDPPFQITFN GRENKIFNGIPDWVYEEEMLATKYALWWSPNG KFLAYAEFNDTDIPVIAYSYYGDEQYPRTINI PYPKAGAKNPVVRIFIIDTTYPAYVGPQEVPV PAMIASSDYYFSWLTWVTDERVCLQWLKRVQN VSVLSICDFREDWQTWDCPKTQEHIEESRTGW AGGFFVSTPVFSYDAISYYKIFSDKDGYKHIH YIKDTVENAIQITSGKWEAINIFRVTQDSLFY SSNEFEEYPGRRNIYRISIGSYPPSKKCVTCH LRKERCQYYTASFSDYAKYYALVCYGPGIPIS TLHDGRTDQEIKILEENKELENALKNIQLPKE EIKKLEVDEITLWYKMILPPQFDRSKKYPLLI QVYGGPCSQSVRSVFAVNWISYLASKEGMVIA LVDGRGTAFQGDKLLYAVYRKLGVYEVEDQIT AVRKFIEMGFIDEKRIAIWGWSYGGYVSSLAL ASGTGLFKCGIAVAPVSSWEYYASVYTERFMG LPTKDDNLEHYKNSTVMARAEYFRNVDYLLIH GTADDNVHFQNSAQIAKALVNAQVDFQAMWYS DQNHGLSGLSTNHLYTHMTHFLKQCFSLSDGK KKKKKGHHHHHH |
| 82 | mouse FAP | UniProt no. P97321 |
| 83 | Murine FAP ectodomain + poly-lys-tag + his6-tag ("His6" disclosed as SEQ ID NO: 168) | RPSRVYKPEGNTKRALTLKDILNGTFSYKTYF PNWISEQEYLHQSEDDNIVFYNIETRESYIIL SNSTMKSVNATDYGLSPDRQFVYLESDYSKLW RYSYTATYYIYDLQNGEFVRGYELPRPIQYLC WSPVGSKLAYVYQNNIYLKQRPGDPPFQITYT GRENRIFNGIPDWVYEEEMLATKYALWWSPDG KFLAYVEFNDSDIPIIAYSYYGDGQYPRTINI PYPKAGAKNPVVRVFIVDTTYPHHVGPMEVPV PEMIASSDYYFSWLTWVSSERVCLQWLKRVQN VSVLSICDFREDWHAWECPKNQEHVEESRTGW AGGFFVSTPAFSQDATSYYKIFSDKDGYKHIH YIKDTVENAIQITSGKWEAIYIFRVTQDSLFY SSNEFEGYPGRRNIYRISIGNSPPSKKCVTCH LRKERCQYYTASFSYKAKYYALVCYGPGLPIS TLHDGRTDQEIQVLEENKELENSLRNIQLPKV |

TABLE C-continued

| | (Sequences): | |
|---|---|---|

| SEQ ID NO: | Name | Sequence |
|---|---|---|
| | | EIKKLKDGGLTFWYKMILPPQFDRSKKYPLLI QVYGGPCSQSVKSVFAVNWITYLASKEGIVIA LVDGRGTAFQGDKFLHAVYRKLGVYEVEDQLT AVRKFIEMGFIDEERIAIWGWSYGGYVSSLAL ASGTGLFKCGIAVAPVSSWEYYASIYSERFMG LPTKDDNLEHYKNSTVMARAEYFRNVDYLLIH GTADDNVHFQNSAQIAKALVNAQVDFQAMWYS DQNHGILSGRSQNHLYTHMTHFLKQCFSLSDG KKKKKGHHHHHH |
| 84 | Cynomolgus FAP ectodomain + poly-lys-tag + his₆-tag ("His6" disclosed as SEQ ID NO: 168) | RPPRVHNSEENTMRALTLKDILNGTFSYKTFF PNWISGQEYLHQSADNNIVLYNIETGQSYTIL SNRTMKSVNASNYGLSPDRQFVYLESDYSKLW RYSYTATYYIYDLSNGEFVRGNELPRPIQYLC WSPVGSKLAYVYQNNIYLKQRPGDPPFQITFN GRENKIFNGIPDWVYEEEMLATKYALWWSPNG KFLAYAEFNDTDIPVIAYSYYGDEQYPRTINI PYPKAGAKNPFVRIFIIDTTYPAYVGPQEVPV PAMIASSDYYFSWLTWVTDERVCLQWLKRVQN VSVLSICDFREDWQTWDCPKTQEHIEESRTGW AGGFFVSTPVFSYDAISYYKIFSDKDGYKHIH YIKDTVENAIQITSGKWEAINIFRVTQDSLFY SSNEFEDYPGRRNIYRISIGSYPPSKKCVYCH LRKERCQYYTASFSDYAKYYALVCYGPGIPIS TLHDGRTDQEIKILEENKELENALKNIQLPKE EIKKLEVDEITLWYKMILPPQFDRSKKYPLLI QVYGGPCSQSVRSVFAVNWISYLASKEGMVIA LVDGRGTAFQGDKLLYAVYRKLGVYEVEDQIT AVRKFIEMGFIDEKRIAIWGWSYGGYVSSLAL ASGTGLFKCGIAVAPVSSWEYYASVYTERFMG LPTKDDNLEHYKNSTVMARAEYFRNVDYLLIH GTADDNVHFQNSAQIAKALVNAQVDFQAMWYS DQNHGLSGLSTNHLYTHMTHFLKQCFSLSDGK KKKKKGHHHHHH |
| 85 | human CEA | UniProt no. P06731 |
| 86 | full length 4-1BBL | UniProt No. P41273 |
| 87 | 4-1BBL (50-254) | ACPWAVSGARASPGSAASPRLREGPELSPDDP AGLLDLRQGMFAQLVAQNVLLIDGPLSWYSDP GLAGVSLTGGLSYKEDTKELVVAKAGVYYVFF QLELRRVVAGEGSGSVSLALHLQPLRSAAGAA ALALTVDLPPASSEARNSAFGFQGRLLHLSAG QRLGVHLHTEARARHAWQLTQGATVLGLFRVT PEIPAGLPSPRSE |
| 88 | human 4-1BB | UniProt accession No. Q07011 |
| 89 | murine 4-1BB | UniProt accession No. P20334 |
| 90 | cynomolgus 4-1BB | Uniprot accession No. F6W5G6 |
| 91 | G4S peptide linker (SEQ ID NO: 91) | GGGGS |
| 92 | (G4S)2 (SEQ ID NO: 92) | GGGGSGGGGS |
| 93 | (SG4)2 (SEQ ID NO: 93) | SGGGGSGGGG |
| 94 | peptide linker | GGGGSGGGGSGGGG |
| 95 | peptide linker | GSPGSSSSGS |
| 96 | (G4S)3 peptide linker (SEQ ID NO: 96) | GGGGSGGGGSGGGGS |
| 97 | (G4S)4 peptide linker (SEQ ID NO: 97) | GGGGSGGGGSGGGGSGGGGS |
| 98 | peptide linker | GSGSGSGS |
| 99 | peptide linker | GSGSGNGS |
| 100 | peptide linker | GGSGSGSG |

TABLE C-continued

| (Sequences): | | |
|---|---|---|
| SEQ ID NO: | Name | Sequence |
| 101 | peptide linker | GGSGSG |
| 102 | peptide linker | GGSG |
| 103 | peptide linker | GGSGNGSG |
| 104 | peptide linker | GGNGSGSG |
| 105 | peptide linker | GGNGSG |
| 106 | human CD3ε | UniProt No. P07766 |
| 107 | cynomolgus CD3ε | NCBI GenBank no. BAB71849.1 Uniprot Q05LI5 |
| 108 | anti-CEACAM5 Fc hole chain (Construct 5.4) | QVQLVQSGAEVKKPGSSVKVSCKASGFNIKDT YMHWVRQAPGQGLEWMGRIDPANGNSKYVPKF QGRVTITADTSTSTAYMELSSLRSEDTAVYYC APFGYYVSDYAMAYWGQGTLVTVSSASTKGPS VFPLAPSSKSTSGGTAALGCLVKDYFPEPVTV SWNSGALTSGVHTFPAVLQSSGLYSLSSVVTV PSSSLGTQTYICNVNHKPSNTKVDKKVEPKSC DKTHTCPPCPAPEAAGGPSVFLFPPKPKDTLM ISRTPEVTCVVVDVSHEDPEVKFNWYVDGVEV HNAKTKPREEQYNSTYRVVSVLTVLHQDWLNG KEYKCKVSNKALGAPIEKTISKAKGQPREPQV CTLPPSRDELTKNQVSLSCAVKGFYPSDIAVE WESNGQPENNYKTTPPVLDSDGSFFLVSKLTV DKSRWQQGNVFSCSVMHEALHNHYTQKSLSLS PGK |
| 109 | anti-CEACAM5 light chain (Construct 5.4) | EIVLTQSPATLSLSPGERATLSCRAGESVDIF GVGFLHWYQQKPGQAPRLLIYRASNRATGIPA RFSGSGSGTDFTLTISSLEPEDFAVYYCQQTN EDPYTFGQGTKLEIKRTVAAPSVFIFPPSDEQ LKSGTASVVCLLNNFYPREAKVQWKVDNALQS GNSQESVTEQDSKDSTYSLSSTLTLSKADYEK HKVYACEVTHQGLSSPVTKSFNRGEC |
| 110 | human PD-L1 (Uniprot Q9NZQ7) | MRIFAVFIFMTYWHLLNAFTVTVPKDLYVVEY GSNMTIECKFPVEKQLDLAALIVYWEMEDKNI IQFVHGEEDLKVQHSSYRQRARLLKDQLSLGN AALQITDVKLQDAGVYRCMISYGGADYKRITV KVNAPYNKINQRILVVDPVTSEHELTCQAEGY PKAEVIWTSSDHQVLSGKTTTTNSKREEKLFN VTSTLRINTTTNEIFYCTFRRLDPEENHTAEL VIPELPLAHPPNERTHLVILGAILLCLGVALT FIFRLRKGRMMDVKKCGIQDTNSKKQSDTHLE ET |
| 111 | human PD-1 (Uniprot Q15116) | MQIPQAPWPVVWAVLQLGWRPGWFLDSPDRPW NPPTFSPALLVVTEGDNATFTCSFSNTSESFV LNWYRMSPSNQTDKLAAFPEDRSQPGQDCRFR VTQLPNGRDFHMSVVRARRNDSGTYLCGAISL APKAQIKESLRAELRVTERRAEVPTAHPSPSP RPAGQFQTLVVGVVGGLLGSLVLLVWVLAVIC SRAARGTIGARRTGQPLKEDPSAVPVFSVDYG ELDFQWREKTPEPPVPCVPEQTEYATIVFPSG MGTSSPARRGSADGPRSAQPLRPEDGHCSWPL |
| 112 | VH (PD-L1) | EVQLVESGGGLVQPGGSLRLSCAASGFTFSDS WIHWVRQAPGKGLEWVAWISPYGGSTYYADSV KGRFTISADTSKNTAYLQMNSLRAEDTAVYYC ARRHWPGGFDYWGQGTLVTVSS |
| 113 | VL (PD-L1) | DIQMTQSPSSLSASVGDRVTITCRASQDVSTA VAWYQQKPGKAPKLLIYSASFLYSGVPSRFSG SGSGTDFTLTISSLQPEDFATYYCQQYLHPA TFGQGTKVEIK |
| 114 | VH (PD-L1) | EVQLVESGGGLVQPGGSLRLSCAASGFTFSRY WMSWVRQAPGKGLEWVANIKQDGSEKYYVDSV KGRFTISRDNAKNSLYLQMNSLRAEDTAVYYC AREGGWFGELAFDYWGQGTLVTVSS |

TABLE C-continued

| SEQ ID NO: | Name | Sequence |
|---|---|---|
| | (Sequences): | |
| 115 | VL (PD-L1) | EIVLTQSPGTLSLSPGERATLSCRASQRVSSS YLAWYQQKPGQAPRLLIYDASSRATGIPDRFS GSGSGTDFTLTISRLEPEDFAVYYCQQYGSLP WTFGQGTKVEIK |
| 116 | VH (PD-1) | QVQLVQSGVEVKKPGASVKVSCKASGYTFTNY YMYWVRQAPGQGLEWMGGINPSNGGTNFNEKF KNRVTLTTDSSTTTAYMELKSLQFDDTAVYYC ARRDYRFDMGFDYWGQGTTVTVSS |
| 117 | VL (PD-1) | EIVLTQSPATLSLSPGERATLSCRASKGVSTS GYSYLHWYQQKPGQAPRLLIYLASYLESGVPA RFSGSGSGTDFTLTISSLEPEDFAVYYCQHSR DLPLTFGGGTKVEIK |
| 118 | VH (PD-1) | QVQLVESGGGVVQPGRSLRLDCKASGITFSNS GMHWVRQAPGKGLEWVAVIWYDGSKRYYADSV KGRFTISRDNSKNTLFLQMNSLRAEDTAVYYC ATNDDYWGQGTLVTVSS |
| 119 | VL (PD-1) | EIVLTQSPATLSLSPGERATLSCRASQSVSSY LAWYQQKPGQAPRLLIYDASNRATGIPARFSG SGSGTDFTLTISSLEPEDFAVYYCQQSSNWPR TFGQGTKVEIK |
| 120 | DP47 light chain | EIVLTQSPGTLSLSPGERATLSCRASQSVSSS YLAWYQQKPGQAPRLLIYGASSRATGIPDRFS GSGSGTDFTLTISRLEPEDFAVYYCQQYGSSP LTFGQGTKVEIKRTVAAPSVFIFPPSDEQLKS GTASVVCLLNNFYPREAKVQWKVDNALQSGNS QESVTEQDSKDSTYSLSSTLTLSKADYEKHKV YACEVTHQGLSSPVTKSFNRGEC |
| 121 | (CH2527) CD3-HCDR1 | TYAMN |
| 122 | (CH2527) CD3-HCDR2 | RIRSKYNNYATYYADSVKG |
| 123 | (CH2527) CD3-HCDR3 | HGNFGNSYVSWFAY |
| 124 | (16D5) FolR1-HCDR1 | NAWMS |
| 125 | (16D5) FolR1-HCDR2 | RIKSKTDGGTTDYAAPVKG |
| 126 | (16D5) FolR1-HCDR3 | PWEWSWYDY |
| 127 | (CH2527-VL7-46-13)-LCDR1 | GSSTGAVTTSNYAN |
| 128 | (CH2527-VL7-46-13)-LCDR2 | GTNKRAP |
| 129 | (CH2527-VL7-46-13)-LCDR3 | ALWYSNLWV |
| 130 | (CH2527) CD3 VH | EVQLLESGGGLVQPGGSLRLSCAASGFTFSTY AMNWVRQAPGKGLEWVSRIRSKYNNYATYYAD SVKGRFTISRDDSKNTLYLQMNSLRAEDTAVY YCVRHGNFGNSYVSWFAYWGQGTLVTVSS |
| 131 | (16D5) FolR1 VH | EVQLVESGGGLVKPGGSLRLSCAASGFTFSNA WMSWVRQAPGKGLEWVGRIKSKTDGGTTDYAA PVKGRFTISRDDSKNTLYLQMNSLKTEDTAVY YCTTPWEWSWYDYWGQGTLVTVSS |
| 132 | (CH2527-VL7-46-13)VL | QAVVTQEPSLTVSPGGTVTLTCGSSTGAVTTS NYANWVQEKPGQAFRGLIGGTNKRAPGTPARF SGSLLGGKAALTLSGAQPEDEAEYYCALWYSN LWVFGGGTKLTVL |
| 133 | (16D5)VH-CH1-(CH2527)VH-CH1 Fc knob PGLALA | EVQLVESGGGLVKPGGSLRLSCAASGFTFSNA WMSWVRQAPGKGLEWVGRIKSKTDGGTTDYAA PVKGRFTISRDDSKNTLYLQMNSLKTEDTAVY YCTTPWEWSWYDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD GGGGSGGGGSEVQLLESGGGLVQPGGSLRLSC |

TABLE C-continued (Sequences):

| SEQ ID NO: | Name | Sequence |
|---|---|---|
| | | AASGFTFSTYAMNWVRQAPGKGLEWVSRIRSK YNNYATYYADSVKGRFTISRDDSKNTLYLQMN SLRAEDTAVYYCVRRHGNFGNSYVSWFAYWGQ GTLVTVSSASTKGPSVFPLAPSSKSTSGGTAA LGCLVKDYFPEPVTVSWNSGALTSGVHTFPAV LQSSGLYSLSSVVTVPSSSLGTQTYICNVNHK PSNTKVDKKVEPKSCDKTHTCPPCPAPEAAGG PSVFLFPPKPKDTLMISRTPEVTCVVVDVSHE DPEVKFNWYVDGVEVHNAKTKPREEQYNSTYR VVSVLTVLHQDWLNGKEYKCKVSNKALGAPIE KTISKAKGQPREPQVYTLPPCRDELTKNQVSL WCLVKGFYPSDIAVEWESNGQPENNYKTTPPV LDSDGSFFLYSKLTVDKSRWQQGNVFSCSVMH EALHNHYTQKSLSLSPGK |
| 134 | (16D5)VH-CH1-Fc hole PGLALA H435R-Y436F | EVQLVESGGGLVKPGGSLRLSCAASGFTFSNA WMSWVRQAPGKGLEWVGRIKSKTDGGTTDYAA PVKGRFTISRDDSKNTLYLQMNSLKTEDTAVY YCTTPWEWSWYDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALGAPIEKTISKAKGQPREPQVC TLPPSRDELTKNQVSLSCAVKGFYPSDIAVEW ESNGQPENNYKTTPPVLDSDGSFFLVSKLTVD KSRWQQGNVFSCSVMHEALHNRFTQKSLSLSP GK |
| 135 | (CH2527-VL7-46-13)VL-CL (common light chain) | QAVVTQEPSLTVSPGGTVTLTCGSSTGAVTTS NYANWVQEKPGQAFRGLIGGTNKRAPGTPARF SGSLLGGKAALTLSGAQPEDEAEYYCALWYSN LWVFGGGTKLTVLGQPKAAPSVTLFPPSSEEL QANKATLVCLISDFYPGAVTVAWKADSSPVKA GVETTTPSKQSNNKYAASSYLSLTPEQWKSHR SYSCQVTHEGSTVEKTVAPTECS |
| 136 | di-mu4-1BBL-CL Fc knob chain | see Table 21 |
| 137 | mono-mu4-1BBL-CH1 chain | see Table 21 |
| 138 | VHCH1 (4B9) Fc hole chain | see Table 21 |
| 139 | VLCL(4B9) Light chain | see Table 21 |
| 140 | VHCH1 (MU137-1)-Heavy chain Fc-DD-VL (28H1) | see Table 23 |
| 141 | VHCH1 (20H4.9)-Heavy chain Fc-KK-VH (28H1) | see Table 23 |
| 142 | VLCL-Light chain (MU137-1) | see Table 23 |
| 143 | VHCH1 (MU137-1)-Heavy chain Fc-DD-VH (28H1) | see Table 24 |
| 144 | VHCH1 (MU137-1)-Heavy chain Fc-KK-VL (28H1) | see Table 24 |
| 145 | murine PD-L1 antibody heavy chain | EVQLVESGGGLVQPGGSLRLSCAASGFTFSDS WIHWVRQAPGKGLEWVAWISPYGGSTYYADSV KGRFTISADTSKNTAYLQMNSLRAEDTAVYYC ARRHWPGGFDYWGQGTLVTVSSAAKTTPPSVYP LAPGSAAQTNSMVTLGCLVKGYFPEPVTVTWN SGSLSSGVHTFPAVLQSDLYTLSSSVTVPSST WPSETVTCNVAHPASSTKVDKKIVPRDCGCKP CICTVPEVSSVFIFPPKPKDVLTITLTPKVTC VVVDISKDAPEVQFSWFVDDVEVHTAQTQPRE EQFNSTFRSVSELPIMHQDWLNGKEFKCRVNS AAFGAPIEKTISKTKGRPKAPQVYTIPPPKEQ |

TABLE C-continued

| | | (Sequences): |
|---|---|---|

| SEQ ID NO: | Name | Sequence |
|---|---|---|
| | | MAKDKVSLTCMITDFFPEDITVEWQWNGQPAE NYKNTQPIMDTDGSYFVYSKLNVQKSNWEAGN TFTCSVLHEGLHNHHTEKSLSHSPGK |
| 146 | murine PD-L1 antibody light chain | DIQMTQSPSSLSASVGDRVTITCRASQDVSTA VAWYQQKPGKAPKLLIYSASFLYSGVPSRFSG SGSGTDFTLTISSLQPEDFATYYCQQYLYHPA TFGQGTKVEIKRADAAPTVSIFPPSSEQLTSG GASVVCFLNNFYPKDINVKWKIDGSERQNGVL NSWTDQDSKDSTYSMSSTLTLTKDEYERHNSY TCEATHKTSTSPIVKSFNRNEC |
| 147 | MCSP CD3 TCB (MCSP) light chain | DIQMTQSPSSLSASVGDRVTITCRASQGIRNY LNWYQQKPGKAPKLLIYYTSSLHSGVPSRFSG SGSGTDYTLTISSLQPEDFATYYCQQYSALPW TFGQGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| 148 | MCSP CD3 TCB (CD3) light chain | QAVVTQEPSLTVSPGGTVTLTCGSSTGAVTTS NYANWVQEKPGQAFRGLIGGTNKRAPGTPARF SGSLLGGKAALTLSGAQPEDEAEYYCALWYSN LWVFGGGTKLTVLSSASTKGPSVFPLAPSSKS TSGGTAALGCLVKDYFPEPVTVSWNSGALTSG VHTFPAVLQSSGLYSLSSVVTVPSSSLGTQTY ICNVNHKPSNTKVDKKVEPKSC |
| 149 | MCSP CD3 TCB heavy chain 1 | QVQLQESGPGLVKPSQTLSLTCTVSGGSITSG YYWNWIRQHPGKGLEWIGYITFDGSNNYNPSL KSRVTISRDTSKNQFSLKLSSVTAADTAVYYC ADFDYWQGQGTLVTVSSASTKGPSVFPLAPSS KSTSGGTAALGCLVKDYFPEPVTVSWNSGALT SGVHTFPAVLQSSGLYSLSSVVTVPSSSLGTQ TYICNVNHKPSNTKVDKKVEPKSCDGGGGSGG GGSEVQLLESGGGLVQPGGSLRLSCAASGFTF STYAMNWVRQAPGKGLEWVSRIRSKYNNYATY YADSVKGRFTISRDDSKNTLYLQMNSLRAEDT AVYYCVRHGNFGNSYVSWFAYWGQGTLVTVSS ASVAAPSVFIFPPSDEQLKSGTASVVCLLNNF YPREAKVQWKVDNALQSGNSQESVTEQDSKDS TYSLSSTLTLSKADYEKHKVYACEVTHQGLSS PVTKSFNRGECDKTHTCPPCPAPEAAGGPSVF LFPPKPKDTLMISRTPEVTCVVVDVSHEDPEV KFNWYVDGVEVHNAKTKPREEQYNSTYRVVSV LTVLHQDWLNGKEYKCKVSNKALGAPIEKTIS KAKGQPREPQVYTLPPCRDELTKNQVSLWCLV KGFYPSDIAVEWESNGQPENNYKTTPPVLDSD GSFFLYSKLTVDKSRWQQGNVFSCSVMHEALH NHYTQKSLSLSPGK |
| 150 | MCSP CD3 TCB heavy chain 2 | QVQLQESGPGLVKPSQTLSLTCTVSGGSITSG YYWNWIRQHPGKGLEWIGYITFDGSNNYNPSL KSRVTISRDTSKNQFSLKLSSVTAADTAVYYC ADFDYWGQGTLVTSSASTKGPSVFPLAPSSKS TSGGTAALGCLVKDYFPEPVTVSWNSGALTSG VHTFPAVLQSSGLYSLSSVVTVPSSSLGTQTY ICNVNHKPSNTKVDKKVEPKSCDKTHTCPPCP APEAAGGPSVFLFPPKPKDTLMISRTPEVTCV VVDVSHEDPEVKFNWYVDGVEVHAKTKPREEQ YNSTYRVVSVLTVLHQDWLNGKEYKCKVSNKA LGAPIEKTISKAKGQPREPQVCTLPPSRDELT KNQVSLSCAVKGFYPSDIAVEWESNGQPENNY KTTPPVLDSDGSFFLVSKLTVDKSRWQQGNVF SCSVMHEALHNHYTQKSLSLSPGK |
| 151 | MCSP-HCDR1 | SGYYWN |
| 152 | MCSP-HCDR2 | YITFDGSNNY NPSLKS |
| | MCSP-HCDR3 | FDY |
| 154 | MCSP-LCDR1 | RASQGIRNYLN |
| 155 | MCSP-LCDR2 | YTSSLHS |

TABLE C-continued

| (Sequences): | | |
|---|---|---|
| SEQ ID NO: | Name | Sequence |
| 156 | MCSP-LCDR3 | QQYSALPWT |
| 157 | MCSP VH | QVQLQESGPGLVKPSQTLSLTCTVSGGSITSG YYWNWIRQHPGKGLEWIGYITFDGSNNYNPSL KSRVTISRDTSKNQFSLKLSSVTAADTAVYYC ADFDYWGQGTLVTVSS |
| 158 | MCSP VL | DIQMTQSPSSLSASVGDRVTITCRASQGIRNY LNWYQQKPGKAPKLLIYYTSSLHSGVPSRFSG SGSGTDYTLTISSLQPEDFATYYCQQYSALPW TFGQGTKVEIK |
| 159 | CD20 | UniProt accession No. P11836 |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, MD (1991)) as defined above.

Aspects of the Invention

In the following, some of the aspects of the invention are listed.

1. A T-cell activating anti-CD3 bispecific antibody specific for a tumor-associated antigen for use in a method for treating or delaying progression of cancer, wherein the T-cell activating anti-CD3 bispecific antibody specific for a tumor-associated antigen is used in combination with a 4-1BB (CD137) agonist.

2. The T-cell activating anti-CD3 bispecific antibody specific for a tumor-associated antigen for use in a method of aspect 1, wherein the T-cell activating anti-CD3 bispecific antibody specific for a tumor-associated antigen is an anti-CEA/anti-CD3 bispecific antibody.

3. The anti-CEA/anti-CD3 bispecific antibody for use in a method of aspects 1 or 2, wherein the T-cell activating anti-CD3 bispecific antibody and the 4-1BB agonist are administered together in a single composition or administered separately in two or more different compositions.

4. The anti-CEA/anti-CD3 bispecific antibody for use in a method of the preceding aspects, wherein the 4-1BB agonist comprises three ectodomains of 4-1BBL or fragments thereof.

5. The anti-CEA/anti-CD3 bispecific antibody for use in a method of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

6. The anti-CEA/anti-CD3 bispecific antibody for use in a method of the preceding aspects, wherein the 4-1BB agonist is an antigen binding molecule comprising three ectodomains of 4-1BBL or fragments thereof and at least one antigen binding domain capable of specific binding to a tumor-associated antigen.

7. The anti-CEA/anti-CD3 bispecific antibody for use in a method of the preceding aspects, wherein the 4-1BB agonist is an antigen binding molecule comprising three ectodomains of 4-1BBL or fragments thereof and at least one antigen binding domain capable of specific binding to Fibroblast activation protein (FAP).

8. The anti-CEA/anti-CD3 bispecific antibody for use in a method of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises (a) a heavy chain variable region ($V_HFAP$) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region ($V_LFAP$) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region ($V_HFAP$) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region ($V_LFAP$) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

9. The anti-CEA/anti-CD3 bispecific antibody for use in a method of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_HFAP$) comprising an amino acid sequence of SEQ ID NO:21 and a light chain variable region ($V_LFAP$) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

10. The anti-CEA/anti-CD3 bispecific antibody for use in a method of the preceding aspects, wherein the 4-1BB agonist is an antigen binding molecule comprising an IgG Fc domain, specifically an IgG1 Fc domain or an IgG4 Fc domain.

11. The anti-CEA/anti-CD3 bispecific antibody for use in a method of the preceding aspects, wherein the 4-1BB agonist is an antigen binding molecule comprising a Fc domain that comprises one or more amino acid substitution that reduces binding to an Fe receptor and/or effector function.

12. The anti-CEA/anti-CD3 bispecific antibody for use in a method of the preceding aspects, wherein the 4-1BB agonist is an antigen binding molecule comprising (a) at least one antigen binding domain capable of specific binding to FAP, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

13. The anti-CEA/anti-CD3 bispecific antibody for use in a method of any one of the preceding aspects, wherein the 4-1BB agonist is an antigen binding molecule comprising (a) at least one Fab domain capable of specific binding to CD19, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

14. The anti-CEA/anti-CD3 bispecific antibody for use in a method of the preceding aspects, wherein the 4-1BB agonist is an antigen binding molecule comprising (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

15. The anti-CEA/anti-CD3 bispecific antibody for use in a method of the preceding aspects, wherein the 4-1BB agonist is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72.

16. The anti-CEA/anti-CD3 bispecific antibody for use in a method of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

17. The anti-CEA/anti-CD3 bispecific antibody for use in a method of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

18. The anti-CEA/anti-CD3 bispecific antibody for use in a method of the preceding aspects, wherein the 4-1BB agonist is an anti-FAP/anti-4-1BB bispecific antibody.

19. The anti-CEA/anti-CD3 bispecific antibody for use in a method of the preceding aspects, wherein the 4-1BB agonist is an antigen binding molecule comprising three ectodomains of 4-1BBL or fragments thereof and at least one antigen binding domain capable of specific binding to CEA.

20. The anti-CEA/anti-CD3 bispecific antibody for use in a method of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises (a) a heavy chain variable region ($V_H$CEA) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region ($V_L$CEA) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

21. The anti-CEA/anti-CD3 bispecific antibody for use in a method of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:55 and a light chain variable region ($V_L$CEA) comprising an amino acid sequence of SEQ ID NO:56.

22. The anti-CEA/anti-CD3 bispecific antibody for use in a method of the preceding aspects, wherein the 4-1BB agonist is an antigen binding molecule comprising an IgG Fc domain, specifically an IgG1 Fc domain or an IgG4 Fc domain.

23. The anti-CEA/anti-CD3 bispecific antibody for use in a method of the preceding aspects, wherein the 4-1BB agonist is an antigen binding molecule comprising a Fc domain that comprises one or more amino acid substitution that reduces binding to an Fc receptor and/or effector function.

24. The anti-CEA/anti-CD3 bispecific antibody for use in a method of the preceding aspects, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

25. The anti-CEA/anti-CD3 bispecific antibody for use in a method of any one of the preceding aspects, wherein the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

26. The anti-CEA/anti-CD3 bispecific antibody for use in a method of the preceding aspects, wherein the 4-1BB agonist is an antigen binding molecule comprising (a) at least one Fab domain capable of specific binding to CEA comprising a heavy chain variable region ($V_H$CEA) comprising the amino acid sequence of SEQ ID NO:55 and a light chain variable region ($V_L$CEA) comprising the amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

27. The anti-CEA/anti-CD3 bispecific antibody for use in a method of the preceding aspects, wherein the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

28. The anti-CEA/anti-CD3 bispecific antibody for use in a method of the preceding aspects, wherein the 4-1BB agonist is an antigen binding molecule comprising
(a) at least one antigen binding domain capable of specific binding to CEA,
(b) a polypeptide comprising three ectodomains of 4-1BBL or fragments thereof that are connected to each other by peptide linkers.

29. The anti-CEA/anti-CD3 bispecific antibody for use in a method of the preceding aspects, wherein the 4-1BB agonist is an antigen binding molecule comprising
(a) at least one antigen binding domain capable of specific binding to CEA,
(b) a polypeptide comprising three ectodomains of 4-1BBL or fragments thereof that are connected to each other by peptide linkers, and
(c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

30. The anti-CEA/anti-CD3 bispecific antibody for use in a method of the preceding aspects, wherein the 4-1BB agonist is an anti-CEA/anti-4-1BB bispecific antibody.

31. The anti-CEA/anti-CD3 bispecific antibody for use in a method of the preceding aspects, wherein the anti-CEA/anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$CEA) and a light chain variable region ($V_L$CEA).

32. The anti-CEA/anti-CD3 bispecific antibody for use in a method of the preceding aspects, wherein the first antigen binding domain comprises a heavy chain variable region ($V_H$CD3) comprising CDR-H1 sequence of SEQ ID NO:33, CDR-H2 sequence of SEQ ID NO:34, and CDR-H3 sequence of SEQ ID NO:35; and/or a light chain variable region ($V_L$CD3) comprising CDR-L1 sequence of SEQ ID NO:36, CDR-L2 sequence of SEQ ID NO:37, and CDR-L3 sequence of SEQ ID NO:38.

33. The anti-CEA/anti-CD3 bispecific antibody for use in a method of the preceding aspects, wherein the first antigen binding domain comprises a heavy chain variable region ($V_H$CD3) comprising the amino acid sequence of SEQ ID NO:39 and/or a light chain variable region ($V_L$CD3) comprising the amino acid sequence of SEQ ID NO:40.

34. The anti-CEA/anti-CD3 bispecific antibody for use in a method of the preceding aspects, wherein the second antigen binding domain comprises
(a) a heavy chain variable region ($V_H$CEA) comprising CDR-H1 sequence of SEQ ID NO:41, CDR-H2 sequence of SEQ ID NO:42, and CDR-H3 sequence of SEQ ID NO:43, and/or a light chain variable region ($V_L$CEA) comprising CDR-L1 sequence of SEQ ID NO:44, CDR-L2 sequence of SEQ ID NO:45, and CDR-L3 sequence of SEQ ID NO:46, or
(b) a heavy chain variable region ($V_H$CEA) comprising CDR-H1 sequence of SEQ ID NO:49, CDR-H2 sequence of SEQ ID NO:50, and CDR-H3 sequence of SEQ ID NO:51, and/or a light chain variable region ($V_L$CEA) comprising CDR-L1 sequence of SEQ ID NO:52, CDR-L2 sequence of SEQ ID NO:53, and CDR-L3 sequence of SEQ ID NO:54.

35. The anti-CEA/anti-CD3 bispecific antibody for use in a method of the preceding aspects, wherein the second antigen binding domain comprises a heavy chain variable region ($V_H$CEA) comprising the amino acid sequence of SEQ ID NO:47 and/or a light chain variable region ($V_L$CEA) comprising the amino acid sequence of SEQ ID NO:48 or wherein the second antigen binding domain comprises a heavy chain variable region ($V_H$CEA) comprising the amino acid sequence of SEQ ID NO:55 and/or a light chain variable region ($V_L$CEA) comprising the amino acid sequence of SEQ ID NO:56.

36. The anti-CEA/anti-CD3 bispecific antibody for use in a method of the preceding aspects, wherein the anti-CEA/anti-CD3 bispecific antibody comprises a third antigen binding domain that binds to CEA.

37. The anti-CEA/anti-CD3 bispecific antibody for use in a method of the preceding aspects, wherein the third antigen binding domain comprises a heavy chain variable region ($V_H$CEA) comprising the amino acid sequence of SEQ ID NO:47 and/or a light chain variable region ($V_L$CEA) comprising the amino acid sequence of SEQ ID NO:48 or wherein the second antigen binding domain comprises a heavy chain variable region ($V_H$CEA) comprising the amino acid sequence of SEQ ID NO:55 and/or a light chain variable region ($V_L$CEA) comprising the amino acid sequence of SEQ ID NO:56.

38. The anti-CEA/anti-CD3 bispecific antibody for use in a method of any one of the preceding aspects, wherein the first antigen binding domain is a cross-Fab molecule wherein the variable domains or the constant domains of the Fab heavy and light chain are exchanged, and the second and third, if present, antigen binding domain is a conventional Fab molecule.

39. The anti-CEA/anti-CD3 bispecific antibody for use in a method of any one of the preceding aspects, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

40. The anti-CEA/anti-CD3 bispecific antibody for use in a method of the preceding aspects, wherein the anti-CEA/anti-CD3 bispecific antibody comprises an Fc domain comprising one or more amino acid substitutions that reduce binding to an Fc receptor and/or effector function.

41. The anti-CEA/anti-CD3 bispecific antibody for use in a method of any one of the preceding aspects, wherein the anti-CEA/anti-CD3 bispecific antibody comprises an IgG1 Fc domain comprising the amino acid substitutions L234A, L235A and P329G.

42. An anti-CEA/anti-CD3 bispecific antibody for use in a method of any one of the preceding aspects, wherein the anti-CEA/anti-CD3 bispecific antibody is used in combination with a 4-1BB (CD137) agonist and wherein the combination is administered at intervals from about one week to three weeks.

43. The T-cell activating anti-CD3 bispecific antibody specific for a tumor-associated antigen for use in a method of any one of the preceding aspects, wherein the T-cell activating anti-CD3 bispecific antibody specific for a tumor-associated antigen is used in combination with a 4-1BB (CD137) agonist and in combination with an agent blocking PD-L1/PD-1 interaction.

44. The T-cell activating anti-CD3 bispecific antibody specific for a tumor-associated antigen for use in a method of aspect 43, wherein the agent blocking PD-L1/PD-1 interaction is a anti-PD-L1 antibody or an anti-PD1 antibody.

45. A pharmaceutical product comprising (A) a first composition comprising as active ingredient an anti-CEA/anti-CD3 bispecific antibody and a pharmaceutically acceptable carrier; and (B) a second composition comprising as active ingredient a 4-1BB agonist and a pharmaceutically acceptable carrier, for use in the combined, sequential or simultaneous, treatment of a disease, in particular cancer.

46. A pharmaceutical composition comprising anti-CEA/anti-CD3 bispecific antibody and a 4-1BB agonist.

47. The pharmaceutical composition of aspect 46 for use in the treatment of solid tumors.

48. The pharmaceutical composition of any one of the preceding aspects, wherein the 4-1BB agonist comprises three ectodomains of 4-1BBL or fragments thereof.

49. The pharmaceutical composition of any one of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

50. The pharmaceutical composition of any one of the preceding aspects, wherein the 4-1BB agonist is an antigen binding molecule comprising three ectodomains of 4-1BBL or fragments thereof and at least one antigen binding domain capable of specific binding to a tumor associated antigen.

51. The pharmaceutical composition of any one of the preceding aspects, wherein the tumor associated antigen is FAP.

52. The pharmaceutical composition of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises
(a) a heavy chain variable region (V$_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region (V$_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or
(b) a heavy chain variable region (V$_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region (V$_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

53. The pharmaceutical composition of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region (V$_H$FAP) comprising an amino acid sequence of SEQ ID NO:21 and a light chain variable region (V$_L$FAP) comprising an amino acid sequence of SEQ ID NO:22 or wherein the antigen binding domain capable of specific binding to FAP comprises a heavy chain variable region (V$_H$FAP) comprising an amino acid sequence of SEQ ID NO:23 and a light chain variable region (V$_L$FAP) comprising an amino acid sequence of SEQ ID NO:24.

54. The pharmaceutical composition of any one of the preceding aspects, wherein the 4-1BB agonist is an antigen binding molecule further comprising a Fc domain composed of a first and a second subunit capable of stable association.

55. The pharmaceutical composition of any one of the preceding aspects, wherein the 4-1BB agonist is an antigen binding molecule comprising an IgG Fc domain, specifically an IgG1 Fc domain or an IgG4 Fc domain.

56. The pharmaceutical composition of any one of the preceding aspects, wherein the 4-1BB agonist is an antigen binding molecule comprising a Fc domain that comprises one or more amino acid substitution that reduces binding to an Fc receptor and/or effector function.

57. The pharmaceutical composition of any one of the preceding aspects, wherein the 4-1BB agonist is an antigen binding molecule comprising an IgG1 Fc domain comprising the amino acid substitutions L234A, L235A and P329G.

58. The pharmaceutical composition of any one of the preceding aspects, wherein the 4-1BB agonist is an antigen binding molecule comprising
(a) at least one antigen binding domain capable of specific binding to FAP,
(b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

59. The pharmaceutical composition of any one of the preceding aspects, wherein the 4-1BB agonist is an antigen binding molecule comprising
(a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

60. The pharmaceutical composition of any one of the preceding aspects, wherein the 4-1BB agonist is an antigen binding molecule comprising (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

61. The pharmaceutical composition of any one of the preceding aspects, wherein wherein the 4-1BB agonist is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72. 62. The pharmaceutical composition of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

63. The pharmaceutical composition of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

64. The pharmaceutical composition of any one of the preceding aspects, wherein the 4-1BB agonist is an anti-FAP/anti-4-1BB bispecific antibody.

65. The pharmaceutical composition of any one of the preceding aspects, wherein the tumor associated antigen is CEA.

66. The pharmaceutical composition of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region ($V_L$CEA) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

67. The pharmaceutical composition of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:55 and a light chain variable region ($V_L$CEA) comprising an amino acid sequence of SEQ ID NO:56.

68. The pharmaceutical composition of any one of the preceding aspects, wherein the 4-1BB agonist is an antigen binding molecule further comprising a Fc domain composed of a first and a second subunit capable of stable association.

69. The pharmaceutical composition of any one of the preceding aspects, wherein the 4-1BB agonist is an antigen binding molecule comprising an IgG Fc domain, specifically an IgG1 Fc domain or an IgG4 Fc domain.

70. The pharmaceutical composition of any one of the preceding aspects, wherein the 4-1BB agonist is an antigen binding molecule comprising a Fc domain that comprises one or more amino acid substitution that reduces binding to an Fc receptor and/or effector function.

71. The pharmaceutical composition of any one of the preceding aspects, wherein the 4-1BB agonist is an antigen binding molecule comprising an IgG1 Fc domain comprising the amino acid substitutions L234A, L235A and P329G.

72. The pharmaceutical composition of any one of the preceding aspects, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

73. The pharmaceutical composition of any one of the preceding aspects, wherein the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

74. The pharmaceutical composition of any one of the preceding aspects, wherein the 4-1BB agonist is an antigen binding molecule comprising (a) (a) at least one Fab domain capable of specific binding to CEA comprising a heavy chain variable region ($V_H$CEA) comprising the amino acid sequence of SEQ ID NO:55 and a light chain variable region ($V_L$CEA) comprising the amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

75. The pharmaceutical composition of any one of the preceding aspects, wherein wherein the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

76. The pharmaceutical composition of any one of the preceding aspects, wherein the 4-1BB agonist is an antigen binding molecule comprising (a) at least one antigen binding domain capable of specific binding to CEA, (b) a polypeptide comprising ectodomains of 4-1BBL or fragments thereof that are connected to each other by peptide linkers.

77. The pharmaceutical composition of any one of the preceding aspects, wherein the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

78. The pharmaceutical composition of any one of the preceding aspects, wherein the 4-1BB agonist is an anti-CEA/anti-4-1BB bispecific antibody.

79. The pharmaceutical composition of any one of the preceding aspects, wherein the anti-CEA/anti-CD3 bispecific antibody comprises a first antigen binding domain that binds to CD3, and a second antigen binding domain that binds to CEA.

80. The pharmaceutical composition of any one of the preceding aspects, wherein the anti-CEA/anti-CD3 bispecific antibody comprises a first antigen binding domain comprising a heavy chain variable region (V$_H$CD3) and a light chain variable region (V$_L$CD3), and a second antigen binding domain comprising a heavy chain variable region (V$_H$CEA) and a light chain variable region (V$_L$CEA).

81. The pharmaceutical composition of any one of the preceding aspects, wherein the first antigen binding domain comprises a heavy chain variable region (V$_H$CD3) comprising CDR-H1 sequence of SEQ ID NO:33, CDR-H2 sequence of SEQ ID NO:34, and CDR-H3 sequence of SEQ ID NO:35; and/or a light chain variable region (V$_L$CD3) comprising CDR-L1 sequence of SEQ ID NO:36, CDR-L2 sequence of SEQ ID NO:37, and CDR-L3 sequence of SEQ ID NO:38.

82. The pharmaceutical composition of any one of the preceding aspects, wherein the first antigen binding domain comprises a heavy chain variable region (V$_H$CD3) comprising the amino acid sequence of SEQ ID NO:39 and/or a light chain variable region (V$_L$CD3) comprising the amino acid sequence of SEQ ID NO:40.

83. The pharmaceutical composition of any one of the preceding aspects, wherein the second antigen binding domain comprises (a) a heavy chain variable region (V$_H$CEA) comprising CDR-H1 sequence of SEQ ID NO:41, CDR-H2 sequence of SEQ ID NO:42, and CDR-H3 sequence of SEQ ID NO:43, and/or a light chain variable region (V$_L$CEA) comprising CDR-L1 sequence of SEQ ID NO:44, CDR-L2 sequence of SEQ ID NO:45, and CDR-L3 sequence of SEQ ID NO:46, or (b) a heavy chain variable region (V$_H$CEA) comprising CDR-H1 sequence of SEQ ID NO:49, CDR-H2 sequence of SEQ ID NO:50, and CDR-H3 sequence of SEQ ID NO:51, and/or a light chain variable region (V$_L$CEA) comprising CDR-L1 sequence of SEQ ID NO:52, CDR-L2 sequence of SEQ ID NO:53, and CDR-L3 sequence of SEQ ID NO:54.

84. The pharmaceutical composition of any one of the preceding aspects, wherein the second antigen binding domain comprises a heavy chain variable region (V$_H$CEA) comprising the amino acid sequence of SEQ ID NO:47 and/or a light chain variable region (V$_L$CEA) comprising the amino acid sequence of SEQ ID NO:48 or wherein the second antigen binding domain comprises a heavy chain variable region (V$_H$CEA) comprising the amino acid sequence of SEQ ID NO:55 and/or a light chain variable region (V$_L$CEA) comprising the amino acid sequence of SEQ ID NO:56.

85. The pharmaceutical composition of any one of the preceding aspects, wherein the anti-CEA/anti-CD3 bispecific antibody comprises a third antigen binding domain that binds to CEA.

86. The pharmaceutical composition of any one of the preceding aspects, wherein the third antigen binding domain comprises (a) a heavy chain variable region (V$_H$CEA) comprising CDR-H1 sequence of SEQ ID NO:41, CDR-H2 sequence of SEQ ID NO:42, and CDR-H3 sequence of SEQ ID NO:43, and/or a light chain variable region (V$_L$CEA) comprising CDR-L1 sequence of SEQ ID NO:44, CDR-L2 sequence of SEQ ID NO:45, and CDR-L3 sequence of SEQ ID NO:46, or (b) a heavy chain variable region (V$_H$CEA) comprising CDR-H1 sequence of SEQ ID NO:49, CDR-H2 sequence of SEQ ID NO:50, and CDR-H3 sequence of SEQ ID NO:51, and/or a light chain variable region (V$_L$CEA) comprising CDR-L1 sequence of SEQ ID NO:52, CDR-L2 sequence of SEQ ID NO:53, and CDR-L3 sequence of SEQ ID NO:54.

87. The pharmaceutical composition of any one of the preceding aspects, wherein the third antigen binding domain comprises a heavy chain variable region (V$_H$CEA) comprising the amino acid sequence of SEQ ID NO:47 and/or a light chain variable region (V$_L$CEA) comprising the amino acid sequence of SEQ ID NO:48 or wherein the second antigen binding domain comprises a heavy chain variable region (V$_H$CEA) comprising the amino acid sequence of SEQ ID NO:55 and/or a light chain variable region (V$_L$CEA) comprising the amino acid sequence of SEQ ID NO:56.

88. The pharmaceutical composition of any one of the preceding aspects, wherein the first antigen binding domain is a cross-Fab molecule wherein the variable domains or the constant domains of the Fab heavy and light chain are exchanged, and the second and third, if present, antigen binding domain is a conventional Fab molecule.

89. The pharmaceutical composition of any one of the preceding aspects, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

90. The pharmaceutical composition of any one of the preceding aspects, wherein the anti-CEA/anti-CD3 bispecific antibody comprises an Fc domain comprising one or more amino acid substitutions that reduce binding to an Fc receptor and/or effector function.

91. The pharmaceutical composition of any one of the preceding aspects, wherein the anti-CEA/anti-CD3 bispecific antibody comprises an IgG1 Fc domain comprising the amino acid substitutions L234A, L235A and P329G.

92. The pharmaceutical composition of any one of the preceding aspects, wherein the anti-CEA/anti-CD3 bispecific antibody is used in combination with a 4-1BB (CD137) agonist and wherein the combination is administered at intervals from about one week to three weeks.

93. The pharmaceutical composition of any one of the preceding aspects for use in treating or delaying progression of a proliferative disease, in particular cancer.

94. The pharmaceutical composition of any one of the preceding aspects for use in the treatment of colon cancer, lung cancer, ovarian cancer, gastric cancer, bladder cancer, pancreatic cancer, endometrial cancer, breast cancer, kidney cancer, esophageal cancer, or prostate cancer.

95. A kit for treating or delaying progression of cancer in a subject, comprising a package comprising (A) a first composition comprising as active ingredient an anti-CEA/anti-CD3 bispecific antibody and a pharmaceutically acceptable carrier; (B) a second composition comprising as active ingredient a 4-1BB agonist and a pharmaceutically acceptable carrier, and (C) instructions for using the compositions in a combination therapy.

96. Use of a combination of an anti-CEA/anti-CD3 bispecific antibody and a 4-1BB agonist in the manufacture of a medicament for treating or delaying progression of a proliferative disease, in particular cancer.

97. Use of a combination of an anti-CEA/anti-CD3 bispecific antibody and a 4-1BB agonist in the manufacture of a medicament, wherein the medicament is for the treatment of solid tumors.

98. A method for treating or delaying progression of cancer in a subject comprising administering to the subject an effective amount of an anti-CEA/anti-CD3 antibody and a 4-1BB agonist.

99. A method for treating or delaying progression of cancer in a subject comprising administering to the subject an effective amount of an anti-CEA/anti-CD3 antibody and a 4-1BB agonist, wherein the 4-1BB agonist is an antigen binding molecule.

100. The method of any one of the preceding aspects, wherein the 4-1BB agonist is an antigen binding molecule comprising a Fc domain.

101. The method of any one of the preceding aspects, wherein the 4-1BB agonist is an antigen binding molecule comprising a Fc domain with modifications reducing Fcγ receptor binding and/or effector function.

102. The method of any one of the preceding aspects, wherein the 4-1BB agonist is an antigen binding molecule comprising three ectodomains of 4-1BBL or fragments thereof.

103. The method of any one of the preceding aspects, wherein the −1BB agonist is an antigen binding molecule comprising three ectodomains of 4-1BBL or fragments thereof and an antigen binding domain capable of specific binding to a tumor associated antigen.

104. The method of any one of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

105. The method of any one of the preceding aspects, wherein the 4-1BB agonist is an antigen binding molecule comprising three ectodomains of 4-1BBL or fragments thereof and at least one moiety capable of specific binding to FAP, wherein the antigen binding domain capable of specific binding to FAP comprises (a) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

106. The method of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

107. The method of any one of the preceding aspects, wherein the 4-1BB agonist is an antigen binding molecule further comprising a Fc domain composed of a first and a second subunit capable of stable association.

108. The method of any one of the preceding aspects, wherein the 4-1BB agonist is an antigen binding molecule comprising an IgG Fc domain, specifically an IgG1 Fc domain or an IgG4 Fc domain.

109. The method of any one of the preceding aspects, wherein the 4-1BB agonist is an antigen binding molecule comprising a Fc domain that comprises one or more amino acid substitution that reduces binding to an Fc receptor and/or effector function.

110. The method of any one of the preceding aspects, wherein the 4-1BB agonist is an antigen binding molecule comprising (a) at least one antigen binding domain capable of specific binding to FAP, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

111. The method of any one of the preceding aspects, wherein the 4-1BB agonist is an antigen binding molecule comprising (a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

112. The method of any one of the preceding aspects, wherein the 4-1BB agonist is an antigen binding molecule comprising (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

113. The method of any one of the preceding aspects, wherein the 4-1BB agonist is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72.

114. The method of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

115. The method of any one of the preceding aspects, wherein the 4-1BB agonist is an anti-FAP/anti-4-1BB bispecific antibody.

116. The method of any one of the preceding aspects, wherein the 4-1BB agonist is an antigen binding molecule comprising three ectodomains of 4-1BBL or fragments thereof and at least one moiety capable of specific binding to CEA, wherein the antigen binding domain capable of specific binding to CEA comprises a heavy chain variable region ($V_H$CEA) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region ($V_L$CEA) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

117. The method of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:55 and a light chain variable region ($V_L$CEA) comprising an amino acid sequence of SEQ ID NO:56.

118. The method of any one of the preceding aspects, wherein the 4-1BB agonist is an antigen binding molecule further comprising a Fc domain composed of a first and a second subunit capable of stable association.

119. The method of any one of the preceding aspects, wherein the 4-1BB agonist is an antigen binding molecule comprising an IgG Fc domain, specifically an IgG1 Fc domain or an IgG4 Fc domain.

120. The method of any one of the preceding aspects, wherein the 4-1BB agonist is an antigen binding molecule comprising a Fc domain that comprises one or more amino acid substitution that reduces binding to an Fc receptor and/or effector function.

121. The method of any one of the preceding aspects, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

122. The method of any one of the preceding aspects, wherein the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

123. The method of any one of the preceding aspects, wherein the 4-1BB agonist is an antigen binding molecule comprising (a) at least one Fab domain capable of specific binding to CEA comprising a heavy chain variable region ($V_H$CEA) comprising an amino acid sequence of SEQ ID NO:55 and a light chain variable region ($V_L$CEA) comprising an amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

124. The method of any one of the preceding aspects, wherein the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

125. The method of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

126. The method of any one of the preceding aspects, wherein the 4-1BB agonist is an anti-CEA/anti-4-1BB bispecific antibody.

127. The method of any one of the preceding aspects, wherein the anti-CEA/anti-CD3 bispecific antibody comprises a first antigen binding domain that binds to CD3, and a second antigen binding domain that binds to CEA.

128. The method of any one of the preceding aspects, wherein the anti-CEA/anti-CD3 bispecific antibody comprises a first antigen binding domain comprising a heavy chain variable region ($V_H$CD3) and a light chain variable region ($V_L$CD3), and a second antigen binding domain comprising a heavy chain variable region ($V_H$CEA) and a light chain variable region ($V_L$CEA).

129. The method of any one of the preceding aspects, wherein the first antigen binding domain comprises a heavy chain variable region ($V_H$CD3) comprising CDR-H1 sequence of SEQ ID NO:33, CDR-H2 sequence of SEQ ID NO:34, and CDR-H3 sequence of SEQ ID NO:35; and/or a light chain variable region ($V_L$CD3) comprising CDR-L1 sequence of SEQ ID NO:36, CDR-L2 sequence of SEQ ID NO:37, and CDR-L3 sequence of SEQ ID NO:38.

130. The method of any one of the preceding aspects, wherein the first antigen binding domain comprises a heavy chain variable region ($V_H$CD3) comprising the amino acid sequence of SEQ ID NO:39 and/or a light chain variable region ($V_L$CD3) comprising the amino acid sequence of SEQ ID NO:40.

131. The method of any one of the preceding aspects, wherein the second antigen binding domain comprises (a) a heavy chain variable region ($V_H$CEA) comprising CDR-H1 sequence of SEQ ID NO:41, CDR-H2 sequence of SEQ ID NO:42, and CDR-H3 sequence of SEQ ID NO:43, and/or a light chain variable region ($V_L$CEA) comprising CDR-L1 sequence of SEQ ID NO:44, CDR-L2 sequence of SEQ ID NO:45, and CDR-L3 sequence of SEQ ID NO:46, or (b) a heavy chain variable region ($V_H$CEA) comprising CDR-H1 sequence of SEQ ID NO:49, CDR-H2 sequence of SEQ ID NO:50, and CDR-H3 sequence of SEQ ID NO:51, and/or a light chain variable region ($V_L$CEA) comprising CDR-L1 sequence of SEQ ID NO:52, CDR-L2 sequence of SEQ ID NO:53, and CDR-L3 sequence of SEQ ID NO:54.

132. The method of any one of the preceding aspects, wherein the second antigen binding domain comprises a heavy chain variable region ($V_H$CEA) comprising the amino acid sequence of SEQ ID NO:47 and/or a light chain variable region ($V_L$CEA) comprising the amino acid sequence of SEQ ID NO:48 or wherein the second antigen binding domain comprises a heavy chain variable region (V$_H$CEA) comprising the amino acid sequence of SEQ ID NO:55 and/or a light chain variable region (V$_L$CEA) comprising the amino acid sequence of SEQ ID NO:56.

133. The method of any one of the preceding aspects, wherein the anti-CEA/anti-CD3 bispecific antibody comprises a third antigen binding domain that binds to CEA.

134. The method of any one of the preceding aspects, wherein the third antigen binding domain comprises (a) a heavy chain variable region (V$_H$CEA) comprising CDR-H1 sequence of SEQ ID NO:41, CDR-H2 sequence of SEQ ID NO:42, and CDR-H3 sequence of SEQ ID NO:43, and/or a light chain variable region (V$_L$CEA) comprising CDR-L1 sequence of SEQ ID NO:44, CDR-L2 sequence of SEQ ID NO:45, and CDR-L3 sequence of SEQ ID NO:46, or (b) a heavy chain variable region (V$_H$CEA) comprising CDR-H1 sequence of SEQ ID NO:49, CDR-H2 sequence of SEQ ID NO:50, and CDR-H3 sequence of SEQ ID NO:51, and/or a light chain variable region (V$_L$CEA) comprising CDR-L1 sequence of SEQ ID NO:52, CDR-L2 sequence of SEQ ID NO:53, and CDR-L3 sequence of SEQ ID NO:54.

135. The method of any one of the preceding aspects, wherein the third antigen binding domain comprises a heavy chain variable region (V$_H$CEA) comprising the amino acid sequence of SEQ ID NO:47 and/or a light chain variable region (V$_L$CEA) comprising the amino acid sequence of SEQ ID NO:48 or wherein the third antigen binding domain comprises a heavy chain variable region (V$_H$CEA) comprising the amino acid sequence of SEQ ID NO:55 and/or a light chain variable region (V$_L$CEA) comprising the amino acid sequence of SEQ ID NO:56.

136. The method of any one of the preceding aspects, wherein the first antigen binding domain is a cross-Fab molecule wherein the variable domains or the constant domains of the Fab heavy and light chain are exchanged, and the second and third, if present, antigen binding domain is a conventional Fab molecule.

137. The method of any one of the preceding aspects, wherein (i) the second antigen binding domain is fused at the C-terminus of the Fab heavy chain to the N-terminus of the Fab heavy chain of the first antigen binding domain, the first antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain, or (ii) the first antigen binding domain is fused at the C-terminus of the Fab heavy chain to the N-terminus of the Fab heavy chain of the second antigen binding domain, the second antigen binding domain is fused at the C-terminus of the Fab heavy chain to the N-terminus of the first subunit of the Fc domain, and the third antigen binding domain is fused at the C-terminus of the Fab heavy chain to the N-terminus of the second subunit of the Fc domain.

138. The method of any one of the preceding aspects, wherein the anti-CEA/anti-CD3 bispecific antibody comprises an Fc domain comprising one or more amino acid substitutions that reduce binding to an Fc receptor and/or effector function.

139. The method of any one of the preceding aspects, wherein the anti-CEA/anti-CD3 bispecific antibody comprises an IgG1 Fc domain comprising the amino acid substitutions L234A, L235A and P329G.

140. The method of any one of the preceding aspects, wherein the anti-CEA/anti-CD3 bispecific antibody is used in combination with a 4-1BB (CD137) agonist and wherein the combination is administered at intervals from about one week to three weeks.

141. The method of any one of the preceding aspects, wherein the anti-CEA/anti-CD3 bispecific antibody and the 4-1BB agonist are administered together in a single composition or administered separately in two or more different compositions.

142. The method of any one of the preceding aspects, wherein the anti-CEA/anti-CD3 bispecific antibody and the 4-1BB (CD137) agonist are administered intravenously or subcutaneously.

143. The method of any one of the preceding aspects, wherein the anti-CEA/anti-CD3 bispecific antibody is administered concurrently with, prior to, or subsequently to the 4-1BB agonist.

144. The method of any one of the preceding aspects, wherein the T-cell activating anti-CD3 bispecific antibody specific for a tumor-associated antigen is used in combination with a 4-1BB (CD137) agonist and in combination with an agent blocking PD-L1/PD-1 interaction.

145. The method of any one of the preceding aspects, wherein the agent blocking PD-L1/PD-1 interaction is an anti-PD-L1 antibody or an anti-PD1 antibody.

146. The method of any one of the preceding aspects, wherein the agent blocking PD-L1/PD-1 interaction is selected from the group consisting of atezolizumab, durvalumab, pembrolizumab and nivolumab.

147. The method of any one of the preceding aspects, wherein the agent blocking PD-L1/PD-1 interaction is atezolizumab.

148. A T-cell activating anti-CD3 bispecific antibody specific for a tumor-associated antigen for use in a method for treating or delaying progression of cancer of any of the preceding aspects, wherein the T-cell activating anti-CD3 bispecific antibody specific for a tumor-associated antigen is used in combination with a 4-1BB (CD137) agonist and wherein the 4-1BB agonist acts synergistically with the T-cell activating anti-CD3 bispecific antibody.

149. The T-cell activating anti-CD3 bispecific antibody specific for a tumor-associated antigen for use in a method for treating or delaying progression of cancer of the preceding aspects, wherein the T-cell activating anti-CD3 bispecific antibody is an anti-FolR1/anti-CD3 bispecific antibody.

150. The T-cell activating anti-CD3 bispecific antibody specific for a tumor-associated antigen for use in a method for treating or delaying progression of cancer of the preceding aspects, wherein the T-cell activating anti-CD3 bispecific antibody comprises a first antigen binding domain comprising a heavy chain variable region (V$_H$CD3), a second antigen binding domain comprising a heavy chain variable region (V$_H$FolR1) and a common light chain variable region.

151. The T-cell activating anti-CD3 bispecific antibody specific for a tumor-associated antigen for use in a method for treating or delaying progression of cancer of the preceding aspects, wherein the first antigen binding domain comprises a heavy chain variable region (V$_H$CD3) comprising CDR-H1 sequence of SEQ ID NO:121, CDR-H2 sequence of SEQ ID NO:122, and CDR-H3 sequence of SEQ ID NO:123; the second antigen binding domain comprises a heavy chain variable region (V$_H$FolR1) comprising CDR-H1 sequence of SEQ ID NO:124, CDR-H2 sequence of SEQ ID NO:125, and CDR-H3 sequence of SEQ ID NO:126; and wherein the common light chain comprises a CDR-L1 sequence of SEQ ID NO:127, CDR-L2 sequence of SEQ ID NO:128, and CDR-L3 sequence of SEQ ID NO:129.

152. The T-cell activating anti-CD3 bispecific antibody specific for a tumor-associated antigen for use in a method for treating or delaying progression of cancer of the preceding aspects, wherein the first antigen binding domain comprises a heavy chain variable region (V$_H$CD3) comprising the sequence of SEQ ID NO:130; the second antigen binding domain comprises a heavy chain variable region (V$_H$FolR1) comprising the sequence of SEQ ID NO:131; and wherein the common light chain comprises the sequence of SEQ ID NO:132.

153. The T-cell activating anti-CD3 bispecific antibody specific for a tumor-associated antigen for use in a method for treating or delaying progression of cancer of the preceding aspects, wherein the anti-FolR1/anti-CD3 bispecific antibody comprises a third antigen binding domain that binds to FolR1.

154. The T-cell activating anti-CD3 bispecific antibody specific for a tumor-associated antigen for use in a method for treating or delaying progression of cancer of the preceding aspects, wherein the anti-FolR1/anti-CD3 bispecific antibody comprises a first heavy chain comprising the amino acid sequence of SEQ ID NO:133, a second heavy chain comprising the amino acid sequence of SEQ ID NO:134 and a common light chain of SEQ ID NO: 135.

155. A pharmaceutical product comprising (A) a first composition comprising as active ingredient an anti-FolR1/anti-CD3 bispecific antibody and a pharmaceutically acceptable carrier; and (B) a second composition comprising as active ingredient a 4-1BB agonist and a pharmaceutically acceptable carrier, for use in the combined, sequential or simultaneous, treatment of a disease, in particular cancer.

156. A pharmaceutical composition comprising anti-FolR1/anti-CD3 bispecific antibody and a 4-1BB agonist.

157. A method for treating or delaying progression of cancer in a subject comprising administering to the subject an effective amount of an anti-FolR1/anti-CD3 antibody and a 4-1BB agonist, wherein the 4-1BB agonist is an antigen binding molecule.

158. A 4-1BB agonist comprising at least one antigen binding domain capable of specific binding to a tumor-associated antigen for use in a method for treating or delaying progression of cancer, wherein the 4-1BB agonist comprising at least one antigen binding domain capable of specific binding to a tumor-associated antigen is used in combination with an agent blocking PD-L1/PD-1 interaction.

159. The 4-1BB agonist comprising at least one antigen binding domain capable of specific binding to a tumor-associated antigen for use in a method of aspect 158, wherein the agent blocking PD-L1/PD-1 interaction is an anti-PD-L1 antibody or an anti-PD1 antibody.

160. The 4-1BB agonist comprising at least one antigen binding domain capable of specific binding to a tumor-associated antigen for use in a method of the preceding aspects, wherein the agent blocking PD-L1/PD-1 interaction is selected from the group consisting of atezolizumab, durvalumab, pembrolizumab and nivolumab.

161. The 4-1BB agonist comprising at least one antigen binding domain capable of specific binding to a tumor-associated antigen for use in a method of any one of the preceding aspects, wherein the agent blocking PD-L1/PD-1 interaction is atezolizumab.

162. The 4-1BB agonist comprising at least one antigen binding domain capable of specific binding to a tumor-associated antigen for use in a method of the preceding aspects, wherein the tumor-associated antigen is selected from Fibroblast activation protein (FAP) or CEA.

163. The 4-1BB agonist comprising at least one antigen binding domain capable of specific binding to a tumor-associated antigen for use in a method of the preceding aspects, wherein the 4-1BB agonist is an antigen binding molecule comprising three ectodomains of 4-1BBL or fragments thereof and at least one antigen binding domain capable of specific binding to Fibroblast activation protein (FAP).

164. The 4-1BB agonist comprising at least one antigen binding domain capable of specific binding to a tumor-associated antigen for use in a method of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises (a) a heavy chain variable region (V$_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region (V$_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region (V$_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region (V$_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

165. The 4-1BB agonist comprising at least one antigen binding domain capable of specific binding to a tumor-associated antigen for use in a method of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region (V$_H$FAP) comprising an amino acid sequence of SEQ ID NO:21 and a light chain variable region (V$_L$FAP) comprising an amino acid sequence of SEQ ID NO:22 or wherein the antigen binding domain capable of specific binding to FAP comprises a heavy chain variable region (V$_H$FAP) comprising an amino acid sequence of SEQ ID NO:23 and a light chain variable region (V$_L$FAP) comprising an amino acid sequence of SEQ ID NO:24.

166. The 4-1BB agonist comprising at least one antigen binding domain capable of specific binding to a tumor-associated antigen for use in a method of the preceding aspects, wherein the 4-1BB agonist is an antigen binding molecule comprising an IgG Fc domain, specifically an IgG1 Fc domain or an IgG4 Fc domain.

167. The 4-1BB agonist comprising at least one antigen binding domain capable of specific binding to a tumor-associated antigen for use in a method of the preceding aspects, wherein the 4-1BB agonist is an antigen binding molecule comprising a Fc domain that comprises one or more amino acid substitution that reduces binding to an Fc receptor and/or effector function.

168. The 4-1BB agonist comprising at least one antigen binding domain capable of specific binding to a tumor-associated antigen for use in a method of the preceding aspects, wherein the 4-1BB agonist is an antigen binding molecule comprising (a) at least one antigen binding domain capable of specific binding to FAP, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

169. The 4-1BB agonist comprising at least one antigen binding domain capable of specific binding to a tumor-associated antigen for use in a method of the preceding aspects, wherein the 4-1BB agonist is an antigen binding molecule comprising (a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

170. The 4-1BB agonist comprising at least one antigen binding domain capable of specific binding to a tumor-associated antigen for use in a method of the preceding aspects, wherein the 4-1BB agonist is an antigen binding molecule comprising (a) at least one Fab domain capable of specific binding to FAP comprising a heavy chain variable region (V$_H$FAP) comprising the amino acid sequence of SEQ ID NO:21 and a light chain variable region (V$_L$FAP) comprising the amino acid sequence of SEQ ID NO:22 or a heavy chain variable region (V$_H$FAP) comprising the amino acid sequence of SEQ ID NO:23 and a light chain variable region (V$_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

171. The 4-1BB agonist comprising at least one antigen binding domain capable of specific binding to a tumor-associated antigen for use in a method of the preceding aspects, wherein the 4-1BB agonist is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72.

172. The 4-1BB agonist comprising at least one antigen binding domain capable of specific binding to a tumor-associated antigen for use in a method of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

173. The 4-1BB agonist comprising at least one antigen binding domain capable of specific binding to a tumor-associated antigen for use in a method of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

174. The 4-1BB agonist comprising at least one antigen binding domain capable of specific binding to a tumor-associated antigen for use in a method of the preceding aspects, wherein the 4-1BB agonist is an anti-FAP/anti-4-1BB bispecific antibody.

175. The 4-1BB agonist comprising at least one antigen binding domain capable of specific binding to a tumor-associated antigen for use in a method of the preceding aspects, wherein the 4-1BB agonist is an antigen binding molecule comprising three ectodomains of 4-1BBL or fragments thereof and at least one antigen binding domain capable of specific binding to CEA.

176. The 4-1BB agonist comprising at least one antigen binding domain capable of specific binding to a tumor-associated antigen for use in a method of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises (a) a heavy chain variable region ($V_H$CEA) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region ($V_L$CEA) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

177. The 4-1BB agonist comprising at least one antigen binding domain capable of specific binding to a tumor-associated antigen for use in a method of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_H$CEA) comprising an amino acid sequence of SEQ ID NO:55 and a light chain variable region ($V_L$CEA) comprising an amino acid sequence of SEQ ID NO:56.

178. The 4-1BB agonist comprising at least one antigen binding domain capable of specific binding to a tumor-associated antigen for use in a method of the preceding aspects, wherein the 4-1BB agonist is an antigen binding molecule comprising an IgG Fc domain, specifically an IgG1 Fc domain or an IgG4 Fc domain.

179. The 4-1BB agonist comprising at least one antigen binding domain capable of specific binding to a tumor-associated antigen for use in a method of the preceding aspects, wherein the 4-1BB agonist is an antigen binding molecule comprising a Fc domain that comprises one or more amino acid substitution that reduces binding to an Fc receptor and/or effector function.

180. The 4-1BB agonist comprising at least one antigen binding domain capable of specific binding to a tumor-associated antigen for use in a method of the preceding aspects, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

181. The 4-1BB agonist comprising at least one antigen binding domain capable of specific binding to a tumor-associated antigen for use in a method of the preceding aspects, wherein the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

182. The 4-1BB agonist comprising at least one antigen binding domain capable of specific binding to a tumor-associated antigen for use in a method of the preceding aspects, wherein the 4-1BB agonist is an antigen binding molecule comprising (a) at least one Fab domain capable of specific binding to CEA comprising a heavy chain variable region ($V_H$CEA) comprising the amino acid sequence of SEQ ID NO:55 and a light chain variable region (V$_L$CEA) comprising the amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

183. The 4-1BB agonist comprising at least one antigen binding domain capable of specific binding to a tumor-associated antigen for use in a method of the preceding aspects, wherein the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

184. The 4-1BB agonist comprising at least one antigen binding domain capable of specific binding to a tumor-associated antigen for use in a method of the preceding aspects, wherein the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers.

185. The 4-1BB agonist comprising at least one antigen binding domain capable of specific binding to a tumor-associated antigen for use in a method of the preceding aspects, wherein the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

186. The 4-1BB agonist comprising at least one antigen binding domain capable of specific binding to a tumor-associated antigen for use in a method of the preceding aspects, wherein the 4-1BB agonist is an anti-CEA/anti-4-1BB bispecific antibody.

187. A pharmaceutical product comprising (A) a first composition comprising as active ingredient an agent blocking PD-L1/PD-1 interaction and a pharmaceutically acceptable carrier; and (B) a second composition comprising as active ingredient a 4-1BB agonist comprising at least one antigen binding domain capable of specific binding to a tumor-associated antigen and a pharmaceutically acceptable carrier, for use in the combined, sequential or simultaneous, treatment of a disease, in particular cancer.

188. A pharmaceutical composition comprising an agent blocking PD-L1/PD-1 interaction and a 4-1BB agonist comprising at least one antigen binding domain capable of specific binding to a tumor-associated antigen.

189. The pharmaceutical composition of aspect 188 for use in the treatment of solid tumors.

190. The pharmaceutical composition of any one of the preceding aspects, wherein the agent blocking PD-L1/PD-1 interaction is an anti-PD-L1 antibody or an anti-PD1 antibody.

191. The pharmaceutical composition of any one of the preceding aspects, wherein the agent blocking PD-L1/PD-1 interaction is selected from the group consisting of atezolizumab, durvalumab, pembrolizumab and nivolumab.

192. The pharmaceutical composition of any one of the preceding aspects, wherein the agent blocking PD-L1/PD-1 interaction is atezolizumab.

193. The pharmaceutical composition of any one of the preceding aspects, wherein the 4-1BB agonist comprising at least one antigen binding domain capable of specific binding to a tumor-associated antigen is an antigen binding molecule comprising three ectodomains of 4-1BBL or fragments thereof.

194. The pharmaceutical composition of any one of the preceding aspects, wherein the 4-1BB agonist comprising at least one antigen binding domain capable of specific binding to a tumor-associated antigen is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

195. The pharmaceutical composition of any one of the preceding aspects, wherein the 4-1BB agonist is an antigen binding molecule an antigen binding molecule comprising three ectodomains of 4-1BBL or fragments thereof and at least one antigen binding domain capable of specific binding to FAP.

196. The pharmaceutical composition of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises (a) a heavy chain variable region (V$_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region (V$_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region (V$_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region (V$_L$FAP) comprising (iv)

CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

197. The pharmaceutical composition of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region ($V_H$FAP) comprising an amino acid sequence of SEQ ID NO:21 and a light chain variable region ($V_L$FAP) comprising an amino acid sequence of SEQ ID NO:22 or wherein the antigen binding domain capable of specific binding to FAP comprises a heavy chain variable region ($V_H$FAP) comprising an amino acid sequence of SEQ ID NO:23 and a light chain variable region ($V_L$FAP) comprising an amino acid sequence of SEQ ID NO:24.

198. The pharmaceutical composition of any one of the preceding aspects, wherein the 4-1BB agonist is an antigen binding molecule comprising an IgG Fc domain, specifically an IgG1 Fc domain or an IgG4 Fc domain.

199. The pharmaceutical composition of any one of the preceding aspects, wherein the 4-1BB agonist is an antigen binding molecule comprising a Fc domain that comprises one or more amino acid substitution that reduces binding to an Fc receptor and/or effector function.

200. The pharmaceutical composition of any one of the preceding aspects, wherein the 4-1BB agonist is an antigen binding molecule comprising an IgG1 Fc domain comprising the amino acid substitutions L234A, L235A and P329G.

201. The pharmaceutical composition of any one of the preceding aspects, wherein the 4-1BB agonist is an antigen binding molecule comprising (a) at least one antigen binding domain capable of specific binding to FAP, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

202. The pharmaceutical composition of any one of the preceding aspects, wherein the 4-1BB agonist is an antigen binding molecule comprising (a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

203. The pharmaceutical composition of any one of the preceding aspects, wherein the 4-1BB agonist is an antigen binding molecule comprising (a) at least one Fab domain capable of specific binding to FAP comprising a heavy chain variable region ($V_H$FAP) comprising the amino acid sequence of SEQ ID NO:21 and a light chain variable region ($V_L$FAP) comprising the amino acid sequence of SEQ ID NO:22 or a heavy chain variable region ($V_H$FAP) comprising the amino acid sequence of SEQ ID NO:23 and a light chain variable region ($V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

204. The pharmaceutical composition of any one of the preceding aspects, wherein wherein the 4-1BB agonist is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72.

205. The pharmaceutical composition of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

206. The pharmaceutical composition of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

207. The pharmaceutical composition of any one of the preceding aspects, wherein the 4-1BB agonist is an anti-FAP/anti-4-1BB bispecific antibody.

208. The pharmaceutical composition of any one of the preceding aspects, wherein the the 4-1BB agonist is an antigen binding molecule comprising three ectodomains of 4-1BBL or fragments thereof and at least one antigen binding domain capable of specific binding to CEA.

209. The pharmaceutical composition of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_HCEA$) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region ($V_LCEA$) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

210. The pharmaceutical composition of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region ($V_HCEA$) comprising an amino acid sequence of SEQ ID NO:55 and a light chain variable region ($V_LCEA$) comprising an amino acid sequence of SEQ ID NO:56.

211. The pharmaceutical composition of any one of the preceding aspects, wherein the 4-1BB agonist is an antigen binding molecule comprising an IgG Fc domain, specifically an IgG1 Fc domain or an IgG4 Fc domain.

212. The pharmaceutical composition of any one of the preceding aspects, wherein the 4-1BB agonist is an antigen binding molecule comprising a Fc domain that comprises one or more amino acid substitution that reduces binding to an Fc receptor and/or effector function.

213. The pharmaceutical composition of any one of the preceding aspects, wherein the 4-1BB agonist is an antigen binding molecule comprising an IgG1 Fc domain comprising the amino acid substitutions L234A, L235A and P329G.

214. The pharmaceutical composition of any one of the preceding aspects, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

215. The pharmaceutical composition of any one of the preceding aspects, wherein the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

216. The pharmaceutical composition of any one of the preceding aspects, wherein the 4-1BB agonist is an antigen binding molecule comprising (a) at least one Fab domain capable of specific binding to CEA comprising a heavy chain variable region ($V_{H^-}$ CEA) comprising the amino acid sequence of SEQ ID NO:55 and a light chain variable region (V$_L$CEA) comprising the amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

217. The pharmaceutical composition of any one of the preceding aspects, wherein wherein the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

218. The pharmaceutical composition of any one of the preceding aspects, wherein the 4-1BB agonist is an antigen binding molecule comprising (a) at least one antigen binding domain capable of specific binding to CEA, (b) a polypeptide comprising ectodomains of 4-1BBL or fragments thereof that are connected to each other by peptide linkers.

219. The pharmaceutical composition of any one of the preceding aspects, wherein the 4-1BB agonist is an antigen binding molecule comprising (a) at least one antigen binding domain capable of specific binding to CEA, (b) a polypeptide comprising three ectodomains of 4-1BBL or fragments thereof that are connected to each other by peptide linkers, and (c) a Fc domain composed of a first and a second subunit capable of stable association, wherein the polypeptide comprising the three ectodomains of 4-1BBL or fragments thereof that are connected to each other by peptide linkers is fused to the N- or C-terminal amino acid of one of the two subunits of the Fc domain, optionally through a peptide linker.

220. The pharmaceutical composition of any one of the preceding aspects, wherein the 4-1BB agonist is an anti-CEA/anti-4-1BB bispecific antibody.

221. Use of a combination of an agent blocking PD-L1/PD-1 interaction and a 4-1BB agonist comprising at least one antigen binding domain capable of specific binding to a tumor-associated antigen in the manufacture of a medicament for treating or delaying progression of a proliferative disease, in particular cancer.

222. Use of a combination of an agent blocking PD-L1/PD-1 interaction and a 4-1BB agonist comprising at least one antigen binding domain capable of specific binding to a tumor-associated antigen in the manufacture of a medicament, wherein the medicament is for the treatment of solid tumors.

223. A method for treating or delaying progression of cancer in a subject comprising administering to the subject an effective amount of an agent blocking PD-L1/PD-1 interaction and a 4-1BB agonist comprising at least one antigen binding domain capable of specific binding to a tumor-associated antigen.

224. A method for treating or delaying progression of cancer in a subject comprising administering to the subject an effective amount of an agent blocking PD-L1/PD-1 interaction and a 4-1BB agonist, wherein the 4-1BB agonist is an antigen binding molecule comprising three ectodomains of 4-1BBL or fragments thereof and an antigen binding domain capable of specific binding to a tumor associated antigen.

225. The method of any one of the preceding aspects, wherein the 4-1BB agonist is a molecule comprising three ectodomains of 4-1BBL or fragments thereof and wherein the ectodomains of 4-1BBL comprise an amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

226. The method of any one of the preceding aspects, wherein the 4-1BB agonist is an antigen binding molecule comprising three ectodomains of 4-1BBL or fragments thereof and at least one moiety capable of specific binding to FAP, wherein the antigen binding domain capable of specific binding to FAP comprises (a) a heavy chain variable region (V$_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO: 11, and a light chain variable region (V$_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14, or (b) a heavy chain variable region (V$_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region (V$_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20.

227. The method of any one of the preceding aspects, wherein the 4-1BB agonist is an antigen binding molecule comprising three ectodomains of 4-1BBL or fragments thereof and at least one antigen binding domain capable of specific binding to FAP, wherein the antigen binding domain capable of specific binding to FAP comprises a heavy chain variable region (V$_H$FAP) comprising an amino acid sequence of SEQ ID NO:21 and a light chain variable region (V$_L$FAP) comprising an amino acid sequence of SEQ ID NO:22 or wherein the antigen binding domain capable of specific binding to FAP comprises a heavy chain variable region (V$_H$FAP) comprising an amino acid sequence of SEQ ID NO:23 and a light chain variable region (V$_L$FAP) comprising an amino acid sequence of SEQ ID NO:24.

228. The method of any one of the preceding aspects, wherein the 4-1BB agonist is an antigen binding molecule comprising an IgG Fc domain, specifically an IgG1 Fc domain or an IgG4 Fc domain.

229. The method of any one of the preceding aspects, wherein the 4-1BB agonist is an antigen binding molecule comprising a Fc domain that comprises one or more amino acid substitution that reduces binding to an Fc receptor and/or effector function.

230. The method of any one of the preceding aspects, wherein the 4-1BB agonist is an antigen binding molecule comprising (a) at least one antigen binding domain capable of specific binding to FAP, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

231. The method of any one of the preceding aspects, wherein the 4-1BB agonist is an antigen binding molecule comprising (a) at least one Fab domain capable of specific binding to FAP, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

232. The method of any one of the preceding aspects, wherein the 4-1BB agonist is an antigen binding molecule comprising (a) at least one Fab domain capable of specific binding to FAP comprising a heavy chain variable region $(V_H$FAP) comprising the amino acid sequence of SEQ ID NO:21 and a light chain variable region $(V_L$FAP) comprising the amino acid sequence of SEQ ID NO:22 or a heavy chain variable region $(V_H$FAP) comprising the amino acid sequence of SEQ ID NO:23 and a light chain variable region $(V_L$FAP) comprising the amino acid sequence of SEQ ID NO:24, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

233. The method of any one of the preceding aspects, wherein the 4-1BB agonist is an antigen binding molecule selected from the group consisting of a) a molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:67 and a second light chain comprising the amino acid sequence of SEQ ID NO:68; and b) a molecule comprising a first heavy chain comprising the amino acid sequence of SEQ ID NO:69, a first light chain comprising the amino acid sequence of SEQ ID NO:70, a second heavy chain comprising the amino acid sequence of SEQ ID NO:71 and a second light chain comprising the amino acid sequence of SEQ ID NO:72.

234. The method of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

235. The method of any one of the preceding aspects, wherein the 4-1BB agonist is an anti-FAP/anti-4-1BB bispecific antibody.

236. The method of any one of the preceding aspects, wherein the 4-1BB agonist is an antigen binding molecule comprising three ectodomains of 4-1BBL or fragments thereof and at least one moiety capable of specific binding to CEA, wherein the antigen binding domain capable of specific binding to CEA comprises a heavy chain variable region $(V_H$CEA) comprising (i) CDR-H1 comprising the amino acid sequence of SEQ ID NO:49, (ii) CDR-H2 comprising the amino acid sequence of SEQ ID NO:50, and (iii) CDR-H3 comprising the amino acid sequence of SEQ ID NO:51, and a light chain variable region $(V_L$CEA) comprising (iv) CDR-L1 comprising the amino acid sequence of SEQ ID NO:52, (v) CDR-L2 comprising the amino acid sequence of SEQ ID NO:53, and (vi) CDR-L3 comprising the amino acid sequence of SEQ ID NO:54.

237. The method of any one of the preceding aspects, wherein the 4-1BB agonist is an antigen binding molecule comprising three ectodomains of 4-1BBL or fragments thereof and at least one antigen binding domain capable of specific binding to CEA, wherein the antigen binding domain capable of specific binding to CEA comprises a heavy chain variable region $(V_H$CEA) comprising an amino acid sequence of SEQ ID NO:55 and a light chain variable region $(V_L$CEA) comprising an amino acid sequence of SEQ ID NO:56.

238. The method of any one of the preceding aspects, wherein the 4-1BB agonist is an antigen binding molecule comprising an IgG Fc domain, specifically an IgG1 Fc domain or an IgG4 Fc domain.

239. The method of any one of the preceding aspects, wherein the 4-1BB agonist is an antigen binding molecule comprising a Fc domain that comprises one or more amino acid substitution that reduces binding to an Fc receptor and/or effector function.

240. The method of any one of the preceding aspects, wherein the 4-1BB agonist is an antigen binding molecule comprising (a) at least one antigen binding domain capable of specific binding to CEA, (b) a first and a second polypeptide that are linked to each other by a disulfide bond, wherein the first polypeptide comprises two ectodomains of 4-1BBL or fragments thereof that are connected to each other by a peptide linker and in that the second polypeptide comprises one ectodomain of 4-1BBL or a fragment thereof.

241. The method of any one of the preceding aspects, wherein the 4-1BB agonist is an antigen binding molecule comprising (a) at least one Fab domain capable of specific binding to CEA, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to the CH1 or CL domain by a peptide linker and wherein the second polypeptide comprises one ectodomain of 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or fragments thereof that are connected to each other and to the C-terminus of the CH3 domain by a peptide linker and wherein the second polypeptide comprises one ectodomain of 4-1BBL or a fragment thereof connected via a peptide linker to the C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or fragments thereof that are connected to each other and to VH or VL by a peptide linker and wherein the second polypeptide comprises one ectodomain of 4-1BBL or a fragment thereof connected via a peptide linker to VL or VH of said polypeptide.

242. The method of any one of the preceding aspects, wherein the 4-1BB agonist is an antigen binding molecule comprising (a) at least one Fab domain capable of specific binding to CEA comprising a heavy chain variable region ($V_H$-

CEA) comprising an amino acid sequence of SEQ ID NO:55 and a light chain variable region ($V_L$CEA) comprising an amino acid sequence of SEQ ID NO:56, and (b) a first and a second polypeptide that are linked to each other by a disulfide bond, wherein the antigen binding molecule is characterized in that the first polypeptide comprises the amino acid sequence selected from the group consisting of SEQ ID NO:25, SEQ ID NO:26, SEQ ID NO:27, SEQ ID NO:28, SEQ ID NO:29, SEQ ID NO:30, SEQ ID NO:31 and SEQ ID NO:32 and in that the second polypeptide comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

243. The method of any one of the preceding aspects, wherein the 4-1BB agonist is an antigen binding molecule comprising a first heavy chain comprising the amino acid sequence of SEQ ID NO:65, a first light chain comprising the amino acid sequence of SEQ ID NO:66, a second heavy chain comprising the amino acid sequence of SEQ ID NO:108 and a second light chain comprising the amino acid sequence of SEQ ID NO:109.

244. The method of any one of the preceding aspects, wherein the 4-1BB agonist is an antigen binding molecule comprising (a) at least one antigen binding domain capable of specific binding to FAP, (b) a polypeptide comprising three ectodomains of 4-1BBL or fragments thereof that are connected to each other by peptide linkers.

245. The method of any one of the preceding aspects, wherein the 4-1BB agonist is an anti-CEA/anti-4-1BB bispecific antibody.

246. The T-cell activating anti-CD3 bispecific antibody specific for a tumor-associated antigen for use in a method for treating or delaying progression of cancer, wherein the T-cell activating anti-CD3 bispecific antibody specific for a tumor-associated antigen is used in combination with a 4-1BB agonist and wherein a pretreatment with an Type II anti-CD20 antibody is performed prior to the combination treatment, wherein the period of time between the pretreatment and the combination treatment is sufficient for the reduction of B-cells in the individual in response to the Type II anti-CD20 antibody.

247. The T-cell activating anti-CD3 bispecific antibody for use in a method of aspect 246, wherein the Type II anti-CD20 antibody is obinutuzumab.

247. A method for treating or delaying progression of cancer in a subject comprising administering to the subject a combination of an effective amount of a T-cell activating anti-CD3 bispecific antibody specific for a tumor-associated antigen and of an effective amount of a 4-1BB agonist comprising at least one antigen binding domain capable of specific binding to a tumor-associated antigen, wherein a pretreatment with an Type II anti-CD20 antibody is performed prior to the treatment with the combination, wherein the period of time between the pretreatment and the combination treatment is sufficient for the reduction of B-cells in the individual in response to the Type II anti-CD20 antibody.

248. A method for treating or delaying progression of cancer in a subject comprising administering to the subject a combination of an effective amount of an agent blocking PD-L1/PD-1 interaction and of an effective amount of a 4-1BB agonist comprising at least one antigen binding domain capable of specific binding to a tumor-associated antigen, wherein a pretreatment with an Type II anti-CD20 antibody is performed prior to the treatment with the combination, wherein the period of time between the pretreatment and the combination treatment is sufficient for the reduction of B-cells in the individual in response to the Type II anti-CD20 antibody.

249. The method of aspects 247 or 248, wherein the Type II anti-CD20 antibody is obinutuzumab.

EXAMPLES

The following are examples of methods and compositions of the invention. It is understood that various other embodiments may be practiced, given the general description provided above.

Recombinant DNA techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A SEPHAROSE™ column (GE healthcare) and washed with PBS. Elution of antibodies was achieved at pH 2.8 followed by immediate neutralization of the sample. Aggregated protein was separated from monomeric antibodies by size exclusion chromatography (SUPERDEX™ 200, GE Healthcare) in PBS or in 20 mM Histidine, 150 mM NaCl pH 6.0. Monomeric antibody fractions were pooled, concentrated (if required) using e.g., a MILLIPORE® Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a SUPERDEX™ 200 column (GE Healthcare) in 2×PBS on a DIONEX® HPLC-System. The eluted protein was quantified by UV absorbance and integration of peak areas. BioRad Gel Filtration Standard 151-1901 served as a standard.

Mass Spectrometry

This section describes the characterization of the multi-specific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 µg deglycosylated VH/VL CrossMabs in a Tris buffer pH 8 at room temperature for 120 hours and at 37° C. for 40 min, respectively. Prior to mass spectrometry the samples were desalted via HPLC on a SEPHADEX™ G25 column (GE Healthcare). The total mass was determined via ESI-MS on a maXis 4G UHR-QTOF MS system (Bruker Daltonik) equipped with a TriVersa NanoMate source (Advion).

Determination of Binding and Binding Affinity of Multispecific Antibodies to the respective Antigens Using Surface Plasmon Resonance (SPR) (BIACORE®)

Binding of the generated antibodies to the respective antigens is investigated by surface plasmon resonance using a BIACORE® instrument (GE Healthcare Biosciences AB, Uppsala, Sweden). Briefly, for affinity measurements Goat-Anti-Human IgG, JIR 109-005-098 antibodies are immobilized on a CM5 chip via amine coupling for presentation of the antibodies against the respective antigen. Binding is measured in HBS buffer (HBS-P (10 mM HEPES, 150 mM NaCl, 0.005% TWEEN® 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective
BIACORE® Evaluation Software is used for analysis of
sensorgrams and for calculation of affinity data.

Further details of the invention are illustrated by the
following non-limiting Examples. The disclosures of all
citations in the specification are expressly incorporated
herein by reference.

Example 1

Preparation, Purification and Characterization of FAP-4-
1BBL Antigen Binding Molecules FAP-targeted 4-1BB ligand trimer-containing Fc fusion
antigen binding molecules were prepared as described in
International Patent Appl. Publ. No. WO 2016/075278 A1.

In particular, the following molecules were made:

a) Monovalent FAP-targeted and untargeted 4-1BB ligand
trimer-containing Fc fusion antigen binding molecules A polypeptide encoding a dimeric 4-1BB ligand fused to
human CL domain was subcloned in frame with the human
IgG1 heavy chain CH2 and CH3 domains on the knob
(Merchant, Zhu et al. 1998, Nature Biotechnol. 16, 677-
681). A polypeptide containing one ectodomain of the
4-1BB ligand was fused to the human IgG1-CH1 domain. In
Construct 2.4, in order to improve correct pairing the
following mutations were additionally introduced in the
crossed CH-CL (charged variant). In the dimeric 4-1BB
ligand fused to human CL, E123R and Q124K, in the
monomeric 4-1BB ligand fused to human CH1, K147E and
K213E.

The variable region of heavy and light chain DNA
sequences encoding a binder specific for FAP, clone 28H1 or
clone 4B9, were subcloned in frame with either the constant
heavy chain of the hole or the constant light chain of human
IgG1. The Pro329Gly, Leu234Ala and Leu235Ala mutations
have been introduced in the constant region of the knob and
hole heavy chains to abrogate binding to Fc gamma recep-
tors according to the method described in WO 2012/130831.
Combination of the dimeric ligand-Fc knob chain containing
the S354C/T366W mutations, the monomeric CH1 fusion,
the targeted anti-FAP-Fc hole chain containing the Y349C/
T366S/L368A/Y407V mutations and the anti-FAP light
chain allows generation of a heterodimer, which includes an
assembled trimeric 4-1BB ligand and a FAP binding Fab
(FIG. 1B). An untargeted version has been prepared accord-
ingly by replacing the FAP binder by germline DP47 (FIG.
1D).

TABLE 1

Monovalent Constructs used in the experiments

| | Example in WO 2016/075278 | composed of |
|---|---|---|
| mono FAP(4B9)-4-1BBL (Charged variant) | Example 2.1.4 (Construct 2.4) | SEQ ID NO: 65, SEQ ID NO: 66 SEQ ID NO: 67 and SEQ ID NO: 68 |
| mono FAP(28H1)-4-1BBL | Example 1.1 (Construct 1.2) | SEQ ID NO: 69, SEQ ID NO: 70 SEQ ID NO: 71 and SEQ ID NO: 72 |
| mono untargeted DP47-4-1BBL | Example 1.4 (Control B) | SEQ ID NO: 69, SEQ ID NO: 70 SEQ ID NO: 73 and SEQ ID NO: 120 | a) Bivalent FAP-Targeted and Untargeted 4-1BB Ligand
Trimer-Containing Fc Fusion Antigen Binding Molecules The DNA sequences encoding the heavy and light chain
variable regions of heavy and light chain specific a binder
specific for FAP, clone 28H1 or clone 4B9, were subcloned
in frame with either the constant heavy chain of the hole, the
knob or the constant light chain of human IgG1. The
Pro329Gly, Leu234Ala and Leu235Ala mutations were
introduced in the constant region of the knob and hole heavy
chains to abrogate binding to Fc gamma receptors according
to the method described in WO 2012/130831. Furthermore,
a polypeptide comprising two ectodomains of 4-1BB ligand
was fused to the C-terminus of human IgG1 Fe hole chain
and a polypeptide comprising one ectodomain of 4-1BB
ligand was fused to the C-terminus of human IgG1 Fe knob
chain. Combination of the anti-FAP huIgG1 hole dimeric
ligand heavy chain containing the Y349C/T366S/L368A/
Y407V mutations, the anti-FAP huIgG1 knob monomeric
ligand heavy chain containing the S354C/T366W mutations
and the anti-FAP light chains allowed generation of a
heterodimer, which included an assembled trimeric 4-1BB
ligand and two FAP binding Fabs (FIG. 1C). An untargeted
version has been prepared accordingly by replacing the FAP
binder by germline DP47 (FIG. 1E).

TABLE 2

Bivalent Constructs used in the experiments

| | Example in WO 2016/075278 | composed of |
|---|---|---|
| bi FAP(4B9)-4-1BBL | Example 2.1.3 (Construct 2.3) | 2 × SEQ ID NO: 68, SEQ ID NO: 74 and SEQ ID NO: 75 |
| bi FAP(28H1)-4-1BBL | Example 1.1 (Construct 1.5) | 2 × SEQ ID NO: 72 SEQ ID NO: 76 and SEQ ID NO: 77 |
| bi untargeted DP47-4-1BBL | Example 2.2 (Control C) | 2 × SEQ ID NO: 73 SEQ ID NO: 78 and SEQ ID NO: 79 |

The production and characterization of the FAP-targeted
and untargeted 4-1BB ligand trimer-containing Fc fusion
antigen binding molecules is described in detail in WO
2016/075278, Examples 1 to 6, respectively.

Example 2

Preparation, purification and characterization of T-cell bis-
pecific (TCB) antibodies TCB molecules have been prepared according to the
methods described in WO 2014/131712 A1 or WO 2016/
079076 A1.

The preparation of the anti-CEA/anti-CD3 bispecific anti-
body (CEA CD3 TCB or CEA TCB) used in the experiments
is described in Example 3 of WO 2014/131712 A1. CEA
CD3 TCB is a "2+1 IgG CrossFab" antibody and is com-
prised of two different heavy chains and two different light
chains. Point mutations in the CH3 domain ("knobs into
holes") were introduced to promote the assembly of the two
different heavy chains. Exchange of the VH and VL domains
in the CD3 binding Fab were made in order to promote the
correct assembly of the two different light chains. 2+1 means
that the molecule has two antigen binding domains specific
for CEA and one antigen binding domain specific for CD3.
CEACAM5 CD3 TCB has the same format, but comprises
another CEA binder and comprises point mutations in the
CH and CL domains of the CD3 binder in order to support
correct pairing of the light chains.

CEA CD3 TCB comprises the amino acid sequences of SEQ ID NO:61, SEQ ID NO:62, SEQ ID NO:63 and SEQ ID NO:64. CEACAM5 CD TCB comprises the amino acid sequences of SEQ ID NO:57, SEQ ID NO:58, SEQ ID NO:59 and SEQ ID NO:60. A schematic scheme of the bispecific antibody in 2+1 format is shown in FIG. 1A.

The preparation of the anti-FolR1/anti-CD3 bispecific antibody (FolR1 CD3 TCB or FolR1 TCB) used in the experiments is described in WO 2016/079076 A1. FolR1 CD3 TCB is shown as "FolR1 TCB 2+1 classical (common light chain)" in FIG. 1D of WO 2016/079076 and is comprised of two different heavy chains and three times the same VLCL light chain (common light chain). Point mutations in the CH3 domain ("knobs into holes") were introduced to promote the assembly of the two different heavy chains. 2+1 means that the molecule has two antigen binding domains specific for FolR1 and one antigen binding domain specific for CD3. The CD3 binder is fused at the C-terminus of the Fab heavy chain to the N-terminus of the first subunit of the Fc domain comprising the knob mutation.

FolR1 CD3 TCB comprises a first heavy chain comprising the amino acid sequence of SEQ ID NO:133, a second heavy chain comprising the amino acid sequence of SEQ ID NO:134 and three times a common light chain of SEQ ID NO: 135.

The preparation of the anti-MCSP/anti-CD3 bispecific antibody (MCSP CD3 TCB) used in the experiments is also described in WO 2014/131712 A1. As CEA CD3 TCB, it is a "2+1 IgG CrossFab" antibody and is comprised of two different heavy chains and two different light chains. MCSP CD3 TCB comprises the amino acid sequences of SEQ ID NO:147, SEQ ID NO:148, SEQ ID NO:149 and SEQ ID NO:150.

Example 3

Potent anti-tumor effect by combination therapy of FAP-4-1BBL and CEA TCB in vivo
a) Experiments with mono- and bivalent FAP(4B9)-4-1BBL The human monovalent FAP-targeted 4-1BBL (mono FAP-4-1BBL, FAP binder 4B9) was tested as single agent and in combination with the human CEA CD3 TCB against the bivalent FAP-targeted 4-1BBL (bi FAP-4-1BBL, FAP binder 4B9) and the monovalent and bivalent untargeted-4-1BBL as single agent and in combination. Human gastric MKN45 cancer cells were cografted subcutaneously with a mouse fibroblast cell line (3T3) in NOG humaniced mice from the Jackson Laboratory.

Human MKN45 cells (human gastric carcinoma) were originally obtained from ATCC and after expansion deposited in the Glycart internal cell bank. Cells were cultured in DMEM containing 10% FCS at 37° C. in a water-saturated atmosphere at 5% $CO_2$. In vitro passage 9 was used for subcutaneous injection at a viability of 97%. Human fibroblasts NIH-3T3 were originally obtained from ATCC, engineered at Roche Nutley to express human FAP and cultured in DMEM containing 10% Calf serum, 1×Sodium Pyruvate and 1.5 ug/ml Puromycin. Clone 39 was used at an in vitro passage number 16 and at a viability of 98%.

50 microliters cell suspension (1×106 MKN45 cells+1×106 3T3-huFAP) mixed with 50 microliters Matrigel were injected subcutaneously in the flank of anaesthetized mice with a 22G to 30G needle.

NSG female mice transferred with human stem cells were delivered by Jackson laboratories; Mice were maintained under specific-pathogen-free condition with daily cycles of 12 h light/12 h darkness according to committed guidelines (GV-Solas; Felasa; TierschG). Experimental study protocol was reviewed and approved by local government (P ZH193/2014). After arrival animals were maintained for one week to get accustomed to new environment and for observation. Continuous health monitoring was carried out on regular basis.

7 days before cell injection mice were bled and screened for the amount of human t-cells in the blood. Mice were injected sub cutaneously on study day 0 with 1×106 MKN45 cells mixed with 1×106 3T3 fibroblasts. Tumors were measured 2 to 3 times per week during the whole experiment by Caliper. On day 6 mice were randomized for tumor size and human T-cell count with an average T-cell count/µl blood of 165 and an average tumor size of 190-200 mm³. On the day of randomization mice were injected i.v. with Vehicle, CEA CD3 TCB, monovalent FAP-4-1BBL, bivalent FAP-4-1BBL, monovalent untargeted (DP47) 4-1BBL, bivalent untargeted 4-1BBL or the combinations of the 4-1BBL constructs with CEA CD3 TCB for 3 weeks.

All mice were injected i.v. with 200 µl of the appropriate solution. The mice in the vehicle group were injected with Histidine Buffer and the treatment groups with the 4-1BBL containing constructs, the CEA CD3 TCB or the combinations. To obtain the proper amount of compound per 200 µl, the stock solutions were diluted with Histidine Buffer when necessary. The dose and schedule used for CEA TCB was 2.5 mg/kg, twice/week whereas the 4-1BBL constructs were given at a dose of 10 mg/kg, once/week.

The experiment was terminated at study day 23. Tumors, blood and spleen were harvested in PBS, single cell suspensions were generated and stained for different immune cell markers and analysed by FACS.

Parts of tumors at termination were formalin fixed and afterwards embedded in Paraffin. Samples were cut and stained for CD3 and CD8.

TABLE 3

Compositions used in the in vivo experiments

| Compound | Dose (mg/kg) | Formulation buffer | Concentration (mg/mL) |
|---|---|---|---|
| monovalent untargeted 4-1BBL (DP47)-4-1BBL | 10 | 20 mM Histidine, 140 mM NaCl, 0.01% TWEEN ® 20, pH 6.0 | 3.64 (= stock concentration) |
| bivalent untargeted 4-1BBL (DP47)-4-1BBL | 10 | 20 mM Histidine, 140 mM NaCl, pH 6.0, 0.01% TWEEN ® 20 | 3.17 (= stock concentration) |
| monovalent FAP (4B9) 4-1BBL | 10 | 20 mM Histidine, 140 mM NaCl, pH 6.0, 0.01% TWEEN ® 20 | 3.96 (= stock concentration) |
| bivalent FAP (4B9) 4-1BBL | 10 | 20 mM Histidine, 140 mM NaCl, pH 6.0, 0.01% TWEEN ® 20 | 1.14 (= stock concentration) |
| CEA CD3 TCB | 2.5 | 20 mM Histidine, 140 mM NaCl, pH 6.0 | 4.77 (= stock concentration) |

Figure 2:
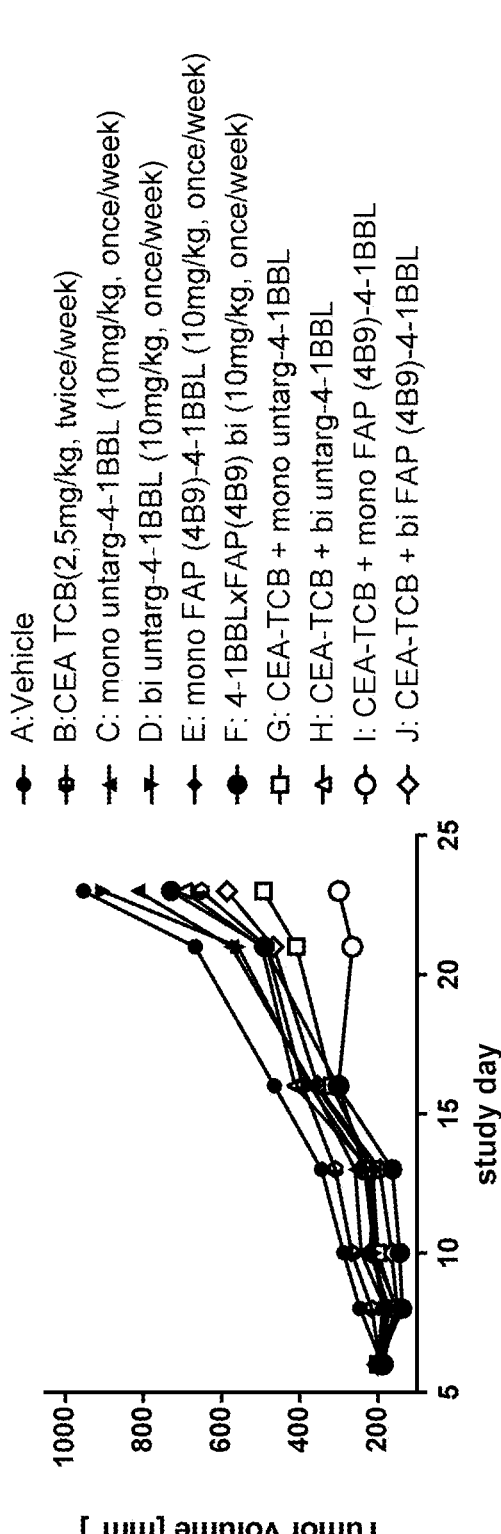
FIG. 2 shows that the groups treated with combinations of CEA CD3 TCB with monovalent FAP(4B9)-4-1BBL showed improved efficacy in terms of tumor growth inhibition compared to the other groups.

FIG. 2 shows that the combination CEA CD3 TCB+mono FAP (4B9)-4-1BBL mediated superior efficacy in terms of Tumor growth inhibition compared to all other groups.

TABLE 4

| Tumor growth inhibition (TGI) at study day 21 and 23 | | |
| --- | --- | --- |
| Group | TGI day 21 [%] | TGI day 23 [%] |
| CEA CD3 TCB | 43.5 | 39 |
| monovalent untarg.4-1BBL | 16.9 | 13.6 |
| bivalent untarg.4-1BBL | 23.1 | 9.5 |
| monovalent FAP 4-1BBL | 2.1 | −5.5 |
| bivalent FAP 4-1BBL | 53.3 | 34.8 |
| CEA CD3 TCB monovalent untarg. 4-1BBL | 54.6 | 68 |
| CEA CD3 TCB bivalent untarg. 4-1BBL | 45.2 | 39 |
| CEA CD3 TCB monovalent FAP 4-1BBL | 93.1 | 91.2 |
| CEA CD3 TCB bivalent FAP 4-1BBL | 65.4 | 57.3 |

Figures 3A, 3B:
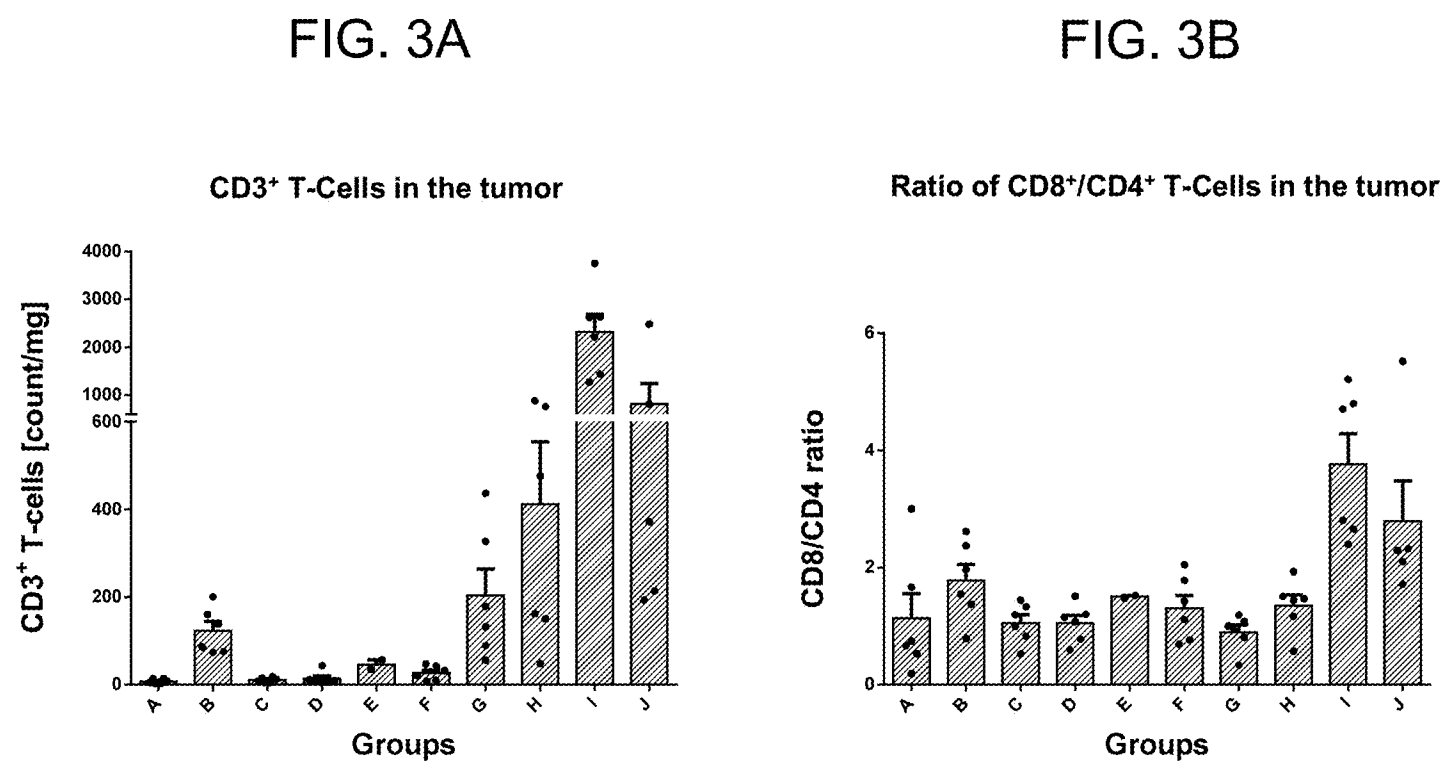
Figures 3C, 3D, 3E, 3F:
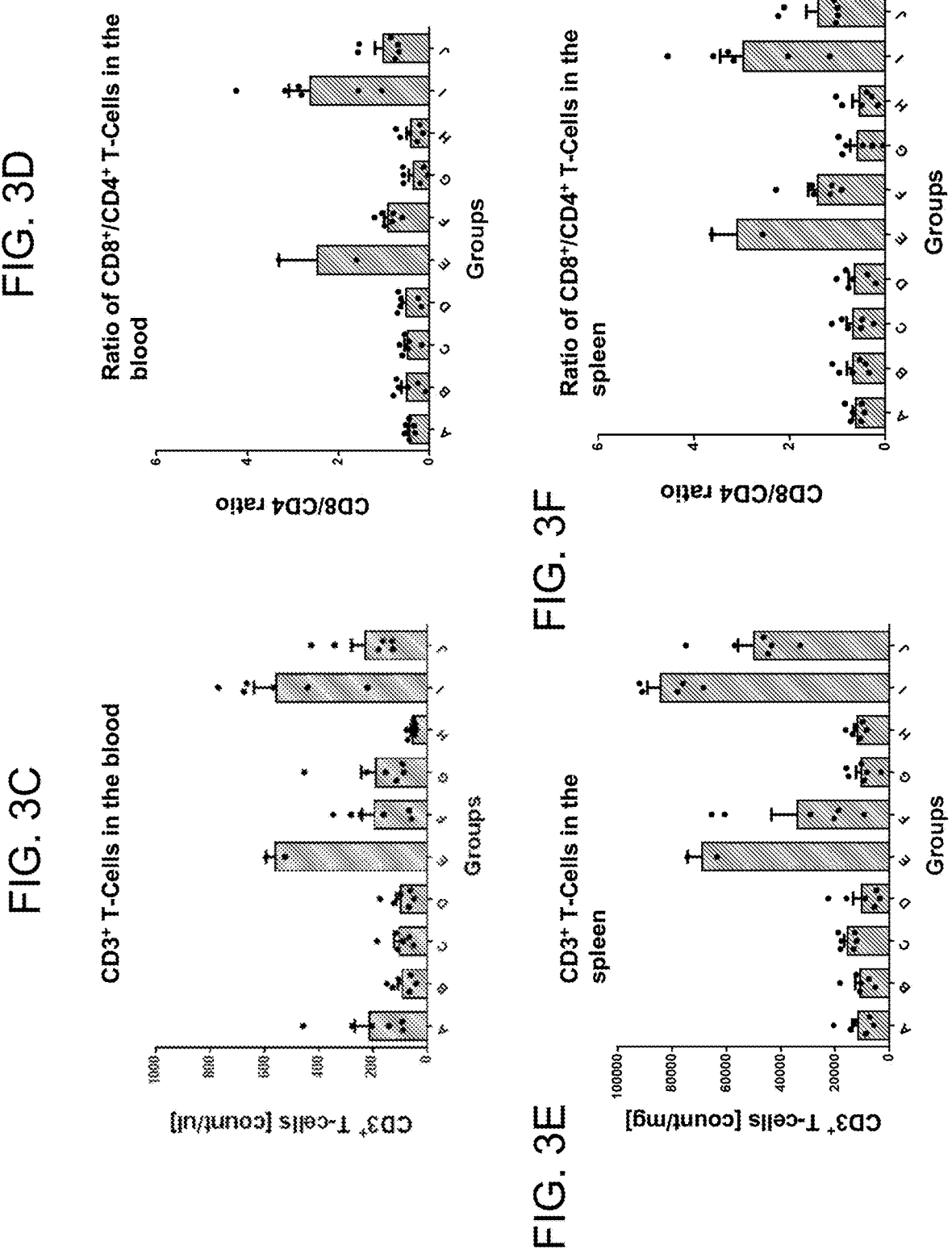

The T cell infiltration in tumor (FIGS. 3A and 3B), blood (FIGS. 3C and 3D) and spleen (FIGS. 3E and 3F) at study termination has been analyzed. The combination of FAP-targeted 4-1BBL compounds with CEA CD3 TCB increases intra-tumoral T-cell frequencies compared to mono-therapies (appr. 300-fold increase compared to vehicle). This increase is mainly due to CD8$^+$ T-cell increase. The FAP-targeted 4-1BBL monovalent compound, when combined with CEA CD3 TCB, is superior in mediating the increase in intra-tumoral CD8$^+$ T-cell frequency. Intra-tumoral CD8$^+$/CD4$^+$ ratio strongly increases in the group receiving combination treatment of FAP-targeted 4-1BBL (especially in the monovalent format) with CEA CD3 TCB. FAP-targeted 4-1BBL compounds (especially in the monovalent format) also mediated an increase in T-cell frequency in spleen and blood of the treated mice. A strong increase in intra-tumoral T-cell frequency paralleled by a strong increase in intra-tumoral CD8$^+$/CD4$^+$ T-cell ratio can be identified as an immuno-PD biomarker of anti-tumor activity of FAP-targeted 4-1BBL compounds, with the monovalent format showing superior activity than the bivalent format. The results of a histological analysis at the end of the study are shown in FIG. 4.

b) Experiments with FAP(28H1)-4-1BBL

The human monovalent FAP (28H1) 4-1BBL (mono FAP-4-1BBL) was tested as single agent and in combination with the human CEA CD3 TCB against the bivalent FAP (28H1) 4-1BBL (bi FAP-4-1BBL) and the monovalent untargeted-4-1BBL as single agent and in combination. Human gastric MKN45 cells were injected subcutaneously in NOG mice from Taconic. 2 Days before the first therapy mice were injected with human PBMCs isolated from buffy coat.

Human MKN45 cells (human gastric carcinoma) were originally obtained from ATCC and after expansion deposited in the Glycart internal cell bank. Cells were cultured in DMEM containing 10% FCS, cells were cultured at 37° C. in a water-saturated atmosphere at 5% CO$_2$. In vitro passage 8 was used for subcutaneous injection, at a viability of 97%. 50 microliters cell suspension (1×106 MKN45 cells) mixed with 50 microliters Matrigel were injected subcutaneously in the flank of anaesthetized mice with a 22G to 30G needle on day 0.

Buffy coats were obtained from Züricher Blutspende and PBMCs purified freshly before injection on day 9. 10 Mio PBMCs were injected i.p. in 200 ul volume of RPMI w/o at a viability of 94.3%. Buffy coat number H0140143019428 was used.

NOG female mice were delivered by Taconic. Mice were maintained under specific-pathogen-free condition with daily cycles of 12 h light/12 h darkness according to committed guidelines (GV-Solas; Felasa; TierschG). Experimental study protocol was reviewed and approved by local government (P ZH193/2014). After arrival animals were maintained for one week to get accustomed to new environment and for observation. Continuous health monitoring was carried out on regular basis.

Mice were injected sub cutaneously on study day 0 with 1×106 MKN45 cells. Tumors were measured 2 to 3 times per week during the whole experiment by Caliper. Freshly purified PBMCs were injected on day 9, 2 days before the first therapy. One day after randomization, on day 11, mice were injected i.v. with Vehicle, CEA tcb, mono FAP-4-1BBL, bi-FAP-4-1BBL, mono untarg.4-1BBL or the combinations of the 4-1BBL constructs with CEA tcb for up to 3 weeks.

All mice were injected i.v. with 200 µl of the appropriate solution. The mice in the vehicle group were injected with Histidine Buffer and the treatment groups with the 4-1BBL containing constructs, the CEA tcb or the combinations. To obtain the proper amount of compound per 200 µl, the stock solutions were diluted with Histidine Buffer when necessary. The dose and schedule used for CEA tcb was 2.5 mg/kg, twice/week whereas the 4-1BBL constructs were given at a dose of 10 mg/kg, once/week.

TABLE 5

| Compositions used in the in vivo experiments | | | |
| --- | --- | --- | --- |
| Compound | Dose (mg/kg) | Formulation buffer | Concentration (mg/mL) |
| monovalent untargeted 4-1BBL (DP47)-4-1BBL | 10 | 20 mM Histidine, 140 mM NaCl, 0.01% TWEEN ® 20, pH 6.0 | 3.07 (= stock concentration) |
| monovalent FAP (28H1) 4-1BBL | 10 | 20 mM Histidine, 140 mM NaCl, pH 6.0, 0.01% TWEEN ® 20 | 2.3 (= stock concentration) |
| bivalent FAP (28H1) 4-1BBL | 10 | 20 mM Histidine, 140 mM NaCl, pH 6.0, 0.01% TWEEN ® 20 | 3.07 (= stock concentration) |
| CEA CD3 TCB | 2.5 | 20 mM Histidine, 140 mM NaCl, pH 6.0 | 4.87 (= stock concentration) |

The experiment was terminated at study day 25. Tumors, blood and spleen were harvested in PBS, single cell suspensions were stained for different immune cell markers and analysed by FACS.

Parts of tumors at termination were formalin fixed and afterwards embedded in Paraffin. Samples were cut and stained for CD3 and CD8.

Figure 5:
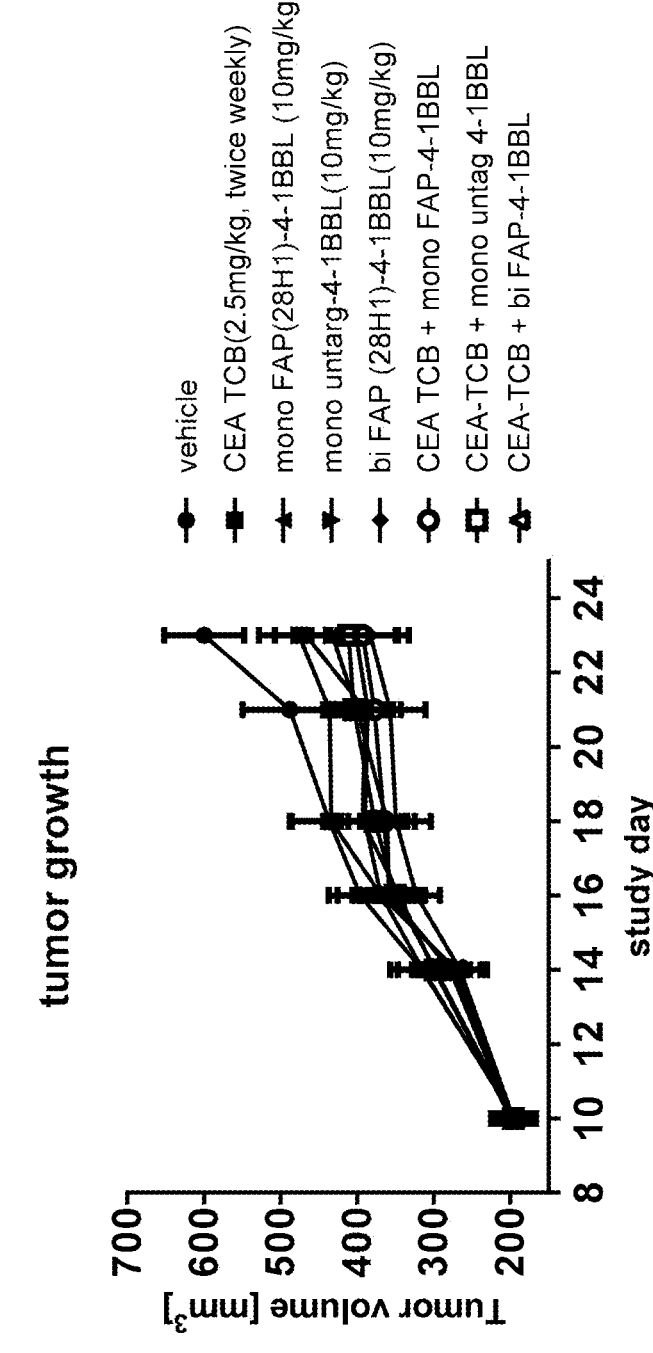
FIG. 5 shows that the groups treated with combinations of CEA CD3 TCB with monovalent FAP(28H1)-4-1BBL showed improved efficacy in terms of tumor growth inhibition compared to groups treated with the single agents.

FIG. 5 shows that the combination CEA CD3 TCB+mono FAP (28H1)-4-1BBL mediated superior efficacy in terms of Tumor growth inhibition compared to all other groups.

TABLE 6

| Tumor growth inhibition (TGI) at study day 21 and 23 | | |
| --- | --- | --- |
| Group | TGI day 21 [%] | TGI day 23 [%] |
| CEA CD3 TCB | 26.7 | 36.4 |
| monovalent untarg. 4-1BBL | 24.1 | 32.2 |
| monovalent FAP 4-1BBL | 28.1 | 27.8 |

TABLE 6-continued

| Tumor growth inhibition (TGI) at study day 21 and 23 | | |
| --- | --- | --- |
| Group | TGI day 21 [%] | TGI day 23 [%] |
| bivalent FAP 4-1BBL | 48.4 | 51.9 |
| CEA CD3 TCB monovalent untarg. 4-1BBL | 13.2 | 72.1 |
| CEA CD3 TCB monovalent FAP 4-1BBL | 28.6 | 44.7 |
| CEA CD3 TCB bivalent FAP 4-1BBL | 40.7 | 53.5 |

To test for significant differences in group means for multiple comparisons, the standard analysis of variance (ANOVA) is automatically produced, using the Dunnett's method. Dunnett's method tests whether means are different from the mean of a control group.

TABLE 7

| p-values: Comparison with a control using Dunnett's method | |
| --- | --- |
| Group | p-value day 23 vs group A |
| A: Vehicle | 1 |
| B: CEA CD3 TCB | 0.255 |
| C: monovalent FAP 4-1BBL | 0.247 |
| D: monovalent untarg.4-1BBL | 0.087 |
| E: Bivalent FAP-4-1BBL | 0.010* |
| F: CEA CD3 TCB + monovalent FAP-4-1BBL | 0.015* |
| G: CEA CD3 TCB + monovalent untarg 4-BBL | 0.033* |
| H: CEA CD3 TCB + bivalent FAP-4-1BBL | 0.022* |

Figure 6A:
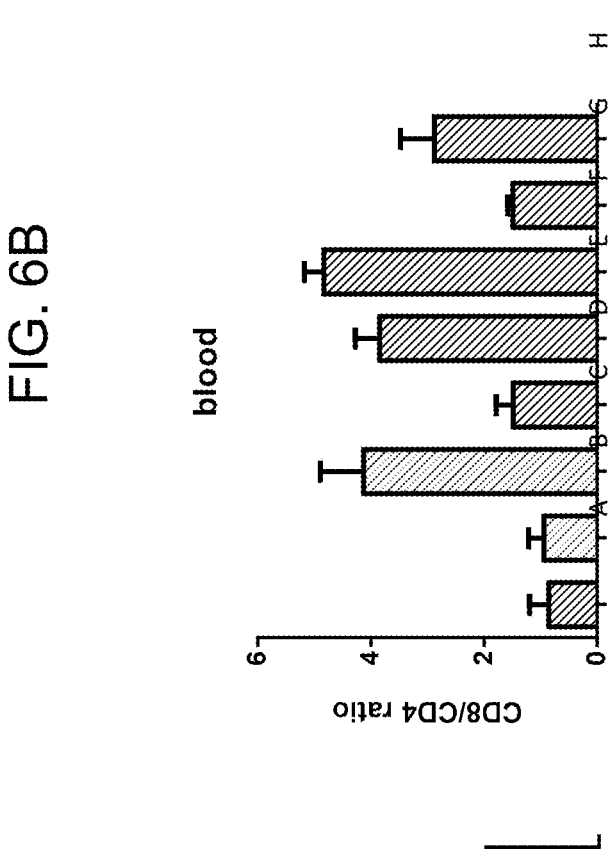
FIGS. 6A and 6B show that treatment with combinations of CEA CD3 TCB with monovalent or bivalent FAP(4B9)-4-1BBL led to increased infiltration of CD8 and CD4 positive T-cells in the tumor (FIG. 6A) and blood (FIG. 6B) compared to treatment with the single agents.
Figure 6B:
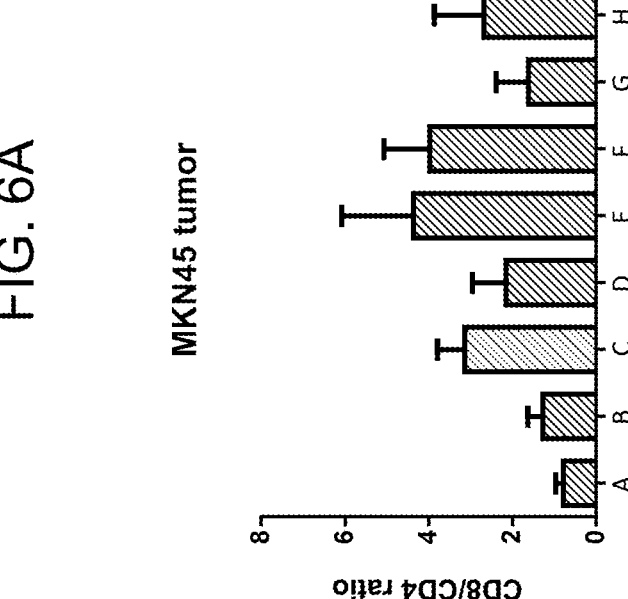
Figure 7:
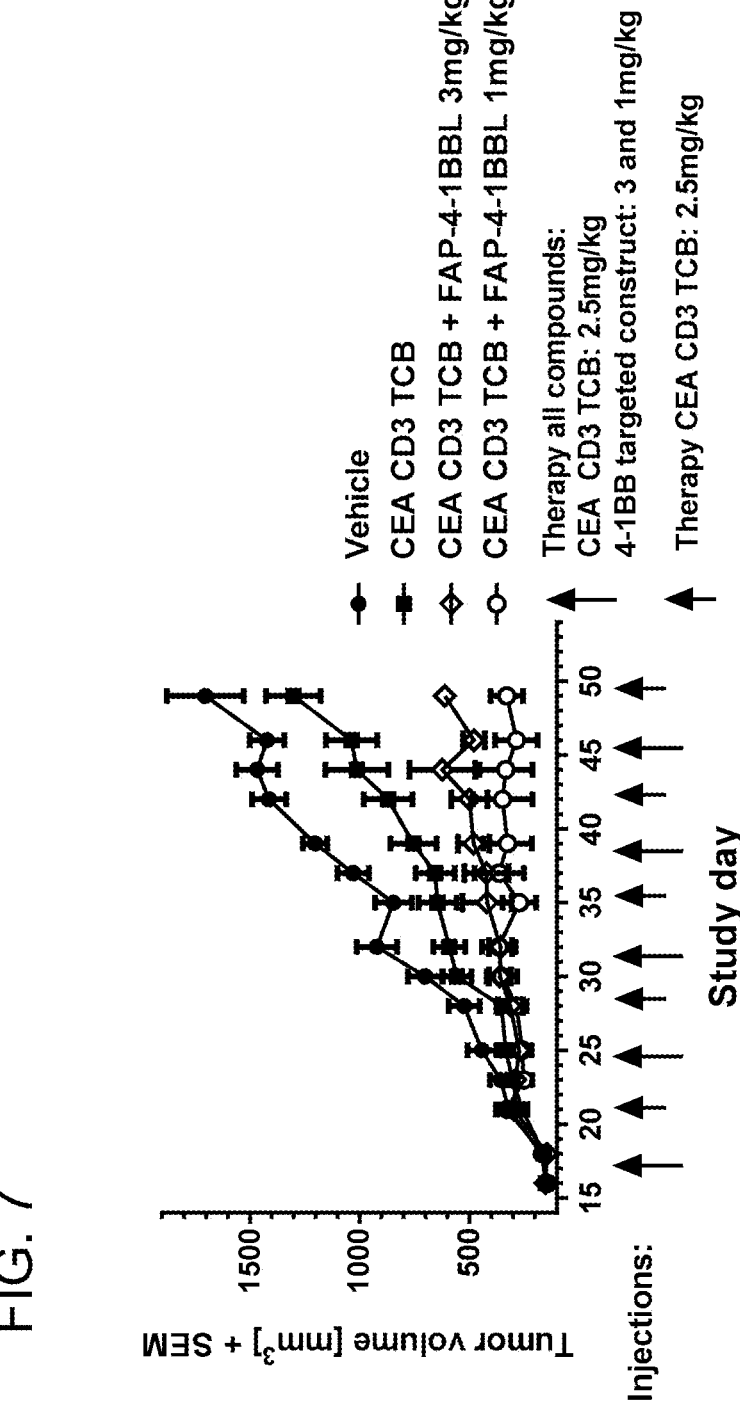
FIG. 7 shows that treatment with the combinations of CEA CD3 TCB+FAP(4B9)-4-1BBL at different doses mediates superior efficacy in terms of tumor growth inhibition compared to treatment with single agents. Mice were inoculated with MKN45 and 3T3 cells in a ratio of 1:1. At day 17 after tumor cell injection mice were randomized and treated with vehicle, CEA CD3 TCB, FAP-4-1BBL or the combinations. CEA CD3 TCB+FAP-4-1BBL at a dose of 3 and 1 mg/kg mediated superior efficacy in terms of tumor growth inhibition compared to the other group, whereas the combination in the group with 1 mg/kg is more efficacious then the combination with 3 mg/kg.

The T cell infiltration (CD8/CD4 ratio) in tumor and blood after termination of the study (at day 25) is shown in FIGS. 6A and 6B.

Example 4

Combination Therapy of Different Concentrations of FAP-4-1BBL and CEA TCB In Vivo
a) Experimental Procedure
The human monovalent FAP-targeted 4-1BBL (FAP-4-1BBL, FAP binder 4B9) was tested in 2 different concentrations in combination with the human CEA CD3 TCB. Human gastric MKN45 cancer cells were cografted subcutaneously with a mouse fibroblast cell line (3T3) in NOG mice humaniced mice with human stem cells.

Human MKN45 cells (human gastric carcinoma) were originally obtained from ATCC and after expansion deposited in the Glycart internal cell bank. Cells were cultured in DMEM containing 10% FCS at 37° C. in a water-saturated atmosphere at 5% $CO_2$. In vitro passage 12 was used for subcutaneous injection at a viability of 97%. Human fibroblasts NIH-3T3 were originally obtained from ATCC, engineered at Roche Nutley to express human FAP and cultured in DMEM containing 10% Calf serum, 1× Sodium Pyruvate and 1.5 ug/ml Puromycin. Clone 39 was used at an in vitro passage number 18 and at a viability of 98.2%.

50 microliters cell suspension (1×106 MKN45 cells+1× 106 3T3-huFAP) mixed with 50 microliters Matrigel were injected subcutaneously in the flank of anaesthetized mice with a 22G to 30G needle.

NOG female mice (purchased from Taconic), aged 5 weeks at start of the experiments, were maintained under specific-pathogen-free condition with daily cycles of 12 h light/12 h darkness according to committed guidelines (GV-Solas; Felasa; TierschG). Experimental study protocol was reviewed and approved by local government authorities (2011-128). After arrival, animals were maintained for one week to get accustomed to the new environment and for observation. Continuous health monitoring was carried out on a daily basis.

For humanization, mice were injected with Busulfan (20 mg/kg) followed 24 hours later by injection of 100,000 human HSC (purchased from StemCell Technologies). 15 weeks after stem cell injection, humanized mice were screened for human T-cell frequencies in blood by flow cytometry, and were randomized in the different study groups (see 5.4). Only humanized mice that revealed a humanization rate greater than 20% (i.e. 20% circulating human immune cells within all leucocytes) were used for the experiment.

7-14 days before cell injection mice were bled and screened for the amount of human t-cells in the blood. Mice were randomized for human T cells with an average T cell count/ul blood of 75-81. Mice were injected sub cutaneously on study day 0 with 1×106 MKN45 cells mixed with 1×106 3T3 fibroblasts. Tumors were measured 2 to 3 times per week during the whole experiment by Caliper. On day 16 mice were randomized for tumor size with an average tumor size of 150 mm3. One day after randomization, day 17, mice were injected i.v. with Vehicle, CEA CD3 TCB and the combinations of the 3 mg/kg or 1 mg/kg FAP-4-1BBL with CEA CD3 TCB for 5 weeks.

All mice were injected i.v. with 200 µl of the appropriate solution. The mice in the vehicle group were injected with Histidine Buffer and the treatment groups with the CEA CD3 TCB or the combination of CEA CD3 TCB and FAP-4-1BBL in 2 different doses. To obtain the proper amount of compound per 200 µl, the stock solutions were diluted with Histidine Buffer when necessary. The dose and schedule used for CEA CD3 TCB was 2.5 mg/kg, twice/week whereas the 4-1BBL construct was given at a dose of 3 mg/kg or 1 mg/kg once/week.

The experiment was terminated at study day 52. From vehicle group 6/9 mice were alive, from CEA CD3 treated group 6/9 mice were alive, from CEA CD3 TCB+FAP-4-1BBL 3 mg/kg treated group 3/9 were alive and from the combination group with 1 mg/kg 2/9 mice were alive. Some mice had to be sacrificed due to bad health status during the experiment.

Spleen and tumor from all remaining mice per group were analysed by flow cytometry at termination. Single cell suspensions were stained for CD45, CD3, CD4 and CD8 and the amount of cells was analysed. Parts of tumors at termination and from animals during the experiment were formalin fixed and afterwards embedded in Paraffin. Samples were cut and stained for CD3 and CD8.

Immunohistochemical images of human MKN45 gastric subcutaneous tumors cografted with 3T3 murine fibroblasts derived from the indicated treatment groups in humanized NOG mice were generated. Tissue samples were prepared for immunohistochemical staining. Subcutaneous tumors were harvested from animals at day 52 and during the experiment, fixed in formalin 10% (Sigma, Germany) and later processed for FFPET (Leica 1020, Germany). 4 µm paraffin sections were subsequently cut in a microtome (Leica RM2235, Germany). HuCD8 and HuCD3 immunohistochemistry was performed with anti-human CD8 (Cell Marque Corporation, California) and anti-human CD3 (ThermoFischer Scientific, USA) in the Leica autostainer (Leica ST5010, Germany) following the manufacture's protocols. Quantification of huCD3 and huCD8 positive T cells was performed with Definiens software (Definiens, Germany). Statistics were analyzed by one way ANOVA with multiple comparison tests. Results showed very low number of T cells in the MNK45/3T3 sc tumors from untreated mice. There is a significant increase of positive CD3 (A) and CD8 (B) T cell number in the CEA CD3 TCB+FAP-4-1BBL 3 mg/kg group compared to vehicle and CEA CD3 TCB monotherapy. (statistics One Way ANOVA, Tukey's multiple comparison test, p<0.05). Animals analysed in histology are from different experiment days to increase the number of samples. (Vehicle: 5× day 52; CEA CD3 TCB: 5× day 52; CEA CD3 TCB+FAP-4-1BBL 3 mg/kg: 2×day 52, 1×day 32, 2×day 29; CEA CD3 TCB+FAP-4-1BBL 1 mg/kg: 1×day 52, 2×day 50, 1×day 37, 1×day 35)

b) Results

Already in previous experiments it was shown that CEA CD3 TCB can mediate efficacy in xenograft mouse models via T cell dependent killing of tumor cells. For testing our human constructs human immune cells and specially T cells have to be present in the mouse system. For this reason we use humanized mice meaning mice transferred with human stemcells. These mice develop over time a partially human immune system consisting mainly of T and B cells.

We coinjected MKN45, a CEA expressing human gastric cancer cell line, and 3T3 fibroblasts which improve the stroma component and FAP expression in the tumor. CEA is targeted by the CEA CD3 TCB, crosslinking T cells with tumor cells and inducing T cell mediated killing of tumor cells and T cell activation. Upon T cell activation 4-1BB is upregulated mainly on CD8 positive T cells. FAP-4-1BBL crosslinks FAP expressing fibroblasts and 4-1BB expressing T cells and therefor is inducing 4-1BB signaling. This leads to improved killing capacity, survival and proliferation of the T cells.

We could prove in this study that combination therapy of FAP-4-1BBL in a dose of 3 mg/kg or 1 mg/kg and CEA CD3 TCB leads to superior efficacy compared to the monotherapy of CEA CD3 TCB. As is shown in FIGS. 10A and 10B, T cell infiltration in the tumor at the end of the study is significantly increased in the combination groups compared to all other groups shown by flow cytometry. In histology, the significant increase could only be observed in the combination of CEA CD3 TCB and FAP-4-1BBL 3 mg/kg.

TABLE 8

| Compositions used in the in vivo experiments | | | |
| --- | --- | --- | --- |
| Compound | Dose | Formulation buffer | Concentration (mg/mL) |
| FAP (4B9)-4-1BBL | 3 mg/kg and 1 mg/kg | 20 mM Histidine, 140 mM NaCl, pH 6.0 0.01% TWEEN ® 20 | 1.77 (= stock solution) |
| CEA CD3 TCB | 2.5 mg/kg | 20 mM Histidine, 240 mM Sucrose, 10 mM Methionine, 0.05% TWEEN ® 20, pH 5.5 | 4.92 (= stock solution) |

Tumor growth inhibition based on medians was calculated at study day 35, 39 and 46. In the CEA CD3 TCB monotherapy group 9/9 mice were alive on study day 35 and 39 and 8/9 mice at study day 46. In the combination group with 3 mg/kg FAP-4-1BBL at day 35 4/9 and at day 39 and 46 3/9 mice were alive. In the combination group with 1 mg/kg at day 35 6/9 mice were alive and at day 39 and 46 5/9 mice were alive. The Group treated with CEA CD3 TCB+FAP-4-1BBL 1 mg/kg shows the strongest inhibition of tumor growth.

TABLE 9

| Tumor growth inhibition (TGI) at study day 35, 39 and 46 | | | |
| --- | --- | --- | --- |
| Group | CEA CD3 TCB | CEA CD3 TCB + FAP-1-1BBL 3 mg/kg | CEA CD3 TCB + FAP-4-1BBL 1 mg/kg |
| TGI day 35 [%] | 33.6 | 69.8 | 85.2 |
| TGI day 39 [%] | 44.6 | 65.2 | 94.6 |
| TGI day 46 [%] | 27.7 | 69.5 | 98.5 |

To test for significant differences in group means for multiple comparisons, the standard analysis of variance (ANOVA) is automatically produced, using the Dunnett's method. Dunnett's method tests whether means are different from the mean of a control group.

TABLE 10

| p-values: Comparison with a control using Dunnett's method (AUC = area under the curve) | | | | |
| --- | --- | --- | --- | --- |
| Comparison with | | Day 35 | | Day 46 |
| CEA CD3 TCB using Dunnett's method (AUC) | Mice alive | p-value | Mice alive | p-value |
| CEA CD3 TCB | 9/9 | 1 | 8/9 | 1 |
| Vehicle | 8/9 | 0.3936 | 8/9 | 0.0769 |
| CEA CD3 TCB + FAP-41BBL (LEAD) 3 mg/kg | 4/9 | 0.4896 | 3/9 | 0.0510 |
| CEA CD3 TCB + FAP-41BBL (LEAD) 1 mg/kg | 6/9 | 0.0280* | 5/9 | 0.0006* |

Figure 8B:
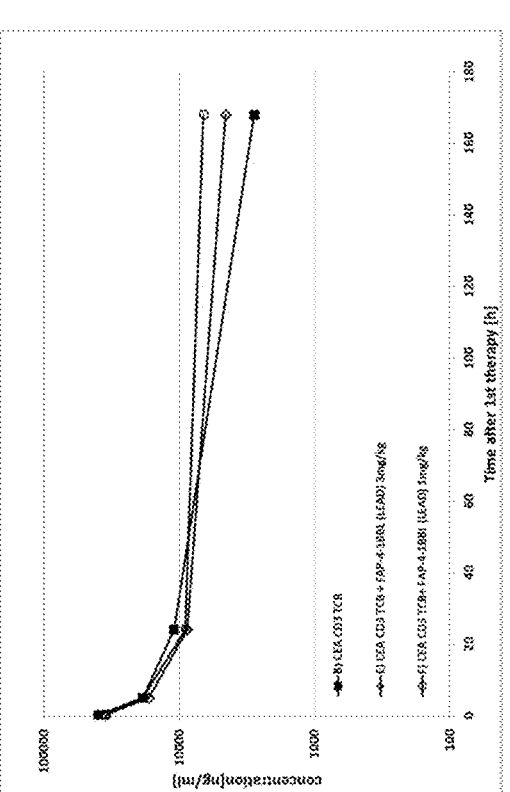
FIGS. 8A and 8B show the pharmacokinetic profile of injected compounds during the first week. 2 mice per Group were bled 10 min, 6 h, 24h, 96h and 7d after the first therapy and injected compounds were analysed by ELISA. 4-1BBL was detected via 4-1BB binding (FIG. 8A), whereas CEA CD3 TCB was detected via binding to anti-CD3 CDR antibody (FIG. 8B). All groups injected with compounds show comparable exposure of the molecules between the different groups (dose dependent), either FAP-4-1BBL or CEA CD3 TCB.
Figure 8A:
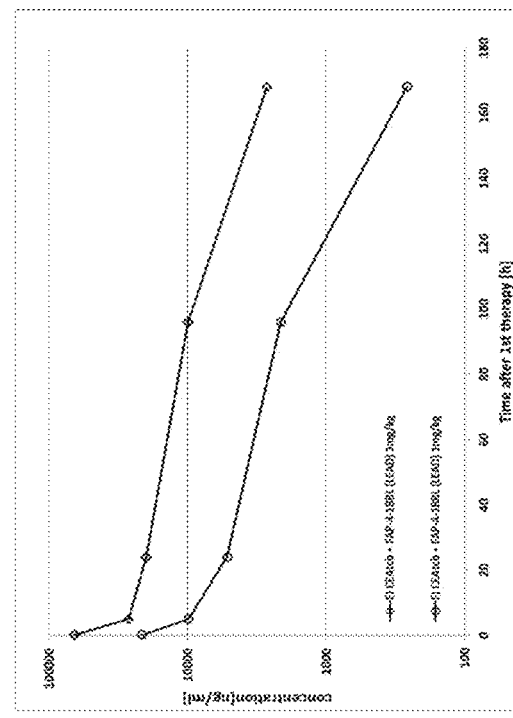
Figures 9A, 9B:
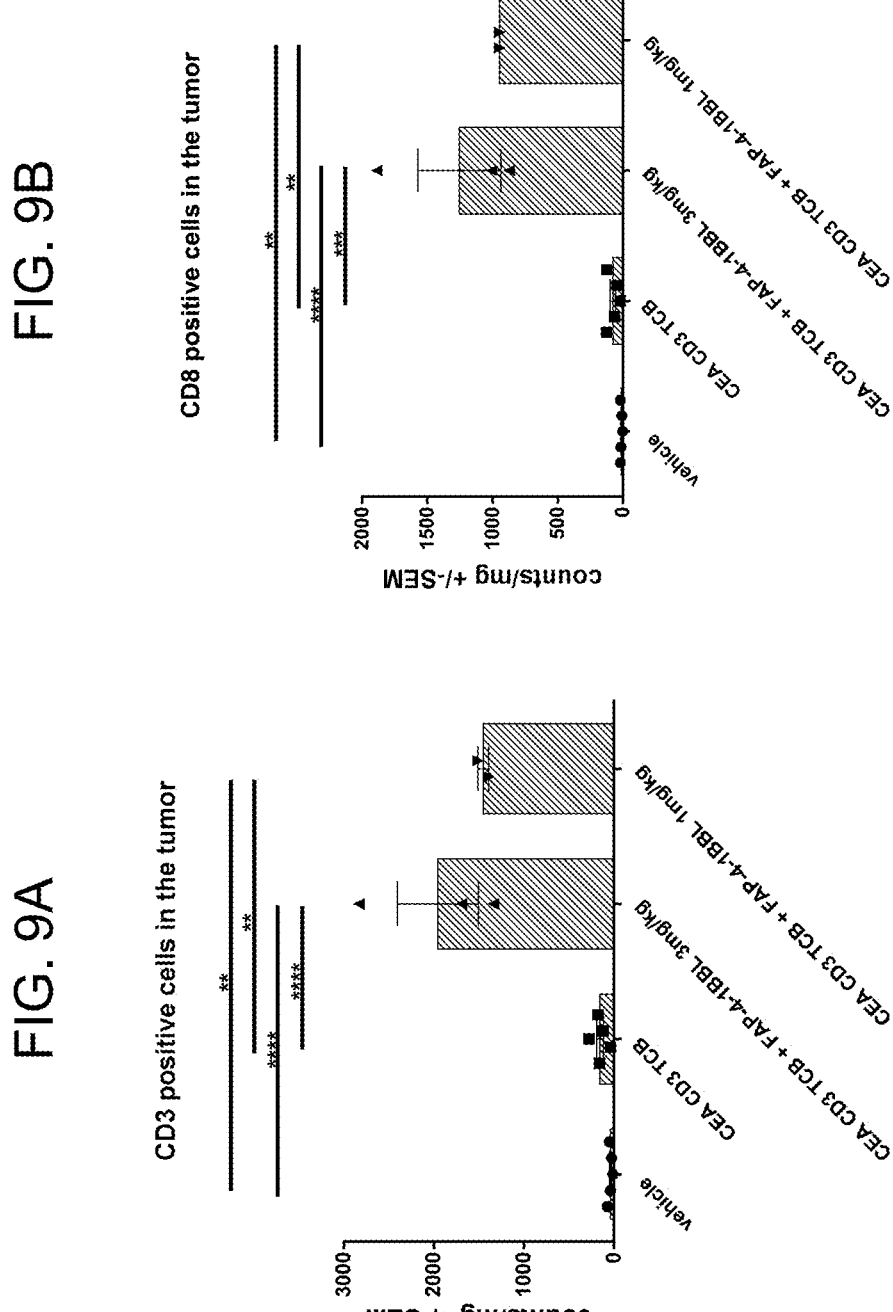
In FIGS. 9A to 9D is shown the T cell infiltration in tumor and spleen at study termination. Spleen and tumor from 2-5 mice/group were analysed by flow cytometry at termination. Single cell suspensions were stained for CD45, CD3, CD4 and CD8 and the amount of cells was analysed. Combining FAP-4-1BBL with CEA CD3 TCB leads to a statistically increased infiltration of CD3, CD8 and CD4 positive T-cells in the tumor at the end of the experiment compared to all other groups. Also in the spleen the combination leads to an increase of CD3 positive T cells compared to vehicle and CEA CD3 TCB monotherapy. (statistics One Way ANOVA, Tukey's multiple comparison test, p<0.05).
Figures 9C, 9D:
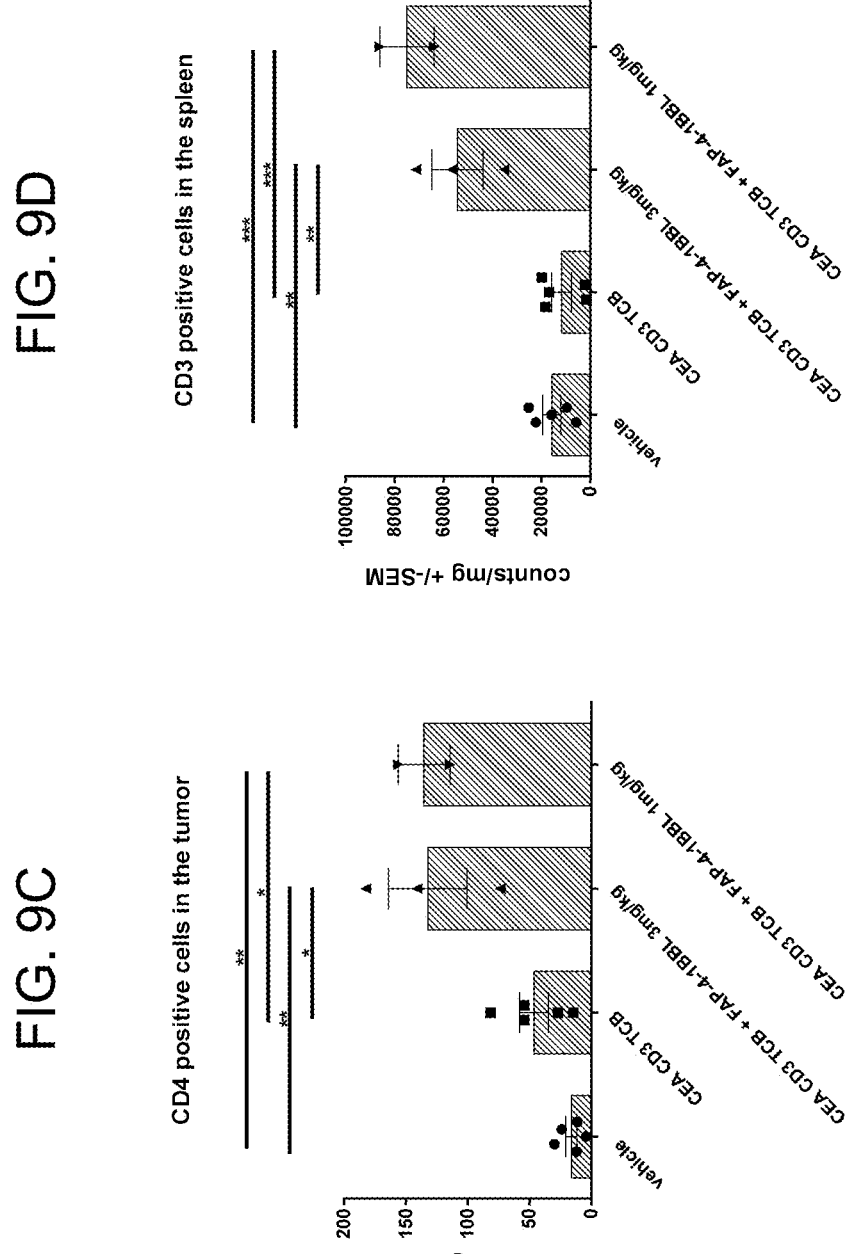

In FIGS. 8A and 8B the pharmacokinetic profile of the injected compounds during the first week is shown. The T cell infiltration in tumor and spleen at study termination is illustrated in FIG. 9.

Example 5

Combination Therapy of Different Concentrations of FAP-4-1BBL and CEACAM5 TCB In Vivo a) Experimental Procedure The human FAP-targeted 4-1BBL (FAP-4-1BBL, FAP binder 4B9) was tested in a concentration of 10 mg/kg and 1 mg/kg in combination with the human CEACAM5 CD3 TCB in a human gastric MKN45 cancer model. MKN45 cells were cografted sub cutaneously with a mouse fibroblast cell line (3T3) in NSG humanized mice.

Human MKN45 cells (human gastric carcinoma) were originally obtained from DSMZ and after expansion deposited in the Glycart internal cell bank. Cells were cultured in DMEM containing 10% FCS at 37° C. in a water-saturated atmosphere at 5% C02. In vitro passage 14 was used for subcutaneous injection at a viability of 99.2%. Human fibroblasts NIH-3T3 were originally obtained from ATCC, engineered at Roche Nutley to express human FAP and cultured in DMEM containing 10% Calf serum, 1× Sodium Pyruvate and 1.5 ug/ml Puromycin. Clone 39 was used at an in vitro passage number 9 and at a viability of 98.2%.

50 microliters cell suspension (1×106 MKN45 cells+1× 106 3T3-huFAP) mixed with 50 microliters Matrigel were injected subcutaneously in the flank of anaesthetized mice with a 22G to 30G needle.

NSG female mice (purchased from Charles River), age 5 weeks at start of the experiment, were maintained under specific-pathogen-free condition with daily cycles of 12 h light/12 h darkness according to committed guidelines (GV-Solas; Felasa; TierschG). Experimental study protocol was reviewed and approved by local government authorities. After arrival, animals were maintained for one week to get accustomed to the new environment and for observation. Continuous health monitoring was carried out on a daily basis.

For humanization, mice were injected with Busulfan (20 mg/kg) followed 24 hours later by injection of 100,000 human HSC (purchased from StemCell Technologies.

7-14 days before cell injection mice were bled and screened for the amount of human t-cells in the blood. Mice were randomized for human T cells with an average T cell count/ul blood of 40-42. Mice were injected sub cutaneously on study day 0 with $1\times10^6$ MKN45 cells mixed with $1\times10^6$ 3T3 fibroblasts. Tumors were measured 2 to 3 times per week during the whole experiment by Caliper. On day 23 mice were randomized for tumor size with an average tumor size of 350 mm³. On day of randomization mice were injected weekly i.v. with Vehicle, CEACAM5 CD3 TCB, FAP-4-1BBL 10 mg/kg, FAP-4-1BBL 1 mg/kg and the combinations of FAP-4-1BBL 10 mg/kg or 1 mg/kg with CEACAM5 CD3 TCB for 4 weeks.

TABLE 11

| Compositions used in the in the in vivo experiments | | | |
|---|---|---|---|
| Compound | Dose | Formulation buffer | Concentration (mg/mL) |
| FAP (4B9)-4-1BBL | 10 mg/kg and 1 mg/kg | 20 mM Histidine, 140 mM NaCl, pH 6.0 0.01% TWEEN ® 20 | 1.6 (= stock solution) |
| CEACAM5 CD3 TCB | 0.5 mg/kg | 20 mM Histidine, 140 mM NaCl, pH 6.0 0.01% TWEEN ® 20 | 3.1 (= stock solution) |

All mice were injected i.v. with 200 µl of the appropriate solution. The mice in the vehicle group were injected with Histidine Buffer and the treatment groups with the CEACAM5 CD3 TCB, FAP-4-1BBL or the combinations. To obtain the proper amount of compound per 200 µl, the stock solutions were diluted with Histidine Buffer when necessary. The dose and schedule used for CEACAM5 CD3 TCB was 0.5 mg/kg once/week whereas FAP-4-1BBL was given at a dose of 10 mg/kg or 1 mg/kg once/week.

Four additional mice were treated in the vehicle group, CEACAM5 CD3 TCB group and the combination groups. The additional mice were taken as scouts on day 33, 72h after the second treatment. The tumors of scouts were analysed for cytokines by Multiplex and T cell infiltration by histology and FACS.

The experiment was terminated at study day 50.

TABLE 12

| | | | | | CEACAM5 CD3 TCB + FAP-4-1BBL 10 mg/kg | CEACAM5 CD3 TCB + FAP-4-1BBL 1 mg/kg |
|---|---|---|---|---|---|---|
| | | | FAP-4-1BBL 10 mg/kg | FAP-4-1BBL 1 mg/kg | | |
| Group | Vehicle | CEACAM5 CD3 TCB | | | | |
| mice alive day 50 | 1/10 | 8/9 | 3/8 | 3/8 | 5/10 | 3/9 |

*Mice alive on day 50*

Some mice had to be sacrificed due to bad health status during the experiment.

Spleen and tumor from all remaining mice per group were analysed by flow cytometry and histology at termination day 50. Single cell suspensions were stained for CD45, CD3, CD4 and CD8 and the amount of cells was analysed. Parts of tumors at termination and from animals during the experiment were formalin fixed and afterwards embedded in Paraffin. Samples were cut and stained for CD3 and CD8.

b) Results

In previous experiments it was shown that FAP-4-1BBL can improve the efficacy of CEA CD3 TCB in xenograft mouse models. In this study we wanted to confirm that FAP-4-1BBL can also enhance efficacy of CEACAM5 CD3 TCB mainly mediated by T cells. We used a suboptimal dosis of CEACAM5 CD3 TCB as this construct is already very potent on its own.

To test our human constructs human immune cells and specifically T cells have to be present in the mouse system. For this reason we use humanized mice meaning mice transferred with human stemcells. These mice develop over time a partially human immune system consisting mainly of T and B cells.

We coinjected MKN45, a CEA expressing human gastric cancer cell line, and 3T3 fibroblasts which improve the stroma component and FAP expression in the tumor. CEA is targeted by the CEA CD3 TCB, crosslinking T cells with tumor cells and inducing T cell mediated killing of tumor cells and T cell activation. Upon T cell activation 4-1BB is upregulated mainly on CD8 positive T cells. FAP-4-1BBL crosslinks FAP expressing fibroblasts and 4-1BB expressing T cells and therefor is inducing 4-1BB signaling. This leads to improved killing capacity, survival and proliferation of the T cells.

We could prove in this study that combination therapy of FAP-4-1BBL in a dose of 10 mg/kg and CEACAM5 CD3 TCB leads to slightly improved efficacy compared to the monotherapy of CEACAM5 CD3 TCB (see FIG. 11). T cell infiltration in the tumor in scouts on day 33 as well as at the end of the study is significantly increased in the combination groups (one or both, depending on time point and analysis) compared to all other groups shown by flow cytometry and histology. A strong increase of intratumoral cytokines and chemokines could be observed in scouts at day 33 in the combination of CEACAM5 CD3 TCB and FAP-4-1BBL 10 mg/kg.

TABLE 13

Tumor growth inhibition (TGI) at study day 44 and 47

| Group | CEACAM5 CD3 TCB | FAP-1-1BBL 10 mg/kg | FAP-4-1BBL 1 mg/kg | CEACAM5 CD3 TCB + FAP-4-1BBL 10 mg/kg | CEACAM5 CD3 TCB + FAP-4-1BBL 1 mg/kg |
|---|---|---|---|---|---|
| Mice alive day 44 | 8/9 | 4/8 | 4/8 | 6/10 | 6/9 |
| TGI day44 [%] | 47.8 | −5.9 | 36.7 | 62.1 | 12.4 |
| Mice alive day47 | 8/9 | 3/8 | 3/8 | 5/10 | 4/9 |
| TGI day47 [%] | 49.0 | 5.2 | 33.0 | 75.9 | 15.4 |

To test for significant differences in group means for multiple comparisons, the standard analysis of variance (ANOVA) is automatically produced, using the Dunnett's method. Dunnett's method tests whether means are different from the mean of a control group.

TABLE 14 p-values: Comparison with a control using Dunnett's method (AUC = area under the curve)

| Comparison with Vehicle using Dunnett's method (AUC) | Day 47 | |
|---|---|---|
| | Mice alive | p-value |
| CEACAM5 CD3 TCB | 8/9 | 0.1683 |
| FAP-1-1BBL 10 mg/kg | 3/8 | 0.9508 |
| FAP-4-1BBL 1 mg/kg | 3/8 | 0.7808 |
| CEACAM5 CD3 TCB + FAP-4-1BBL 1 mg/kg | 4/10 | 0.5380 |
| CEACAM5 CD3 TCB + FAP-4-1BBL 10 mg/kg | 5/9 | 0.0500 |

In order to study the pharmacokinetic profile of injected compounds during the first week, 2 mice per Group were bled 1h and 72h after 1st and 2nd therapy. Injected compounds were analysed by ELISA (see FIGS. 12A and 12B).

(A) Biotinylated human 4-1BB, test sample, Digoxigenin labelled anti-huCH1 antibody and anti-Digoxigenin detection antibody (POD) are added stepwise to a 96-well streptavidin-coated microtiter plate and incubated after every step for 1h at room temperature. The plate is washed three times after each step to remove unbound substances. Finally, the peroxidase-bound complex is visualized by adding ABTS substrate solution to form a colored reaction product. The reaction product intensity, which is photometrically determined at 405 nm (with reference wavelength at 490 nm), is proportional to the analyte concentration in the serum sample.

(B) Biotinylated anti-huCD3-CDR antibody, test sample, Digoxigenin labelled anti-huFc antibody and anti-Digoxigenin detection antibody (POD) are added stepwise to a 96-well streptavidin-coated microtiter plate and incubated after every step for 1h at room temperature. The plate is washed three times after each step to remove unbound substances. Finally, the peroxidase-bound complex is visualized by adding ABTS substrate solution to form a colored reaction product. The reaction product intensity, which is photometrically determined at 405 nm (with reference wavelength at 490 nm), is proportional to the analyte concentration in the serum sample.

4-1BBL was detected via 4-1BB binding (A), whereas CEA CD3 TCB was detected via binding to anti-CD3 CDR antibody (B).

All groups injected with compounds show comparable exposure of the molecules between the different groups (dose dependent), either FAP-4-1BBL or CEA CD3 TCB.

The T cell infiltration in tumor at study termination was analysed by FACS. Tumors from 3-4 mice/group were analysed by flow cytometry at day 33 and at termination on day 50. Single cell suspensions were stained for CD45, CD3, CD4 and CD8 and the amount of cells was analysed. One Way ANOVA and Tukey's multiple comparison test (with $p < 0.05$) was used as statistical methods (see FIGS. 13A and 13B).

Combining FAP-4-1BBL 10 mg/kg with CEACAM CD3 TCB leads to a statistically increased infiltration of CD8 and CD4 positive T-cells in the tumor at day 33 and/or day 50 compared to vehicle or the TCB (dependent on timepoint).

Immunohistochemical images of human MKN45 gastric subcutaneous tumors cografted with 3T3 murine fibroblasts derived from the indicated treatment groups in humanized NOG mice were generated. Tissue samples were prepared for immunohistochemical staining. Subcutaneous tumors were harvested from animals at day 33 (vehicle, CEACAM5 CD3 TCB and the combinations) and at the end of the experiment (except vehicle, only one tumor still available at that timepoint). Tumors were fixed in formalin 10% (Sigma, Germany) and later processed for FFPET (Leica 1020, Germany). 4 µm paraffin sections were subsequently cut in a microtome (Leica RM2235, Germany). HuCD8 immunohistochemistry was performed with anti-human CD8 (Cell Marque Corporation, California) in the Leica autostainer (Leica ST5010, Germany) following the manufacture's protocols. Quantification of huCD8 positive T cells was performed with Definiens software (Definiens, Germany). Statistics were analyzed by one way ANOVA with multiple comparison tests. Results showed very low number of T cells in the MNK45/3T3 sc tumors from untreated mice at day 33 and at termination day 50. Also monotherapies of FAP-4-1BBL don't show an increase of T-cells in the tumor at the end of the experiment. There is a significant increase of positive CD8 T cells in the CEACAM5 CD3 TCB+FAP-4-1BBL 1 mg/kg group compared to CEACAM5 CD3 TCB monotherapy on day 33 (see FIG. 14A). At study termination on day 50 both combination groups show a significant increase of CD8 T cells compared to CEACAM5 CD3 TCB monotherapy (see FIG. 14B). (statistics One Way ANOVA, Tukey's multiple comparison test, $p < 0.05$).

No differences could be observed in CD4 T cell infiltration (data not shown).

For the Cytokine Analysis in tumor and serum at the end of the study, serum was collected and 20-30 mg of snap-frozen tumor tissues were processed for whole protein isolation at day 33. Briefly, tissue samples were meshed by using the Tissue Lyser system and stainless steel beads in a total volume of 150 ul of lysis buffer. Meshed samples were cleared by centrifugation and whole protein content was analysis by BCA protein assay kit in the supernatant. At total of 200 µg of whole protein of tumor and spleen lysates as well as a 1:10 dilution of serum samples were used for the analysis of different cytokines/chemokines by the Bio-Plex system following instructions of manufacturer (Bio-Plex Pro™ Human Cytokine 40-plex Assay, BioRad).

An increase of several cytokines was observed in the serum and in tumor upon combination of CEACAM5 CD3 TCB and FAP-4-1BBL compared to the monotherapy of CEACAM5 CD3 TCB.

Statistical significant increased cytokines in the tumor CEACAM5 CD3 TCB+FAP-4-1BBL 10 mg/kg vs. CEACAM5 CD3 TCB alone were: CXCL10, 13, 5, CCL1, 11, 21, 22, IL12, MIP-3a, MIP-1a, TECK, MCP3 and MCP4 (statistics analysed with One-way ANOVA, values not shown).

In FIGS. 15A, 15B and 15C examples of increases of intratumoral cytokines are shown: CCL1, TECK, CCL2, CXCL13, CXCL12, 1116, MIP-3a.

Example 6

Preparation, Purification and Characterization of CEA-4-1BBL Antigen Binding Molecules CEA-targeted 4-1BB ligand trimer-containing Fc fusion antigen binding molecules were prepared as described in International Patent Appl. Publ. No. WO 2016/075278 A1.

In particular, monovalent CEA-targeted and untargeted 4-1BB ligand trimer-containing Fc fusion antigen binding molecules were made.

A polypeptide encoding a dimeric 4-1BB ligand fused to the human CL domain was subcloned in frame with the human IgG1 heavy chain CH2 and CH3 domains on the knob (Merchant, Zhu et al. 1998, Nature Biotechnol. 16, 677-681). A polypeptide containing one ectodomain of the 4-1BB ligand was fused to the human IgG1-CH1 domain. In order to improve correct pairing the following mutations were additionally introduced in the crossed CH-CL (charged variant): In the dimeric 4-1BB ligand fused to human CL, E123R and Q124K, in the monomeric 4-1BB ligand fused to human CH1, K147E and K213E.

The variable region of heavy and light chain DNA sequences encoding a binder specific for CEA, clone T84.66-LCHA (CEACAM5), were subcloned in frame with either the constant heavy chain of the hole or the constant light chain of human IgG1. The Pro329Gly, Leu234Ala and Leu235Ala mutations were introduced in the constant region of the knob and hole heavy chains to abrogate binding to Fc gamma receptors according to the method described in WO 2012/130831. Combination of the dimeric ligand-Fc knob chain containing the S354C/T366W mutations, the mono-meric CH1 fusion, the targeted anti-CEA-Fc hole chain containing the Y349C/T366S/L368A/Y407V mutations and the anti-CEA light chain allows generation of a heterodimer, which includes an assembled trimeric 4-1BB ligand and a CEA binding Fab (in analogy to FIG. 1B, anti-FAP replaced by anti-CEA).

TABLE 15

Monovalent Construct used in the experiments

| | Example in WO 2016/075278 | composed of |
|---|---|---|
| mono CEA (T84.66-LCHA)-4-1BBL (Charged variant) | Example 11.2.4 (Construct 5.4) | SEQ ID NO: 65, SEQ ID NO: 66 SEQ ID NO: 108 and SEQ ID NO: 109 |

The production and characterization of the CEA-targeted and untargeted 4-1BB ligand trimer-containing Fc fusion antigen binding molecules is described in detail in WO 2016/075278, Examples 11 to 13, respectively.

Example 7

Combination Therapy of Different Concentrations of CEA-4-1BBL Antigen Binding Molecules and CEA TCB In Vivo a) Experimental Procedure The human CEA targeted 4-1BBL (CEA-4-1BBL, CEA binder T84.66-LCHA or CEACAM5) was tested in a concentration of 10, 3 and 1 mg/kg in combination with the human CEA CD3 TCB in a human gastric MKN45 cancer model. The binder used in the CEA CD3 TCB is CH1A1A 98/99×2F1 and not competing with the binder used in the CEA-4-1BBL. MKN45 cells were cografted subcutaneously with a mouse fibroblast cell line (3T3) in NSG humanized mice.

Human MKN45 cells (human gastric carcinoma) were originally obtained from DSMZ and after expansion deposited in the Glycart internal cell bank. Cells were cultured in DMEM containing 10% FCS at 37° C. in a water-saturated atmosphere at 5% CO2. In vitro passage 13 was used for subcutaneous injection at a viability of 99.1%. Human fibroblasts NIH-3T3 were originally obtained from ATCC, engineered at Roche Nutley to express human FAP and cultured in DMEM containing 10% Calf serum, 1× Sodium Pyruvate and 1.5 ug/ml Puromycin. Clone 39 was used at in vitro passage number 8 and at a viability of 97.6%.

50 microliters cell suspension ($1\times10^6$ MKN45 cells+$1\times 10^6$ 3T3-huFAP) mixed with 50 microliters Matrigel were injected subcutaneously in the flank of anaesthetized mice with a 22G to 30G needle.

NSG female mice (purchased from Charles River), age 5 weeks at start of the experiment, were maintained under specific-pathogen-free condition with daily cycles of 12 h light/12 h darkness according to committed guidelines (GV-Solas; Felasa; TierschG). Experimental study protocol was reviewed and approved by local government authorities. After arrival, animals were maintained for one week to get accustomed to the new environment and for observation. Continuous health monitoring was carried out on a daily basis.

For humanization, mice were injected with Busulfan (20 mg/kg) followed 24 hours later by injection of 100,000 human HSC (purchased from StemCell Technologies).

7-14 days before cell injection mice were bled and screened for the amount of human t-cells in the blood. Mice were randomized for human T cells with an average T cell count/ul blood of 131, Mice were injected sub cutaneously on study day 0 with $1\times10^6$ MKN45 cells mixed with $1\times10^6$ 3T3 fibroblasts. Tumors were measured 2 to 3 times per week during the whole experiment by Caliper. On day 17 mice were randomized for tumor size with an average tumor size of 205 mm³. On day of randomization mice were injected weekly i.v. with Vehicle, CEA CD3 TCB and the combinations of CEA CD3 TCB with CEA-4-1BBL at a dose of 10 mg/kg, 3 mg/kg or 1 mg/kg for up to 4 weeks. All mice were injected i.v. with 200 µl of the appropriate solution. The mice in the vehicle group were injected with Histidine Buffer and the treatment groups with the CEA CD3 TCB and the combinations of CEA CD3 TCB plus CEA-4-1BBL. To obtain the proper amount of compound per 200 µl, the stock solutions were diluted with Histidine Buffer when necessary. The dose and schedule used for CEA CD3 TCB was 2.5 mg/kg twice/week whereas CEA-4-1BBL was given at a dose of 10 mg/kg, 3 mg/kg or 1 mg/kg once/week.

The experiment was terminated at study day 44.

TABLE 16

| | | | CEA CD3 TCB + CEA-4-1BBL 10 mg/kg | CEA CD3 TCB + CEA-4-1BBL 3 mg/kg | CEA CD3 TCB + CEA-4-1BBL 1 mg/kg |
|---|---|---|---|---|---|
| | | Mice alive on day 44 | | | |
| Group | Vehicle | CEA CD3 TCB | | | |
| mice alive day 44 | 7/9 | 5/9 | 5/10 | 7/9 | 7/9 |

Some mice had to be sacrificed due to bad health status during the experiment.

3-4 Tumors from remaining mice per group were analysed by flow cytometry and histology at termination day 44 if tumors provided enough material. Single cell suspensions were stained for CD45, CD3, CD4 and CD8 and the amount of cells was analysed. Parts of tumors at termination and from animals during the experiment were formalin fixed and afterwards embedded in Paraffin. Samples were cut and stained for CD3 and CD8.

b) Results

In this study we wanted to prove for the first time that a tumor targeted 4-1BBL (CEA) can improve efficacy of a T-cell bispecific (TCB). We choose as a target for the TCB as well as for the 4-1BBL CEA although using different and not competing binders. The CEA-4-1BBL was given weekly at 3 different doses (10, 3 and 1 mg/kg) to evaluate dose dependency whereas the CEA CD3 TCB was given at the optimal does of 2.5 mg/kg twice per week.

To test our human constructs human immune cells and specifically T cells have to be present in the mouse system. For this reason we used humanized mice meaning mice transferred with human stem cells. These mice develop over time a partially human immune system consisting mainly of T and B cells.

We coinjected MKN45, a CEA expressing human gastric cancer cell line, and 3T3 fibroblasts which improve the stroma component in the tumor. CEA is targeted by the CEA CD3 TCB, crosslinking T cells with tumor cells and inducing T cell mediated killing of tumor cells and T cell activation. Upon T cell activation 4-1BB is upregulated mainly on CD8 positive T cells. CEA-4-1BBL crosslinks CEA expressing tumor cells and 4-1BB expressing T cells and is therefore inducing 4-1BB signaling. This leads to improved killing capacity, survival and proliferation of the T cells.

We could prove in this study that the combination of CEA-4-1BBL in a dose of 10 mg/kg, 3 mg/kg or 1 mg/kg and CEA CD3 TCB leads to improved efficacy compared to the monotherapy of CEA CD3 TCB (see FIG. 16). The combination with CEA-4-1BBL at 10 mg/kg or 3 mg/kg leads to stronger tumor growth inhibition than the combination with 1 mg/kg. T-cell infiltration in the tumor at termination on day 44 is significantly increased in the combination groups compared to vehicle and CEA CD3 TCB monotherapy shown by flow cytometry (see FIGS. 18A-18C). The analysis by histology shows only a significant increase of CD8 and CD3 positive T-cells (see FIGS.

19A and 19B, respectively) in the combination groups with 10 and 3 mg/kg but not with 1 mg/kg.

TABLE 17

| | | | Concentration |
|---|---|---|---|
| Compositions used in the in vivo experiments | | | |
| Compound | Dose | Formulation buffer | (mg/mL) |
| CEA-4-1BBL | 10 mg/kg, 3 mg/kg and 1 mg/kg | 20 mM Histidine, 140 mM NaCl, pH 6.0 0.01% TWEEN ® 20 | 3.78 (=stock solution) |
| CEA CD3 TCB | 2.5 mg/kg | 20 mM Histidine, 140 mM NaCl, 0.01% TWEEN ® 20, pH 6.0 | 4.82 (=stock solution) |

Tumor growth inhibition based on medians was calculated at study day 36, 38, 41 and 43. The Group treated with CEA CD3 TCB+CEA-4-1BBL 10 mg/kg shows the strongest inhibition of tumor growth.

TABLE 18

| | | | | |
|---|---|---|---|---|
| Tumor growth inhibition (TGI) at study day 36, 38, 41 and 43 | | | | |
| Group | Day 36 | Day 38 | Day 41 | Day 43 |
| CEA CD3 TCB | 62.8 | 55.1 | 47.3 | 32.7 |
| CEA CD3 TCB + CEA-4-1BBL 10 mg/kg | 93.8 | 93.0 | 92.7 | 112.5 |
| CEA CD3 TCB + CEA-4-1BBL 3 mg/kg | 67.6 | 85.0 | 86.2 | 102.1 |
| CEA CD3 TCB + CEA-4-1BBL 1 mg/kg | 51.6 | 66.2 | 73.1 | 83.5 |

To test for significant differences in group means for multiple comparisons, the standard analysis of variance (ANOVA) is automatically produced, using the Dunnett's method. On day 43 the combination of CEA CD3 TCB+CEA-4-1BBL 10 mg/kg is significantly different from CEA CD3 TCB monotherapy (see Table 19).

TABLE 19

| | |
|---|---|
| One Way Analysis of tumor volumes on day 43, comparison with CEA CD3 TCB | |
| Means Comparisons with a control using Dunnett's Method (d43) (Control Group = CEA CD3 TCB) | p-Value |
| Vehicle | 0.1197 |
| CEA CD3 TCB | 1.0000 |
| CEA CD3 TCB + CEA-4-1BBL 1 mg/kg | 0.3451 |
| CEA CD3 TCB + CEA-4-1BBL 3 mg/kg | 0.0713 |
| CEA CD3 TCB + CEA-4-1BBL 10 mg/kg | 0.0167 |

The combination of CEA CD3 TCB+CEA-4-1BBL 10 mg/kg and 3 mg/kg are significantly different from vehicle considering the area under the curve (AUC) until day 43 as shown in Table 20.

178

TABLE 20

One Way Analysis of sAUC until day 43, comparison
with Vehicle (AUC = area under the curve)

| Comparisons with a control using Dunnett's Method (sAUC) (Control Group = vehicle) | p-Value |
|---|---|
| Vehicle | 1.0000 |
| CEA CD3 TCB | 0.0563 |
| CEA CD3 TCB + CEA-4-1BBL 1 mg/kg | 0.0527 |
| CEA CD3 TCB + CEA-4-1BBL 3 mg/kg | 0.0084 |
| CEA CD3 TCB + CEA-4-1BBL 10 mg/kg | 0.0005 |

In FIGS. 17A and 17B the pharmacokinetic profile of the injected compounds during the first week is shown. In order to study the pharmacokinetic profile of injected compounds during the first week, 2 mice per Group were bled 1 h and 72h after 1st and 2nd therapy.

Injected compounds were analysed by ELISA.

(A) Biotinylated human 4-1BB, test sample, Digoxigenin labelled anti-huCH1 antibody and anti-Digoxigenin detection antibody (POD) are added stepwise to a 96-well streptavidin-coated microtiter plate and incubated after every step for 1 h at room temperature. The plate is washed three times after each step to remove unbound substances. Finally, the peroxidase-bound complex is visualized by adding ABTS substrate solution to form a colored reaction product. The reaction product intensity which is photometrically determined at 405 nm (with reference wavelength at 490 nm) is proportional to the analyte concentration in the serum sample.

(B) Biotinylated anti-huCD3-CDR antibody, test sample, Digoxigenin labelled anti-huFc antibody and anti-Digoxigenin detection antibody (POD) are added stepwise to a 96-well streptavidin-coated microtiter plate and incubated after every step for 1 h at room temperature. The plate is washed three times after each step to remove unbound substances. Finally, the peroxidase-bound complex is visualized by adding ABTS substrate solution to form a colored reaction product. The reaction product intensity which is photometrically determined at 405 nm (with reference wavelength at 490 nm) is proportional to the analyte concentration in the serum sample.

4-1BBL was detected via 4-1BB binding (A), whereas CEA CD3 TCB was detected via binding to anti-CD3 CDR antibody (B).

All groups injected with compounds show comparable exposure of the molecules between the different groups (dose dependent), either CEA-4-1BBL or CEA CD3 TCB.

Figure 18C:
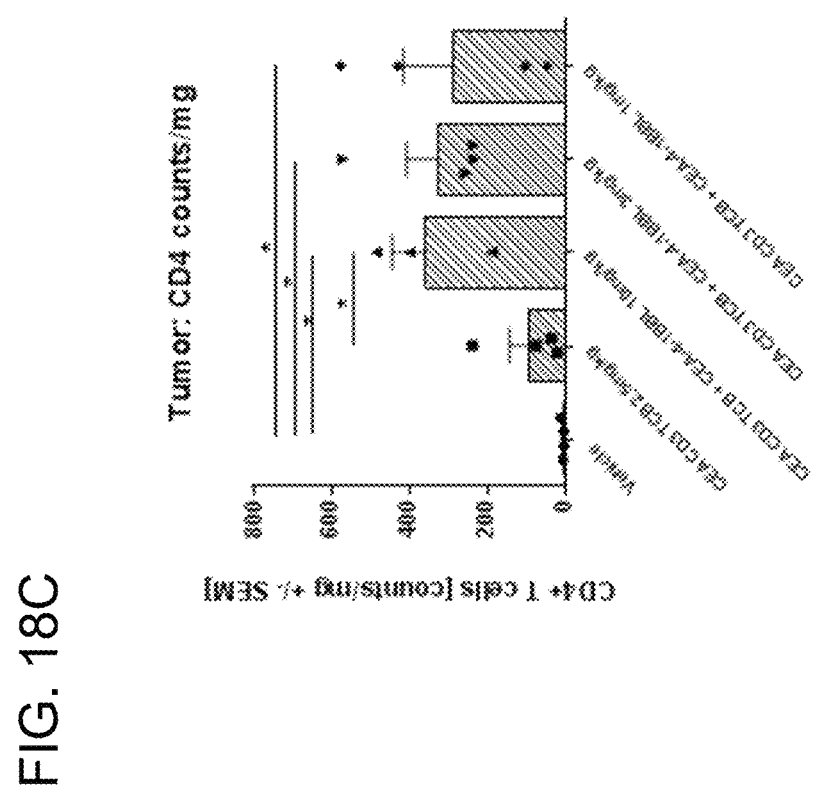

The T cell infiltration in tumor at study termination was analysed by FACS. Tumors from 3-4 mice/group were analysed by flow cytometry at day 44. Single cell suspensions were stained for CD45, CD3, CD4 and CD8 and the amount of cells was analysed. One Way ANOVA and Tukey's multiple comparison test (with p<0.05) was used as statistical methods. The T cell infiltration in tumor at study termination is illustrated in FIGS. 18A, 18B and 18C.

Combining CEA-4-1BBL in doses 10, 3 or 1 mg/kg with CEA CD3 TCB leads to a statistically increased infiltration of CD3, CD8 and CD4 (in particular for combination with 10 mg/kg CEA-4-1BBL) positive T-cells in the tumor at day 44 compared to CEA CD3 TCB monotherapy.

Immunohistochemical images of human MKN45 gastric subcutaneous tumors cografted with 3T3 murine fibroblasts derived from the indicated treatment groups in humanized NOG mice were generated. Tissue samples were prepared for immunohistochemical staining. Subcutaneous tumors were harvested from animals at the end of the study, day 44 (vehicle, CEA CD3 TCB and the combinations). Tumors were fixed in formalin 10% (Sigma, Germany) and later processed for FFPET (Leica 1020, Germany). 4 μm paraffin sections were subsequently cut in a microtome (Leica RM2235, Germany). HuCD8 and HuCD3 immunohistochemistry was performed with anti-human CD8 (Cell Marque Corporation, California) and anti-human CD3 (ThermoFischer Scientific, USA) in the Leica autostainer (Leica ST5010, Germany) following the manufacture's protocols. Quantification of huCD8 and CD3 positive T cells was performed with Definiens software (Definiens, Germany). Statistics were analyzed by one way ANOVA with multiple comparison tests. Results showed very low number of T cells in the MNK45/3T3 sc tumors from untreated mice at termination day 44. There is a significant increase of CD3 positive T cells (FIG. 19A) and CD8 positive T cells (FIG. 19B) in the groups treated with CEA CD3 TCB+CEA-4-1BBL 10 mg/kg and 3 mg/kg group compared to CEA CD3 TCB monotherapy and vehicle (statistics One Way ANOVA, Tukey's multiple comparison test, p<0.05).

Example 8

In Vitro Co-Culture Assays with Human Immune Effector Cells

The immune functions of T cells were tested in in vitro co-culture assays with human immune effector cells (resting PBMC, CD4 or CD8 T cells, NLV specific CD8 T effector memory cells), target antigen positive tumor cells and FAP positive fibroblasts in the presence of TCBs (CEA CD3 TCB (2), CEA TCB CD3) and FAP 4-1BBL). The evaluated tumor cell line was the gastric cancer cell line MKN-45. The mouse embryonic fibroblast cell line NIH/3T3 transduced to express human FAP was used as FAP positive fibroblast. Effector cells were resting human PBMC, isolated resting CD4 or CD8 T cells. In some cases also antigen specific effector memory CD8 T cells were used. In some assays, TNF-α sensor cells were added to monitor TNF-α, induction. Tumor cell lysis (kinetic high content life imaging, endpoint flow cytometry), expression of cell surface activation and maturation markers (endpoint flow cytometry) and cytokine secretion (kinetic high content life imaging, endpoint cytometric bead array) was used to monitor the extent of T cell function induced by TCBs and modulated by FAP targeted immune modulators.

a) Target cell lines and fibroblasts

The MKN45 NucLight Red (NLR) cells naturally express CEA. MKN-45 (ATCC, Cat. No. TCP-1008) were transduced with the Essen CellPlayer NucLight Red Lentivirus (Essenbioscience, Cat. No. 4476; EF1α, puromycin)) at an MOI of 3 (TU/cell) in the presence of 8 μg/ml polybrene following the manufacturers instructions to stable express the NucLight Red fluorescent protein restricted to the nucleus. This enables easy separation from non-fluorescent effector T cells or fibroblasts and monitoring of the tumor cell growth by high through put life fluorescence microscopy. Quantification of red events or mena integrated red fluorescence per well over time allows thus real-time assessment of tumor cell lysis or proliferation.

MKN45 NucLight Red cells were cultured in DMEM (GIBCO, Cat. No 42430-082) containing 10% Fetal Bovine Serum (FBS, Gibco by Life Technology, Cat. No. 16000-044, gamma-irradiated, *mycoplasma*-free and heat inactivated at 56° C. for 35 min), 1% (v/v) GlutaMAX I (GIBCO by Life Technologies, Cat. No. 35050 038), 1 mM sodium pyruvate (SIGMA, Cat. No. S8636) and 0.5 ug/mL Puromycin (Sigma-Aldrich, Cat. No. ant-pr-1).

The crosslinking of FAP-binding antibodies by cell surface FAP was provided by human fibroblast activating protein (huFAP) expressing NIH/3T3-huFAP clone 19. This cell line was generated by the transfection of the mouse embryonic fibroblast NIH/3T3 cell line (ATCC CRL-1658) with the expression vector pETR4921 to express huFAP. Cells were cultured in DMEM (GIBCO, Cat. No. 42430-082) containing 10% calf serum (Sigma-Aldrich, Cat. No. C8056-500 ml, gamma-irradiated, *mycoplasma*-free and heat inactivated at 56° C. for 35 min) and 1.5 µg/mL Puromycin (Sigma-Aldrich, Cat. No. ant-pr-1).

b) Preparation of Effector cells

Buffy coats were obtained from the Zürich blood donation center. To isolate fresh peripheral blood mononuclear cells (PBMCs) the buffy coat was diluted with the same volume of DPBS (Gibco by Life Technologies, Cat. No. 14190 326). 50 mL polypropylene centrifuge tubes (TPP, Cat.-No. 91050) were supplied with 15 mL Histopaque 1077 (SIGMA Life Science, Cat.-No. 10771, polysucrose and sodium diatrizoate, adjusted to a density of 1.077 g/mL) and the buffy coat solution was layered above the Histopaque 1077. The tubes were centrifuged for 30 min at 400× g, room temperature and with low acceleration and no break. Afterwards the PBMCs were collected from the interface, washed three times with DPBS and resuspended in T cell medium consisting of RPMI 1640 medium (Gibco by Life Technology, Cat. No. 42401-042) supplied with 10% Fetal Bovine Serum (FBS, Gibco by Life Technology, Cat. No. 16000-044, Lot 941273, gamma-irradiated, *mycoplasma*-free and heat inactivated at 56° C. for 35 min), 1% (v/v) GlutaMAX I (GIBCO by Life Technologies, Cat. No. 35050 038), 1 mM Sodium Pyruvate (SIGMA, Cat. No. S8636), 1% (v/v) MEM non-essential amino acids (SIGMA, Cat.-No. M7145) and 50 µM β-Mercaptoethanol (SIGMA, M3148). In some cases, RPMI1640 was replaced by FluoroBrite DMEM media (GIBCO, Invitrogen, Cat No A18967-01) for improved high content live microscopy with reduced background fluorescence.

PBMCs were used as effector cells directly after isolation (resting human PBMCs) or certain subfractions, as resting CD4 T cells or CD8 T cells, were isolated using the untouched human CD4+ T cell isolation kit (Miltenyi, Ca. No. 130-096-533) and untouched human CD8+ T cell isolation kit (Miltenyi, Ca. No. 130-096-495) according to manufacturers instructions, respectively. Briefly, human PBMC were centrifuged for 8 min at 400× g, 4° C. and were washed once with MACS buffer (PBS+BSA (0.5% v/w, Sigma-Aldrich, Cat. No. A9418)+EDTA ([2 nM], Ambion, AM9261)). The pellet was resuspended with the respective provided streptavidin labeled negative antibody cocktail and incubated for 5 minutes at 4° C. (per 1*107 cells 40 µL MACS buffer and 10 µL antibody mix) followed by a subsequent incubation with biotinylated magnetic capture beads (per 1*107 cells 30 µL MACS buffer and 20 µL bead mix) for 10 min at 4° C. Labeled non-CD4 or non-C8 T cells were removed by magnetic separation using an LS column (Miltenyi, Ca. No. 130-042-401) according to manufacturer's instructions. The column flow through, containing unlabeled resting CD4 and CD8 T cells, respectively, was centrifuged and washed once with MACS buffer as described above. Cells were adjusted to 2 mio cells/mL in RPMI1640 or Fuorobright DMEM based T cell media.

c) Isolation and culture of antigen-specific CD8 T cells

In some assays antigen specific CD8 T cells were used as effector cells. Fresh blood was obtained from a HLA-A2+

CMV-infected volunteer. PBMCs were isolated as described above. CD8 T cells were purified from PBMCs using a negative selection human CD8 T cell isolation Kit according to manufacturer's recommendations (Miltenyi Biotec, Cat. No. 130-094-156) as described above. Ten million of isolated CD8 T cells were resuspended in 1 mL sterile DPBS supplemented with 1% (v/v) FBS along with 50 µL of PE-labeled HLA-A2-pentamer containing the CMV-derived NLVPMVATV peptide (SEQ ID NO: 169) (ProImmune, Cat. No. F008-2B) and incubated for 10 min at room temperature. Cells were washed twice with 3 mL sterile DPBS supplied with 1% (v/v) FBS. Cells were resuspended in 1 mL cells DPBS supplied with 1% (v/v) FBS containing 1 µg/mL anti-human CD8-FITC (clone LT8, Abcam, Cat. No. Ab28010) and incubated for 30 minutes at 4° C. Cells were washed twice, resuspended to a concentration of 5×10⁶ cells/mL in DPBS supplied with 1% (v/v) FBS, and filtrated through a 30 µm pre-separation nylon-net cell strainer (Miltenyi Biotec, Cat. No. 130-041-407). NLV-peptide-specific CD8⁺ T cells were isolated by FACS sorting using an ARIA cell sorter (BD Bioscience with DIVA software) with the following settings: 100 µm nozzle and purity sort mask. Sorted cells were collected in a 15 ml polypropylene centrifuge tube (TPP, Cat. No. 91015) containing 5 ml RPMI 1640 medium supplied with 10% (v/v) FBS, 1% (v/v) GlutaMAX-I and 400 U/mL Proleukin. Sorted cells were centrifuged for 7 minutes at 350× g at room temperature and resuspended in same medium to a concentration of 0.53×10⁶ cells/mL. 100 µL/well of this cell suspension were added to each well of a previously prepared feeder plate.

PHA-L-activated irradiated allogeneic feeder cells were prepared from PBMCs as previously described (Levitsky et al., 1998) and distributed to 96 well culture plates at 2×10⁵ feeder cells per well.

After one day of culturing 100 µL medium/well were removed from well containing sorted CD8⁺ T-cells and replaced by new RPMI 1640 medium supplemented with 10% (v/v) FBS and 1% (v/v) GlutaMAX-I and 400 U/mL Proleukin, this was repeated during culture on a regular basis (every 2-4 days). As soon as cells start to proliferate, they were transferred to 24-well flat-bottom tissue culture plate (TPP, 92024). Cells were expanded/split and reactivated with new feeder cell preparation on a regular basis.

d) TNF-α sensor cells

TNF-α, sensor cells were HEK 293T cells (ATCC, Cat. No. xxx) transduced with the reporter plasmid pETR14327 encoding for green fluorescent protein (GFP) under the control of an NFκB sensitive promotor element. HEK 293T cells express naturally the TNF receptor to which TNF-α secreted by activated T cells can bind. This leads to dose dependent activation of NFκB and translocation to the nucleus, which in turn switches on dose dependent GFP production. The GFP fluorescence can be quantified by high through put life fluorescence microscopy over time and allows thus real-time assessment of TNF-α secretion. e) Cytotoxicity and T cell activation assay Mouse embryonic fibroblast NIH/3T3-huFAP cells, TNF-α, sensor cells and MKN45 NLR cells were harvested using cell dissociation buffer (Invitrogen, Cat.-No. 13151-014) for 10 minutes at 37° C. Cells were washed once with DPBS. TNF-α sensor cells or fibroblasts were irradiated in an xRay irradiator using a dose of 4500 RAD to prevent later overgrowth of effector or tumor cell lines. Target cell lines, NIH/3T3-huFAP and in some assays TNF-α sensor cells were cultured at a density of 0.1*105 cells per well in T cell media in a sterile 96-well flat bottom adhesion tissue culture plate (TPP, Cat. No. 92097) overnight at 37° C. and in 5% $CO_2$ in an incubator (Hera Cell 150).

Resting human PBMC, human CD4 T cells, human CD8 T cells or NLV-specific T cells were prepared as described above and were added at a density of 0.5*105 cells per well. A serial dilution row of TCBs (CEA CD3 TCB or CEA CD3 TCB (2)) and a fixed concentration of FAP 4-1BBL (2 nM) was added to a total volume of 200 uL per well. Cells were cocultured for up to 72 hours at 37° C. and 5% $CO_2$ in an incubator (Hera Cell 150).

In some assays, plates were monitored by fluorescence microscopy high content life imaging using the Incucyte Zoom System (Essenbioscience, HD phase-contrast, green fluorescence and red fluorescence, 10× objective) in a 3 hours interval for up to 72 hours at 37° C. and 5% $CO_2$. The integrated red fluorescence of healthy tumor cells (RCU× um2/image), which is proportional to the amount of $NLR^+$ cells per well, was quantified using the IncucyteZoom Software to monitor tumor cell growth vs lysis by T cells. Values were plotted for the respective time point and conditions against the used TCB concentration to analyse effects on the cytolytic potential of T cells.

In some assays where TNF-α sensor cells were present, the integrated green RCU×um2/image was quantified using the IncucyteZoom Software to monitor TNF-α, induced production of GFP by the TNF-α sensor cells. Values were plotted for the respective time point and conditions against the used TCB concentration to analyze effects on TNF-α, secretion by T cells.

After 72 hrs, the supernatant was collected for subsequent analysis of selected cytokine using the cytometric bead array according to manufacturer's instructions. Evaluated cytokines were IL-2 (Human IL-2 CBA Flex-set (Bead A4), BD Bioscience, Ca. No. 558270), IL-17A (Human IL-17A CBA Flex-set (Bead B5), BD Bioscience, Ca. No. 560383), TNF-α, (Human TNF-α CBA Flex-set (Bead C4), BD Bioscience, Ca. No. 560112), IFN-γ (IFN-γ CBA Flex-set (Bead E7), BD Bioscience, Ca. No. 558269), IL-4 (Human IL-4 CBA Flex-set (Bead A5), BD Bioscience, Ca. No. 558272), IL-10 (Human IL-10 CBA Flex-set (Bead B7), BD Bioscience, Ca. No. 558274) and IL-9 (Human IL-9 CBA Flex-set (Bead B6), BD Bioscience, Ca. No. 558333).

Thereafter, all cells were detached from the wells by incubation with cell dissociation buffer for 10 minutes at 37° C. followed by centrifugation at 400×g at 4° C. Pellets were washed with ice cold FACS buffer (DPBS (Gibco by Life Technologies, Cat. No. 14190 326) w/ BSA (0.1% v/w, Sigma-Aldrich, Cat. No. A9418). Cells were surface-stained with fluorescent dye-conjugated antibodies anti-human CD4 (clone RPA-T4, BioLegend, Cat.-No. 300532), CD8 (clone RPa-T8, BioLegend, Cat.-No. 3010441), CD62L (clone DREG-56, BioLegend, Cat.-No. 304834), CD127 (clone 019D5, BioLegend, Cat.-No. A019D5), CD134 (clone Ber-ACT35, BioLegend, Cat.-No. 350008), CD137 (clone 4B4-1, BioLegend, Cat.-No. 309814), GITR (clone 621, BioLegend, Cat.-No. 3311608) and CD25 (clone M-A251, BioLegend, Cat.-No. 356112) for 20 min at 4° C. in FACS buffer. Then, they were washed once with FACS buffer before being resuspended in 85 µL/well FACS buffer containing containing 0.2 µg/mL DAPI (Santa Cruz Biotec, Cat. No. Sc-3598) before they were acquired the same day using 5-laser LSR-Fortessa (BD Bioscience with DIVA software). Living CD4 and CD8 T cells were gated (DAPI-, NucLight RED-, CD4 or $CD8^+$) and counts, the mean fluorescence intensity (MFI) of activation marker (CD134, CD137, GITR, CD25) or maturation marker (CD127, CD62L) or the percentage of positive cells were plotted for the respective conditions against the used TCB concentration to analyze effects on T activation.

Results 8.1 T Cell Bispecific Antibodies Induce a Dose Dependent Upregulation of 4-1BB on CD8 and CD4 T Cells Different human immune effector cell preparations (resting PBMC, CD4 or CD8 T cells, NLV specific CD8 T effector memory cells) were cocultured with MKN-45 NucLight Red cells and irradiated NIH/3T3 huFAP in the presence of a serial dilution row of CEACAM5 CD3 TCB for 48 hrs. The amount of living tumor cells was quantified by fluorescence microscopy high content life imaging using the Incucyte Zoom System and the integrated red fluorescence of healthy tumor cells was used to calculate the specific lysis (FIG. 20). The expression of 4-1BB was evaluated by flow cytometry on CD4 and CD8 positive T cells (FIGS. 21A to 21D).

CEACAM5 CD3 TCB was able to induce lysis of MKN45 NucLight red cells in all used immune effector cell preparations, as shown in FIG. 20 for the 42 hours time point. The $EC_{50}$ values and the magnitude of lysis differed slightly between the different effector cell preparations and was highest for isolated CD8 T cells and lowest for CD4 T cells. Concomitant to tumor cell lysis, T cells increased surface expression of activation markers including 4-1BB (FIGS. 21A to 21D). Surface expression of 4-1BB was highest on CD8 positive T cells, but was also detected to a lower extent on CD4 positive T cells. The extent of 4-1BB expression was not depending on the presence of helper cells (no difference of expression levels in PBMC vs isolated populations for CD4 or CD8 T cells). The extent of 4-1BB expression was less strong upon restimulation of fully differentiated effector memory NLV spec. CD8 T cells compared to stimulation of resting CD8 T cells. However, this might also be due to a single endpoint analysis, as the kinetics of 4-1BB on memory and naïve cells differ slightly.

8.2 The presence of FAP-targeted 4-1BBL does not influence the cytolytic potential of T cells Next we evaluated the influence of 4-1BB costimulation on TCB mediated tumor cell lysis. As described in 8.1, T cells were cocultured for 48 hours with MKN-45 NucLight Red cells and irradiated NIH/3T3 huFAP in the presence of a serial dilution row of CEACAM5 CD3 TCB with or without a fixed concentration of FAP 4-1BBL, respectively.

The amount of living tumor cells was quantified by fluorescence microscopy high content life imaging using the Incucyte Zoom System in 3 hour intervals and the integrated red fluorescence of healthy tumor cells was used to calculate the specific lysis.

The presence of 4-1BBL costimulation did neither speed up tumor cell lysis nor increase the magnitude of tumor cell lysis nor decrease the TCB concentration necessary to achieve lysis of a certain percentage of tumor cells (e.g. shift in $EC_{50}$ values). This was true for all evaluated effector cell preparations and is shown exemplary for the 42 hours time point in FIGS. 22A to 22D.

8.3 The presence of FAP targeted 4-1BBL does influence the secretion of cytokines In some assays, TNF-α sensor cells were cultured additionally to the above described setting. TNF-α sensor cells naturally express the TNF-α receptor and were genetically modified with GFP under the control of an NFκB sensitive promotor element. Binding of TNF-α secreted by activated T cells leads to dose dependent activation of NFκB and subsequently to expression of GFP. The GFP fluorescence can be quantified by high through put life fluorescence microscopy over time and allows thus real-time assessment of TNF-α secretion. As described in 8.1 above, CD4 T cells were cocultured for 48 hours with MKN-45 NucLight Red cells as target cells and irradiated NIH/3T3 huFAP in the presence of a serial dilution row of CEACAM5 CD3 TCB and CEA CD3 TCB, respectively, with or without a fixed concentration of FAP 4-1BBL.

Activation of T cells by the present TCB led to dose dependent release of TNF-α, which led to a dose dependent increase of GFP fluorescence over time in the TNF-α sensor cells. Additional costimulation with FAP 4-1BBL further increased the GFP fluorescence and thus the TNF-α secretion by activated T cells (FIGS. 23A to 23D). This effect increased the magnitude of TCB mediated TNF-α, secretion but did not lower the TCB concentration itself at which TNF-α secretion was induced. For an easier comparison over time the area under curve (AUC) was calculated for each time point with and w/o 4-1BB costimulation and was plotted against time (FIGS. 24A to 24B).

The supernatants of all samples were evaluated at the end point (48 hours) using the cytometric bead array system (BD Bioscience) to quantify the effect on secretion of several cytokines beyond TNF-α. Evaluated cytokines were IL-2 and TNF-α, as marker for general T cell activation, IFN-γ (Th1 cytokine), IL-4 (Th2 cytokine), IL-9 (Th9 cytokine) and IL-17A (Th17 cytokine) to monitor a differentiation towards a certain Th subclass, and IL-10 as immunesuppressive cytokine.

Activation of T cells by the present TCB led, next to TNF-α, to a dose dependent release of all evaluated cytokines, namely IL-2, IL-4, IFN-γ, IL-17a and IL-10 (FIGS. 25A to 25D, FIGS. 26A to 26D). Additional co-stimulation with FAP 4-1BBL modulated the extent of dose-dependent cytokine secretion, but did not lower the TCB threshold concentration needed for cytokine secretion. Thereby, an increase of pro-inflammatory IL-2, TNF-α, and IFN-γ secretion was observed, whereby the concentration of immune-suppressive IL-10 was lowered. For an easier comparison, the changes in cytokine concentration in samples with 4-1BB costimulation were calculated relative to those without costimulation for the TCB plateau concentration (FIG. 27).

We also tested the ability of 4-1BBL costimulation to modulate the cytokine secretion of resting CD8 T cells and fully differentiated effector memory NLV spec. CD8 T cells. As described in 8.1, resting human PBMC, isolated CD4 or CD8 T cells and NLV specific CD8 effector memory CD8 T cells were cocultured for 72 hours with MKN-45 NucLight Red cells and irradiated NIH/3T3 huFAP in the presence of a serial dilution row of CEACAM5 CD3 TCB with or without a fixed concentration of FAP 4-1BBL. The supernatant was evaluated at 72 hours using the cytometric bead array as described above.

4-1BB costimulation supported the secretion of pro-inflammatory cytokines in resting human PBMC, CD4 and CD8 T cells (dose dependency, see FIGS. 28A to 28H and FIGS. 29A to 29H), comparison for top TCB concentration see FIG. 30). A especially remarkable impact was shown on IL-2 and TNF-α, production in resting CD8 T cells. Albeit to a lower extent, 4-1BB costimulation was also able to modulate the cytokine secretion of fully differentiated CD8 T cells.

Thus, costimulation via 4-1BBL does not increase directly the cytolytic potential of T cells in a time range of 48-72 hours in the in vitro cytotoxicity assay, but it increases the ability to secrete cytokines and modulated the cytokine microenvironment. A more proinflammatory cytokine mileau in the tumor can shift the tumor microenvironment towards a more immune activating and less immunesuppressive state, e.g. a lower level of IL-10 and increased concentrations of IFN-γ can allow myeloid cells in the tumor to mature to Th1 and cytotoxic T cell supporting antigen presenting cells. A shift to a supportive cytokine network will restore a successfully and sustained tumor cell elimination.

Example 9

In vitro co-culture assays with MKN45 cells expressing CEA and PDL-1

FAP-expressing NIH/3T3-huFAP cells were harvested using PBS-based dissociation buffer (Gibco by Life Technologies, Cat.-No: 13151-014), resuspended in assay medium consisting of RPMI (GIBCO, Invitrogen by Life Technologies, Cat.-No 42401-042) supplied with 10% (v/v) FBS and 1% (v/v) GlutaMAX-I (GIBCO, Invitrogen by Life Technologies, Cat-No. 35050-038), 1 mM Sodium pyruvate (SIGMA, Cat.-No. S8636), 1% (v/v) MEM non-essential amino acids (SIGMA, Cat.-No. M7145) and 50 μM $-Mer-captoethanol (SIGMA, M3148) and irradiated with 50 Gy using X-Ray Irradiator RS 2000 (Rad source). CEACAM5-expressing MKN45-huPD-L1 cells harvested, labeled with PKH-26 red (Sigma Cat.-No. PKH26GL-1KT) and resuspended in assay medium and irradiated with 50 Gy. Human PBMCs were isolated from buffy coat using Ficoll density centrifugation and were labeled with 40 nM CFDA-SE in 37° C. warm PBS (GIBCO by Life Technologies, Cat-No. 14190-136) for 15 min. After labeled CFSE-labeled PBMCs were washed and resuspended in assay medium. In a 96-well round bottom TC-treated plate in each well 0.01×106 irradiated NIH/3T3-huFAP cells, 0.01×106 PKH-26 red labeled and irradiated MKN45-huPDL-1 cells, 0.05×106 CFSE-labeled PBMCs, 100 nM CEA CD3 TCB or 20 nM CEACAM5 CD3 TCB and 1 nM FAP-4-1BBL or 1 nM DP47-4-1BBL or no Ab were seeded in 200 mL assay medium. The cells were incubated for 4 days. Afterwards cells were stained for flow cytometry analysis with LIVE/ DEATH Fixable Aqua (Molecular Probes, Cat.-No. L34957), Per-CPCy5.5 conjugated anti-human CD137 mouse IgG1 (BioLegend, Cat.-No. 309814), PE/Cy7-conjugated anti-human CD8 mouse IgG1 (BioLegend, 301012), APC-conjugated anti-human CD25 mouse IgG1 (BioLegend, Cat.-No. 302610), APC/Cy7-conjugated anti-human OX40 (BioLegend, Cat.-No. 350022) and BV421-conjugated anti-human CD4-BV421 (BioLegend, Cat.-No. 300532). Cells were acquired using MACS Quant Analzyer 10 (Mitenyi Biotec) and analyzed using FlowJo and GraphPad Prism. Statistics were analyzed using Significance test: One-way Anova with Tukey's multiple comparison test of twelves technical replicates.

The results are shown in FIG. 31 for CEA CD3 TCB and in FIG. 32 for CEACAM5 CD3 TCB.

Example 10

In vitro PBMC activation assay combining FAP-4-1BBL with CEA CD3 TCB and/or Atezolizumab In this assay FAP-4-1BBL was tested for its potential to activate human PBMCs (isolated from buffy coat, frozen and stored in liquid nitrogen) in the presence or absence of CEA CD3 TCB and Atezolizumab (Tecentriq, anti-human PD-L1-specific humanized human IgG1x antibody) similar as described in Example 9. To mimic the tumor environment PBMCs of five different donors were incubated with FAP-expression NIH/3T3-huFAP fibroblast cell line and with CEA-expressing MKN45-PDL1 gastric cancer cell line for four days in the presence of absence of 1 nM FAP-4-1BBL or 1 nM DP47-4-1BBL and/or 100 nM CEA CD3 TCB and/or 80 nM Atezolizumab. For determining PBMC activation CD4 and CD8 T cells were analyzed by flow cytometry for proliferation (CFSE-dilution), CD25 (IL-2R(X), 4-1BB (CD137) and PD-1 expression. Supernatant was analyzed by Multiplex for IFN$\gamma$, TNF$\alpha$, GM-CSF, IL-4, IL-2, IL-6, IL-8 and IL-10.

a) Preparation of PBMCs

Buffy coats were obtained from the Zürich blood donation center. To isolate fresh peripheral blood mononuclear cells (PBMCs) the buffy coat was diluted with the same volume of DPBS (Gibco by Life Technologies, Cat. No. 14190 326). 50 mL Falcon centrifuge tubes (TPP, Cat.-No. 91050) were supplied with 15 mL Histopaque 1077 (SIGMA Life Science, Cat.-No. 10771, polysucrose and sodium diatrizoate, adjusted to a density of 1.077 g/mL) and the buffy coat solution was over-layered on 15 mL Histopaque 1077. The tubes were centrifuged for 30 min at 450× g, room temperature and with low acceleration and no break. Afterwards the PBMCs were collected from the interface, washed three times with DPBS and resuspended in T cell freezing medium consisting of RPMI 1640 medium (Gibco by Life Technology, Cat. No. 42401-042) supplied with 20% Dimethyl sulfoxide (Sigma, Cat.-No. D2650), 10% (v/v) Fetal Bovine Serum (FBS, Gibco by Life Technology, Cat. No. 16000-044, Lot 941273, gamma-irradiated, *mycoplasma*-free and heat inactivated at 56° C. for 35 min), 1% (v/v) GlutaMAX I (GIBCO by Life Technologies, Cat. No. 35050 038). 1-1.5 mL were transferred quickly to sterile Cryovials, transferred to Cryoboxes and stored for at least 48 h at −80° C. Afterwards vials were transferred to liquid nitrogen containers or Vapor phase containers.

Vials from 8 donors were thawed and washed in assay medium consisting of RPMI 1640 medium supplied with 10% (v/v) Fetal Bovine Serum (FBS), 1% (v/v) GlutaMAX I, 1 mM Sodium pyruvate (SIGMA, Cat. No. S8636), 1% (v/v) MEM non-essential amino acids (SIGMA, Cat.-No. M7145) and 50 μM $-Mercaptoethanol (SIGMA, M3148). Cells were counted, washed with DPBS and resuspended in 37° C. DPBS to 1×10$^6$ cells/mL. CFDA-SE was added to a final concentration of 40 nM and incubated for 15 min at 37° C. Afterwards FBS was added, cells were washed and set in assay medium (2×10$^6$ cells/mL) and rested overnight in 6 well tissue-culture plates at 37° C. and 5% CO$_2$ in cell incubator. The next day PBMCs were harvested, counted and resuspended in assay medium to 1×10$^6$ cells/mL.

b) Target Cell Lines

T150 flasks containing NIH/3T3-huFAP clone 19 were washed with DPBS and incubated with enzyme-free PBS-based dissociation buffer for 8 min at 37° C. Cells were collected, washed, resuspended in assay medium and irradiated with 50 Gy using X-Ray Irradiator RS 2000. Cells were set in assay medium to 0.4×10$^6$ cells/mL.

T150 flasks containing MKN45-PD-L1 were washed with DPBS and incubated with enzyme-free PBS-based dissociation buffer for 8 min at 37° C. Cells were collected, washed with DPBS and resuspended in C diluent (at least 250 μL, 8×10$^7$ cells/mL or lower). The same amount of C diluent was supplied with 4 μL/mL PKH-26 dye and mixed well. This dye solution was added to the cells and mixed well and immediately. Cells were incubated for 5 min at room temperature. Afterwards FBS was added, cells were washed in assay, resuspended in assay medium and irradiated with 50 Gy with the X-Ray Irradiator RS 2000 (Rad source). Cells were set in assay medium to 0.4×10$^6$ cells/mL.

c) Assay Setup

For the test compounds master solutions were prepared of each component in assay medium as follows 4 nM FAP-4-1BBL, 4 nM DP47-4-1BBL, 800 nM CEA CD3 TCB and 640 nM Atezolizumab. Cells and components were combined in 96-well round bottom tissue culture plates (TTP, Cat.-No. 92097) in amounts of 25 μL of PKH-26red labeled MKN45-PD-L1 (10'000 cells/well), 25 μL of NIH/3T3-huFAP clone 19 (10'000 cells/well), 50 μL of PBMC of one donor (50'000 cells/well), 50 μL of 4 nM FAP-4-1BBL or 4 nM DP47-4-1BBL solution or assay medium (final concentration 1 nM), 25 μL of 800 nM CEA CD3 TCB solution or assay medium (final concentration 100 nM), and 25 μL of 640 nM Atezolizumab solution or assay medium (final concentration 80 nM). Plates were then incubated for four days at 37° C. and 5% CO$_2$ in a humidified cell incubator.

After four days 50 μL supernatant was removed and stored at −80° C. to be later analyzed for cytokine content (see below). To perform a flow cytometry analysis of T cell proliferation and surface expression plates were centrifuged and washed once with cold DPBS. Samples are stained for 30 min at 4° C. in 100 μL/well DPBS supplied with 1:1000 diluted LIVE/DEAD Fixable Aqua Dead Cell Stain. Cells were washed once with 200 μL/well DPBS (centrifugation 350× g 4 min 4° C., flick off). Cells were resuspended in 50 μL/well staining solution composed of FACS-buffer containing 1 μg/mL anti-human CD137-PerCP/Cy5.5 and 0.67 μg/mL anti-human PD-1-PE/Cy7, 0.5 μg/mL anti-human CD25-APC, 0.67 μg/mL anti-human CD8-APC-Cy7 and 0.67 μg/mL anti-human CD4-BV421 and incubated for 30 min at 4° C. Cells were washed twice with 200 μL/well DPBS (centrifugation 350× g 4 min 4° C., flick off) and resuspended in 40 μL/well 1% PFA in PBS and incubated at 4° C. to fix the staining. Cells were centrifuged and resuspended in 100 μL FACS-buffer before cells were acquired using the MACS Quant Analyzer 10 (Miltenyi Biotec) and an automated Cytomat (ThermoFischer, set to 4° C.) plate-handling system. Data was analyzed using FlowJo v10.3 for PC (FlowJo LLC), Microsoft Excel (professional Plus 2010) and GraphPad Prism v6.07 (GraphPad Software, Inc) for total count and percentage of proliferation CD4 and CD8 T cells (CFSE dilution), as well as CD25 (IL-2R(x), CD137 (4-1BB) and PD-1 expressing CD4 and CD8 T cells.

To analyze the released cytokines in the supernatant, the previous frozen samples were taken and analyzed for IFN$\gamma$, GM-CSF, TNF$\alpha$, IL-4, IL-2, IL-6, IL-8 and IL-10 using Bio-RAD Bio-Plex Pro™ Human Cytokine 8 plex assay (Bio-Rad Laboratories AG, Switzerland). Thawed samples were analyzed as following: The Bio-Plex system was calibrated according to the manufacturer's instructions. The assay buffer, wash buffer and sample diluent of the Bio-RAD Bio-Plex Pro Human Cytokine 8 plex were brought to RT. The Vacuum manifolder (Milipore) for 96-well filter plates was set to −1 to −3" Hg. The standard vial was diluted with 500 μL Standard Diluent, vortexed and stored on ice. A four-fold standard diluent was performed in T cell activation assay medium (same medium as the supernatant, see above) including a blank control (medium only). Thawed supernatant were diluted in T cell activation assay medium 1:1.2 and 1:1.5 (two different dilutions were tested). The 10× Bio-Plex coupled beads were vortexed and diluted in Bio-Plex assay buffer and kept protected from light.

A Multi-Screen Filter plate (Millipore) was pre-wetted using Bio-Plex assay buffer and the vacuum manifolder. 50

µL/well of the prepared Bio-Plex coupled bead solution was added and filter plates were washed twice with 100 µL/well Bio-Plex assay buffer using the vacuum manifolder. Diluted supernatants, standards and blank control were added to the wells (50 µL/well) according to the plate layout. The plate was incubated for 1 h in the dark on a plate shaker (850 rpm) to allow the cytokines to bind to the Bio-Plex coupled beads. In the meanwhile Bio-Plex detection antibody was diluted 1:20 in Bio-Plex detection antibody diluent. The incubated filter plate was washed three times with 100 µL/well Bio-Plex assay buffer using the vacuum manifolder. Afterwards the prepared detection antibody solution was vortexed and 25 µL/well were added. The plate was incubated for 30 min in the dark on a plate shaker (850 rpm) to allow the biotin-labeled detection antibody to bind. In the meanwhile the SA-PE (PE-conjugated Streptavidin) solution was prepared by dilution it 1:200 in Bio-Plex assay buffer and protected from light. After the incubation the plate was washed three times with 100 µL/well Bio-Plex assay buffer using the vacuum manifolder. 50 µL/well SA-PE solution were added and the plate was incubated for 10 min in the dark on a plate shaker (850 rpm) to allow the SA-PE to bind to biotin-labeled detection antibodies.

Afterwards plates were washed three times as described above. Finally 100 µL Bio-Plex assay buffer were added to each well, the plate was shaked for 30 sec at 850 rpm on the plate shaker, then applied to the Bio-Plex system and the analysis was started. The data was analyzed using Bio-Plex Manager Software and GraphPad Prism v6.07 (GraphPad Software, Inc).

Results

Figure 33:
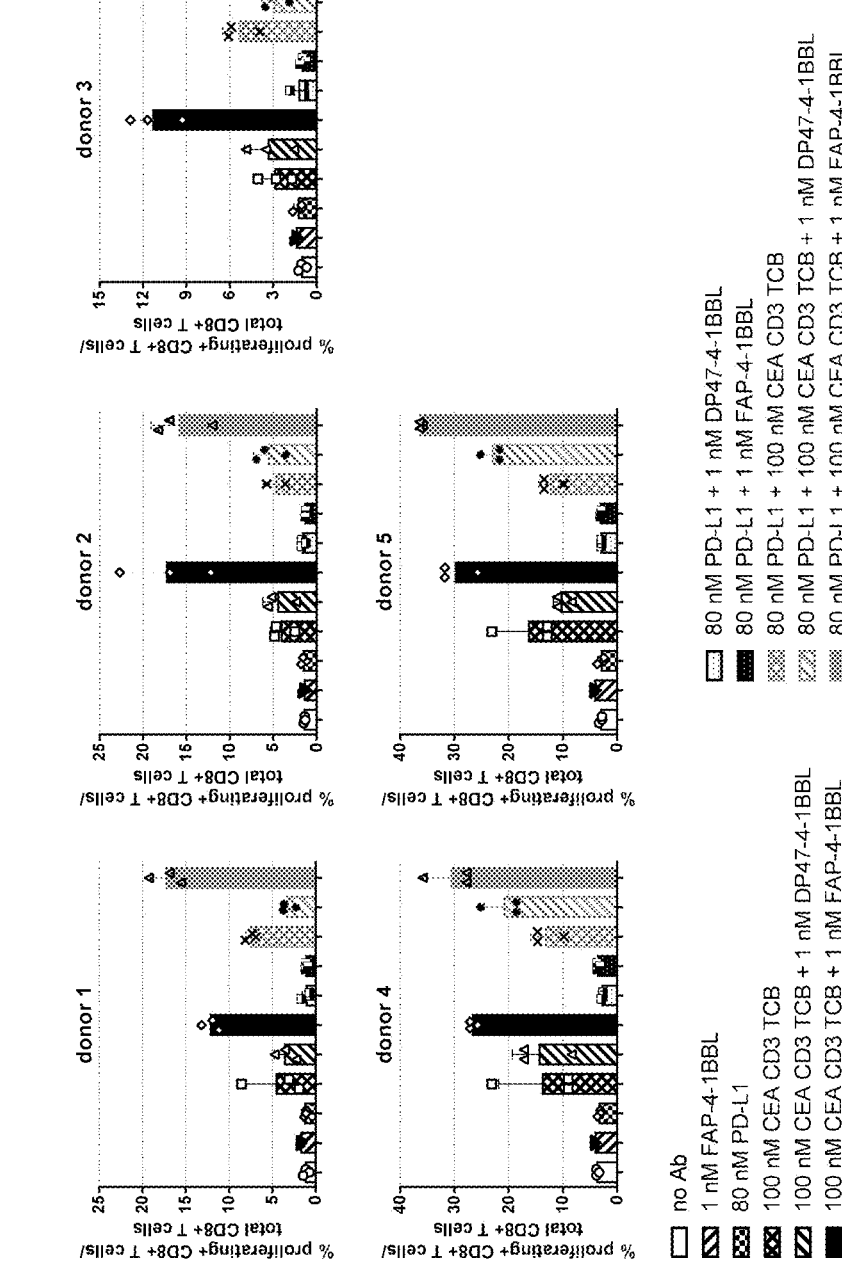
Figure 34:
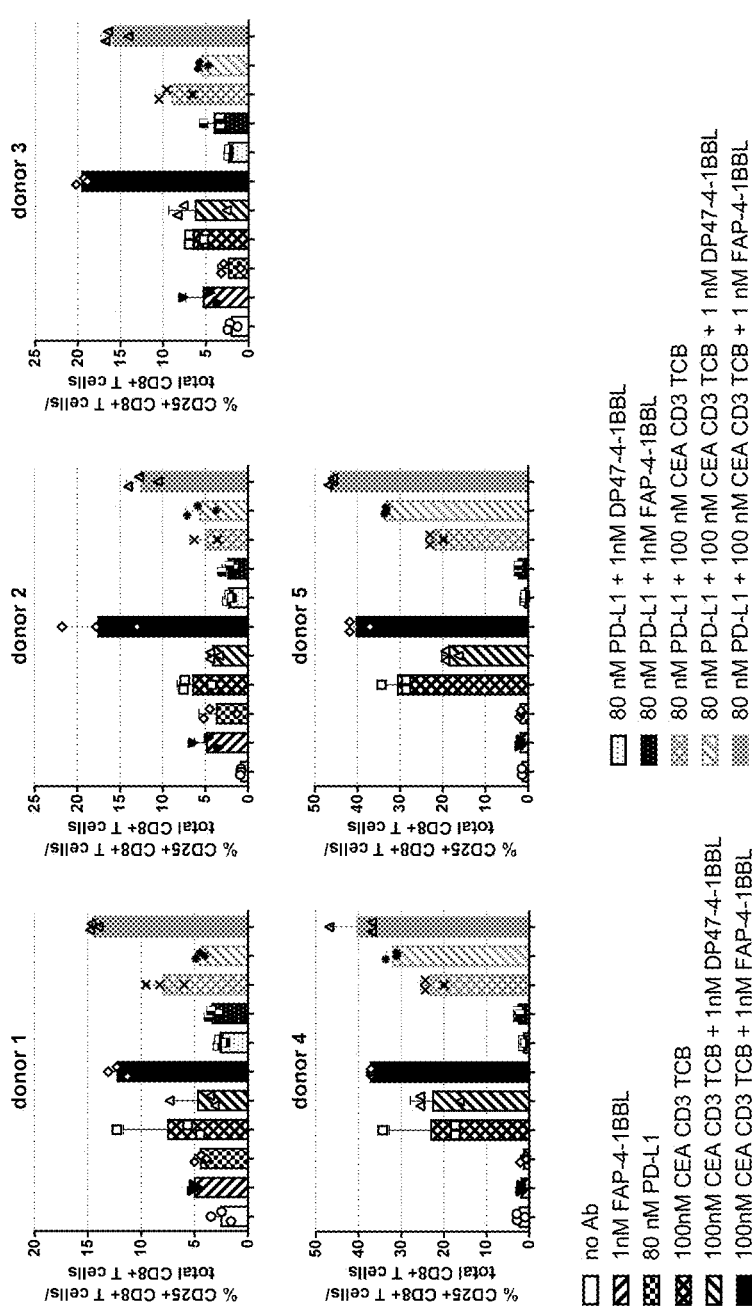
Figure 35:
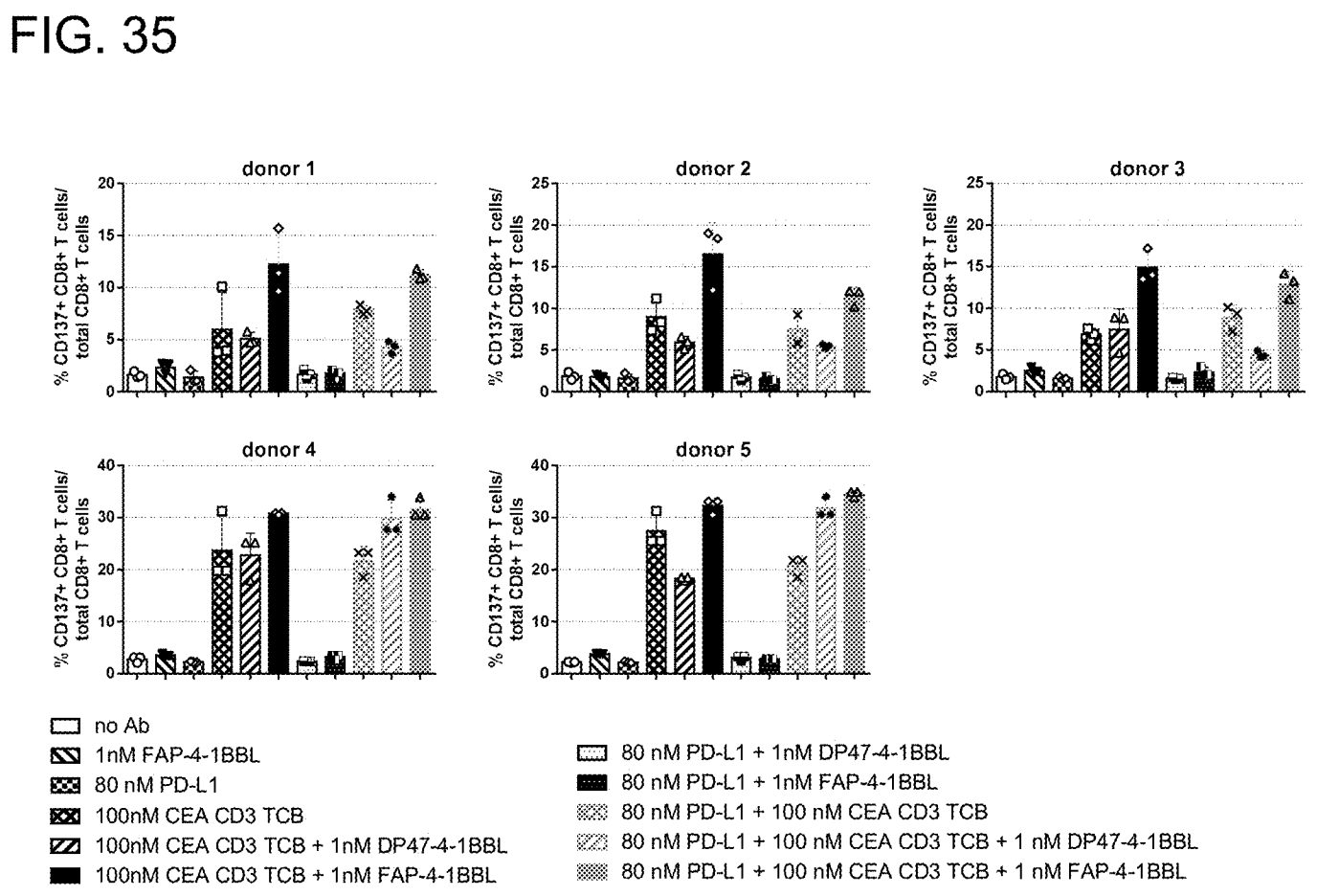

As shown in FIGS. 33, 34 and 35, the addition of 10 nM CEA CD3 TCB (black chassed bars, open squares) but not 1 nM FAP-4-1BBL alone (black and white diagonal striped bar (stripes sloping down to the right), black down-facing triangles) could increase the proliferation as well as the expression of CD25 and CD137 (4-1BB) on CD8 T cells. The combination of 10 nM CEA CD3 TCB with 1 nM FAP-4-1BBL (black bars, open diamonds) led to a further increase of CD25 and CD137 (to a lesser extent) and increased proliferation of CD8 T cells. Stronger effects were seen when analyzing the cytokines (FIGS. 36, 37 and 38). Fold increase of cytokine release comparing the combination of CEA CD3 TCB and FAP-4-1BBL with CEA CD3 TCB alone is shown in FIG. 39. The combination of these two components induced synergistic effects mainly for CD8 T cells in proliferation, activation (CD25, CD137) and cytokine release (especially IFNγ, GM-CSF and TNF(x). Untargeted DP47-4-1BBL in combination with CEA CD3 TCB (black/white striped bar, stripes sloping up to the right) could not induce the same effects as the combination of targeted FAP-4-1BBL and CEA CD3 TCB showing that the synergistic effect of FAP-41-BBL is dependent on FAP-targeting and crosslinking.

As also shown in FIGS. 33, 34 and 35 the triple combination (grey bar, grey filled up-facing triangles) of CEA CD3 TCB with FAP-4-1BBL and PD-L1 antibody (Atezolizumab) had no additional effect on T cell proliferation or activation (CD137, CD25 expression) but could induce further increased secretion of IFNγ, TNFα and GMC-CSF if compared to single treatments or treatment with the combination of CEA CD3 TCB and FAP-4-1-BBL (see FIGS. 36, 37 and 38). Fold increase of this cytokines comparing the triple combination with the combination of CEA CD3 TCB and FAP-4-1BBL is shown in FIG. 40. The triple combination showed a very strong synergistic effect on cytokine release (mainly IFNγ, TNFα and GM-CSF).

Example 11

Preparation, purification and characterization of FAP targeted mouse 4-1BBL antigen binding molecule (Hybrid surrogate)

A bispecific antigen binding molecule comprising an agonistic mouse 4-1BB ligand with monovalent binding for FAP, also termed hybrid surrogate or FAP-mu4-1BBL, was prepared as described in International Patent Appl. Publ. No. WO 2016/075278 A1. The targeted mouse 4-1BBL was prepared as described for the human ligand by replacing the human ligand with the mouse ectodomain.

The DNA sequence encoding part of the ectodomain (amino acid 104-309, including the C160S mutation) of mouse 4-1BB ligand was synthetized according to the Q3U1Z9-1 sequence of Uniprot database. The FAP binder used to target the 4-1BB ligand was clone 4B9. The amino acid sequences for the hybrid surrogate FAP-mu4-1BBL can be found in Table 21.

TABLE 21

Amino acid sequences of mature hybrid
surrogate FAP-mu4-1BBL

| SEQ ID NO: | Description | Sequence |
|---|---|---|
| 136 | di-mu4-1BBL-CL Fc knob chain | RTEPRPALTITTSPNLGTRENN ADQVTPVSHIGCPNTTQQGSPV FAKLLAKNQASLSNTTLNWHSQ DGAGSSYLSQGLRYEEDKKELV VDSPGLYYVFLELKLSPTFTNT GHKVQGWVSLVLQAKPQVDDFD NLALTVELFPCSMENKLVDRSW SQLLLLLKAGHRLSVGLRAYLHG AQDAYRDWELSYPNTTSFGLFL VKPDNPWEGGGGSGGGGSRTEP RPALTITTSPNLGTRENNADQV TPVSHIGCPNTTQQGSPVFAKL LAKNQASLSNTTLNWHSQDGAG SSYLSQGLRYEEDKKELVVDSP GLYYVFLELKLSPTFTNTGHKV QGWVSLVLQAKPQVDDFDNLAL TVELFPCSMENKLVDRSWSQLL LLKAGHRLSVGLRAYLHGAQDA YRDWELSYPNTTSFGLFLVKPD NPWEGGGGSGGGGSRTVAAPSV FIFPPSDRKLKSGTASVVCLLN NFYPREAKVQWKVDNALQSGNS QESVTEQDSKDSTYSLSSTLTL SKADYEKHKVYACEVTHQGLSS PVTKSFNRGECDKTHTCPPCPA PEAAGGPSVFLFPPKPKDTLMI SRTPEVTCVVVDVSHEDPEVKF NWYVDGVEVHNAKTKPREEQYN STYRVVSVLTVLHQDWLNGKEY KCKVSNKALGAPIEKTISKAKG QPREPQVYTLPPCRDELTKNQV SLWCLVKGFYPSDIAVEWESNG QPENNYKTTPPVLDSDGSFFLY SKLTVDKSRWQQGNVFSCSVMH EALHNHYTQKSLSLSPGK |
| 137 | mono-mu4-1BBL-CH1 chain | RTEPRPALTITTSPNLGTRENN ADQVTPVSHIGCPNTTQQGSPV FAKLLAKNQASLSNTTLNWHSQ DGAGSSYLSQGLRYEEDKKELV VDSPGLYYVFLELKLSPTFTNT GHKVQGWVSLVLQAKPQVDDFD NLALTVELFPCSMENKLVDRSW SQLLLLLKAGHRLSVGLRAYLHG AQDAYRDWELSYPNTTSFGLFL |

TABLE 21-continued

Amino acid sequences of mature hybrid
surrogate FAP-mu4-1BBL

| SEQ ID NO: | Description | Sequence |
|---|---|---|
| | | VKPDNPWEGGGGSGGGGSASTK GPSVFPLAPSSKSTSGGTAALG CLVEDYFPEPVTVSWNSGALTS GVHTFPAVLQSSGLYSLSSVVT VPSSSLGTQTYICNVNHKPSNT KVDEKVEPKSC |
| 138 | VHCH1 (4B9) Fc hole chain | EVQLLESGGGLVQPGGSLRLSC AASGFTFSSYAMSWVRQAPGKG LEWVSAIIGSGASTYYADSVKG RFTISRDNSKNTLYLQMNSLRA EDTAVYYCAKGWFGGFNYWGQG TLVTVSSASTKGPSVFPLAPSS KSTSGGTAALGCLVKDYFPEPV TVSWNSGALTSGVHTFPAVLQS SGLYSLSSVVTVPSSSLGTQTY ICNVNHKPSNTKVDKKVEPKSC DKTHTCPPCPAPEAAGGPSVFL FPPKPKDTLMISRTPEVTCVVV DVSHEDPEVKFNWYVDGVEVHN AKTKPREEQYNSTYRVVSVLTV LHQDWLNGKEYKCKVSNKALGA PIEKTISKAKGQPREPQVCTLP PSRDELTKNQVSLSCAVKGFYP SDIAVEWESNGQPENNYKTTPP VLDSDGSFFLVSKLTVDKSRWQ QGNVFSCSVMHEALHNHYTQKS LSLSPGK |
| 139 | VLCL(4B9) Light chain | EIVLTQSPGTLSLSPGERATLS CRASQSVTSSYLAWYQQKPGQA PRLLINVGSRRATGIPDRFSGS GSGTDFTLTISRLEPEDFAVYY CQQGIMLPPTFGQGTKVEIKRT VAAPSVFIFPPSDEQLKSGTAS VVCLLNNFYPREAKVQWKVDNA LQSGNSQESVTEQDSKDSTYSL SSTLTLSKADYEKHKVYACEVT HQGLSSPVTKSFNRGEC |

The hybrid surrogate FAP-mu4-1BBL was produced by co-transfecting CHO-K1 cells growing in suspension with the mammalian expression vectors using eviFect (Evitria AG).

The cells were transfected with the corresponding expression vectors in a 1:1:1:1 ratio ("vector Fc-hole heavy chain": "vector FAP light chain": "vector 4-1BBL Fc-knob heavy chain": "vector mu4-1BBL light chain").

For transfection CHO-K1 cells are cultivated in suspension serum free in eviMake culture medium (Evitria AG). After 7 days at 37° C. in an incubator with a 5% CO$_2$ atmosphere, cultivation supernatant is collected for purification by centrifugation and the solution is sterile filtered (0.22 mm filter) and kept at 4° C.

Secreted proteins were purified from cell culture supernatants by affinity chromatography using Protein A, followed by size exclusion chromatography. For affinity chromatography, the supernatant was loaded on a Protein A MabSelectSure column (GE Healthcare) equilibrated with 20 mM sodium phosphate, 20 mM sodium citrate pH 7.5. Unbound protein was removed by washing with 20 mM sodium phosphate, 20 mM sodium citrate containing buffer (pH 7.5). The bound protein was eluted using a linear pH-gradient of sodium chloride of 20 mM sodium citrate, 100 mM NaCl, 100 mM Glycine, 0.01% TWEEN® 20 pH 3.0. The column was then washed with 20 mM sodium citrate, 100 mM NaCl, 100 mM Glycine, 0.01% TWEEN®

20 pH 3.0. The pH of collected fractions was adjusted by adding 1/40 (v/v) of 2M Tris, pH8.0. The protein was concentrated and filtered prior to loading on a HILOAD™ SUPERDEX™ column (GE Healthcare) equilibrated with 20 mM Histidine, 140 mM NaCl, 0.01% TWEEN® 20 pH6.0.

The protein concentration of purified bispecific constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM K2HPO4, 125 mM NaCl, 200 mM L-Arginine Monohydrocloride, 0.02% (w/v) NaN$_3$, pH 6.7 running buffer at 25° C.

TABLE 22

Biochemical analysis of hybrid surrogate FAP-mu4-1BBL

| Molecule | Monomer [%] | Yield [mg/l] | CE-SDS (non-red) |
|---|---|---|---|
| FAP-mu4-1BBL | 95 | 3.2 | 92 |

11.1 Functional characterization of hybrid surrogate FAP-mu4-1BBL by surface plasmon resonance The capacity of binding simultaneously murine 4-1BB Fc(kih) and human or murine FAP was assessed by surface plasmon resonance (SPR) in the manner as described in WO 2016/075278 A1. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). Biotinylated murine 4-1BB Fc(kih) was directly coupled to a flow cell of a streptavidin (SA) sensor chip. Immobilization levels up to 600 resonance units (RU) were used.

The FAP-targeted mu4-1BBL construct was passed at a concentration range of 200 nM with a flow of 30 μL/minute through the flow cells over 90 seconds and dissociation was set to zero sec. Human or murine FAP was injected as second analyte with a flow of 30 μL/minute through the flow cells over 90 seconds at a concentration of 500 nM. The dissociation was monitored for 120 sec. Bulk refractive index differences were corrected for by subtracting the response obtained in a reference flow cell, where no protein was immobilized.

As can be seen in the graphs of FIGS. 41A and 41B, the hybrid surrogate FAP-mu4-1BBL can bind simultaneously murine 4-1BB and murine/human FAP.

Example 12

Preparation, Purification and Characterization of Bispecific Antigen Binding Molecules with bivalent binding to mouse 4-1BB and monovalent binding to FAP Bispecific agonistic mouse 4-1BB antibodies with bivalent binding for 4-1BB and monovalent binding for FAP, also termed 2+1, have been prepared in analogy to FIGS. 1A and 1B. In this example, the first heavy chain HCl of the construct was comprised of the following components: VHCH1 of an anti-4-1BB (clone MU137-1) followed by Fc containing the mutations Lys392Asp and Lys409Asp (termed Fc-DD), at which C-terminus a VL, or VH, of anti-FAP binder (clone 28H1) was fused. The second heavy chain HC2 was comprised of VHCH1 of anti-4-1BB (clone MU137-1) followed by Fc containing the mutation Glu356Lys and Asp399Lys (termed Fc-KK), at which C-terminus a VH, or VL, of anti-FAP binder (clone 28H1) was fused. The DDKK mutations for enhancing antibody Fc heterodimer formation are inter alia described by Gunasekaran et al., J. Biol. Chem. 2010, 19637-19646. Combination of the targeted anti-FAP-Fc DD with the anti-4-1BB-Fc KK chain allows generation of a heterodimer, which includes a FAP binding moiety and two murine mouse 4-1BB binding Fabs. DAPG mutations were introduced in the constant regions of the heavy chains to abrogate binding to mouse Fc gamma receptors according to the method described e.g. in Baudino et al. J. Immunol. (2008), 181, 6664-6669, or in WO 2016/030350 A1. Briefly, the Asp265Ala and Pro329Gly mutations have been introduced in the constant region of the Fc-DD and Fc-KK heavy chains to abrogate binding to Fc gamma receptors (numbering according to Kabat EU index; i.e. D265A, P329G).

The amino acid sequences for 2+1 anti-4-1BB(MU137-1), anti-FAP(28H1) construct with a-FAP(28H1) VH fused to Fc-KK and VL fused to Fc-DD chain can be found respectively in Table 23. The amino acid sequences for 2+1 anti-4-1BB(MU137-1), anti-FAP(28H1) construct with a-FAP(28H1) VL fused to Fc-KK and VH fused to Fc-DD chain can be found respectively in Table 24.

TABLE 23

Sequences of bispecific, bivalent anti-4-1BB
(MU137-1)/anti-FAP (28H1) mouse IgG1 DAPG
antigen binding molecules (Constructs
with FAP VL fused to Fc-DD chain and
VH fused to Fc-KK chain, also
termed below Fc-DD-VL)

| SEQ ID NO: | Description | Sequence |
|---|---|---|
| 140 | VHCH1 (MU137-1)-Heavy chain Fc-DD-VL (28H1) | DVQLVESGGGLVQPGRSLKLSC AASGFIFSYFDMAWVRQAPTKG LEWVASISPSGDIPYYRDSVKG RFTVSRENAKSSLYLQMDSLRS EDTATYYCARRSYGGYSELDYW GQGVMVTVSSAKTTPPSVYPLA PGSAAQTNSMVTLGCLVKGYFP EPVTVTWNSGSLSSGVHTFPAV LQSDLYTLSSSVTVPSSTWPSQ TVTCNVAHPASSTKVDKKIVPR DCGCKPCICTVPEVSSVFIFPP KPKDVLTITLTPKVTCVVVAIS KDDPEVQFSWFVDDVEVHTAQT KPREEQINSTFRSVSELPIMHQ DWLNGKEFKCRVNSAAFGAPIE KTISKTKGRPKAPQVYTIPPPK EQMAKDKVSLTCMITNFFPEDI TVEWQWNGQPAENYDNTQPIMD TDGSYFVYSDLNVQKSNWEAGN TFTCSVLHEGLHNHHTEKSLSH SPGGGGSGGGGSGGGGSGGGG SEIVLTQSPGTLSLSPGERATL SCRASQSVSRSYLAWYQQKPGQ APRLLIIGASTRATGIPDRFSG SGSGTDFTLTISRLEPEDFAVY YCQQGQVIPPTFGQGTKVEIK |
| 141 | VHCH1 (20H4.9)-Heavy chain Fc-KK-VH (28H1) | DVQLVESGGGLVQPGRSLKLSC AASGFIFSYFDMAWVRQAPTKG LEWVASISPSGDIPYYRDSVKG RFTVSRENAKSSLYLQMDSLRS EDTATYYCARRSYGGYSELDYW GQGVMVTVSSAKTTPPSVYPLA PGSAAQTNSMVTLGCLVKGYFP EPVTVTWNSGSLSSGVHTFPAV LQSDLYTLSSSVTVPSSTWPSQ TVTCNVAHPASSTKVDKKIVPR |

TABLE 23-continued

Sequences of bispecific, bivalent anti-4-1BB
(MU137-1)/anti-FAP (28H1) mouse IgG1 DAPG
antigen binding molecules (Constructs
with FAP VL fused to Fc-DD chain and
VH fused to Fc-KK chain, also
termed below Fc-DD-VL)

| SEQ ID NO: | Description | Sequence |
|---|---|---|
| | | DCGCKPCICTVPEVSSVFIFPP KPKDVLTITLTPKVTCVVVAIS KDDPEVQFSWFVDDVEVHTAQT KPREEQINSTFRSVSELPIMHQ DWLNGKEFKCRVNSAAFGAPIE KTISKTKGRPKAPQVYTIPPPK KQMAKDKVSLTCMITNFFPEDI TVEWQWNGQPAENYKNTQPIMK TDGSYFVYSKLNVQKSNWEAGN TFTCSVLHEGLHNHHTEKSLSH SPGGGGSGGGGSGGGGSGGGG SEVQLLESGGGLVQPGGSLRLS CAASGFTFSSHAMSWVRQAPGK GLEWVSAIWASGEQYYADSVKG RFTISRDNSKNTLYLQMNSLRA EDTAVYYCAKGWLGNFDYWGQG TLVTVSS |
| 142 | VLCL-Light chain (MU137-1) | DIQMTQSPASLSASLEEIVTIT CQASQDIGNWLAWYHQKPGKSP QLLIYGTSSLADGVPSRFSGSS SGSQYSLKISRLQVEDIGIYYC LQAYGAPWTFGGGTKLELKRAD AAPTVSIFPPSSEQLTSGGASV VCFLNNFYPKDINVKWKIDGSE RQNGVLNSWTDQDSKDSTYSMS STLTLTKDEYERHNSYTCEATH KTSTSPIVKSFNRNEC |

TABLE 24

Sequences of bispecific, bivalent anti-4-1BB
(MU137-1)/monovalent anti-FAP (28H1) mouse
IgG1 DAPG antigen binding molecules
(Constructs with FAP VH fused to
Fc DD chain and VL fused to Fc
KK chain, termed Fc-DD-VH)

| SEQ ID NO: | Description | Sequence |
|---|---|---|
| 143 | VHCH1 (MU137-1)-Heavy chain Fc-DD-VH (28H1) | DVQLVESGGGLVQPGRSLKLSC AASGFIFSYFDMAWVRQAPTKG LEWVASISPSGDIPYYRDSVKG RFTVSRENAKSSLYLQMDSLRS EDTATYYCARRSYGGYSELDYW GQGVMVTVSSAKTTPPSVYPLA PGSAAQTNSMVTLGCLVKGYFP EPVTVTWNSGSLSSGVHTFPAV LQSDLYTLSSSVTVPSSTWPSQ TVTCNVAHPASSTKVDKKIVPR DCGCKPCICTVPEVSSVFIFPP KPKDVLTITLTPKVTCVVVAIS KDDPEVQFSWFVDDVEVHTAQT KPREEQINSTFRSVSELPIMHQ DWLNGKEFKCRVNSAAFGAPIE KTISKTKGRPKAPQVYTIPPPK EQMAKDKVSLTCMITNFFPEDI TVEWQWNGQPAENYDNTQPIMD TDGSYFVYSDLNVQKSNWEAGN TFTCSVLHEGLHNHHTEKSLSH SPGGGGSGGGGSGGGGSGGGG |

TABLE 24-continued

Sequences of bispecific, bivalent anti-4-1BB
(MU137-1)/monovalent anti-FAP (28H1) mouse
IgG1 DAPG antigen binding molecules
(Constructs with FAP VH fused to
Fc DD chain and VL fused to Fc
KK chain, termed Fc-DD-VH)

| SEQ ID NO: | Description | Sequence |
|---|---|---|
| | | SEVQLLESGGGLVQPGGSLRLS CAASGFTFSSHAMSWVRQAPGK GLEWVSAIWASGEQYYADSVKG RFTISRDNSKNTLYLQMNSLRA EDTAVYYCAKGWLGNFDYWGQG TLVTVSS |
| 144 | VHCH1 (MU137-1)-Heavy chain Fc-KK-VL (28H1) | DVQLVESGGGLVQPGRSLKLSC AASGFIFSYFDMAWVRQAPTKG LEWVASISPSGDIPYYRDSVKG RFTVSRENAKSSLYLQMDSLRS EDTATYYCARRSYGGYSELDYW GQGVMVTVSSAKTTPPSVYPLA PGSAAQTNSMVTLGCLVKGYFP EPVTVTWNSGSLSSGVHTFPAV LQSDLYTLSSSVTVPSSTWPSQ TVTCNVAHPASSTKVDKKIVPR DCGCKPCICTVPEVSSVFIFPP KPKDVLTITLTPKVTCVVVAIS KDDPEVQFSWFVDDVEVHTAQT KPREEQINSTFRSVSELPIMHQ DWLNGKEFKCRVNSAAFGAPIE KTISKTKGRPKAPQVYTIPPPK KQMAKDKVSLTCMITNFFPEDI TVEWQWNGQPAENYKNTQPIMK TDGSYFVYSKLNVQKSNWEAGN TFTCSVLHEGLHNHHTEKSLSH SPGGGGSGGGGSGGGGSGGGG SEIVLTQSPGTLSLSPGERATL SCRASQSVSRSYLAWYQQKPGQ APRLLIIGASTRATGIPDRFSG SGSGTDFTLTISRLEPEDFAVY YCQQGQVIPPTFGQGTKVEIK |
| 142 | VLCL-Light chain (MU137-1) | see Table 23 |

The bispecific 2+1 anti-4-1BB anti-FAP muIgG1 DAPG was produced by co-transfecting CHO-K1 cells growing in suspension with the mammalian expression vectors using eviFect (Evitria AG). The cells were transfected with the corresponding expression vectors in a 1:1:1 ratio ("vector Fc-DD heavy chain": "vector light chain":"vector Fc-KK heavy chain").

For transfection CHO-K1 cells are cultivated in suspension serum free in eviMake (Evitria AG) culture medium. After 7 days at 37° C. in an incubator with a 5% $CO_2$ atmosphere, cultivation supernatant is collected for purification by centrifugation and the solution is sterile filtered (0.22 mm filter) and kept at 4° C.

Secreted proteins were purified from cell culture supernatants by affinity chromatography using Protein A, followed by size exclusion chromatography. For affinity chromatography, the supernatant was loaded on a Protein A MabSelectSure column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate containing buffer (pH 7.5). The bound protein was eluted using a linear pH-gradient of sodium chloride (from 20 to 100 mM) created over 15 column volumes of 20 mM sodium citrate, 100 mM NaCl, 100 mM Glycine, pH 3.0. The column was then washed with 10 column volumes of 20 mM sodium citrate, 100 mM NaCl, 100 mM Glycine, pH 3.0. The pH of collected fractions was adjusted by adding 1/40 (v/v) of 2M Tris, pH8.0. The protein was concentrated and filtered prior to loading on a HILOAD™ SUPERDEX™ 16/600 5200 column (GE Healthcare) equilibrated with 20 mM Histidine, 140 mM NaCl, pH6.0.

The protein concentration of purified bispecific constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM $K_2HPO_4$, 125 mM NaCl, 200 mM L-Arginine Monohydrocloride, 0.02% (w/v) NaN3, pH 6.7 running buffer at 25° C.

TABLE 25

Biochemical analysis of bispecific antigen binding molecules with a bivalent binding to 4-1BB and a monovalent binding to FAP (2 + 1) anti-4-1BB (MU137-1), anti-FAP(28H1) mouse IgG1 DAPG

| Molecule | Monomer [%] | Yield [mg/l] | CE-SDS (non-red) |
|---|---|---|---|
| 4-1BB (MU137-1)/FAP(28H1) DAPG IgG1 2 + 1 (Fc-DD-VL), in the following named muFAP-4-1BB | 98 | 3.6 | 92 |

12.1 Functional characterization of mouse surrogate muFAP-4-1BB by surface plasmon resonance The capacity of binding simultaneously murine 4-1BB Fc(kih) and murine FAP was assessed by surface plasmon resonance (SPR) in the manner as described in WO 2016/075278 A1. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). Biotinylated murine 4-1BB Fc(kih) was directly coupled to a flow cell of a streptavidin (SA) sensor chip. Immobilization levels up to 600 resonance units (RU) were used.

The FAP-targeted 4-1BB constructs were passed at a concentration range of 200 nM with a flow of 30 µL/minute through the flow cells over 90 seconds and dissociation was set to zero sec. Murine FAP was injected as second analyte with a flow of 30 µL/minute through the flow cells over 90 seconds at a concentration of 500 nM. The dissociation was monitored for 120 sec. Bulk refractive index differences were corrected for by subtracting the response obtained in a reference flow cell, where no protein was immobilized. As can be seen in the graph of FIG. 41C, the mouse surrogate muFAP-4-1BB can bind simultaneously murine 4-1BB and murine FAP.

Example 13

Pharmacokinetic profile of muFAP-4-1BB after single injection in C57BL/6 mice

A single dose of 2.5 mg/kg of muFAP-4-1BB (prepared according to Example 12) was injected into C57BL/6 mice. All mice were injected i.v. with 200 µl of the appropriate solution. To obtain the proper amount of compounds per 200 µl, the stock solution (Table 26, muFAP-4-1BB) was diluted with histidine buffer. Three mice per time point were bled at 10 min, 1 hr, 6 hr, 24 hr, 48 hr, 72 hr, 96 hr, 6 days and 9 days. The injected compound was analyzed in serum samples by ELISA. Biotinylated murine 4-1BB, test serum sample, detection antibody anti-msIgG labelled with HRP were added stepwise to a 96-well streptavidin-coated microtiter plate and incubated after every step for 1h at room temperature. The plate was washed three times after each step to remove unbound substances. Finally, the peroxidase-bound complex was visualized by adding ABTS substrate solution to form a colored reaction product. The reaction product intensity was photometrically determined at 405 nm (with reference wavelength at 490 nm) and was proportional to the analyte concentration in the serum sample. The result is shown in FIG. 42. muFAP-4-1BB showed a stable PK-behavior which suggested a once weekly schedule for subsequent efficacy studies.

Example 14

Anti-Tumor Effect by Combination Therapy of muFAP-4-1BB and Anti-PD-L1 Antibody In Vivo An efficacy study with the combination of muFAP-4-1BB and a PD-L1 antibody was carried out in the MC38-CEA model.

An anti-mouse PD-L1 antibody based on the YW243.55.S70 PD-L1 antibody described in WO 2010/077634 (sequence shown in FIG. 11 of said document) was used in the in vivo tumor models. This antibody contained a DAPG mutation as described in Example 12 to abolish FcγR interaction. The variable region of YW243.55.S70 was attached to a murine IgG1 constant domain with DAPG Fc mutations. The anti-PD-L1 antibody used in this example comprises heavy chains according to SEQ ID NO: 145 and light chains according to SEQ ID NO: 146.

MC38-huCEA (murine colon carcinoma) cells were obtained from the City of Hope and expanded at Roche Innovation Center Zurich and maintained in RPMI medium supplemented with 10% FCS, 4 ug/ml Puromycin and 50 ug/ml Hygromycin. Passage 10 at a viability of 96% was used for in vivo cell injection. $0.5 \times 10^6$ cells were resuspended in 100 μl of RPMI (w/o) 50%+GFR matrigel 50% and injected s.c. (subcutaneously).

Immunocompetent human CEA transgenic (hCEATg) C57BL/6J mice were obtained under license agreement from Beckmann Research Institute of City of Hope and bred at Charles River Laboratories. Mice at an age of 8-10 weeks at start of the experiment were maintained under specific-pathogen-free condition with daily cycles of 12 h light/12 h darkness according to committed guidelines (GV-Solas; Felasa; TierschG). The experimental study protocol was reviewed and approved by local government. After arrival, animals were maintained for one week to get accustomed to the new environment and for observation. Continuous health monitoring was carried out on a regular basis.

According to the protocol (FIG. 43), female hCEATg mice were injected with tumor cells s.c. as described above and treated once weekly with the compounds or PBS (Vehicle) when tumor size reached appr. 180 mm³ (day 15). All mice were injected i.v. with 200 μl of the appropriate solution once per week. To obtain the proper amount of compounds per 200 μl, the stock solutions (Table 26) were diluted with histidine buffer when necessary.

TABLE 26

Compositions used in the in vivo experiments

| Compound | Formulation buffer | Concentration (mg/mL) |
|---|---|---|
| muFAP-4-1BBL | 20 mM Histidine, 140 mM NaCl, pH 6.0 | 1.81 (=stock solution) |
| PD-L1 antibody | 20 mM Histidine, 140 mM NaCl, pH 6.0 | 23.4 (=stock solution) |

TABLE 27

Study groups in the in vivo experiments

| Group | No. of animals | Compound | Dose/ mouse (mg/kg) | Route/ Mode of admini- stration | No of treatments |
|---|---|---|---|---|---|
| A | 10 | vehicle | — | i.v. | 3 |
| B | 10 | muFAP-4-1BB | 3 | i.v. | 3 |
| C | 10 | anti-PD-L1 | 10 | i.v. | 3 |
| D | 10 | anti-PD-L1 + muFAP-4-1BB | 10/3 | i.v. | 3 |

For combination therapy (Group D) with muFAP-4-1BB and anti-PD-L1, therapies were injected concomitant. Tumor growth was measured three times per week using a caliper (Example 2, FIG. 2) and tumor volume was calculated as followed:

$$T_v: (W^2/2) \times L \ (W: \text{Width}, L: \text{Length})$$

Figure 44C:
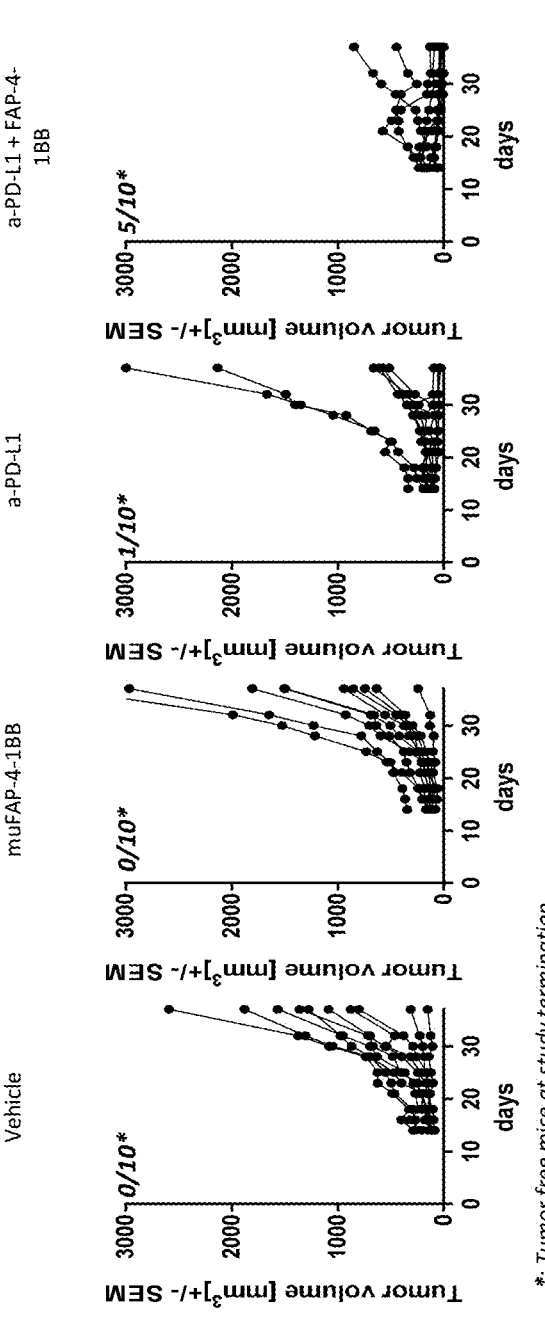

The study was stopped after 3 weeks of treatment (day 37 after tumor cell injection). FIG. 44A shows the tumor growth kinetics (Mean+/−SEM) in all treatment groups, the individual tumor growth kinetics of each animal for all groups is shown in FIG. 44C and as a waterfall plot indicating the tumor growth change from start of treatment at day 15 until day 37 in FIG. 44B. Monotherapy of muFAP-4-1BB did not reveal any tumor growth inhibition. a-PD-L1 treatment alone induced tumor growth inhibition (TGI: 40 and TCR: 0.37) with one mouse being tumor free at day 37. However, the combination of muFAP-4-1BB and a-PD-L1 induced strong tumor regression in 8 out of 10 mice (TGI: 98 and TCR: 0.05) resulting in 50% tumor free mice by day 37.

Statistical analysis was carried out using JMP software:

$$TGI: \frac{100 - Av\left(T\_\text{treatment}^{[day\ x]} - T\_\text{treatment}^{[baseline]}\right)}{Av\left(T\_\text{Vehicle}^{[day\ x]} - T\_\text{Vehicle}^{[baseline]}\right)} * 100$$

$$TCR: \frac{Av\left(T\_\text{treatment}^{[day\ x]}\right)}{Av\left(T\_\text{Vehicle}^{[day\ x]}\right)}$$

The resulting TGI and TCR values are shown in Table 28 (TGI means tumor growth inhibition, TGI>100 means tumor regression and TGI=100 is defined as tumor stasis, TCR means treatment to control ratio, TCR=1 means no effect and TCR=0 is defined as complete regression).

TABLE 28

| TGI and TCR at study day 37 (Vehicle as Control Group) | | |
|---|---|---|
| Group | TGI | TCR |
| muFAP-4-1BB | −28 | 1.17 |
| anti-PD-L1 | 40 | 0.37 |
| muFAP-4-1BB + anti-PD-L1 | 98 | 0.05 |

Example 15

Anti-tumor effect by combination therapy of FAP-4-1BBL and FolR1 CD3 TCB in vivo a) Experiments with monovalent FAP(28H1)-4-1BBL The human monovalent FAP-targeted 4-1BBL (mono FAP-4-1BBL, FAP binder 28H1) was tested as single agent and in combination with the human FolR1 CD3 TCB against the untargeted 4-1BBL (binder DP47) as single agent and in combination. Human ovarian cancer cells (SKOV3) were engrafted subcutaneously in NOG mice from Taconic. 2 days before beginning of therapy mice were injected with human PBMCs.

Human SKOV3 cells (ovarian carcinoma) were originally obtained from ATCC and after expansion deposited in the Roche internal cell bank. Cells were cultured in RPMI containing 10% FCS, 1% Glutamax at 37° C. in a water-saturated atmosphere at 5% $CO_2$. In vitro passage 42 was used for subcutaneous injection at a viability of 96.9%, 50 microliters cell suspension ($5\times10^6$ SKOV3 cells) mixed with 50 microliters Matrigel were injected subcutaneously in the flank of anaesthetized mice with a 22G to 30G needle 70 NOG female mice having an age of 6-8 weeks at start of experiment (purchased from Taconic, SOPF facility) were maintained under specific-pathogen-free condition with daily cycles of 12 h light/12 h darkness according to committed guidelines (GV-Solas; Felasa; TierschG). Experimental study protocol was reviewed and approved by local government (P 2005086). After arrival animals were maintained for one week to get accustomed to new environment and for observation. Continuous health monitoring was carried out on regular basis.

Mice were injected subcutaneously on study day 0 with $5\times10^6$ SKOV3 cells and tumors were measured 2 to 3 times per week during the whole experiment by Caliper Buffy coats were obtained from Züricher Blutspende and PBMCs purified freshly before injection on day 28. 9.1 Mio PBMCs were injected i.p. in 200 μl volume of RPMI. Therapies were administered intravenously (i.v.) starting at day 29. Subsequently, the animals were treated weekly until study end. On the day of randomization mice were injected i.v. with Vehicle, untargeted 4-1BBL (9.85 mg/kg), FOLR1 CD3 TCB, mono FAP-4-1BBL (9.85 mg/kg), FOLR1 CD3 TCB+ untargeted 4-1BBL (9.85 mg/kg), FOLR1 CD3 TCB+FAP-4-1BBL (9.85 mg/kg) or FOLR1-TCB+FAP-4-1BBL (0.985 mg/kg).

All mice were injected i.v. with 200 μl of the appropriate solution. The mice in the vehicle group were injected with Histidine Buffer and the treatment groups with the 4-1BBL containing constructs, the FOLR1 CD3 TCB or the combinations. To obtain the proper amount of compound per 200 μl, the stock solutions were diluted with Histidine Buffer when necessary. The dose and schedule used for FOLR1 CD3 TCB was 5 μg/kg, once/week whereas the 4-1BBL constructs were given at a dose of 9.85 mg/kg or 0.985 mg/kg once/week 2-3 mice/group were bled 10 min, 1h, 8 h, 24 h and 7d after first therapy to determine the pharmacokinetic profile of the compounds during the first week. Mouse serum samples were analyzed with ELISA method. Biotinylated 4-1BB (Roche Innovation Center Zürich), test sample, Digoxigenin labelled anti-huCH1 antibody (Roche Diagnostics GmbH) and anti-Digoxigenin detection antibody (Roche Diagnostics GmbH) were added stepwise to a 96-well streptavidin-coated microtiter plate. The peroxidase-bound complex was visualized by adding ABTS substrate solution to form a colored reaction product.

The experiment was terminated at study day 44, 1 day after the $3^{rd}$ therapy. Tumors were harvested in PBS, single cell suspensions were generated and stained for different immune cell markers and analysed by FACS (staining antibodies Biolegend: Anti-human CD45 AF488, Anti-human CD3 Percp-Cy5.5, Anti-human CD8 PE-Cy7, Anti-human CD4 BV421).

Parts of tumors at termination were formalin fixed and afterwards embedded in Paraffin. Samples were cut and stained for CD3 and CD8.

TABLE 29

| Compositions used in the in vivo experiments | | | |
|---|---|---|---|
| Compound | Dose | Formulation buffer | Concentration (mg/mL) |
| monovalent untargeted 4-1BBL (DP47)-4-1BBL | 9.85 mg/kg | 20 mM Histidine, 140 mM NaCl, 0.01% TWEEN ® 20, pH 6.0 | 3.07 (=stock concentration) |
| monovalent FAP (28H1) 4-1BBL | 9.85 mg/kg or 0.985 mg/kg | 20 mM Histidine, 140 mM NaCl, pH 6.0, 0.01% TWEEN ® 20 | 2.3 (=stock concentration) |
| FolR1 CD3 TCB | 5 μg/kg | 20 mM Histidine, 140 mM NaCl, pH 6.0, 0.01% TWEEN ® 20 | 3.88 (=stock concentration) |

TABLE 30

| Study groups in the in vivo experiments | | | | | | |
|---|---|---|---|---|---|---|
| Group | No. of animals | Mouse strain | Compound | Dose/ mouse | Route/ Mode of administration | No of treatments |
| A | 9 | NOG | vehicle | — | i.v. | 3 |
| B | 10 | NOG | untargeted 4-1BBL | 197 μg | i.v. | 3 |
| C | 9 | NOG | FolR1 CD3 TCB | 0.1 μg | i.v. | 3 |
| D | 10 | NOG | FAP (28H1) 4-1BBL | 197 μg | i.v. | 3 |
| E | 10 | NOG | FolR1 CD3 TCB + untargeted 4-1BBL | 0.1 μg 197 μg | i.v. | 3 |
| F | 10 | NOG | FolR1 CD3 TCB + FAP (28H1) 4-1BBL | 0.1 μg 197 μg | i.v. | 3 |
| G | 9 | NOG | FolR1 CD3 TCB + FAP (28H1) 4-1BBL | 0.1 μg 19.7 μg | i.v. | 3 |

TABLE 31

| Study Plan | |
| --- | --- |
| Study Day | Experimental Procedure |
| Day 0 | Harvesting and preparation of SKOV3 |
| Day 0 | SKOV3 injection s.c. |
| Day 27 | Injection of PBMCs i.p. |
| Day 29 | Injection of 1$^{st}$ therapy |
| Day 29-36 | Bleed 2 mice/group 10 min, 1 h, 8 h, 24 h and 7 d after 1$^{st}$ therapy |
| Day 36 | Injection of 2$^{nd}$ therapy |
| Day 43 | Injection of 3$^{rd}$ therapy |
| Day 44, end of experiment | Termination of experiment |

FIG. 45 shows that the combination FolR1 CD3 TCB+ mono FAP (28H1)-4-1BBL mediated superior efficacy in terms of Tumor growth inhibition compared to the vehicle group. All combination groups (FolR1 CD3 TCB+FAP (28H1)-4-1BBL and FolR1 CD3 TCB+untargeted 4-1BBL) are significantly different from Vehicle control.

TABLE 32

| Tumor growth inhibition (TGI) at study days 35, 40 and 42 | | | |
| --- | --- | --- | --- |
| Group | TGI day 35 [%] | TGI day 40 [%] | TGI day 42 [%] |
| B (monovalent untarg. 4-1BBL) | 41.2 | 28.1 | 19.3 |
| C (FolR1 CD3 TCB) | 58.8 | 75.5 | 73.0 |
| D (monovalent FAP 4-1BBL) | 79.5 | 56.4 | 51.6 |
| E (FolR1 CD3 TCB + monovalent untarg. 4-1BBL) | 79.2 | 86.9 | 90.5 |
| F (FolR1 CD3 TCB + monovalent FAP 4-1BBL) | 73.2 | 89.1 | 90.9 |
| G (FolR1 CD3 TCB + monovalent FAP 4-1BBL, low dose) | 51.9 | 75.5 | 70.0 | b) Experiments with mono- and bivalent FAP(28H1)-4-1BBL

The human monovalent and bivalent FAP-targeted 4-1BBL (mono FAP(28H1)-4-1BBL and bi FAP(28H1)-4-1BBL) were tested as single agent and in combination with the human FolR1 CD3 TCB against the mono- and bivalent untargeted 4-1BBL (mono untarg-4-1BBL and bi untarg-4-1BBL). Human ovarian SKOV3 cells were injected subcutaneously in NOG mice from Taconic. 2 Days before the first therapy mice were injected with human PBMCs isolated from buffy coat.

Human SKOV3 cells (ovarian carcinoma) were originally obtained from ATCC and after expansion deposited in the Roche internal cell bank. Cells were cultured in RPMI containing 10% FCS, 1% Glutamax at 37° C. in a water-saturated atmosphere at 5% $CO_2$. In vitro passage 44 was used for subcutaneous injection at a viability of 99.3%. 50 microliters cell suspension ($5\times10^6$ SKOV3 cells) mixed with 50 microliters Matrigel were injected subcutaneously in the flank of anaesthetized mice with a 22G to 30G needle.

Buffy coats were obtained from Züricher Blutspende and PBMCs purified freshly before injection on day 28. 10 Mio PBMCs were injected i.p. in 200 ul volume of RPMI.

80 NOG female mice were delivered by Taconic. Mice were maintained under specific-pathogen-free condition with daily cycles of 12 h light/12 h darkness according to committed guidelines (GV-Solas; Felasa; TierschG). Experimental study protocol was reviewed and approved by local government (P 2005086). After arrival animals were maintained for one week to get accustomed to new environment and for observation. Continuous health monitoring was carried out on regular basis.

Mice were injected sub cutaneously on study day 0 with $1\times10^6$ SKOV3 cells. Tumors were measured 2 to 3 times per week during the whole experiment by Caliper. Freshly purified PBMCs were injected on day 27, 2 days before the first therapy. One day after randomization, on day 29, mice were injected i.v. with Vehicle, FolR1 CD3 TCB, mono untarg-4-1BBL, bi-untarg-4-1BBL, mono FAP-4-1BBL, bi FAP-4-1BBL, mono untarg-4-1BBL+FolR1 CD3 TCB, mono FAP-4-1BBL+FolR1 CD3 TCB or bi FAP-4-1BBL+ FolR1 CD3 TCB up to 2 weeks.

All mice were injected i.v. with 200 µl of the appropriate solution. The mice in the vehicle group were injected with Histidine Buffer and the treatment groups with the 4-1BBL containing constructs, the FOLR1-TCB or the combinations. To obtain the proper amount of compound per 200 µl, the stock solutions were diluted with Histidine Buffer when necessary. The dose and schedule used for FolR1 CD3 TCB was 5 µg/kg, once/week whereas the 4-1BBL constructs were given at a dose of 10 mg/kg once/week.

TABLE 33

| Compositions used in the in vivo experiments | | | |
| --- | --- | --- | --- |
| Compound | Dose | Formulation buffer | Concentration (mg/mL) |
| monovalent untargeted 4-1BBL (DP47)-4-1BBL | 10 mg/kg | 20 mM Histidine, 140 mM NaCl, 0.01% TWEEN ® 20, pH 6.0 | 3.07 (=stock concentration) |
| bivalent untargeted 4-1BBL (DP47)-4-1BBL | 10 mg/kg | 20 mM Histidine, 140 mM NaCl, 0.01% TWEEN ® 20, pH 6.0 | 2.57 (=stock concentration) |
| monovalent FAP (28H1) 4-1BBL (mono FAP-4-1BBL) | 10 mg/kg | 20 mM Histidine, 140 mM NaCl, pH 6.0 | 4.5 (=stock concentration) |
| bivalent FAP (28H1) 4-1BBL (bi FAP-4-1BBL) | 10 mg/kg | 20 mM Histidine, 140 mM NaCl, pH 6.0 | 3.07 (=stock concentration) |
| FolR1 CD3 TCB | 5 µg/kg | 20 mM Histidine, 140 mM NaCl, pH 6.0, 0.01% TWEEN ® 20 | 0.76 (=stock concentration) |

2 mice/group were bled 10 min, 1 h, 7 h, 72 h and 7d after first therapy to determine the pharmacokinetic profile of the compounds during the first week. Mouse serum samples were analyzed with ELISA method. Biotinylated hu 4-1BB (Roche Innovation Center Zürich), test sample, Digoxigenin labelled anti-huCH1 antibody (Roche Diagnostics GmbH) and anti-Digoxigenin detection antibody (Roche Diagnostics GmbH) were added stepwise to a 96-well streptavidin-coated microtiter plate. The peroxidase-bound complex was visualized by adding ABTS substrate solution to form a colored reaction product.

The experiment was terminated at study day 42, 6 days after the second therapy. Tumors were harvested in PBS, single cell suspensions were generated and stained for different immune cell markers and analysed by FACS (staining antibodies Biolegend: Anti-human CD45 AF488, Anti-human CD3 Percp-Cy5.5, Anti-human CD8 PE-Cy7, Anti-human CD4 B V421).

TABLE 34

Study groups in the in vivo experiments

| Group | No. of animals | Mouse strain | Compound | Dose (mg/kg) | Route/ Mode of admini- stration | No of treat- ments |
|---|---|---|---|---|---|---|
| A | 8 | NOG | vehicle | — | i.v. | 2 |
| B | 9 | NOG | FolR1 CD3 TCB | 5 μg/kg | i.v. | 2 |
| C | 9 | NOG | mono untargeted 4-1BBL | 10 mg/kg | i.v. | 2 |
| D | 9 | NOG | bi untargeted 4-1BBL | 10 mg/kg | i.v. | 2 |
| E | 9 | NOG | mono FAP (28H1) 4-1BBL | 10 mg/kg | i.v. | 2 |
| F | 9 | NOG | bi FAP (28H1) 4-1BBL | 10 mg/kg | i.v. | 2 |
| G | 9 | NOG | FolR1 CD3 TCB + mono untargeted 4-1BBL | 5 μg/kg + 10 mg/kg | i.v. | 2 |
| H | 9 | NOG | FolR1 CD3 TCB + mono FAP (28H1) 4-1BBL | 5 μg/kg + 10 mg/kg | i.v. | 2 |
| I | 9 | NOG | FolR1 CD3 TCB + bi FAP (28H1) 4-1BBL | 5 μg/kg + 10 mg/kg | i.v. | 2 |

TABLE 35

Study Plan

| Study Day | Experimental Procedure |
|---|---|
| Day 0 | Harvesting and preparation of SKOV3 |
| Day 0 | SKOV3 injection s.c. |
| Day 27 | Injection of PBMCs i.p. |
| Day 29 | Injection of 1$^{st}$ therapy |
| Day 29-36 | Bleed 2mice/group 10 min, 1 h, 8 h, 24 h and 7 d after 1$^{st}$ therapy |
| Day 36 | Injection of 2$^{nd}$ therapy |
| Day42 | Termination of experiment |

FIG. 49 shows that all combinations with FolR1 CD3 TCB showed slightly improved efficacy in terms of Tumor growth inhibition compared to the vehicle group and FolR1 CD3 TCB alone. No statistical differences could be observed between the different combinations.

TABLE 36

Tumor growth inhibition (TGI) at study days 39 and 41

| Group | TGI day 39 [%] | TGI day 41 [%] |
|---|---|---|
| FolR1 CD3 TCB | 31.9 | 39.5 |
| monovalent untarg. 4-1BBL | 5.2 | −9.1 |
| bivalent untarg. 4-1BBL | −15.2 | −23.6 |
| monovalent FAP 4-1BBL | 10.6 | 12.4 |
| bivalent FAP 4-1BBL | 17.7 | 4.4 |
| FolR1 CD3 TCB + monovalent untarg. 4-1BBL | 59.8 | 73.1 |
| FolR1 CD3 TCB + monovalent FAP 4-1BBL | 52.4 | 66.8 |
| FolR1 CD3 TCB + bivalent FAP 4-1BBL | 59.8 | 77.1 |

Example 16

Assessing the ability of FAP 4-1BBL to support TCB-mediated target cell killing in vitro To assess the capacity of FAP 4-1BBL to support TCB-mediated tumor cell killing, purified CD8$^+$ T cells or pan T cells served as effector cells and RFP-expressing MV3 melanoma cells served as tumor targets. Effector cells were purified by negative selection (Miltenyi) from buffy coats of healthy donors. 105 effector cells per well were co-cultured with 5000 MV3 target cells in flat bottom 96 well plates. Killing of MV3 target cells in presence of 5 μM MCSP CD3 TCB alone or in combination with 1 nM FAP 4-1BBL was monitored over the course of 5 days capturing 4 images per well every 3 hours using an IncuCyte live cell imager (Essen Biosciences), counting RFP$^+$ target cells using the IncuCyte ZOOM software (Essen Biosciences). RFP$^+$ object counts per image over time served as proxy for target cell death. TCB-mediated target cell killing was distinguished from spontaneous target cell death by monitoring counts of MV3 target cells in presence of effector T cells alone over time (=baseline control). Killing by TCB was calculated as 100−x, x being % targets relative to the baseline control. Statistical analyses were performed using student's t-test, comparing the areas under the curves (AUC) of % killing over time.

MCSP CD3 TCB mediated target cell killing was significantly increased by FAP 4-1BBL for CD8$^+$ T cells (3 out of 3 donors) and pan T cells (3 out of 3 donors). Despite observable target cell killing by MCSP CD3 TCB alone throughout the experiment, killing was not effective at termination of the experiment, with target cell growth achieving baseline levels in 3/3 donors using purified pan T cells and 1/3 donors using purified CD8$^+$ T cells. In contrast, target cell killing was effective in all donors with the combination of MCSP CD3 TCB and FAP 4-1BBL, achieving average plateaus at 89% killing (CD8$^+$ T cells) and 72% killing (pan T cells), indicative of a strong supportive capacity of FAP 4-1BBL for MCSP CD3 TCB mediated target cell killing (see FIGS. 52 and 53).

SEQUENCE LISTING

```
Sequence total quantity: 169
SEQ ID NO: 1            moltype = AA  length = 184
FEATURE                 Location/Qualifiers
source                  1..184
                        mol_type = protein
                        organism = Homo sapiens
SEQUENCE: 1
```

```
REGPELSPDD PAGLLDLRQG MFAQLVAQNV LLIDGPLSWY SDPGLAGVSL TGGLSYKEDT    60
KELVVAKAGV YYVFFQLELR RVVAGEGSGS VSLALHLQPL RSAAGAAALA LTVDLPPASS   120
EARNSAFGFQ GRLLHLSAGQ RLGVHLHTEA RARHAWQLTQ GATVLGLFRV TPEIPAGLPS   180
PRSE                                                                184

SEQ ID NO: 2              moltype = AA  length = 170
FEATURE                   Location/Qualifiers
source                    1..170
                          mol_type = protein
                          organism = Homo sapiens
SEQUENCE: 2
LDLRQGMFAQ LVAQNVLLID GPLSWYSDPG LAGVSLTGGL SYKEDTKELV VAKAGVYYVF    60
FQLELRRVVA GEGSGSVSLA LHLQPLRSAA GAAALALTVD LPPASSEARN SAFGFQGRLL   120
HLSAGQRLGV HLHTEARARH AWQLTQGATV LGLFRVTPEI PAGLPSPRSE              170

SEQ ID NO: 3              moltype = AA  length = 175
FEATURE                   Location/Qualifiers
source                    1..175
                          mol_type = protein
                          organism = Homo sapiens
SEQUENCE: 3
DPAGLLDLRQ GMFAQLVAQN VLLIDGPLSW YSDPGLAGVS LTGGLSYKED TKELVVAKAG    60
VYYVFFQLEL RRVVAGEGSG SVSLALHLQP LRSAAGAAAL ALTVDLPPAS SEARNSAFGF   120
QGRLLHLSAG QRLGVHLHTE ARARHAWQLT QGATVLGLFR VTPEIPAGLP SPRSE        175

SEQ ID NO: 4              moltype = AA  length = 203
FEATURE                   Location/Qualifiers
source                    1..203
                          mol_type = protein
                          organism = Homo sapiens
SEQUENCE: 4
PWAVSGARAS PGSAASPRLR EGPELSPDDP AGLLDLRQGM FAQLVAQNVL LIDGPLSWYS    60
DPGLAGVSLT GGLSYKEDTK ELVVAKAGVY YVFFQLELRR VVAGEGSGSV SLALHLQPLR   120
SAAGAAALAL TVDLPPASSE ARNSAFGFQG RLLHLSAGQR LGVHLHTEAR ARHAWQLTQG   180
ATVLGLFRVT PEIPAGLPSP RSE                                           203

SEQ ID NO: 5              moltype = AA  length = 178
FEATURE                   Location/Qualifiers
source                    1..178
                          mol_type = protein
                          organism = Homo sapiens
SEQUENCE: 5
REGPELSPDD PAGLLDLRQG MFAQLVAQNV LLIDGPLSWY SDPGLAGVSL TGGLSYKEDT    60
KELVVAKAGV YYVFFQLELR RVVAGEGSGS VSLALHLQPL RSAAGAAALA LTVDLPPASS   120
EARNSAFGFQ GRLLHLSAGQ RLGVHLHTEA RARHAWQLTQ GATVLGLFRV TPEIPAGL     178

SEQ ID NO: 6              moltype = AA  length = 164
FEATURE                   Location/Qualifiers
source                    1..164
                          mol_type = protein
                          organism = Homo sapiens
SEQUENCE: 6
LDLRQGMFAQ LVAQNVLLID GPLSWYSDPG LAGVSLTGGL SYKEDTKELV VAKAGVYYVF    60
FQLELRRVVA GEGSGSVSLA LHLQPLRSAA GAAALALTVD LPPASSEARN SAFGFQGRLL   120
HLSAGQRLGV HLHTEARARH AWQLTQGATV LGLFRVTPEI PAGL                    164

SEQ ID NO: 7              moltype = AA  length = 169
FEATURE                   Location/Qualifiers
source                    1..169
                          mol_type = protein
                          organism = Homo sapiens
SEQUENCE: 7
DPAGLLDLRQ GMFAQLVAQN VLLIDGPLSW YSDPGLAGVS LTGGLSYKED TKELVVAKAG    60
VYYVFFQLEL RRVVAGEGSG SVSLALHLQP LRSAAGAAAL ALTVDLPPAS SEARNSAFGF   120
QGRLLHLSAG QRLGVHLHTE ARARHAWQLT QGATVLGLFR VTPEIPAGL               169

SEQ ID NO: 8              moltype = AA  length = 197
FEATURE                   Location/Qualifiers
source                    1..197
                          mol_type = protein
                          organism = Homo sapiens
SEQUENCE: 8
PWAVSGARAS PGSAASPRLR EGPELSPDDP AGLLDLRQGM FAQLVAQNVL LIDGPLSWYS    60
DPGLAGVSLT GGLSYKEDTK ELVVAKAGVY YVFFQLELRR VVAGEGSGSV SLALHLQPLR   120
SAAGAAALAL TVDLPPASSE ARNSAFGFQG RLLHLSAGQR LGVHLHTEAR ARHAWQLTQG   180
ATVLGLFRVT PEIPAGL                                                  197

SEQ ID NO: 9              moltype = AA  length = 5
FEATURE                   Location/Qualifiers
```

-continued

```
REGION                   1..5
                         note = FAP(28H1) CDR-H1
source                   1..5
                         mol_type = protein
                         organism = synthetic construct
SEQUENCE: 9
SHAMS                                                                  5

SEQ ID NO: 10           moltype = AA  length = 16
FEATURE                 Location/Qualifiers
REGION                  1..16
                        note = FAP(28H1) CDR-H2
source                  1..16
                        mol_type = protein
                        organism = synthetic construct
SEQUENCE: 10
AIWASGEQYY ADSVKG                                                      16

SEQ ID NO: 11           moltype = AA  length = 8
FEATURE                 Location/Qualifiers
REGION                  1..8
                        note = FAP(28H1) CDR-H3
source                  1..8
                        mol_type = protein
                        organism = synthetic construct
SEQUENCE: 11
GWLGNFDY                                                               8

SEQ ID NO: 12           moltype = AA  length = 12
FEATURE                 Location/Qualifiers
REGION                  1..12
                        note = FAP(28H1) CDR-L1
source                  1..12
                        mol_type = protein
                        organism = synthetic construct
SEQUENCE: 12
RASQSVSRSY LA                                                          12

SEQ ID NO: 13           moltype = AA  length = 7
FEATURE                 Location/Qualifiers
REGION                  1..7
                        note = FAP(28H1) CDR-L2
source                  1..7
                        mol_type = protein
                        organism = synthetic construct
SEQUENCE: 13
GASTRAT                                                                7

SEQ ID NO: 14           moltype = AA  length = 9
FEATURE                 Location/Qualifiers
REGION                  1..9
                        note = FAP(28H1) CDR-L3
source                  1..9
                        mol_type = protein
                        organism = synthetic construct
SEQUENCE: 14
QQGQVIPPT                                                              9

SEQ ID NO: 15           moltype = AA  length = 5
FEATURE                 Location/Qualifiers
REGION                  1..5
                        note = FAP(4B9) CDR-H1
source                  1..5
                        mol_type = protein
                        organism = synthetic construct
SEQUENCE: 15
SYAMS                                                                  5

SEQ ID NO: 16           moltype = AA  length = 17
FEATURE                 Location/Qualifiers
REGION                  1..17
                        note = FAP(4B9) CDR-H2
source                  1..17
                        mol_type = protein
                        organism = synthetic construct
SEQUENCE: 16
AIIGSGASTY YADSVKG                                                     17

SEQ ID NO: 17           moltype = AA  length = 8
```

```
FEATURE                 Location/Qualifiers
REGION                  1..8
                        note = FAP(4B9) CDR-H3
source                  1..8
                        mol_type = protein
                        organism = synthetic construct
SEQUENCE: 17
GWFGGFNY                                                              8

SEQ ID NO: 18           moltype = AA   length = 12
FEATURE                 Location/Qualifiers
REGION                  1..12
                        note = FAP(4B9) CDR-L1
source                  1..12
                        mol_type = protein
                        organism = synthetic construct
SEQUENCE: 18
RASQSVTSSY LA                                                         12

SEQ ID NO: 19           moltype = AA   length = 7
FEATURE                 Location/Qualifiers
REGION                  1..7
                        note = FAP(4B9) CDR-L2
source                  1..7
                        mol_type = protein
                        organism = synthetic construct
SEQUENCE: 19
VGSRRAT                                                               7

SEQ ID NO: 20           moltype = AA   length = 9
FEATURE                 Location/Qualifiers
REGION                  1..9
                        note = FAP(4B9) CDR-L3
source                  1..9
                        mol_type = protein
                        organism = synthetic construct
SEQUENCE: 20
QQGIMLPPT                                                             9

SEQ ID NO: 21           moltype = AA   length = 116
FEATURE                 Location/Qualifiers
REGION                  1..116
                        note = FAP(28H1) VH
source                  1..116
                        mol_type = protein
                        organism = synthetic construct
SEQUENCE: 21
EVQLLESGGG LVQPGGSLRL SCAASGFTFS SHAMSWVRQA PGKGLEWVSA IWASGEQYYA  60
DSVKGRFTIS RDNSKNTLYL QMNSLRAEDT AVYYCAKGWL GNFDYWGQGT LVTVSS       116

SEQ ID NO: 22           moltype = AA   length = 108
FEATURE                 Location/Qualifiers
REGION                  1..108
                        note = FAP(28H1) VL
source                  1..108
                        mol_type = protein
                        organism = synthetic construct
SEQUENCE: 22
EIVLTQSPGT LSLSPGERAT LSCRASQSVS RSYLAWYQQK PGQAPRLLII GASTRATGIP  60
DRFSGSGSGT DFTLTISRLE PEDFAVYYCQ QGQVIPPTFG QGTKVEIK               108

SEQ ID NO: 23           moltype = AA   length = 117
FEATURE                 Location/Qualifiers
REGION                  1..117
                        note = FAP(4B9) VH
source                  1..117
                        mol_type = protein
                        organism = synthetic construct
SEQUENCE: 23
EVQLLESGGG LVQPGGSLRL SCAASGFTFS SYAMSWVRQA PGKGLEWVSA IIGSGASTYY  60
ADSVKGRFTI SRDNSKNTLY LQMNSLRAED TAVYYCAKGW FGGFNYWGQG TLVTVSS     117

SEQ ID NO: 24           moltype = AA   length = 108
FEATURE                 Location/Qualifiers
REGION                  1..108
                        note = FAP(4B9) VL
source                  1..108
                        mol_type = protein
                        organism = synthetic construct
```

```
SEQUENCE: 24
EIVLTQSPGT LSLSPGERAT LSCRASQSVT SSYLAWYQQK PGQAPRLLIN VGSRRATGIP  60
DRFSGSGSGT DFTLTISRLE PEDFAVYYCQ QGIMLPPTFG QGTKVEIK                108

SEQ ID NO: 25              moltype = AA  length = 378
FEATURE                    Location/Qualifiers
REGION                     1..378
                           note = dimeric hu 4-1BBL (71-254) connected by (G4S)2 linker
source                     1..378
                           mol_type = protein
                           organism = synthetic construct
SEQUENCE: 25
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSREGPEL SPDDPAGLLD LRQGMFAQLV AQNVLLIDGP LSWYSDPGLA  240
GVSLTGGLSY KEDTKELVVA KAGVYYVFFQ LELRRVVAGE GSGSVSLALH LQPLRSAAGA  300
AALALTVDLP PASSEARNSA FGFQGRLLHL SAGQRLGVHL HTEARARHAW QLTQGATVLG  360
LFRVTPEIPA GLPSPRSE                                                378

SEQ ID NO: 26              moltype = AA  length = 350
FEATURE                    Location/Qualifiers
REGION                     1..350
                           note = dimeric hu 4-1BBL (85-254) connected by (G4S)2 linker
source                     1..350
                           mol_type = protein
                           organism = synthetic construct
SEQUENCE: 26
LDLRQGMFAQ LVAQNVLLID GPLSWYSDPG LAGVSLTGGL SYKEDTKELV VAKAGVYYVF  60
FQLELRRVVA GEGSGSVSLA LHLQPLRSAA GAAALALTVD LPPASSEARN SAFGFQGRLL  120
HLSAGQRLGV HLHTEARARH AWQLTQGATV LGLFRVTPEI PAGLPSPRSE GGGGSGGGGS  180
LDLRQGMFAQ LVAQNVLLID GPLSWYSDPG LAGVSLTGGL SYKEDTKELV VAKAGVYYVF  240
FQLELRRVVA GEGSGSVSLA LHLQPLRSAA GAAALALTVD LPPASSEARN SAFGFQGRLL  300
HLSAGQRLGV HLHTEARARH AWQLTQGATV LGLFRVTPEI PAGLPSPRSE             350

SEQ ID NO: 27              moltype = AA  length = 360
FEATURE                    Location/Qualifiers
REGION                     1..360
                           note = dimeric hu 4-1BBL (80-254) connected by (G4S)2 linker
source                     1..360
                           mol_type = protein
                           organism = synthetic construct
SEQUENCE: 27
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEIPAGLP SPRSEGGGGS  180
GGGGSDPAGL LDLRQGMFAQ LVAQNVLLID GPLSWYSDPG LAGVSLTGGL SYKEDTKELV  240
VAKAGVYYVF FQLELRRVVA GEGSGSVSLA LHLQPLRSAA GAAALALTVD LPPASSEARN  300
SAFGFQGRLL HLSAGQRLGV HLHTEARARH AWQLTQGATV LGLFRVTPEI PAGLPSPRSE  360

SEQ ID NO: 28              moltype = AA  length = 416
FEATURE                    Location/Qualifiers
REGION                     1..416
                           note = dimeric hu 4-1BBL (52-254) connected by (G4S)2 linker
source                     1..416
                           mol_type = protein
                           organism = synthetic construct
SEQUENCE: 28
PWAVSGARAS PGSAASPRLR EGPELSPDDP AGLLDLRQGM FAQLVAQNVL LIDGPLSWYS  60
DPGLAGVSLT GGLSYKEDTK ELVVAKAGVY YVFFQLELRR VVAGEGSGSV SLALHLQPLR  120
SAAGAAALAL TVDLPPASSE ARNSAFGFQG RLLHLSAGQR LGVHLHTEAR ARHAWQLTQG  180
ATVLGLFRVT PEIPAGLPSP RSEGGGGSGG GGSPWAVSGA RASPGSAASP RLREGPELSP  240
DDPAGLLDLR QGMFAQLVAQ NVLLIDGPLS WYSDPGLAGV SLTGGLSYKE DTKELVVAKA  300
GVYYVFFQLE LRRVVAGEGS GSVSLALHLQ PLRSAAGAAA LALTVDLPPA SSEARNSAFG  360
FQGRLLHLSA GQRLGVHLHT EARARHAWQL TQGATVLGLF RVTPEIPAGL PSPRSE      416

SEQ ID NO: 29              moltype = AA  length = 366
FEATURE                    Location/Qualifiers
REGION                     1..366
                           note = dimeric hu 4-1BBL (71-248) connected by (G4S)2 linker
source                     1..366
                           mol_type = protein
                           organism = synthetic construct
SEQUENCE: 29
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLGG  180
GGSGGGGSRE GPELSPDDPA GLLDLRQGMF AQLVAQNVLL IDGPLSWYSD PGLAGVSLTG  240
GLSYKEDTKE LVVAKAGVYY VFFQLELRRV VAGEGSGSVS LALHLQPLRS AAGAAALALT  300
```

```
VDLPPASSEA RNSAFGFQGR LLHLSAGQRL GVHLHTEARA RHAWQLTQGA TVLGLFRVTP   360
EIPAGL                                                              366

SEQ ID NO: 30            moltype = AA  length = 338
FEATURE                  Location/Qualifiers
REGION                   1..338
                         note = dimeric hu 4-1BBL (85-248) connected by (G4S)2 linker
source                   1..338
                         mol_type = protein
                         organism = synthetic construct
SEQUENCE: 30
LDLRQGMFAQ LVAQNVLLID GPLSWYSDPG LAGVSLTGGL SYKEDTKELV VAKAGVYYVF   60
FQLELRRVVA GEGSGSVSLA LHLQPLRSAA GAAALALTVD LPPASSEARN SAFGFQGRLL   120
HLSAGQRLGV HLHTEARARH AWQLTQGATV LGLFRVTPEI PAGLGGGGSG GGGSLDLRQG   180
MFAQLVAQNV LLIDGPLSWY SDPGLAGVSL TGGLSYKEDT KELVVAKAGV YYVFFQLELR   240
RVVAGEGSGS VSLALHLQPL RSAAGAAALA LTVDLPPASS EARNSAFGFQ GRLLHLSAGQ   300
RLGVHLHTEA RARHAWQLTQ GATVLGLFRV TPEIPAGL                           338

SEQ ID NO: 31            moltype = AA  length = 348
FEATURE                  Location/Qualifiers
REGION                   1..348
                         note = dimeric hu 4-1BBL (80-248) connected by (G4S)2 linker
source                   1..348
                         mol_type = protein
                         organism = synthetic construct
SEQUENCE: 31
DPAGLLDLRQ GMFAQLVAQN VLLIDGPLSW YSDPGLAGVS LTGGLSYKED TKELVVAKAG   60
VYYVFFQLEL RRVVAGEGSG SVSLALHLQP LRSAAGAAAL ALTVDLPPAS SEARNSAFGF   120
QGRLLHLSAG QRLGVHLHTE ARARHAWQLT QGATVLGLFR VTPEIPAGLG GGGSGGGGSD   180
PAGLLDLRQG MFAQLVAQNV LLIDGPLSWY SDPGLAGVSL TGGLSYKEDT KELVVAKAGV   240
YYVFFQLELR RVVAGEGSGS VSLALHLQPL RSAAGAAALA LTVDLPPASS EARNSAFGFQ   300
GRLLHLSAGQ RLGVHLHTEA RARHAWQLTQ GATVLGLFRV TPEIPAGL                348

SEQ ID NO: 32            moltype = AA  length = 404
FEATURE                  Location/Qualifiers
REGION                   1..404
                         note = dimeric hu 4-1BBL (52-248) connected by (G4S)2 linker
source                   1..404
                         mol_type = protein
                         organism = synthetic construct
SEQUENCE: 32
PWAVSGARAS PGSAASPRLR EGPELSPDDP AGLLDLRQGM FAQLVAQNVL LIDGPLSWYS   60
DPGLAGVSLT GGLSYKEDTK ELVVAKAGVY YVFFQLELRR VVAGEGSGSV SLALHLQPLR   120
SAAGAAALAL TVDLPPASSE ARNSAFGFQG RLLHLSAGQR LGVHLHTEAR ARHAWQLTQG   180
ATVLGLFRVT PEIPAGLGGG GSGGGGSPWA VSGARASPGS AASPRLREGP ELSPDDPAGL   240
LDLRQGMFAQ LVAQNVLLID GPLSWYSDPG LAGVSLTGGL SYKEDTKELV VAKAGVYYVF   300
FQLELRRVVA GEGSGSVSLA LHLQPLRSAA GAAALALTVD LPPASSEARN SAFGFQGRLL   360
HLSAGQRLGV HLHTEARARH AWQLTQGATV LGLFRVTPEI PAGL                    404

SEQ ID NO: 33            moltype = AA  length = 5
FEATURE                  Location/Qualifiers
REGION                   1..5
                         note = CD3-HCDR1
source                   1..5
                         mol_type = protein
                         organism = synthetic construct
SEQUENCE: 33
TYAMN                                                               5

SEQ ID NO: 34            moltype = AA  length = 19
FEATURE                  Location/Qualifiers
REGION                   1..19
                         note = CD3-HCDR2
source                   1..19
                         mol_type = protein
                         organism = synthetic construct
SEQUENCE: 34
RIRSKYNNYA TYYADSVKG                                                19

SEQ ID NO: 35            moltype = AA  length = 14
FEATURE                  Location/Qualifiers
REGION                   1..14
                         note = CD3-HCDR3
source                   1..14
                         mol_type = protein
                         organism = synthetic construct
SEQUENCE: 35
HGNFGNSYVS WFAY                                                     14
```

-continued

```
SEQ ID NO: 36          moltype = AA   length = 14
FEATURE                Location/Qualifiers
REGION                 1..14
                       note = CD3-LCDR1
source                 1..14
                       mol_type = protein
                       organism = synthetic construct
SEQUENCE: 36
GSSTGAVTTS NYAN                                                 14

SEQ ID NO: 37          moltype = AA   length = 7
FEATURE                Location/Qualifiers
REGION                 1..7
                       note = CD3-LCDR2
source                 1..7
                       mol_type = protein
                       organism = synthetic construct
SEQUENCE: 37
GTNKRAP                                                          7

SEQ ID NO: 38          moltype = AA   length = 9
FEATURE                Location/Qualifiers
REGION                 1..9
                       note = CD3-LCDR3
source                 1..9
                       mol_type = protein
                       organism = synthetic construct
SEQUENCE: 38
ALWYSNLWV                                                        9

SEQ ID NO: 39          moltype = AA   length = 125
FEATURE                Location/Qualifiers
REGION                 1..125
                       note = CD3 VH
source                 1..125
                       mol_type = protein
                       organism = synthetic construct
SEQUENCE: 39
EVQLLESGGG LVQPGGSLRL SCAASGFTFS TYAMNWVRQA PGKGLEWVSR IRSKYNNYAT   60
YYADSVKGRF TISRDDSKNT LYLQMNSLRA EDTAVYYCVR HGNFGNSYVS WFAYWGQGTL  120
VTVSS                                                            125

SEQ ID NO: 40          moltype = AA   length = 109
FEATURE                Location/Qualifiers
REGION                 1..109
                       note = CD3 VL
source                 1..109
                       mol_type = protein
                       organism = synthetic construct
SEQUENCE: 40
QAVVTQEPSL TVSPGGTVTL TCGSSTGAVT TSNYANWVQE KPGQAFRGLI GGTNKRAPGT   60
PARFSGSLLG GKAALTLSGA QPEDEAEYYC ALWYSNLWVF GGGTKLTVL            109

SEQ ID NO: 41          moltype = AA   length = 5
FEATURE                Location/Qualifiers
REGION                 1..5
                       note = CEA-HCDR1
source                 1..5
                       mol_type = protein
                       organism = synthetic construct
SEQUENCE: 41
EFGMN                                                            5

SEQ ID NO: 42          moltype = AA   length = 17
FEATURE                Location/Qualifiers
REGION                 1..17
                       note = CEA-HCDR2
source                 1..17
                       mol_type = protein
                       organism = synthetic construct
SEQUENCE: 42
WINTKTGEAT YVEEFKG                                               17

SEQ ID NO: 43          moltype = AA   length = 12
FEATURE                Location/Qualifiers
REGION                 1..12
                       note = CEA-HCDR3
source                 1..12
                       mol_type = protein
```

-continued

```
                          organism = synthetic construct
SEQUENCE: 43
WDFAYYVEAM DY                                                        12

SEQ ID NO: 44            moltype = AA   length = 11
FEATURE                  Location/Qualifiers
REGION                   1..11
                         note = CEA-LCDR1
source                   1..11
                         mol_type = protein
                         organism = synthetic construct
SEQUENCE: 44
KASAAVGTYV A                                                         11

SEQ ID NO: 45            moltype = AA   length = 7
FEATURE                  Location/Qualifiers
REGION                   1..7
                         note = CEA-LCDR2
source                   1..7
                         mol_type = protein
                         organism = synthetic construct
SEQUENCE: 45
SASYRKR                                                              7

SEQ ID NO: 46            moltype = AA   length = 10
FEATURE                  Location/Qualifiers
REGION                   1..10
                         note = CEA-LCDR3
source                   1..10
                         mol_type = protein
                         organism = synthetic construct
SEQUENCE: 46
HQYYTYPLFT                                                           10

SEQ ID NO: 47            moltype = AA   length = 121
FEATURE                  Location/Qualifiers
REGION                   1..121
                         note = CEA VH
source                   1..121
                         mol_type = protein
                         organism = synthetic construct
SEQUENCE: 47
QVQLVQSGAE VKKPGASVKV SCKASGYTFT EFGMNWVRQA PGQGLEWMGW INTKTGEATY    60
VEEFKGRVTF TTDTSTSTAY MELRSLRSDD TAVYYCARWD FAYYVEAMDY WGQGTTVTVS    120
S                                                                   121

SEQ ID NO: 48            moltype = AA   length = 108
FEATURE                  Location/Qualifiers
REGION                   1..108
                         note = CEA VL
source                   1..108
                         mol_type = protein
                         organism = synthetic construct
SEQUENCE: 48
DIQMTQSPSS LSASVGDRVT ITCKASAAVG TYVAWYQQKP GKAPKLLIYS ASYRKRGVPS    60
RFSGSGSGTD FTLTISSLQP EDFATYYCHQ YYTYPLFTFG QGTKLEIK                108

SEQ ID NO: 49            moltype = AA   length = 5
FEATURE                  Location/Qualifiers
REGION                   1..5
                         note = CEA-HCDR1 (CEACAM5)
source                   1..5
                         mol_type = protein
                         organism = synthetic construct
SEQUENCE: 49
DTYMH                                                                5

SEQ ID NO: 50            moltype = AA   length = 17
FEATURE                  Location/Qualifiers
REGION                   1..17
                         note = CEA-HCDR2 (CEACAM5)
source                   1..17
                         mol_type = protein
                         organism = synthetic construct
SEQUENCE: 50
RIDPANGNSK YVPKFQG                                                   17

SEQ ID NO: 51            moltype = AA   length = 12
FEATURE                  Location/Qualifiers
```

```
REGION                      1..12
                            note = CEA-HCDR3 (CEACAM5)
source                      1..12
                            mol_type = protein
                            organism = synthetic construct
SEQUENCE: 51
FGYYVSDYAM AY                                                    12

SEQ ID NO: 52               moltype = AA   length = 15
FEATURE                     Location/Qualifiers
REGION                      1..15
                            note = CEA-LCDR1 (CEACAM5)
source                      1..15
                            mol_type = protein
                            organism = synthetic construct
SEQUENCE: 52
RAGESVDIFG VGFLH                                                 15

SEQ ID NO: 53               moltype = AA   length = 7
FEATURE                     Location/Qualifiers
REGION                      1..7
                            note = CEA-LCDR2 (CEACAM5)
source                      1..7
                            mol_type = protein
                            organism = synthetic construct
SEQUENCE: 53
RASNRAT                                                          7

SEQ ID NO: 54               moltype = AA   length = 9
FEATURE                     Location/Qualifiers
REGION                      1..9
                            note = CEA-LCDR3 (CEACAM5)
source                      1..9
                            mol_type = protein
                            organism = synthetic construct
SEQUENCE: 54
QQTNEDPYT                                                        9

SEQ ID NO: 55               moltype = AA   length = 121
FEATURE                     Location/Qualifiers
REGION                      1..121
                            note = CEA VH (CEACAM5)
source                      1..121
                            mol_type = protein
                            organism = synthetic construct
SEQUENCE: 55
QVQLVQSGAE VKKPGSSVKV SCKASGFNIK DTYMHWVRQA PGQGLEWMGR IDPANGNSKY 60
VPKFQGRVTI TADTSTSTAY MELSSLRSED TAVYYCAPFG YYVSDYAMAY WGQGTLVTVS 120
S                                                               121

SEQ ID NO: 56               moltype = AA   length = 111
FEATURE                     Location/Qualifiers
REGION                      1..111
                            note = CEA VL (CEACAM5)
source                      1..111
                            mol_type = protein
                            organism = synthetic construct
SEQUENCE: 56
EIVLTQSPAT LSLSPGERAT LSCRAGESVD IFGVGFLHWY QQKPGQAPRL LIYRASNRAT 60
GIPARFSGSG SGTDFTLTIS SLEPEDFAVY YCQQTNEDPY TFGQGTKLEI K         111

SEQ ID NO: 57               moltype = AA   length = 232
FEATURE                     Location/Qualifiers
REGION                      1..232
                            note = CD3 VH-CL (CEACAM5 TCB)
source                      1..232
                            mol_type = protein
                            organism = synthetic construct
SEQUENCE: 57
EVQLLESGGG LVQPGGSLRL SCAASGFTFS TYAMNWVRQA PGKGLEWVSR IRSKYNNYAT 60
YYADSVKGRF TISRDDSKNT LYLQMNSLRA EDTAVYYCVR HGNFGNSYVS WFAYWGQGTL 120
VTVSSASVAA PSVFIFPPSD EQLKSGTASV VCLLNNFYPR EAKVQWKVDN ALQSGNSQES 180
VTEQDSKDST YSLSSTLTLS KADYEKHKVY ACEVTHQGLS SPVTKSFNRG EC         232

SEQ ID NO: 58               moltype = AA   length = 449
FEATURE                     Location/Qualifiers
REGION                      1..449
                            note = CEACAM5 VH-CH1(EE)-Fc (hole, P329G LALA)
source                      1..449
```

-continued

```
                         mol_type = protein
                         organism = synthetic construct
SEQUENCE: 58
QVQLVQSGAE VKKPGSSVKV SCKASGFNIK DTYMHWVRQA PGQGLEWMGR IDPANGNSKY    60
VPKFQGRVTI TADTSTSTAY MELSSLRSED TAVYYCAPFG YYVSDYAMAY WGQGTLVTVS   120
SASTKGPSVF PLAPSSKSTS GGTAALGCLV EDYFPEPVTV SWNSGALTSG VHTFPAVLQS   180
SGLYSLSSVV TVPSSSLGTQ TYICNVNHKP SNTKVDEKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVCTLPPSRD   360
ELTKNQVSLS CAVKGFYPSD IAVEWESNGQ PENNYKTTPP VLDSDGSFFL VSKLTVDKSR   420
WQQGNVFSCS VMHEALHNHY TQKSLSLSP                                     449

SEQ ID NO: 59           moltype = AA  length = 674
FEATURE                 Location/Qualifiers
REGION                  1..674
                        note = CEACAM5 VH-CH1(EE)-CD3 VL-CH1-Fc (knob, P329G LALA)
source                  1..674
                        mol_type = protein
                        organism = synthetic construct
SEQUENCE: 59
QVQLVQSGAE VKKPGSSVKV SCKASGFNIK DTYMHWVRQA PGQGLEWMGR IDPANGNSKY    60
VPKFQGRVTI TADTSTSTAY MELSSLRSED TAVYYCAPFG YYVSDYAMAY WGQGTLVTVS   120
SASTKGPSVF PLAPSSKSTS GGTAALGCLV EDYFPEPVTV SWNSGALTSG VHTFPAVLQS   180
SGLYSLSSVV TVPSSSLGTQ TYICNVNHKP SNTKVDEKVE PKSCDGGGGS GGGGSQAVVT   240
QEPSLTVSPG GTVTLTCGSS TGAVTTSNYA NWVQEKPGQA FRGLIGGTNK RAPGTPARFS   300
GSLLGGKAAL TLSGAQPEDE AEYYCALWYS NLWVFGGGTK LTVLSSASTK GPSVFPLAPS   360
SKSTSGGTAA LGCLVKDYFP EPVTVSWNSG ALTSGVHTFP AVLQSSGLYS LSSVVTVPSS   420
SLGTQTYICN VNHKPSNTKV DKKVEPKSCD KTHTCPPCPA PEAAGGPSVF LFPPKPKDTL   480
MISRTPEVTC VVVDVSHEDP EVKFNWYVDG VEVHNAKTKP REEQYNSTYR VVSVLTVLHQ   540
DWLNGKEYKC KVSNKALGAP IEKTISKAKG QPREPQVYTL PPCRDELTKN QVSLWCLVKG   600
FYPSDIAVEW ESNGQPENNY KTTPPVLDSD GSFFLYSKLT VDKSRWQQGN VFSCSVMHEA   660
LHNHYTQKSL SLSP                                                    674

SEQ ID NO: 60           moltype = AA  length = 218
FEATURE                 Location/Qualifiers
REGION                  1..218
                        note = CEACAM5 VL-CL(RK)
source                  1..218
                        mol_type = protein
                        organism = synthetic construct
SEQUENCE: 60
EIVLTQSPAT LSLSPGERAT LSCRAGESVD IFGVGFLHWY QQKPGQAPRL LIYRASNRAT    60
GIPARFSGSG SGTDFTLTIS SLEPEDFAVY YCQQTNEDPY TFGQGTKLEI KRTVAAPSVF   120
IFPPSDRKLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 61           moltype = AA  length = 215
FEATURE                 Location/Qualifiers
REGION                  1..215
                        note = Light chain CEA (CEA TCB)
source                  1..215
                        mol_type = protein
                        organism = synthetic construct
SEQUENCE: 61
DIQMTQSPSS LSASVGDRVT ITCKASAAVG TYVAWYQQKP GKAPKLLIYS ASYRKRGVPS    60
RFSGSGSGTD FTLTISSLQP EDFATYYCHQ YYTYPLFTFG QGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 62           moltype = AA  length = 214
FEATURE                 Location/Qualifiers
REGION                  1..214
                        note = Light chain CD3 (CEA TCB)
source                  1..214
                        mol_type = protein
                        organism = synthetic construct
SEQUENCE: 62
QAVVTQEPSL TVSPGGTVTL TCGSSTGAVT TSNYANWVQE KPGQAFRGLI GGTNKRAPGT    60
PARFSGSLLG GKAALTLSGA QPEDEAEYYC ALWYSNLWVF GGGTKLTVLS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDKKVE PKSC                               214

SEQ ID NO: 63           moltype = AA  length = 694
FEATURE                 Location/Qualifiers
REGION                  1..694
                        note = CEA CD3 crossfab VHck fc knob P329GLALA (CEA TCB)
source                  1..694
                        mol_type = protein
                        organism = synthetic construct
```

```
SEQUENCE: 63
QVQLVQSGAE VKKPGASVKV SCKASGYTFT EFGMNWVRQA PGQGLEWMGW INTKTGEATY    60
VEEFKGRVTF TTDTSTSTAY MELRSLRSDD TAVYYCARWD FAYYVEAMDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDGGGGS GGGGSEVQLL   240
ESGGGLVQPG GSLRLSCAAS GFTFSTYAMN WVRQAPGKGL EWVSRIRSKY NNYATYYADS   300
VKGRFTISRD DSKNTLYLQM NSLRAEDTAV YYCVRHGNFG NSYVSWFAYW GQGTLVTVSS   360
ASVAAPSVFI FPPSDEQLKS GTASVVCLLN NFYPREAKVQ WKVDNALQSG NSQESVTEQD   420
SKDSTYSLSS TLTLSKADYE KHKVYACEVT HQGLSSPVTK SFNRGECDKT HTCPPCPAPE   480
AAGGPSVFLF PPKPKDTLMI SRTPEVTCVV VDVSHEDPEV KFNWYVDGVE VHNAKTKPRE   540
EQYNSTYRVV SVLTVLHQDW LNGKEYKCKV SNKALGAPIE KTISKAKGQP REPQVYTLPP   600
CRDELTKNQV SLWCLVKGFY PSDIAVEWES NGQPENNYKT TPPVLDSDGS FFLYSKLTVD   660
KSRWQQGNVF SCSVMHEALH NHYTQKSLSL SPGK                               694

SEQ ID NO: 64              moltype = AA  length = 451
FEATURE                    Location/Qualifiers
REGION                     1..451
                           note = CEA VHCH1 Fc hole P329GLALA (CEA TCB)
source                     1..451
                           mol_type = protein
                           organism = synthetic construct
SEQUENCE: 64
QVQLVQSGAE VKKPGASVKV SCKASGYTFT EFGMNWVRQA PGQGLEWMGW INTKTGEATY    60
VEEFKGRVTF TTDTSTSTAY MELRSLRSDD TAVYYCARWD FAYYVEAMDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAGG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVCTLPPSRD   360
ELTKNQVSLS CAVKGFYPSD IAVEWESNGQ PENNYKTTPP VLDSDGSFFL VSKLTVDKSR   420
WQQGNVFSCS VMHEALHNHY TQKSLSLSPG K                                  451

SEQ ID NO: 65              moltype = AA  length = 710
FEATURE                    Location/Qualifiers
REGION                     1..710
                           note = Dimeric hu 4-1BBL (71-248) - CL* Fc knob chain
source                     1..710
                           mol_type = protein
                           organism = synthetic construct
SEQUENCE: 65
REGPELSPDD PAGLLDLRQG MFAQLVAQNV LLIDGPLSWY SDPGLAGVSL TGGLSYKEDT    60
KELVVAKAGV YYVFFQLELR RVVAGEGSGS VSLALHLQPL RSAAGAAALA LTVDLPPASS   120
EARNSAFGFQ GRLLHLSAGQ RLGVHLHTEA RARHAWQLTQ GATVLGLFRV TPEIPAGLGG   180
GGSGGGGSRE GPELSPDDPA GLLLDLRQGMF AQLVAQNVLL IDGPLSWYSD PGLAGVSLTG   240
GLSYKEDTKE LVVAKAGVYY VFFQLELRRV VAGEGSGSVS LALHLQPLRS AAGAAALALT   300
VDLPPASSEA RNSAFGFQGR LLHLSAGQRL GVHLHTEARA RHAWQLTQGA TVLGLFRVTP   360
EIPAGLGGGG SGGGGSRTVA APSVFIFPPS DRKLKSGTAS VVCLLNNFYP REAKVQWKVD   420
NALQSGNSQE SVTEQDSKDS TYSLSSTLTL SKADYEKHKV YACEVTHQGL SSPVTKSFNR   480
GECDKTHTCP PCPAPEAAGG PSVFLFPPKP KDTLMISRTP EVTCVVVDVS HEDPEVKFNW   540
YVDGVEVHNA KTKPREEQYN STYRVVSVLT VLHQDWLNGK EYKCKVSNKA LGAPIEKTIS   600
KAKGQPREPQ VYTLPPCRDE LTKNQVSLWC LVKGFYPSDI AVEWESNGQP ENNYKTTPPV   660
LDSDGSFFLY SKLTVDKSRW QQGNVFSCSV MHEALHNHYT QKSLSLSPGK              710

SEQ ID NO: 66              moltype = AA  length = 291
FEATURE                    Location/Qualifiers
REGION                     1..291
                           note = Monomeric hu 4-1BBL (71-248) - CH1*
source                     1..291
                           mol_type = protein
                           organism = synthetic construct
SEQUENCE: 66
REGPELSPDD PAGLLDLRQG MFAQLVAQNV LLIDGPLSWY SDPGLAGVSL TGGLSYKEDT    60
KELVVAKAGV YYVFFQLELR RVVAGEGSGS VSLALHLQPL RSAAGAAALA LTVDLPPASS   120
EARNSAFGFQ GRLLHLSAGQ RLGVHLHTEA RARHAWQLTQ GATVLGLFRV TPEIPAGLGG   180
GGSGGGGSAS TKGPSVFPLA PSSKSTSGGT AALGCLVEDY FPEPVTVSWN SGALTSGVHT   240
FPAVLQSSGL YSLSSVVTVP SSSLGTQTYI CNVNHKPSNT KVDEKVEPKS C            291

SEQ ID NO: 67              moltype = AA  length = 447
FEATURE                    Location/Qualifiers
REGION                     1..447
                           note = anti-FAP (4B9) Fc hole chain
source                     1..447
                           mol_type = protein
                           organism = synthetic construct
SEQUENCE: 67
EVQLLESGGG LVQPGGSLRL SCAASGFTFS SYAMSWVRQA PGKGLEWVSA IIGSGASTYY    60
ADSVKGRFTI SRDNSKNTLY LQMNSLRAED TAVYYCAKGW FGGFNYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APEAAGGPSV   240
FLFPPKPKDT LMISRTPEVT CVVVDVSHED PEVKFNWYVD GVEVHNAKTK PREEQYNSTY   300
```

```
RVVSVLTVLH QDWLNGKEYK CKVSNKALGA PIEKTISKAK GQPREPQVCT LPPSRDELTK  360
NQVSLSCAVK GFYPSDIAVE WESNGQPENN YKTTPPVLDS DGSFFLVSKL TVDKSRWQQG  420
NVFSCSVMHE ALHNHYTQKS LSLSPGK                                     447

SEQ ID NO: 68          moltype = AA  length = 215
FEATURE                Location/Qualifiers
REGION                 1..215
                       note = anti-FAP (4B9) light chain
source                 1..215
                       mol_type = protein
                       organism = synthetic construct
SEQUENCE: 68
EIVLTQSPGT LSLSPGERAT LSCRASQSVT SSYLAWYQQK PGQAPRLLIN VGSRRATGIP  60
DRFSGSGSGT DFTLTISRLE PEDFAVYYCQ QGIMLPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 69          moltype = AA  length = 722
FEATURE                Location/Qualifiers
REGION                 1..722
                       note = Dimeric hu 4-1BBL (71-254) - CL* Fc knob chain
source                 1..722
                       mol_type = protein
                       organism = synthetic construct
SEQUENCE: 69
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSREGPEL SPDDPAGLLD LRQGMFAQLV AQNVLLIDGP LSWYSDPGLA  240
GVSLTGGLSY KEDTKELVVA KAGVYYVFFQ LELRRVVAGE GSGSVSLALH LQPLRSAAGA  300
AALALTVDLP PASSEARNSA FGFQGRLLHL SAGQRLGVHL HTEARARHAW QLTQGATVLG  360
LFRVTPEIPA GLPSPRSEGG GGSGGGGSRT VAAPSVFIFP PSDRKLKSGT ASVVCLLNNF  420
YPREAKVQWK VDNALQSGNS QESVTEQDSK DSTYSLSSTL TLSKADYEKH KVYACEVTHQ  480
GLSSPVTKSF NRGECDKTHT CPPCPAPEAA GGPSVFLPPP KPKDTLMISR TPEVTCVVVD  540
VSHEDPEVKF NWYVDGVEVH NAKTKPREEQ YNSTYRVVSV LTVLHQDWLN GKEYKCKVSN  600
KALGAPIEKT ISKAKGQPRE PQVYTLPPCR DELTKNQVSL WCLVKGFYPS DIAVEWESNG  660
QPENNYKTTP PVLDSDGSFF LYSKLTVDKS RWQQGNVFSC SVMHEALHNH YTQKSLSLSP  720
GK                                                               722

SEQ ID NO: 70          moltype = AA  length = 297
FEATURE                Location/Qualifiers
REGION                 1..297
                       note = Monomeric hu 4-1BBL (71-254) -CH1*
source                 1..297
                       mol_type = protein
                       organism = synthetic construct
SEQUENCE: 70
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSASTKGP SVFPLAPSSK STSGGTAALG CLVEDYFPEP VTVSWNSGAL  240
TSGVHTFPAV LQSSGLYSLS SVVTVPSSSL GTQTYICNVN HKPSNTKVDE KVEPKSC     297

SEQ ID NO: 71          moltype = AA  length = 446
FEATURE                Location/Qualifiers
REGION                 1..446
                       note = anti-FAP(28H1) Fc hole chain
source                 1..446
                       mol_type = protein
                       organism = synthetic construct
SEQUENCE: 71
EVQLLESGGG LVQPGGSLRL SCAASGFTFS SHAMSWVRQA PGKGLEWVSA IWASGEQYYA  60
DSVKGRFTIS RDNSKNTLYL QMNSLRAEDT AVYYCAKGWL GNFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVCTL PPSRDELTKN  360
QVSLSCAVKG FYPSDIAVEW ESNGQPENNY KTTPPVLDSD GSFFLVSKLT VDKSRWQQGN  420
VFSCSVMHEA LHNHYTQKSL SLSPGK                                     446

SEQ ID NO: 72          moltype = AA  length = 215
FEATURE                Location/Qualifiers
REGION                 1..215
                       note = anti-FAP (28H1) light chain
source                 1..215
                       mol_type = protein
                       organism = synthetic construct
SEQUENCE: 72
EIVLTQSPGT LSLSPGERAT LSCRASQSVS RSYLAWYQQK PGQAPRLLII GASTRATGIP  60
```

```
DRFSGSGSGT DFTLTISRLE PEDFAVYYCQ QGQVIPPTFG QGTKVEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                               215

SEQ ID NO: 73             moltype = AA   length = 445
FEATURE                   Location/Qualifiers
REGION                    1..445
                          note = DP47 Fc hole chain
source                    1..445
                          mol_type = protein
                          organism = synthetic construct
SEQUENCE: 73
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKGS GFDYWGQGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP EAAGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALGAPI EKTISKAKGQ PREPQVCTLP PSRDELTKNQ    360
VSLSCAVKGF YPSDIAVEWE SNGQPENNYK TTPPVLDSDG SFFLVSKLTV DKSRWQQGNV    420
FSCSVMHEAL HNHYTQKSLS LSPGK                                          445

SEQ ID NO: 74             moltype = AA   length = 834
FEATURE                   Location/Qualifiers
REGION                    1..834
                          note = anti-FAP (4B9) Fc hole chain fused to dimeric hu
                          4-1BBL (71-254)
source                    1..834
                          mol_type = protein
                          organism = synthetic construct
SEQUENCE: 74
EVQLLESGGG LVQPGGSLRL SCAASGFTFS SYAMSWVRQA PGKGLEWVSA IIGSGASTYY    60
ADSVKGRFTI SRDNSKNTLY LQMNSLRAED TAVYYCAKGW FGGFNYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APEAAGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALGA PIEKTISKAK GQPREPQVCT LPPSRDELTK    360
NQVSLSCAVK GFYPSDIAVE WESNGQPENN YKTTPPVLDS DGSFFLVSKL TVDKSRWQQG    420
NVFSCSVMHE ALHNHYTQKS LSLSPGGGGG SGGGGSREGP ELSPDDPAGL LDLRQGMFAQ    480
LVAQNVLLID GPLSWYSDPG LAGVSLTGGL SYKEDTKELV VAKAGVYYVF FQLELRRVVA    540
GEGSGSVSLA LHLQPLRSAA GAAALALTVD LPPASSEARN SAFGFQGRLL HLSAGQRLGV    600
HLHTEARARH AWQLTQGATV LGLFRVTPEI PAGLPSPRSE GGGGSGGGGS REGPELSPDD    660
PAGLLDLRQG MFAQLVAQNV LLIDGPLSWY SDPGLAGVSL TGGLSYKEDT KELVVAKAGV    720
YYVFFQLELR RVVAGEGSGS VSLALHLQPL RSAAGAAALA LTVDLPPASS EARNSAFGFQ    780
GRLLHLSAGQ RLGVHLHTEA RARHAWQLTQ GATVLGLFRV TPEIPAGLPS PRSE          834

SEQ ID NO: 75             moltype = AA   length = 640
FEATURE                   Location/Qualifiers
REGION                    1..640
                          note = anti-FAP (4B9) Fc knob chain fused to monomeric hu
                          4-1BBL (71-254)
source                    1..640
                          mol_type = protein
                          organism = synthetic construct
SEQUENCE: 75
EVQLLESGGG LVQPGGSLRL SCAASGFTFS SYAMSWVRQA PGKGLEWVSA IIGSGASTYY    60
ADSVKGRFTI SRDNSKNTLY LQMNSLRAED TAVYYCAKGW FGGFNYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APEAAGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALGA PIEKTISKAK GQPREPQVYT LPPCRDELTK    360
NQVSLWCLVK GFYPSDIAVE WESNGQPENN YKTTPPVLDS DGSFFLYSKL TVDKSRWQQG    420
NVFSCSVMHE ALHNHYTQKS LSLSPGGGGG SGGGGSREGP ELSPDDPAGL LDLRQGMFAQ    480
LVAQNVLLID GPLSWYSDPG LAGVSLTGGL SYKEDTKELV VAKAGVYYVF FQLELRRVVA    540
GEGSGSVSLA LHLQPLRSAA GAAALALTVD LPPASSEARN SAFGFQGRLL HLSAGQRLGV    600
HLHTEARARH AWQLTQGATV LGLFRVTPEI PAGLPSPRSE                          640

SEQ ID NO: 76             moltype = AA   length = 833
FEATURE                   Location/Qualifiers
REGION                    1..833
                          note = anti-FAP (28H1) Fc hole chain fused to dimeric hu
                          4-1BBL (71-254)
source                    1..833
                          mol_type = protein
                          organism = synthetic construct
SEQUENCE: 76
EVQLLESGGG LVQPGGSLRL SCAASGFTFS SHAMSWVRQA PGKGLEWVSA IWASGEQYYA    60
DSVKGRFTIS RDNSKNTLYL QMNSLRAEDT AVYYCAKGWL GNFDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PEAAGGPSVF    240
```

```
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVCTL PPSRDELTKN  360
QVSLSCAVKG FYPSDIAVEW ESNGQPENNY KTTPPVLDSD GSFFLVSKLT VDKSRWQQGN  420
VFSCSVMHEA LHNHYTQKSL SLSPGGGGGS GGGGSREGPE LSPDDPAGLL DLRQGMFAQL  480
VAQNVLLIDG PLSWYSDPGL AGVSLTGGLS YKEDTKELVV AKAGVYYFF QLELRRVVAG   540
EGSGSVSLAL HLQPLRSAAG AAALALTVDL PPASSEARNS AFGFQGRLLH LSAGQRLGVH  600
LHTEARARHA WQLTQGATVL GLFRVTPEIP AGLPSPRSEG GGGSGGGGSR EGPELSPDDP  660
AGLLDLRQGM FAQLVAQNVL LIDGPLSWYS DPGLAGVSLT GGLSYKEDTK ELVVAKAGVY  720
YVFFQLELRR VVAGEGSGSV SLALHLQPLR SAAGAAALAL TVDLPPASSE ARNSAFGFQG  780
RLLHLSAGQR LGVHLHTEAR ARHAWQLTQG ATVLGLFRVT PEIPAGLPSP RSE         833
```

```
SEQ ID NO: 77              moltype = AA  length = 639
FEATURE                    Location/Qualifiers
REGION                     1..639
                           note = anti-FAP (28H1) Fc knob chain fused to monomeric hu
                           4-1BBL (71-254)
source                     1..639
                           mol_type = protein
                           organism = synthetic construct
SEQUENCE: 77
EVQLLESGGG LVQPGGSLRL SCAASGFTFS SHAMSWVRQA PGKGLEWVSA IWASGEQYYA  60
DSVKGRFTIS RDNSKNTLYL QMNSLRAEDT AVYYCAKGWL GNFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPCRDELTKN  360
QVSLWCLVKG FYPSDIAVEW ESNGQPENNY KTTPPVLDSD GSFFLYSKLT VDKSRWQQGN  420
VFSCSVMHEA LHNHYTQKSL SLSPGGGGGS GGGGSREGPE LSPDDPAGLL DLRQGMFAQL  480
VAQNVLLIDG PLSWYSDPGL AGVSLTGGLS YKEDTKELVV AKAGVYYFF QLELRRVVAG   540
EGSGSVSLAL HLQPLRSAAG AAALALTVDL PPASSEARNS AFGFQGRLLH LSAGQRLGVH  600
LHTEARARHA WQLTQGATVL GLFRVTPEIP AGLPSPRSE                        639
```

```
SEQ ID NO: 78              moltype = AA  length = 834
FEATURE                    Location/Qualifiers
REGION                     1..834
                           note = DP47 Fc hole chain fused to dimeric hu 4-1BBL
                           (71-254)
source                     1..834
                           mol_type = protein
                           organism = synthetic construct
SEQUENCE: 78
EVQLLESGGG LVQPGGSLRL SCAASGFTFS SYAMSWVRQA PGKGLEWVSA IIGSGASTYY  60
ADSVKGRFTI SRDNSKNTLY LQMNSLRAED TAVYYCAKGW FGGFNYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVCT LPPSRDELTK  360
NQVSLSCAVK GFYPSDIAVE WESNGQPENN YKTTPPVLDS DGSFFLVSKL TVDKSRWQQG  420
NVFSCSVMHE ALHNHYTQKS LSLSPGGGGG SGGGGSREGP ELSPDDPAGL LDLRQGMFAQ  480
LVAQNVLLID GPLSWYSDPG LAGVSLTGGL SYKEDTKELV VAKAGVYYVF FQLELRRVVA  540
GEGSGSVSLA LHLQPLRSAA GAAALALTVD LPPASSEARN SAFGFQGRLL HLSAGQRLGV  600
HLHTEARARH AWQLTQGATV LGLFRVTPEI PAGLPSPRSE GGGGSGGGGS REGPELSPDD  660
PAGLLDLRQG MFAQLVAQNV LLIDGPLSWY SDPGLAGVSL TGGLSYKEDT KELVVAKAGV  720
YYVFFQLELR RVVAGEGSGS VSLALHLQPL RSAAGAAALA LTVDLPPASS EARNSAFGFQ  780
GRLLHLSAGQ RLGVHLHTEA RARHAWQLTQ GATVLGLFRV TPEIPAGLPS PRSE        834
```

```
SEQ ID NO: 79              moltype = AA  length = 640
FEATURE                    Location/Qualifiers
REGION                     1..640
                           note = DP47 Fc knob chain fused to monomeric hu 4-1BBL
                           (71-254)
source                     1..640
                           mol_type = protein
                           organism = synthetic construct
SEQUENCE: 79
EVQLLESGGG LVQPGGSLRL SCAASGFTFS SYAMSWVRQA PGKGLEWVSA IIGSGASTYY  60
ADSVKGRFTI SRDNSKNTLY LQMNSLRAED TAVYYCAKGW FGGFNYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYT LPPCRDELTK  360
NQVSLWCLVK GFYPSDIAVE WESNGQPENN YKTTPPVLDS DGSFFLYSKL TVDKSRWQQG  420
NVFSCSVMHE ALHNHYTQKS LSLSPGGGGG SGGGGSREGP ELSPDDPAGL LDLRQGMFAQ  480
LVAQNVLLID GPLSWYSDPG LAGVSLTGGL SYKEDTKELV VAKAGVYYVF FQLELRRVVA  540
GEGSGSVSLA LHLQPLRSAA GAAALALTVD LPPASSEARN SAFGFQGRLL HLSAGQRLGV  600
HLHTEARARH AWQLTQGATV LGLFRVTPEI PAGLPSPRSE                       640
```

```
SEQ ID NO: 80              moltype = AA  length = 760
FEATURE                    Location/Qualifiers
```

```
source                          1..760
                                mol_type = protein
                                organism = Homo sapiens
SEQUENCE: 80
MKTWVKIVFG VATSAVLALL VMCIVLRPSR VHNSEENTMR ALTLKDILNG TFSYKTFFPN       60
WISGQEYLHQ SADNNIVLYN IETGQSYTIL SNRTMKSVNA SNYGLSPDRQ FVYLESDYSK      120
LWRYSYTATY YIYDLSNGEF VRGNELPRPI QYLCWSPVGS KLAYVYQNNI YLKQRPGDPP      180
FQITFNGREN KIFNGIPDWV YEEEMLATKY ALWWSPNGKF LAYAEFNDTD IPVIAYSYYG      240
DEQYPRTINI PYPKAGAKNP VVRIFIIDTT YPAYVGPQEV PVPAMIASSD YYFSWLTWVT      300
DERVCLQWLK RVQNVSVLSI CDFREDWQTW DCPKTQEHIE ESRTGWAGGF FVSTPVFSYD      360
AISYYKIFSD KDGYKHIHYI KDTVENAIQI TSGKWEAINI FRVTQDSLFY SSNEFEEYPG      420
RRNIYRISIG SYPPSKKCVT CHLRKERCQY YTASFSDYAK YYALVCYGPG IPISTLHDGR      480
TDQEIKILEE NKELENALKN IQLPKEEIKK LEVDEITLWY KMILPPQFDR SKKYPLLIQV      540
YGGPCSQSVR SVFAVNWISY LASKEGMVIA LVDGRGTAFQ GDKLLYAVYR KLGVYEVEDQ      600
ITAVRKFIEM GFIDEKRIAI WGWSYGGYVS SLALASGTGL FKCGIAVAPV SSWEYYASVY      660
TERFMGLPTK DDNLEHYKNS TVMARAEYFR NVDYLLIHGT ADDNVHFQNS AQIAKALVNA      720
QVDFQAMWYS DQNHGLSGLS TNHLYTHMTH FLKQCFSLSD                            760

SEQ ID NO: 81                   moltype = AA   length = 748
FEATURE                         Location/Qualifiers
REGION                          1..748
                                note = hu FAP ectodomain+poly-lys-tag+his6-tag
source                          1..748
                                mol_type = protein
                                organism = synthetic construct
SEQUENCE: 81
RPSRVHNSEE NTMRALTLKD ILNGTFSYKT FFPNWISGQE YLHQSADNNI VLYNIETGQS       60
YTILSNRTMK SVNASNYGLS PDRQFVYLES DYSKLWRYSY TATYYIYDLS NGEFVRGNEL      120
PRPIQYLCWS PVGSKLAYVY QNNIYLKQRP GDPPFQITFN GRENKIFNGI PDWVYEEEML      180
ATKYALWWSP NGKFLAYAEF NDTDIPVIAY SYYGDEQYPR TINIPYPKAG AKNPVVRIFI      240
IDTTYPAYVG PQEVPVPAMI ASSDYYFSWL TWVTDERVCL QWLKRVQNVS VLSICDFRED      300
WQTWDCPKTQ EHIEESRTGW AGGFFVSTPV FSYDAISYYK IFSDKDGYKH IHYIKDTVEN      360
AIQITSGKWE AINIFRVTQD SLFYSSNEFE EYPGRRNIYR ISIGSYPPSK KCVTCHLRKE      420
RCQYYTASFS DYAKYYALVC YGPGIPISTL HDGRTDQEIK ILEENKELEN ALKNIQLPKE      480
EIKKLEVDEI TLWYKMILPP QFDRSKKYPL LIQVYGGPCS QSVRSVFAVN WISYLASKEG      540
MVIALVDGRG TAFQGDKLLY AVYRKLGVYE VEDQITAVRK FIEMGFIDEK RIAIWGWSYG      600
GYVSSLALAS GTGLFKCGIA VAPVSSWEYY ASVYTERFMG LPTKDDNLEH YKNSTVMARA      660
EYFRNVDYLL IHGTADDNVH FQNSAQIAKA LVNAQVDFQA MWYSDQNHGL SGLSTNHLYT      720
HMTHFLKQCF SLSDGKKKKK KGHHHHHH                                        748

SEQ ID NO: 82                   moltype = AA   length = 761
FEATURE                         Location/Qualifiers
source                          1..761
                                mol_type = protein
                                organism = Mus musculus
SEQUENCE: 82
MKTWLKTVFG VTTLAALALV VICIVLRPSR VYKPEGNTKR ALTLKDILNG TFSYKTYFPN       60
WISEQEYLHQ SEDDNIVFYN IETRESYIIL SNSTMKSVNA TDYGLSPDRQ FVYLESDYSK      120
LWRYSYTATY YIYDLQNGEF VRGYELPRPI QYLCWSPVGS KLAYVYQNNI YLKQRPGDPP      180
FQITYTGREN RIFNGIPDWV YEEEMLATKY ALWWSPDGKF LAYVEFNDSD IPIIAYSYYG      240
DGQYPRTINI PYPKAGAKNP VVRVFIVDTT YPHHVGPMEV PVPEMIASSD YYFSWLTWVS      300
SERVCLQWLK RVQNVSVLSI CDFREDWHAW ECPKNQEHVE ESRTGWAGGF FVSTPAFSQD      360
ATSYYKIFSD KDGYKHIHYI KDTVENAIQI TSGKWEAIYI FRVTQDSLFY SSNEFEGYPG      420
RRNIYRISIG NSPPSKKCVT CHLRKERCQY YTASFSYKAK YYALVCYGPG LPISTLHDGR      480
TDQEIQVLEE NKELENSLRN IQLPKVEIKK LKDGGLTFWY KMILPPQFDR SKKYPLLIQV      540
YGGPCSQSVK SVFAVNWITY LASKEGIVIA LVDGRGTAFQ GDKFLHAVYR KLGVYEVEDQ      600
LTAVRKFIEM GFIDEERIAI WGWSYGGYVS SLALASGTGL FKCGIAVAPV SSWEYYASIY      660
SERFMGLPTK DDNLEHYKNS TVMARAEYFR NVDYLLIHGT ADDNVHFQNS AQIAKALVNA      720
QVDFQAMWYS DQNHGISSGR SQNHLYTHMT HFLKQCFSLS D                         761

SEQ ID NO: 83                   moltype = AA   length = 749
FEATURE                         Location/Qualifiers
REGION                          1..749
                                note = Murine FAP ectodomain+poly-lys-tag+his6-tag
source                          1..749
                                mol_type = protein
                                organism = synthetic construct
SEQUENCE: 83
RPSRVYKPEG NTKRALTLKD ILNGTFSYKT YFPNWISEQE YLHQSEDDNI VFYNIETRES       60
YIILSNSTMK SVNATDYGLS PDRQFVYLES DYSKLWRYSY TATYYIYDLQ NGEFVRGYEL      120
PRPIQYLCWS PVGSKLAYVY QNNIYLKQRP GDPPFQITYT GRENRIFNGI PDWVYEEEML      180
ATKYALWWSP DGKFLAYVEF NDSDIPIIAY SYYGDGQYPR TINIPYPKAG AKNPVVRVFI      240
VDTTYPHHVG PMEVPVPEMI ASSDYYFSWL TWVSSERVCL QWLKRVQNVS VLSICDFRED      300
WHAWECPKNQ EHVEESRTGW AGGFFVSTPA FSQDATSYYK IFSDKDGYKH IHYIKDTVEN      360
AIQITSGKWE AIYIFRVTQD SLFYSSNEFE GYPGRRNIYR ISIGNSPPSK KCVTCHLRKE      420
RCQYYTASFS YKAKYYALVC YGPGLPISTL HDGRTDQEIQ VLEENKELEN SLRNIQLPKV      480
EIKKLKDGGL TFWYKMILPP QFDRSKKYPL LIQVYGGPCS QSVKSVFAVN WITYLASKEG      540
IVIALVDGRG TAFQGDKFLH AVYRKLGVYE VEDQLTAVRK FIEMGFIDEE RIAIWGWSYG      600
GYVSSLALAS GTGLFKCGIA VAPVSSWEYY ASIYSERFMG LPTKDDNLEH YKNSTVMARA      660
```

-continued

```
EYFRNVDYLL IHGTADDNVH FQNSAQIAKA LVNAQVDFQA MWYSDQNHGI LSGRSQNHLY   720
THMTHFLKQC FSLSDGKKKK KKGHHHHHH                                     749

SEQ ID NO: 84          moltype = AA  length = 748
FEATURE                Location/Qualifiers
REGION                 1..748
                       note = Cynomolgus FAP ectodomain+poly-lys-tag+his6-tag
source                 1..748
                       mol_type = protein
                       organism = synthetic construct
SEQUENCE: 84
RPPRVHNSEE NTMRALTLKD ILNGTFSYKT FFPNWISGQE YLHQSADNNI VLYNIETGQS   60
YTILSNRTMK SVNASNYGLS PDRQFVYLES DYSKLWRYSY TATYYIYDLS NGEFVRGNEL   120
PRPIQYLCWS PVGSKLAYVY QNNIYLKQRP GDPPFQITFN GRENKIFNGI PDWVYEEEML   180
ATKYALWWSP NGKFLAYAEF NDTDIPVIAY SYYGDEQYPR TINIPYPKAG AKNPFVRIFI   240
IDTTYPAYVG PQEVPVPAMI ASSDYYFSWL TWVTDERVCL QWLKRVQNVS VLSICDFRED   300
WQTWDCPKTQ EHIEESRTGW AGGFFVSTPV FSYDAISYYK IFSDKDGYKH IHYIKDTVEN   360
AIQITSGKWE AINIFRVTQD SLFYSSNEFE DYPGRRNIYR ISIGSYPPSK KCVTCHLRKE   420
RCQYYTASFS DYAKYYALVC YGPGIPISTL HDGRTDQEIK ILEENKELEN ALKNIQLPKE   480
EIKKLEVDEI TLWYKMILPP QFDRSKKYPL LIQVYGGPCS QSVRSVFAVN WISYLASKEG   540
MVIALVDGRG TAFQGDKLLY AVYRKLGVYE VEDQITAVRK FIEMGFIDEK RIAIWGWSYG   600
GYVSSLALAS GTGLFKCGIA VAPVSSWEYY ASVYTERFMG LPTKDDNLEH YKNSTVMARA   660
EYFRNVDYLL IHGTADDNVH FQNSAQIAKA LVNAQVDFQA MWYSDQNHGL SGLSTNHLYT   720
HMTHFLKQCF SLSDGKKKKK KGHHHHHH                                      748

SEQ ID NO: 85          moltype = AA  length = 702
FEATURE                Location/Qualifiers
source                 1..702
                       mol_type = protein
                       organism = Homo sapiens
SEQUENCE: 85
MESPSAPPHR WCIPWQRLLL TASLLTFWNP PTTAKLTIES TPFNVAEGKE VLLLVHNLPQ   60
HLFGYSWYKG ERVDGNRQII GYVIGTQQAT PGPAYSGREI IYPNASLLIQ NIIQNDTGFY   120
TLHVIKSDLV NEEATGQFRV YPELPKPSIS SNNSKPVEDK DAVAFTCEPE TQDATYLWWV   180
NNQSLPVSPR LQLSNGNRTL TLFNVTRNDT ASYKCETQNP VSARRSDSVI LNVLYGPDAP   240
TISPLNTSYR SGENLNLSCH AASNPPAQYS WFVNGTFQQS TQELFIPNIT VNNSGSYTCQ   300
AHNSDTGLNR TTVTTITVYA EPPKPFITSN NSNPVEDEDA VALTCEPEIQ NTTYLWWVNN   360
QSLPVSPRLQ LSNDNRTLTL LSVTRNDVGP YECGIQNELS VDHSDPVILN VLYGPDDPTI   420
SPSYTYYRPG VNLSLSCHAA SNPPAQYSWL IDGNIQQHTQ ELFISNITEK NSGLYTCQAN   480
NSASGHSRTT VKTITVSAEL PKPSISSNNS KPVEDKDAVA FTCEPEAQNT TYLWWVNGQS   540
LPVSPRLQLS NGNRTLTLFN VTRNDARAYV CGIQNSVSAN RSDPVTLDVL YGPDTPIISP   600
PDSSYLSGAN LNLSCHSASN PSPQYSWRIN GIPQQHTQVL FIAKITPNNN GTYACFVSNL   660
ATGRNNSIVK SITVSASGTS PGLSAGATVG IMIGVLVGVA LI                      702

SEQ ID NO: 86          moltype = AA  length = 254
FEATURE                Location/Qualifiers
source                 1..254
                       mol_type = protein
                       organism = Homo sapiens
SEQUENCE: 86
MEYASDASLD PEAPWPPAPR ARACRVLPWA LVAGLLLLLL LAAACAVFLA CPWAVSGARA   60
SPGSAASPRL REGPELSPDD PAGLLDLRQG MFAQLVAQNV LLIDGPLSWY SDPGLAGVSL   120
TGGLSYKEDT KELVVAKAGV YYVFFQLELR RVVAGEGSGS VSLALHLQPL RSAAGAAALA   180
LTVDLPPASS EARNSAFGFQ GRLLHLSAGQ RLGVHLHTEA RARHAWQLTQ GATVLGLFRV   240
TPEIPAGLPS PRSE                                                    254

SEQ ID NO: 87          moltype = AA  length = 205
FEATURE                Location/Qualifiers
source                 1..205
                       mol_type = protein
                       organism = Homo sapiens
SEQUENCE: 87
ACPWAVSGAR ASPGSAASPR LREGPELSPD DPAGLLDLRQ GMFAQLVAQN VLLIDGPLSW   60
YSDPGLAGVS LTGGLSYKED TKELVVAKAG VYYVFFQLEL RRVVAGEGSG SVSLALHLQP   120
LRSAAGAAAL ALTVDLPPAS SEARNSAFGF QGRLLHLSAG QRLGVHLHTE ARARHAWQLT   180
QGATVLGLFR VTPEIPAGLP SPRSE                                        205

SEQ ID NO: 88          moltype = AA  length = 255
FEATURE                Location/Qualifiers
source                 1..255
                       mol_type = protein
                       organism = Homo sapiens
SEQUENCE: 88
MGNSCYNIVA TLLLVLNFER TRSLQDPCSN CPAGTFCDNN RNQICSPCPP NSFSSAGGQR   60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                   255
```

-continued

```
SEQ ID NO: 89              moltype = AA  length = 256
FEATURE                    Location/Qualifiers
source                     1..256
                           mol_type = protein
                           organism = Mus musculus
SEQUENCE: 89
MGNNCYNVVV IVLLLVGCEK VGAVQNSCDN CQPGTFCRKY NPVCKSCPPS TFSSIGGQPN  60
CNICRVCAGY FRFKKFCSST HNAECECIEG FHCLGPQCTR CEKDCRPGQE LTKQGCKTCS  120
LGTFNDQNGT GVCRPWTNCS LDGRSVLKTG TTEKDVVCGP PVVSFSPSTT ISVTPEGGPG  180
GHSLQVLTLF LALTSALLLA LIFITLLLFSV LKWIRKKFPH IFKQPFKKTT GAAQEEDACS  240
CRCPQEEEGG GGGYEL                                                  256

SEQ ID NO: 90              moltype = AA  length = 254
FEATURE                    Location/Qualifiers
source                     1..254
                           mol_type = protein
                           organism = unidentified
                           note = cynomolgus
SEQUENCE: 90
MGNSCYNIVA TLLLVLNFER TRSLQDLCSN CPAGTFCDNN RSQICSPCPP NSFSSAGGQR  60
TCDICRQCKG VFKTRKECSS TSNAECDCIS GYHCLGAECS MCEQDCKQGQ ELTKKGCKDC  120
CFGTFNDQKR GICRPWTNCS LDGKSVLVNG TKERDVVCGP SPADLSPGAS SATPPAPARE  180
PGHSPQIIFF LALTSTVVLF LLFFLVLRFS VVKRSRKKLL YIFKQPFMRP VQTTQEEDGC  240
SCRFPEEEEG GCEL                                                    254

SEQ ID NO: 91              moltype = AA  length = 5
FEATURE                    Location/Qualifiers
REGION                     1..5
                           note = G4S peptide linker
source                     1..5
                           mol_type = protein
                           organism = synthetic construct
SEQUENCE: 91
GGGGS                                                              5

SEQ ID NO: 92              moltype = AA  length = 10
FEATURE                    Location/Qualifiers
REGION                     1..10
                           note = (G4S)2
source                     1..10
                           mol_type = protein
                           organism = synthetic construct
SEQUENCE: 92
GGGGSGGGGS                                                         10

SEQ ID NO: 93              moltype = AA  length = 10
FEATURE                    Location/Qualifiers
REGION                     1..10
                           note = (SG4)2
source                     1..10
                           mol_type = protein
                           organism = synthetic construct
SEQUENCE: 93
SGGGGSGGGG                                                         10

SEQ ID NO: 94              moltype = AA  length = 14
FEATURE                    Location/Qualifiers
REGION                     1..14
                           note = peptide linker
source                     1..14
                           mol_type = protein
                           organism = synthetic construct
SEQUENCE: 94
GGGGSGGGGS GGGG                                                    14

SEQ ID NO: 95              moltype = AA  length = 10
FEATURE                    Location/Qualifiers
REGION                     1..10
                           note = peptide linker
source                     1..10
                           mol_type = protein
                           organism = synthetic construct
SEQUENCE: 95
GSPGSSSSGS                                                         10

SEQ ID NO: 96              moltype = AA  length = 15
FEATURE                    Location/Qualifiers
REGION                     1..15
                           note = peptide linker 2
```

-continued

```
source                   1..15
                         mol_type = protein
                         organism = synthetic construct
SEQUENCE: 96
GGGGSGGGGS GGGGS                                                15

SEQ ID NO: 97            moltype = AA  length = 20
FEATURE                  Location/Qualifiers
REGION                   1..20
                         note = peptide linker 3
source                   1..20
                         mol_type = protein
                         organism = synthetic construct
SEQUENCE: 97
GGGGSGGGGS GGGGSGGGGS                                           20

SEQ ID NO: 98            moltype = AA  length = 8
FEATURE                  Location/Qualifiers
REGION                   1..8
                         note = peptide linker 4
source                   1..8
                         mol_type = protein
                         organism = synthetic construct
SEQUENCE: 98
GSGSGSGS                                                        8

SEQ ID NO: 99            moltype = AA  length = 8
FEATURE                  Location/Qualifiers
REGION                   1..8
                         note = peptide linker 5
source                   1..8
                         mol_type = protein
                         organism = synthetic construct
SEQUENCE: 99
GSGSGNGS                                                        8

SEQ ID NO: 100           moltype = AA  length = 8
FEATURE                  Location/Qualifiers
REGION                   1..8
                         note = peptide linker 6
source                   1..8
                         mol_type = protein
                         organism = synthetic construct
SEQUENCE: 100
GGSGSGSG                                                        8

SEQ ID NO: 101           moltype = AA  length = 6
FEATURE                  Location/Qualifiers
REGION                   1..6
                         note = peptide linker 7
source                   1..6
                         mol_type = protein
                         organism = synthetic construct
SEQUENCE: 101
GGSGSG                                                          6

SEQ ID NO: 102           moltype = AA  length = 4
FEATURE                  Location/Qualifiers
REGION                   1..4
                         note = peptide linker 8
source                   1..4
                         mol_type = protein
                         organism = synthetic construct
SEQUENCE: 102
GGSG                                                            4

SEQ ID NO: 103           moltype = AA  length = 8
FEATURE                  Location/Qualifiers
REGION                   1..8
                         note = peptide linker 9
source                   1..8
                         mol_type = protein
                         organism = synthetic construct
SEQUENCE: 103
GGSGNGSG                                                        8

SEQ ID NO: 104           moltype = AA  length = 8
FEATURE                  Location/Qualifiers
REGION                   1..8
```

-continued

```
                           note = peptide linker 10
source                     1..8
                           mol_type = protein
                           organism = synthetic construct
SEQUENCE: 104
GGNGSGSG                                                                    8

SEQ ID NO: 105             moltype = AA  length = 6
FEATURE                    Location/Qualifiers
REGION                     1..6
                           note = peptide linker 11
source                     1..6
                           mol_type = protein
                           organism = synthetic construct
SEQUENCE: 105
GGNGSG                                                                      6

SEQ ID NO: 106             moltype = AA  length = 207
FEATURE                    Location/Qualifiers
source                     1..207
                           mol_type = protein
                           organism = Homo sapiens
SEQUENCE: 106
MQSGTHWRVL GLCLLSVGVW GQDGNEEMGG ITQTPYKVSI SGTTVILTCP QYPGSEILWQ      60
HNDKNIGGDE DDKNIGSDED HLSLKEFSEL EQSGYYVCYP RGSKPEDANF YLYLRARVCE     120
NCMEMDVMSV ATIVIVDICI TGGLLLLVYY WSKNRKAKAK PVTRGAGAGG RQRGQNKERP     180
PPVPNPDYEP IRKGQRDLYS GLNQRRI                                         207

SEQ ID NO: 107             moltype = AA  length = 198
FEATURE                    Location/Qualifiers
source                     1..198
                           mol_type = protein
                           organism = unidentified
                           note = Macacis fascularis
SEQUENCE: 107
MQSGTRWRVL GLCLLSIGVW GQDGNEEMGS ITQTPYQVSI SGTTVILTCS QHLGSEAQWQ      60
HNGKNKEDSG DRLFLPEFSE MEQSGYYVCY PRGSNPEDAS HHLYLKARVC ENCMEMDVMA     120
VATIVIVDIC ITLGLLLLVY YWSKNRKAKA KPVTRGAGAG GRQRGQNKER PPPVPNPDYE     180
PIRKGQQDLY SGLNQRRI                                                   198

SEQ ID NO: 108             moltype = AA  length = 451
FEATURE                    Location/Qualifiers
REGION                     1..451
                           note = anti-CEACAM5 Fc hole chain
source                     1..451
                           mol_type = protein
                           organism = synthetic construct
SEQUENCE: 108
QVQLVQSGAE VKKPGSSVKV SCKASGFNIK DTYMHWVRQA PGQGLEWMGR IDPANGNSKY      60
VPKFQGRVTI TADTSTSTAY MELSSLRSED TAVYYCAPFG YYVSDYAMAY WGQGTLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHTC PPCPAPEAAG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALGAPIEKTI SKAKGQPREP QVCTLPPSRD     360
ELTKNQVSLS CAVKGFYPSD IAVEWESNGQ PENNYKTTPP VLDSDGSFFL VSKLTVDKSR     420
WQQGNVFSCS VMHEALHNHY TQKSLSLSPG K                                    451

SEQ ID NO: 109             moltype = AA  length = 218
FEATURE                    Location/Qualifiers
REGION                     1..218
                           note = anti-CEACAM5 light chain
source                     1..218
                           mol_type = protein
                           organism = synthetic construct
SEQUENCE: 109
EIVLTQSPAT LSLSPGERAT LSCRAGESVD IFGVGFLHWY QQKPGQAPRL LIYRASNRAT      60
GIPARFSGSG SGTDFTLTIS SLEPEDFAVY YCQQTNEDPY TFGQGTKLEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 110             moltype = AA  length = 290
FEATURE                    Location/Qualifiers
source                     1..290
                           mol_type = protein
                           organism = Homo sapiens
SEQUENCE: 110
MRIFAVFIFM TYWHLLNAFT VTVPKDLYVV EYGSNMTIEC KFPVEKQLDL AALIVYWEME      60
DKNIIQFVHG EEDLKVQHSS YRQRARLLKD QLSLGNAALQ ITDVKLQDAG VYRCMISYGG     120
ADYKRITVKV NAPYNKINQR ILVVDPVTSE HELTCQAEGY PKAEVIWTSS DHQVLSGKTT     180
```

```
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET              290

SEQ ID NO: 111            moltype = AA  length = 288
FEATURE                   Location/Qualifiers
source                    1..288
                          mol_type = protein
                          organism = Homo sapiens
SEQUENCE: 111
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL              288

SEQ ID NO: 112            moltype = AA  length = 118
FEATURE                   Location/Qualifiers
REGION                    1..118
                          note = VH (PD-L1)
source                    1..118
                          mol_type = protein
                          organism = synthetic construct
SEQUENCE: 112
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS   118

SEQ ID NO: 113            moltype = AA  length = 107
FEATURE                   Location/Qualifiers
REGION                    1..107
                          note = VL (PD-L1)
source                    1..107
                          mol_type = protein
                          organism = synthetic construct
SEQUENCE: 113
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIK              107

SEQ ID NO: 114            moltype = AA  length = 121
FEATURE                   Location/Qualifiers
REGION                    1..121
                          note = VH (PD-L1) 2
source                    1..121
                          mol_type = protein
                          organism = synthetic construct
SEQUENCE: 114
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 115            moltype = AA  length = 108
FEATURE                   Location/Qualifiers
REGION                    1..108
                          note = VL (PD-L1) 2
source                    1..108
                          mol_type = protein
                          organism = synthetic construct
SEQUENCE: 115
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK             108

SEQ ID NO: 116            moltype = AA  length = 120
FEATURE                   Location/Qualifiers
REGION                    1..120
                          note = VH (PD-1)
source                    1..120
                          mol_type = protein
                          organism = synthetic construct
SEQUENCE: 116
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 117            moltype = AA  length = 111
FEATURE                   Location/Qualifiers
REGION                    1..111
                          note = VL (PD-1)
source                    1..111
                          mol_type = protein
                          organism = synthetic construct
SEQUENCE: 117
```

```
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI K              111

SEQ ID NO: 118          moltype = AA  length = 113
FEATURE                 Location/Qualifiers
REGION                  1..113
                        note = VH (PD-1) 2
source                  1..113
                        mol_type = protein
                        organism = synthetic construct
SEQUENCE: 118
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSS          113

SEQ ID NO: 119          moltype = AA  length = 107
FEATURE                 Location/Qualifiers
REGION                  1..107
                        note = VL (PD-1) 2
source                  1..107
                        mol_type = protein
                        organism = synthetic construct
SEQUENCE: 119
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIK                 107

SEQ ID NO: 120          moltype = AA  length = 215
FEATURE                 Location/Qualifiers
REGION                  1..215
                        note = DP47 light chain
source                  1..215
                        mol_type = protein
                        organism = synthetic construct
SEQUENCE: 120
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPLTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 121          moltype = AA  length = 5
FEATURE                 Location/Qualifiers
REGION                  1..5
                        note = (CH2527) CD3-HCDR1
source                  1..5
                        mol_type = protein
                        organism = synthetic construct
SEQUENCE: 121
TYAMN                                                                5

SEQ ID NO: 122          moltype = AA  length = 19
FEATURE                 Location/Qualifiers
REGION                  1..19
                        note = (CH2527) CD3-HCDR2
source                  1..19
                        mol_type = protein
                        organism = synthetic construct
SEQUENCE: 122
RIRSKYNNYA TYYADSVKG                                                 19

SEQ ID NO: 123          moltype = AA  length = 14
FEATURE                 Location/Qualifiers
REGION                  1..14
                        note = (CH2527) CD3-HCDR3
source                  1..14
                        mol_type = protein
                        organism = synthetic construct
SEQUENCE: 123
HGNFGNSYVS WFAY                                                      14

SEQ ID NO: 124          moltype = AA  length = 5
FEATURE                 Location/Qualifiers
REGION                  1..5
                        note = (16D5) FolR1-HCDR1
source                  1..5
                        mol_type = protein
                        organism = synthetic construct
SEQUENCE: 124
NAWMS                                                                5

SEQ ID NO: 125          moltype = AA  length = 19
```

-continued

```
FEATURE              Location/Qualifiers
REGION               1..19
                     note = (16D5) FolR1-HCDR2
source               1..19
                     mol_type = protein
                     organism = synthetic construct
SEQUENCE: 125
RIKSKTDGGT TDYAAPVKG                                            19

SEQ ID NO: 126       moltype = AA  length = 9
FEATURE              Location/Qualifiers
REGION               1..9
                     note = (16D5) FolR1-HCDR3
source               1..9
                     mol_type = protein
                     organism = synthetic construct
SEQUENCE: 126
PWEWSWYDY                                                       9

SEQ ID NO: 127       moltype = AA  length = 14
FEATURE              Location/Qualifiers
REGION               1..14
                     note = (CH2527-VL7-46-13)-LCDR1
source               1..14
                     mol_type = protein
                     organism = synthetic construct
SEQUENCE: 127
GSSTGAVTTS NYAN                                                 14

SEQ ID NO: 128       moltype = AA  length = 7
FEATURE              Location/Qualifiers
REGION               1..7
                     note = (CH2527-VL7-46-13)-LCDR2
source               1..7
                     mol_type = protein
                     organism = synthetic construct
SEQUENCE: 128
GTNKRAP                                                         7

SEQ ID NO: 129       moltype = AA  length = 9
FEATURE              Location/Qualifiers
REGION               1..9
                     note = (CH2527-VL7-46-13)-LCDR3
source               1..9
                     mol_type = protein
                     organism = synthetic construct
SEQUENCE: 129
ALWYSNLWV                                                       9

SEQ ID NO: 130       moltype = AA  length = 125
FEATURE              Location/Qualifiers
REGION               1..125
                     note = (CH2527) CD3 VH
source               1..125
                     mol_type = protein
                     organism = synthetic construct
SEQUENCE: 130
EVQLLESGGG LVQPGGSLRL SCAASGFTFS TYAMNWVRQA PGKGLEWVSR IRSKYNNYAT 60
YYADSVKGRF TISRDDSKNT LYLQMNSLRA EDTAVYYCVR HGNFGNSYVS WFAYWGQGTL 120
VTVSS                                                           125

SEQ ID NO: 131       moltype = AA  length = 120
FEATURE              Location/Qualifiers
REGION               1..120
                     note = (16D5) FolR1 VH
source               1..120
                     mol_type = protein
                     organism = synthetic construct
SEQUENCE: 131
EVQLVESGGG LVKPGGSLRL SCAASGFTFS NAWMSWVRQA PGKGLEWVGR IKSKTDGGTT 60
DYAAPVKGRF TISRDDSKNT LYLQMNSLKT EDTAVYYCTT PWEWSWYDYW GQGTLVTVSS 120

SEQ ID NO: 132       moltype = AA  length = 109
FEATURE              Location/Qualifiers
REGION               1..109
                     note = (CH2527-VL7-46-13)VL
source               1..109
                     mol_type = protein
                     organism = synthetic construct
```

-continued

```
SEQUENCE: 132
QAVVTQEPSL TVSPGGTVTL TCGSSTGAVT TSNYANWVQE KPGQAFRGLI GGTNKRAPGT    60
PARFSGSLLG GKAALTLSGA QPEDEAEYYC ALWYSNLWVF GGGTKLTVL               109

SEQ ID NO: 133          moltype = AA  length = 689
FEATURE                 Location/Qualifiers
REGION                  1..689
                        note = (16D5)VH-CH1-(CH2527)VH-CH1 Fc knob PGLALA
source                  1..689
                        mol_type = protein
                        organism = synthetic construct
SEQUENCE: 133
EVQLVESGGG LVKPGGSLRL SCAASGFTFS NAWMSWVRQA PGKGLEWVGR IKSKTDGGTT    60
DYAAPVKGRF TISRDDSKNT LYLQMNSLKT EDTAVYYCTT PWEWSWYDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDGGGGSG GGGSEVQLLE   240
SGGGLVQPGG SLRLSCAASG FTFSTYAMNW VRQAPGKGLE WVSRIRSKYN NYATYYADSV   300
KGRFTISRDD SKNTLYLQMN SLRAEDTAVY YCVRHGNFGN SYVSWFAYWG QGTLVTVSSA   360
STKGPSVFPL APSSKSTSGG TAALGCLVKD YFPEPVTVSW NSGALTSGVH TFPAVLQSSG   420
LYSLSSVVTV PSSSLGTQTY ICNVNHKPSN TKVDKKVEPK SCDKTHTCPP CPAPEAAGGP   480
SVFLFPPKPK DTLMISRTPE VTCVVVDVSH EDPEVKFNWY VDGVEVHNAK TKPREEQYNS   540
TYRVVSVLTV LHQDWLNGKE YKCKVSNKAL GAPIEKTISK AKGQPREPQV YTLPPCRDEL   600
TKNQVSLWCL VKGFYPSDIA VEWESNGQPE NNYKTTPPVL DSDGSFFLYS KLTVDKSRWQ   660
QGNVFSCSVM HEALHNHYTQ KSLSLSPGK                                     689

SEQ ID NO: 134          moltype = AA  length = 450
FEATURE                 Location/Qualifiers
REGION                  1..450
                        note = (16D5)VH-CH1-Fc hole PGLALA H435R-Y436F
source                  1..450
                        mol_type = protein
                        organism = synthetic construct
SEQUENCE: 134
EVQLVESGGG LVKPGGSLRL SCAASGFTFS NAWMSWVRQA PGKGLEWVGR IKSKTDGGTT    60
DYAAPVKGRF TISRDDSKNT LYLQMNSLKT EDTAVYYCTT PWEWSWYDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LGAPIEKTIS KAKGQPREPQ VCTLPPSRDE   360
LTKNQVSLSC AVKGFYPSDI AVEWESNGQP ENNYKTTPPV LDSDGSFFLV SKLTVDKSRW   420
QQGNVFSCSV MHEALHNRFT QKSLSLSPGK                                    450

SEQ ID NO: 135          moltype = AA  length = 215
FEATURE                 Location/Qualifiers
REGION                  1..215
                        note = (CH2527-VL7-46-13)VL-CL
source                  1..215
                        mol_type = protein
                        organism = synthetic construct
SEQUENCE: 135
QAVVTQEPSL TVSPGGTVTL TCGSSTGAVT TSNYANWVQE KPGQAFRGLI GGTNKRAPGT    60
PARFSGSLLG GKAALTLSGA QPEDEAEYYC ALWYSNLWVF GGGTKLTVLG QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECS                              215

SEQ ID NO: 136          moltype = AA  length = 766
FEATURE                 Location/Qualifiers
REGION                  1..766
                        note = di-mu4-1BBL-CL Fc knob chain
source                  1..766
                        mol_type = protein
                        organism = synthetic construct
SEQUENCE: 136
RTEPRPALTI TTSPNLGTRE NNADQVTPVS HIGCPNTTQQ GSPVFAKLLA KNQASLSNTT    60
LNWHSQDGAG SSYLSQGLRY EEDKKELVVD SPGLYYVFLE LKLSPTFTNT GHKVQGWVSL   120
VLQAKPQVDD FDNLALTVEL FPCSMENKLV DRSWSQLLLL KAGHRLSVGL RAYLHGAQDA   180
YRDWELSYPN TTSFGLFLVK PDNPWEGGGG SGGGGSRTEP RPALTITTSP NLGTRENNAD   240
QVTPVSHIGC PNTTQQGSPV FAKLLAKNQA SLSNTTLNWH SQDGAGSSYL SQGLRYEEDK   300
KELVVDSPGL YYVFLELKLS PTFTNTGHKV QGWVSLVLQA KPQVDDFDNL ALTVELFPCS   360
MENKLVDRSW SQLLLLKAGH RLSVGLRAYL HGAQDAYRDW ELSYPNTTSF GLFLVKPDNP   420
WEGGGGSGGG GSRTVAAPSV FIFPPSDRKL KSGTASVVCL LNNFYPREAK VQWKVDNALQ   480
SGNSQESVTE QDSKDSTYSL SSTLTLSKAD YEKHKVYACE VTHQGLSSPV TKSFNRGECD   540
KTHTCPPCPA PEAAGGPSVF LFPPKPKDTL MISRTPEVTC VVVDVSHEDP EVKFNWYVDG   600
VEVHNAKTKP REEQYNSTYR VVSVLTVLHQ DWLNGKEYKC KVSNKALGAP IEKTISKAKG   660
QPREPQVYTL PPCRDELTKN QVSLWCLVKG FYPSDIAVEW ESNGQPENNY KTTPPVLDSD   720
GSFFLYSKLT VDKSRWQQGN VFSCSVMHEA LHNHYTQKSL SLSPGK                  766

SEQ ID NO: 137          moltype = AA  length = 319
FEATURE                 Location/Qualifiers
```

-continued

```
REGION                   1..319
                         note = mono-mu4-1BBL-CH1 chain
source                   1..319
                         mol_type = protein
                         organism = synthetic construct
SEQUENCE: 137
RTEPRPALTI TTSPNLGTRE NNADQVTPVS HIGCPNTTQQ GSPVFAKLLA KNQASLSNTT   60
LNWHSQDGAG SSYLSQGLRY EEDKKELVVD SPGLYYVFLE LKLSPTFTNT GHKVQGWVSL  120
VLQAKPQVDD FDNLALTVEL FPCSMENKLV DRSWSQLLLL KAGHRLSVGL RAYLHGAQDA  180
YRDWELSYPN TTSFGLFLVK PDNPWEGGGG SGGGGSASTK GPSVFPLAPS SKSTSGGTAA  240
LGCLVEDYFP EPVTVSWNSG ALTSGVHTFP AVLQSSGLYS LSSVVTVPSS SLGTQTYICN  300
VNHKPSNTKV DEKVEPKSC                                              319

SEQ ID NO: 138           moltype = AA  length = 447
FEATURE                  Location/Qualifiers
REGION                   1..447
                         note = VHCH1 (4B9) Fc hole chain
source                   1..447
                         mol_type = protein
                         organism = synthetic construct
SEQUENCE: 138
EVQLLESGGG LVQPGGSLRL SCAASGFTFS SYAMSWVRQA PGKGLEWVSA IIGSGASTYY   60
ADSVKGRFTI SRDNSKNTLY LQMNSLRAED TAVYYCAKGW FGGFNYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVCT LPPSRDELTK  360
NQVSLSCAVK GFYPSDIAVE WESNGQPENN YKTTPPVLDS DGSFFLVSKL TVDKSRWQQG  420
NVFSCSVMHE ALHNHYTQKS LSLSPGK                                     447

SEQ ID NO: 139           moltype = AA  length = 215
FEATURE                  Location/Qualifiers
REGION                   1..215
                         note = VLCL(4B9) Light chain
source                   1..215
                         mol_type = protein
                         organism = synthetic construct
SEQUENCE: 139
EIVLTQSPGT LSLSPGERAT LSCRASQSVT SSYLAWYQQK PGQAPRLLIN VGSRRATGIP   60
DRFSGSGSGT DFTLTISRLE PEDFAVYYCQ QGIMLPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 140           moltype = AA  length = 571
FEATURE                  Location/Qualifiers
REGION                   1..571
                         note = VHCH1 (MU137-1)-Heavy chain Fc-DD-VL (28H1)
source                   1..571
                         mol_type = protein
                         organism = synthetic construct
SEQUENCE: 140
DVQLVESGGG LVQPGRSLKL SCAASGFIFS YFDMAWVRQA PTKGLEWVAS ISPSGDIPYY   60
RDSVKGRFTV SRENAKSSLY LQMDSLRSED TATYYCARRS YGGYSELDYW GQGVMVTVSS  120
AKTTPPSVYP LAPGSAAQTN SMVTLGCLVK GYFPEPVTVT WNSGSLSSGV HTFPAVLQSD  180
LYTLSSSVTV PSSTWPSQTV TCNVAHPASS TKVDKKVIPR DCGCKPCICT VPEVSSVFIF  240
PPKPKDVLTI TLTPKVTCVV VAISKDDPEV QFSWFVDDVE VHTAQTKPRE EQINSTFRSV  300
SELPIMHQDW LNGKEFKCRV NSAAFGAPIE KTISKTKGRP KAPQVYTIPP PKEQMAKDKV  360
SLTCMITNFF PEDITVEWQW NGQPAENYDN TQPIMDTDGS YFVYSDLNVQ KSNWEAGNTF  420
TCSVLHEGLH NHHTEKSLSH SPGGGGGSGG GGSGGGGSGG GGSEIVLTQS PGTLSLSPGE  480
RATLSCRASQ SVSRSYLAWY QQKPGQAPRL LIIGASTRAT GIPDRFSGSG SGTDFTLTIS  540
RLEPEDFAVY YCQQGVIPP TFGQGTKVEI K                                 571

SEQ ID NO: 141           moltype = AA  length = 579
FEATURE                  Location/Qualifiers
REGION                   1..579
                         note = VHCH1 (20H4.9)-Heavy chain Fc-KK-VH (28H1)
source                   1..579
                         mol_type = protein
                         organism = synthetic construct
SEQUENCE: 141
DVQLVESGGG LVQPGRSLKL SCAASGFIFS YFDMAWVRQA PTKGLEWVAS ISPSGDIPY   60
RDSVKGRFTV SRENAKSSLY LQMDSLRSED TATYYCARRS YGGYSELDYW GQGVMVTVSS  120
AKTTPPSVYP LAPGSAAQTN SMVTLGCLVK GYFPEPVTVT WNSGSLSSGV HTFPAVLQSD  180
LYTLSSSVTV PSSTWPSQTV TCNVAHPASS TKVDKKIVPR DCGCKPCICT VPEVSSVFIF  240
PPKPKDVLTI TLTPKVTCVV VAISKDDPEV QFSWFVDDVE VHTAQTKPRE EQINSTFRSV  300
SELPIMHQDW LNGKEFKCRV NSAAFGAPIE KTISKTKGRP KAPQVYTIPP PKKQMAKDKV  360
SLTCMITNFF PEDITVEWQW NGQPAENYKN TQPIMKTDGS YFVYSKLNVQ KSNWEAGNTF  420
TCSVLHEGLH NHHTEKSLSH SPGGGGGSGG GGSGGGGSGG GGSEVQLLES GGGLVQPGGS  480
LRLSCAASGF TFSSHAMSWV RQAPGKGLEW VSAIWASGEQ YYADSVKGRF TISRDNSKNT  540
```

```
LYLQMNSLRA EDTAVYYCAK GWLGNFDYWG QGTLVTVSS                              579

SEQ ID NO: 142          moltype = AA   length = 214
FEATURE                 Location/Qualifiers
REGION                  1..214
                        note = VLCL-Light chain (MU137-1)
source                  1..214
                        mol_type = protein
                        organism = synthetic construct
SEQUENCE: 142
DIQMTQSPAS LSASLEEIVT ITCQASQDIG NWLAWYHQKP GKSPQLLIYG TSSLADGVPS      60
RFSGSSSGSQ YSLKISRLQV EDIGIYYCLQ AYGAPWTFGG GTKLELKRAD AAPTVSIFPP      120
SSEQLTSGGA SVVCFLNNFY PKDINVKWKI DGSERQNGVL NSWTDQDSKD STYSMSSTLT      180
LTKDEYERHN SYTCEATHKT STSPIVKSFN RNEC                                  214

SEQ ID NO: 143          moltype = AA   length = 579
FEATURE                 Location/Qualifiers
REGION                  1..579
                        note = VHCH1 (MU137-1)-Heavy chain Fc-DD-VH (28H1)
source                  1..579
                        mol_type = protein
                        organism = synthetic construct
SEQUENCE: 143
DVQLVESGGG LVQPGRSLKL SCAASGFIFS YFDMAWVRQA PTKGLEWVAS ISPSGDIPYY      60
RDSVKGRFTV SRENAKSSLY LQMDSLRSED TATYYCARRS YGGYSELDYW GQGVMVTVSS      120
AKTTPPSVYP LAPGSAAQTN SMVTLGCLVK GYFPEPVTVT WNSGSLSSGV HTFPAVLQSD      180
LYTLSSSVTV PSSTWPSQTV TCNVAHPASS TKVDKKIVPR DCGCKPCICT VPEVSSVFIF      240
PPKPKDVLTI TLTPKVTCVV VAISKDDPEV QFSWFVDDVE VHTAQTKPRE EQINSTFRSV      300
SELPIMHQDW LNGKEFKCRV NSAAFGAPIE KTISKTKGRP KAPQVYTIPP PKEQMAKDKV      360
SLTCMITNFF PEDITVEWQW NGQPAENYDN TQPIMDTDGS YFVSDLNVQ KSNWEAGNTF       420
TCSVLHEGLH NHHTEKSLSH SPGGGGGSGG GGSGGGGSGG GGSEVQLLES GGGLVQPGGS      480
LRLSCAASGF TFSSHAMSWV RQAPGKGLEW VSAIWASGEQ YYADSVKGRF TISRDNSKNT      540
LYLQMNSLRA EDTAVYYCAK GWLGNFDYWG QGTLVTVSS                              579

SEQ ID NO: 144          moltype = AA   length = 571
FEATURE                 Location/Qualifiers
REGION                  1..571
                        note = VHCH1 (MU137-1)-Heavy chain Fc-KK-VL (28H1)
source                  1..571
                        mol_type = protein
                        organism = synthetic construct
SEQUENCE: 144
DVQLVESGGG LVQPGRSLKL SCAASGFIFS YFDMAWVRQA PTKGLEWVAS ISPSGDIPYY      60
RDSVKGRFTV SRENAKSSLY LQMDSLRSED TATYYCARRS YGGYSELDYW GQGVMVTVSS      120
AKTTPPSVYP LAPGSAAQTN SMVTLGCLVK GYFPEPVTVT WNSGSLSSGV HTFPAVLQSD      180
LYTLSSSVTV PSSTWPSQTV TCNVAHPASS TKVDKKIVPR DCGCKPCICT VPEVSSVFIF      240
PPKPKDVLTI TLTPKVTCVV VAISKDDPEV QFSWFVDDVE VHTAQTKPRE EQINSTFRSV      300
SELPIMHQDW LNGKEFKCRV NSAAFGAPIE KTISKTKGRP KAPQVYTIPP PKKQMAKDKV      360
SLTCMITNFF PEDITVEWQW NGQPAENYKN TQPIMKTDGS YFVYSKLNVQ KSNWEAGNTF      420
TCSVLHEGLH NHHTEKSLSH SPGGGGGSGG GGSGGGGSGG GGSEIVLTQS PGTLSLSPGE      480
RATLSCRASQ SVSRSYLAWY QQKPGQAPRL LIIGASTRAT GIPDRFSGSG SGTDFTLTIS      540
RLEPEDFAVY YCQQGQVIPP TFGQGTKVEI K                                     571

SEQ ID NO: 145          moltype = AA   length = 442
FEATURE                 Location/Qualifiers
REGION                  1..442
                        note = murine PD-L1 antibody heavy chain
source                  1..442
                        mol_type = protein
                        organism = synthetic construct
SEQUENCE: 145
EVQLVESGGG LVQPGGSLRL SCAASGFTFS DSWIHWVRQA PGKGLEWVAW ISPYGGSTYY      60
ADSVKGRFTI SADTSKNTAY LQMNSLRAED TAVYYCARRH WPGGFDYWGQ GTLVTVSAAK      120
TTPPSVYPLA PGSAAQTNSM VTLGCLVKGY FPEPVTVTWN SGSLSSGVHT FPAVLQSDLY      180
TLSSSVTVPS STWPSETVTC NVAHPASSTK VDKKIVPRDC GCKPCICTVP EVSSVFIFPP      240
KPKDVLTITL TPKVTCVVVD ISKDAPEVQF SWFVDDVEVH TAQTQPREEQ FNSTFRSVSE      300
LPIMHQDWLN GKEFKCRVNS AAFGAPIEKT ISKTKGRPKA PQVYTIPPPK EQMAKDKVSL      360
TCMITDFFPE DITVEWQWNG QPAENYKNTQ PIMDTDGSYF VYSKLNVQKS NWEAGNTFTC      420
SVLHEGLHNH HTEKSLSHSP GK                                               442

SEQ ID NO: 146          moltype = AA   length = 214
FEATURE                 Location/Qualifiers
REGION                  1..214
                        note = murine PD-L1 antibody light chain
source                  1..214
                        mol_type = protein
                        organism = synthetic construct
SEQUENCE: 146
DIQMTQSPSS LSASVGDRVT ITCRASQDVS TAVAWYQQKP GKAPKLLIYS ASFLYSGVPS      60
```

```
RFSGSGSGTD FTLTISSLQP EDFATYYCQQ YLYHPATFGQ GTKVEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 147        moltype = AA  length = 214
FEATURE               Location/Qualifiers
REGION                1..214
                      note = MCSP CD3 TCB (MCSP) light chain
source                1..214
                      mol_type = protein
                      organism = synthetic construct
SEQUENCE: 147
DIQMTQSPSS LSASVGDRVT ITCRASQGIR NYLNWYQQKP GKAPKLLIYY TSSLHSGVPS  60
RFSGSGSGTD YTLTISSLQP EDFATYYCQQ YSALPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 148        moltype = AA  length = 214
FEATURE               Location/Qualifiers
REGION                1..214
                      note = MCSP CD3 TCB (CD3) light chain
source                1..214
                      mol_type = protein
                      organism = synthetic construct
SEQUENCE: 148
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVLS SASTKGPSVF  120
PLAPSSKSTS GGTAALGCLV KDYFPEPVTV SWNSGALTSG VHTFPAVLQS SGLYSLSSVV  180
TVPSSSLGTQ TYICNVNHKP SNTKVDKKVE PKSC                              214

SEQ ID NO: 149        moltype = AA  length = 685
FEATURE               Location/Qualifiers
REGION                1..685
                      note = MCSP CD3 TCB heavy chain 1
source                1..685
                      mol_type = protein
                      organism = synthetic construct
SEQUENCE: 149
QVQLQESGPG LVKPSQTLSL TCTVSGGSIT SGYYWNWIRQ HPGKGLEWIG YITFDGSNNY  60
NPSLKSRVTI SRDTSKNQFS LKLSSVTAAD TAVYYCADFD YWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDGGGG SGGGGSEVQL LESGGGLVQP  240
GGSLRLSCAA SGFTFSTYAM NWVRQAPGKG LEWVSRIRSK YNNYATYYAD SVKGRFTISR  300
DDSKNTLYLQ MNSLRAEDTA VYYCVRHGNF GNSYVSWFAY WGQGTLVTVS SASVAAPSVF  360
IFPPSDEQLK SGTASVVCLL NNFYPREAKV QWKVDNALQS GNSQESVTEQ DSKDSTYSLS  420
STLTLSKADY EKHKVYACEV THQGLSSPVT KSFNRGECDK THTCPPCPAP EAAGGPSVFL  480
FPPKPKDTLM ISRTPEVTCV VVDVSHEDPE VKFNWYVDGV EVHNAKTKPR EEQYNSTYRV  540
VSVLTVLHQD WLNGKEYKCK VSNKALGAPI EKTISKAKGQ PREPQVYTLP PCRDELTKNQ  600
VSLWCLVKGF YPSDIAVEWE SNGQPENNYK TTPPVLDSDG SFFLYSKLTV DKSRWQQGNV  660
FSCSVMHEAL HNHYTQKSLS LSPGK                                        685

SEQ ID NO: 150        moltype = AA  length = 441
FEATURE               Location/Qualifiers
REGION                1..441
                      note = MCSP CD3 TCB heavy chain 2
source                1..441
                      mol_type = protein
                      organism = synthetic construct
SEQUENCE: 150
QVQLQESGPG LVKPSQTLSL TCTVSGGSIT SGYYWNWIRQ HPGKGLEWIG YITFDGSNNY  60
NPSLKSRVTI SRDTSKNQFS LKLSSVTAAD TAVYYCADFD YWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPEAA GGPSVFLFPP  240
KPKDTLMISR TPEVTCVVVD VSHEDPEVKF NWYVDGVEVH AKTKPREEQY NSTYRVVSVL  300
TVLHQDWLNG KEYKCKVSNK ALGAPIEKTI SKAKGQPREP QVCTLPPSRD ELTKNQVSLS  360
CAVKGFYPSD IAVEWESNGQ PENNYKTTPP VLDSDGSFFL VSKLTVDKSR WQQGNVFSCS  420
VMHEALHNHY TQKSLSLSPG K                                            441

SEQ ID NO: 151        moltype = AA  length = 6
FEATURE               Location/Qualifiers
REGION                1..6
                      note = MCSP-HCDR1
source                1..6
                      mol_type = protein
                      organism = synthetic construct
SEQUENCE: 151
SGYYWN                                                             6

SEQ ID NO: 152        moltype = AA  length = 16
```

-continued

```
FEATURE              Location/Qualifiers
REGION               1..16
                     note = MCSP-HCDR2
source               1..16
                     mol_type = protein
                     organism = synthetic construct
SEQUENCE: 152
YITFDGSNNY NPSLKS                                                       16

SEQ ID NO: 153       moltype =    length =
SEQUENCE: 153
000

SEQ ID NO: 154       moltype = AA   length = 11
FEATURE              Location/Qualifiers
REGION               1..11
                     note = MCSP-LCDR1
source               1..11
                     mol_type = protein
                     organism = synthetic construct
SEQUENCE: 154
RASQGIRNYL N                                                            11

SEQ ID NO: 155       moltype = AA   length = 7
FEATURE              Location/Qualifiers
REGION               1..7
                     note = MCSP-LCDR2
source               1..7
                     mol_type = protein
                     organism = synthetic construct
SEQUENCE: 155
YTSSLHS                                                                 7

SEQ ID NO: 156       moltype = AA   length = 9
FEATURE              Location/Qualifiers
REGION               1..9
                     note = QQYSALPWT
source               1..9
                     mol_type = protein
                     organism = synthetic construct
SEQUENCE: 156
QQYSALPWT                                                               9

SEQ ID NO: 157       moltype = AA   length = 112
FEATURE              Location/Qualifiers
REGION               1..112
                     note = MCSP VH
source               1..112
                     mol_type = protein
                     organism = synthetic construct
SEQUENCE: 157
QVQLQESGPG LVKPSQTLSL TCTVSGGSIT SGYYWNWIRQ HPGKGLEWIG YITFDGSNNY 60
NPSLKSRVTI SRDTSKNQFS LKLSSVTAAD TAVYYCADFD YWGQGTLVTV SS        112

SEQ ID NO: 158       moltype = AA   length = 107
FEATURE              Location/Qualifiers
REGION               1..107
                     note = MCSP VL
source               1..107
                     mol_type = protein
                     organism = synthetic construct
SEQUENCE: 158
DIQMTQSPSS LSASVGDRVT ITCRASQGIR NYLNWYQQKP GKAPKLLIYY TSSLHSGVPS 60
RFSGSGSGTD YTLTISSLQP EDFATYYCQQ YSALPWTFGQ GTKVEIK           107

SEQ ID NO: 159       moltype = AA   length = 297
FEATURE              Location/Qualifiers
source               1..297
                     mol_type = protein
                     organism = Homo sapiens
SEQUENCE: 159
MTTPRNSVNG TFPAEPMKGP IAMQSGPKPL FRRMSSLVGP TQSFFMRESK TLGAVQIMNG 60
LFHIALGGLL MIPAGIYAPI CVTVWYPLWG GIMYIISGSL LAATEKNSRK CLVKGKMIMN 120
SLSLFAAISG MILSIMDILN IKISHFLKME SLNFIRAHTP YINIYNCEPA NPSEKNSPST 180
QYCYSIQSLF LGILSVMLIF AFFQELVIAG IVENEWKRTC SRPKSNIVLL SAEEKKEQTI 240
EIKEEVVGLT ETSSQPKNEE DIEIIPIQEE EEEETETNFP EPPQDQESSP IENDSSP    297

SEQ ID NO: 160       moltype = AA   length = 50
FEATURE              Location/Qualifiers
```

```
source                  1..50
                        mol_type = protein
                        organism = synthetic construct
VARIANT                 1..50
                        note = This sequence may encompass 1-10 GGGGS repeating
                         units
SEQUENCE: 160
GGGGSGGGGS GGGGSGGGGS GGGGSGGGGS GGGGSGGGGS GGGGSGGGGS                   50

SEQ ID NO: 161          moltype = AA  length = 50
FEATURE                 Location/Qualifiers
source                  1..50
                        mol_type = protein
                        organism = synthetic construct
VARIANT                 1..50
                        note = This sequence may encompass 1-10 SGGGG repeating
                         units
SEQUENCE: 161
SGGGGSGGGG SGGGGSGGGG SGGGGSGGGG SGGGGSGGGG SGGGGSGGGG                   50

SEQ ID NO: 162          moltype = AA  length = 54
FEATURE                 Location/Qualifiers
source                  1..54
                        mol_type = protein
                        organism = synthetic construct
VARIANT                 5..54
                        note = This region may encompass 1-10 SGGGG repeating units
SEQUENCE: 162
GGGGSGGGGS GGGGSGGGGS GGGGSGGGGS GGGGSGGGGS GGGGSGGGGS GGGG             54

SEQ ID NO: 163          moltype = AA  length = 24
FEATURE                 Location/Qualifiers
source                  1..24
                        mol_type = protein
                        organism = synthetic construct
VARIANT                 1..24
                        note = This sequence may encompass 3-6 GGGS repeating units
SEQUENCE: 163
GGGSGGGSGG GSGGGSGGGG GGGS                                              24

SEQ ID NO: 164          moltype = AA  length = 25
FEATURE                 Location/Qualifiers
source                  1..25
                        mol_type = protein
                        organism = synthetic construct
VARIANT                 1..25
                        note = This sequence may encompass 2-5 GGGGS repeating units
SEQUENCE: 164
GGGGSGGGGS GGGGSGGGGS GGGGS                                             25

SEQ ID NO: 165          moltype = AA  length = 27
FEATURE                 Location/Qualifiers
source                  1..27
                        mol_type = protein
                        organism = synthetic construct
VARIANT                 1..24
                        note = This region may encompass 3-6 GGGS repeating units
VARIANT                 25..27
                        note = This region may encompass 0-3 residues
SEQUENCE: 165
GGGSGGGSGG GSGGGSGGGG GGGSGGG                                           27

SEQ ID NO: 166          moltype = AA  length = 28
FEATURE                 Location/Qualifiers
source                  1..28
                        mol_type = protein
                        organism = synthetic construct
VARIANT                 1..25
                        note = This region may encompass 2-5 GGGGS repeating units
VARIANT                 26..28
                        note = This region may encompass 0-3 residues
SEQUENCE: 166
GGGGSGGGGS GGGGSGGGGS GGGGSGGG                                          28

SEQ ID NO: 167          moltype = AA  length = 11
FEATURE                 Location/Qualifiers
source                  1..11
                        mol_type = protein
                        organism = synthetic construct
```

```
SEQUENCE: 167
DGGGGSGGGG S                                                                    11

SEQ ID NO: 168          moltype = AA  length = 6
FEATURE                 Location/Qualifiers
source                  1..6
                        mol_type = protein
                        organism = synthetic construct
SEQUENCE: 168
HHHHHH                                                                          6

SEQ ID NO: 169          moltype = AA  length = 9
FEATURE                 Location/Qualifiers
source                  1..9
                        mol_type = protein
                        organism = Cytomegalovirus sp.
SEQUENCE: 169
NLVPMVATV                                                                       9
```

The invention claimed is:

1. A method for treating cancer in a subject, wherein the method comprises administering to the subject an effective amount of a T-cell activating anti-carcinoembryonic antigen (CEA)/anti-CD3 bispecific antibody and an effective amount of a 4-1BB agonist that binds to 4-1BB comprising at least one antigen binding domain capable of specific binding to fibroblast activation protein (FAP), wherein said treating comprises alleviating symptoms of the cancer, diminishing pathological consequences of the cancer, delaying progression of the cancer, decreasing the rate of disease progression of the cancer, amelioration or palliation of the disease state of the cancer, remission of the cancer, or improving prognosis of the cancer; and wherein the at least one antigen binding domain capable of specific binding to FAP comprises:

a heavy chain variable region ($V_H$FAP) comprising (i) CDR-H1 comprising the amino acid sequence of SEQ ID NO:15, (ii) CDR-H2 comprising the amino acid sequence of SEQ ID NO:16, and (iii) CDR-H3 comprising the amino acid sequence of SEQ ID NO:17, and a light chain variable region ($V_L$FAP) comprising (iv) CDR-L1 comprising the amino acid sequence of SEQ ID NO:18, (v) CDR-L2 comprising the amino acid sequence of SEQ ID NO:19, and (vi) CDR-L3 comprising the amino acid sequence of SEQ ID NO:20; and wherein the 4-1BB agonist that binds to 4-1BB comprises a first polypeptide and a second polypeptide that are linked to each other by a disulfide bond, wherein the first polypeptide comprises the amino acid sequence of SEQ ID NO:25, SEQ ID NO:26, SEQ ID NO:27, SEQ ID NO:28, SEQ ID NO:29, SEQ ID NO:30, SEQ ID NO:31, or SEQ ID NO:32 and the second polypeptide comprises the amino acid sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

2. The method of claim 1, wherein the T-cell activating anti-CEA/anti-CD3 bispecific antibody comprises a first antigen binding domain comprising a heavy chain variable region ($V_H$CD3) and a light chain variable region ($V_L$CD3); and a second antigen binding domain comprising a heavy chain variable region ($V_H$CEA) and a light chain variable region ($V_L$CEA).

3. The method of claim 2, wherein the second antigen binding domain comprises a heavy chain variable region ($V_H$CEA) CDR-H1 comprising the amino acid sequence of SEQ ID NO:41, CDR-H2 comprising the amino acid sequence of SEQ ID NO:42, and CDR-H3 comprising the amino acid sequence of SEQ ID NO:43, and a light chain variable region ($V_L$CEA) CDR-L1 comprising the amino acid sequence of SEQ ID NO: 44, CDR-L2 comprising the amino acid sequence of SEQ ID NO: 45, and CDR-L3 comprising the amino acid sequence of SEQ ID NO: 46.

4. The method of claim 2, wherein the second antigen binding domain comprises a heavy chain variable region ($V_H$CEA) comprising the amino acid sequence of SEQ ID NO:47 and a light chain variable region ($V_L$CEA) comprising the amino acid sequence of SEQ ID NO: 48.

5. The method of claim 1, wherein the at least one antigen binding domain capable of specific binding to FAP comprises a heavy chain variable region ($V_H$FAP) comprising the amino acid sequence of SEQ ID NO:23 and a light chain variable region ($V_L$FAP) comprising the amino acid sequence of SEQ ID NO:24.

6. The method of claim 1, wherein the 4-1BB agonist comprising at least one antigen binding domain capable of specific binding to FAP comprises:

(a) a heavy chain variable region ($V_H$FAP) comprising the amino acid sequence of SEQ ID NO:23 and a light chain variable region ($V_L$FAP) comprising the amino acid sequence of SEQ ID NO:24, and (b) a first polypeptide and a second polypeptide that are linked to each other by a disulfide bond, wherein the first polypeptide comprises the amino acid sequence of SEQ ID NO:29 and the second polypeptide comprises the amino acid sequence of SEQ ID NO:5.

7. The method of claim 1, wherein the 4-1BB agonist comprising at least one antigen binding domain capable of specific binding to FAP comprises a first heavy chain comprising the amino acid sequence of SEQ ID NO:65, a first light chain comprising the amino acid sequence of SEQ ID NO:66, and a second heavy chain comprising the amino acid sequence of SEQ ID NO:67 and a second light chain comprising the amino acid sequence of SEQ ID NO:68.

8. The method of claim 1, wherein the T-cell activating anti-CEA/anti-CD3 bispecific antibody comprises the polypeptide sequence of SEQ ID NO:61, the polypeptide sequence of SEQ ID NO:62, the polypeptide sequence of SEQ ID NO:63 and the polypeptide sequence of SEQ ID NO:64.

9. The method of claim 1, wherein the T cell-activating anti-CEA/anti-CD3 bispecific antibody comprises a polypeptide comprising the amino acid sequence of SEQ ID NO: 61, a polypeptide comprising the amino acid sequence of SEQ ID NO: 62, a polypeptide comprising the amino acid sequence of SEQ ID NO: 63 and a polypeptide comprising the amino acid sequence of SEQ ID NO: 64 and wherein the 4-1BB (CD137) agonist comprises a first heavy chain amino acid sequence of SEQ ID NO:65, a first light chain comprising the amino acid sequence of SEQ ID NO:66, a second heavy chain comprising the A amino acid sequence of SEQ ID NO:67 and a second light chain comprising the amino acid sequence of SEQ ID NO:68.

* * * * *